United States Patent
Hosoya et al.

(10) Patent No.: US 9,074,261 B2
(45) Date of Patent: Jul. 7, 2015

(54) METHOD OF DETECTING HEAT-RESISTANT FUNGUS

(75) Inventors: Kouichi Hosoya, Haga-gun (JP);
Motokazu Nakayama, Haga-gun (JP);
Hajime Tokuda, Haga-gun (JP);
Takashi Yaguchi, Chiba (JP); Yusuke Hiro, Chiba (JP)

(73) Assignee: Kao Corporation, Tokyo (JP)

(*) Notice: Subject to any disclaimer, the term of this patent is extended or adjusted under 35 U.S.C. 154(b) by 453 days.

(21) Appl. No.: 12/994,566

(22) PCT Filed: May 28, 2009

(86) PCT No.: PCT/JP2009/059818
§ 371 (c)(1),
(2), (4) Date: Jan. 5, 2011

(87) PCT Pub. No.: WO2009/145279
PCT Pub. Date: Dec. 3, 2009

(65) Prior Publication Data
US 2011/0136117 A1    Jun. 9, 2011

(30) Foreign Application Priority Data

May 28, 2008  (JP) .................. 2008-139995
May 28, 2008  (JP) .................. 2008-139996
May 28, 2008  (JP) .................. 2008-139997
May 28, 2008  (JP) .................. 2008-139998
May 28, 2008  (JP) .................. 2008-139999
May 29, 2008  (JP) .................. 2008-141499

(51) Int. Cl.
*C12Q 1/68* (2006.01)
*C12Q 1/04* (2006.01)
*G01N 33/569* (2006.01)

(52) U.S. Cl.
CPC ............... *C12Q 1/6895* (2013.01); *C12Q 1/04* (2013.01); *G01N 33/56961* (2013.01); *G01N 2333/37* (2013.01); *G01N 2333/38* (2013.01)

(58) Field of Classification Search
None
See application file for complete search history.

(56) References Cited

U.S. PATENT DOCUMENTS 6,117,636 A * 9/2000 Chrzavzez nee Taddei et al. ................. 435/6.12
2005/0118625 A1 6/2005 Mounts

FOREIGN PATENT DOCUMENTS

JP   2006-061152   3/2006
JP   2006-304763   11/2006

(Continued)

OTHER PUBLICATIONS

Peterson, S.W. Mycologia 100(2):205-226 (Mar./Apr. 2008).*

(Continued)

*Primary Examiner* — Diana B Johannsen
(74) *Attorney, Agent, or Firm* — Sterne, Kessler, Goldstein & Fox P.L.L.C.

(57) ABSTRACT

A method of detecting a heat-resistant fungus, which has a step of identifying the heat-resistant fungus using the following nucleic acid (I) or (II):
(I) a nucleic acid including a nucleotide sequence set forth in any one of SEQ ID NOS: 24 to 35 and 83 to 86, or a complementary sequence thereof; or
(II) a nucleic acid including a nucleotide sequence resulting from a deletion, substitution, or addition of one to several nucleotides in the nucleotide sequence set forth in any one of SEQ ID NOS: 24 to 35 and 83 to 86 and being capable of detecting the heat-resistant fungus, or a complementary sequence thereof.

6 Claims, 36 Drawing Sheets

Lane    Strain No.
1; B. nivea  NBRC8815
2; B. nivea  NBRC8972
3; B. nivea  NBRC30569
4; B. nivea  NBRC31351
5; B. nivea  NBRC31832
6; B. nivea  CBS140.65
7; B. nivea  CBS608.71

(56) References Cited

FOREIGN PATENT DOCUMENTS

| JP | 2007-174903 | | 7/2007 |
|---|---|---|---|
| JP | 11-505728 | | 5/2011 |
| WO | WO 96/38587 | | 12/1996 |
| WO | WO 9947706 A1 | * | 9/1999 |
| WO | WO 01/96612 A2 | | 12/2001 |
| WO | WO 2006005770 A2 | * | 1/2006 |
| WO | WO 2007/101664 A2 | | 9/2007 |

OTHER PUBLICATIONS

Peterson, S.W. GenBank Accession No. EU021671 (Jun. 11, 2008).*
Luangsa-ard, J.J. et al. Phylogeny of section *Paecilomyces* based on ribosomal DNA and beta-tubulin gene sequences, PopSet 62999448, including GenBank accession No. AY7553355 (Mar. 30, 2006).*
Translation of International Search Report for PCT/JP2009/059818; I.A. fd: May 28, 2009, mailed Jun. 30, 2009 from the Japanese Patent Office, Tokyo, Japan.
International Preliminary Report on Patentability, Chapter I of the Patent Cooperation Treaty, including a translation of the Written Opinion for PCT/JP2009/059818; I.A. fd: May 28, 2009, issued Jan. 11, 2011 from the International Bureau of WIPO, Geneva, Switzerland.
Aoyama, F., "Identification of Heat resistance Fungi in Fruit Juice based on DNA sequence analysis," Kajitsu Kyohaiho, Association of Fruit Juice Report No. 569, pp. 4-15 (Jan. 2006), Japan Fruit Juice Association, Tokyo, Japan.
Unverified human translation of a report by Aoyama, F., "Identification of Heat resistance Fungi in fruit juice based on DNA sequence analysis,"Kajitsu Kyohaiho, Association of Fruit Juice, Report No. 569, pp. 4-15, Japan Fruit Juice Association, Tokyo, Japan (Jan. 2006).
Extended European Search Report for EP Appl. No. 09754787, mailed Nov. 3, 2011, from the European Patent Office, Rijswijk, Netherlands.
Puel, O et al., "The inability of *Byssochlamys fulva* to produce patulin is related to absence of 6-methylsalicylic acid synthase and isoepoxydon dehydrogenase genes," Int J Food Microbiol. 115(2):131-139 (Apr. 2007), Elsevier, Netherlands.
Glass NL et al., "Development of primer sets designed for use with the PCR to amplify conserved genes from filamentous ascomycetes," Appl. Envir. Microbiol., 61:1323-1330 (Apr. 1995), American Soc. Microbiology, Washington, DC.
Accession No. AY753355; retrieved from EBI accession No. EM_FUN:AY53355, entry created Mar. 30, 2006, updated May 13, 2009, *Byssochlamys nivea* strain CBS 133.37 beta-tubulin gene, partial sequence.
Dombrink-Kurtzman MA et al., "*Byssochlamys nivea* with patulin-producing capability has an isoepoxydon dehydrogenase gene (idh) with sequence homology to *Penicillium expansum* and *P. griseofulvum*,"Mycol. Res.110(Pt 9): 1111-1118 (Sep. 2006), Elsevier, Netherlands.
Accession No. DQ322216; retrieved from EBI accession No. EM_FUN:DQ322216, entry created Sep. 21, 2006, updated Sep. 21, 2006, *Byssochlamys nivea* strain NRRL 32294 18S ribosomal RNA gene, partial sequence; internal transcribed spacer 1, 5.8S ribosomal RNA gene, and internal transcribed spacer 2, complete sequence; and 28S ribosomal RNA gene, partial sequence.
Furuhata, K. et al., "The detection of *Alicyclobacillus acidoterrestris* from the commercial juice by the LAMP method," Abstracts of the 26th Annual General Conference of the Japanese Society of Food Microbiology, p. 42, (Nov. 2005), Nakagawa Print Co., Ltd., Ishikawa, Japan.

Yaguchi, T et al., "Molecular phylogenetics of multiple genes on *Aspergillus* section *Fumigati* isolated from clinical specimens in Japan," Jpn J Med Mycol (Nihon Ishinkin Gakkai Zasshi) 48(1): 37-46, (Jan. 2007), Do Gakkai, Tokyo, Japan.
Extended European search report, including the European search report and the European search opinion, for EP patent application No. 13198462.7, dated Mar. 3, 2014, European Patent Office, Rijswijk, Netherlands.
EMBL Database accession No. AY766254; retrieved from EBI accession No. EM_EST:AY766254, entry created Dec. 31, 2005, last updated (version 2) Nov. 14, 2006, "*Talaromyces thermophilus* beta-tubulin gene, exons 3 through 6 and partial cds".
EMBL Database accession No. AY766252; retrieved from EBI accession No. EM_EST:AY766252, entry created Dec. 31, 2005, last updated (version 2) Nov. 14, 2006, "*Talaromyces flavus* beta-tubulin gene, exons 3 through 6 and partial cds".
Extended European search report, including the European search report and the European search opinion, for EP patent application No. 13198494.0, dated Mar. 3, 2014, European Patent Office, Rijswijk, Netherlands.
EMBL Database accession No. AB176625; retrieved from EBI accession No. EM_STD:AB176625, entry created Jan. 6, 2005, last updated (version 1) Jan. 6, 2005, "*Talaromyces intermedius* genes for ITS 1, 5.8S rRNA, ITS 2, partial and complete sequence, strain-:NBRC 31572".
EMBL Database accession No. AB196360; retrieved from EBI accession No. EM_STD:AB196360, entry created Jun. 9, 2005, last updated (version 1) Jun. 9, 2005, "*Talaromyces flavus* gene for 28S rRNA, partial sequence".
Extended European search report, including the European search report and the European search opinion, for EP patent application No. 13198538.4, dated Mar. 3, 2014, European Patent Office, Rijswijk, Netherlands.
Brandt, ME et al., "Utility of random amplified polymorphic DNA PCR and TaqMan automated detection in molecular identification of *Aspergillus finnigatus*," J. Clin. Microbiol., Jul. 1998, 36(7):2057-2062, American Society for Microbiology, Washington, DC.
EMBL Database accession No. AF057315; retrieved from EBI accession No. EM_EST:AF057315, entry created Apr. 15, 1998, last updated (version 4) Apr. 15, 2005, "*Aspergillus fumigatus* beta tubulin gene, partial cds".
EMBL Database accession No. DQ438538; retrieved from EBI accession No. EM_EST:DQ438538, entry created Mar. 2, 2007, last updated (version 2) Mar. 12, 2008, "*Neosartorya fischeri* isolate FH198 Beta-tubulin gene, partial sequence".
Extended European search report, including the European search report and the European search opinion, for EP patent application No. 13198558.2, dated Mar. 3, 2014, European Patent Office, Rijswijk, Netherlands.
EMBL Database accession No. AY766253; retrieved from EBI accession No. EM_EST:AY766253, entry created Dec. 31, 2005, last updated (version 2) Nov. 14, 2006, "*Hamigera avellanea* beta-tubulin gene, exons 3 through 6 and partial cds".
Arunmozhi Balajee, S., et al., "Mistaken Identity: *Neosartorya pseudofischeri* and Its Anamorph Masquerading as *Aspergillus fumigatus*," J. Clin. Microbiol., Dec. 2005; 43: 5996-5999, American Society for Microbiology, Washington, DC.
Li, J-k et al., "Optimization and establishment of quantitatively competitive PCR system for the detection of *Alicyclobacillus acidoterrestris*," Scientia Agricultura Sinica, 2006, 39(2): 375-380, Chinese Agricultural Society, China.

* cited by examiner

Fig. 1

| | | |
|---|---|---|
| A. fumigatus | AGGGTAACCAAATTGGTGTGCCGCCTTTCTGGTATGTCTCTTGACCTCAAAGCTT | 50 |
| N. fischeri | TGGTAAACCAAATCGGTGCTGCTTTCTGGTATGTCTGTATGTCTTNGACCTCAATTCTT | 50 |
| N. spinosa | TGGTAAACCAAATGGGTGCTGCTTTCTGGTATGTCTGTATGTCTCAACCTCAATGCTT | 50 |
| | **. ***** . **** . * ******** . . ****** . *** | |

| | | |
|---|---|---|
| A. fumigatus | GGATGACGGTGATTGGATCTGTCTGATCTTAGGCAGGCTA-CCTCCATGGG | 99 |
| N. fischeri | GGATGACGGAGAGATTGGGACCTGTC----TTAGCAGGCTGTCCTCCATGGG | 97 |
| N. spinosa | GGATGATGGGAGATTAGGACCTGTCATCTCAGCAGGCTGTCCTCCATGGG | 100 |
| | ***** . *** . *** . *** . ** . ** . . * . ******** . . ********* | |

SEQ ID NO:22 →

| | | |
|---|---|---|
| A. fumigatus | CCTCCCAATTGAGAAAGC-GGCGGAAACACGGAAACAACACGGAAGGA | 249 |
| N. fischeri | CCTCCCAATTGAGAAAGC-GGCGGAAACACGGAAACGACGA-AGGAAGAGAGGA | 246 |
| N. spinosa | CCTCCCAATTGAGAAAGCGGGGGGAAACACGGAAACGACGAAGGAAGGAAGAGGA | 251 |
| | ****************** . ************* . *** . *** . ***** . *** | |

← SEQ ID NO: 23

| | | |
|---|---|---|
| A. fumigatus | CGGGTGTCTGATGGGAAATAATAGCTACAATGGCTCCTCCGATCTCCAGC | 299 |
| N. fischeri | CGGGTGTCTGATGGGGT-TAATAGCTACAATGGCTCCTCCGATCTCCAGC | 295 |
| N. spinosa | CGGGTGCCTGACGGGA---TAATAGCTACAATGGCACCTCCGACCTCCAGC | 299 |
| | ****** . *** . *** . ************* . ******** . ****** | |

Fig. 2 (corrected)

Lane    Strain No.
1; B. fulva JCM12804
2; B. fulva JCM12805
3; B. fulva JCM12806
4; B. fulva NBRC31877
5; B. fulva NBRC7901
6; B. fulva NBRC31878

Lane    Strain No.
1; B. nivea NBRC8815
2; B. nivea NBRC8972
3; B. nivea NBRC30569
4; B. nivea NBRC31351
5; B. nivea NBRC31832
6; B. nivea CBS140.65
7; B. nivea CBS608.71

N. Negative Control
1. *Talaromyces flavus*
2. *T. trachyspermus*
3. *Neosartorya ficheri*
4. *Byssochlamys fulva*
5. *B. nivea*
6. *Penicillium griseofulvum*
7. *P. citirinum*
8. *P. paneum*
9. *P. oxalicum*

| | Talaromyces flavus Strain No. |
|---|---|
| Lane 1. | NBRC 7231 |
| 2. | NBRC 7232 |
| 3. | NBRC 7233 |
| 4. | NBRC 8896 |
| 5. | NBRC 8897 |
| 6. | NBRC 8898 |
| 7. | NBRC 8959 |
| 8. | NBRC 8960 |
| 9. | NBRC 9044 |
| 10. | NBRC 30574 |
| 11. | NBRC 31359 |
| 12. | NBRC 31879 |
| 13. | NBRC 31902 |
| 14. | NBRC 102293 |

FIG. 15
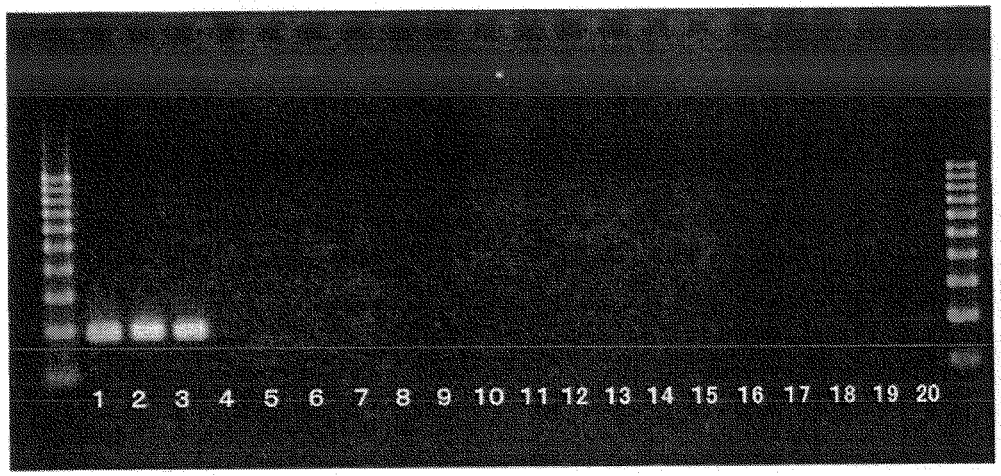
FIG. 16
(a) Primer : N2F/R
(SEQ ID NO:14, 15)
(b) Primer : Af1F/R
(SEQ ID NO:22, 23)
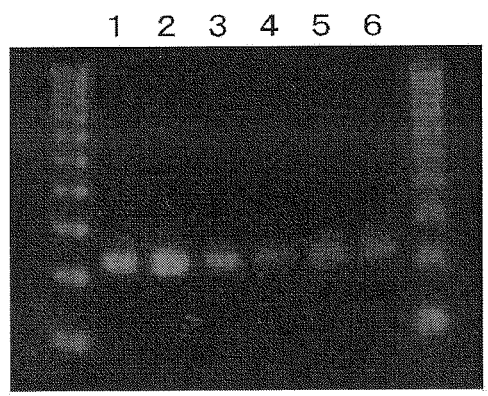
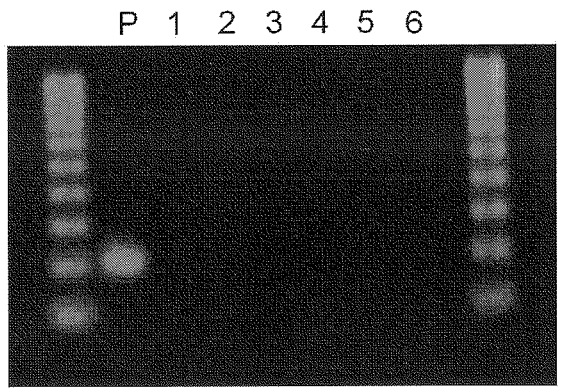
| Lane | Strain No. |
|---|---|
| 1: N. fisheri | CBM-FA-839 96-PE-92-1 |
| 2: N. fisheri | CBM-FA-181 90-BP-127-1 |
| 3: N. fisheri | XY-243-1 |
| 4: N. fisheri | 2000-XY-247-3 |
| 5: N. fisheri | XY-296-1 |
| 6: N. fisheri | XY-298-1 |
| P: A.fumigatus IFM77 (Positive Control) | |

FIG. 17
(a) Primer: N2F/R
(SEQ ID NO:14,15)
(b) Primer: Af1F/R
(SEQ ID NO:22,23)
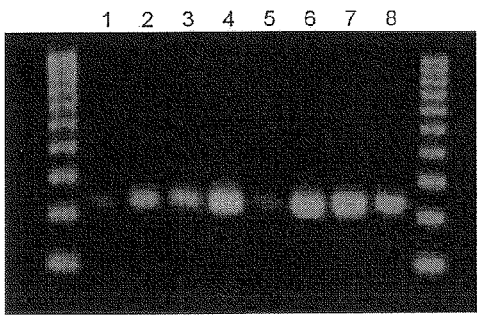
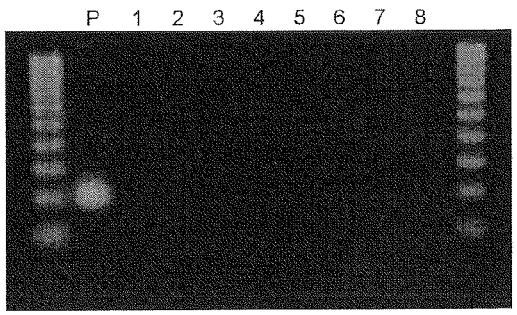
Lane        Strain No.
  1: N. glabra   CBM-FA-665 93-BS590-3
  2: N. glabra   CBM-FA-657 93-BS-1164-3
  3: N. glabra   CBF158
  4: N. glabra   CBM-FA-189
  5: N. glabra   IFM47148
  6: N. glabra   IFM53839
  7: N. glabra   IFM53841
  8: N. glabra   IFM55914
  P: A.fumigatus IFM77 (Positive Control)

FIG. 18
(a) Primer : N2F/R
    (SEQ ID NO:14,15)
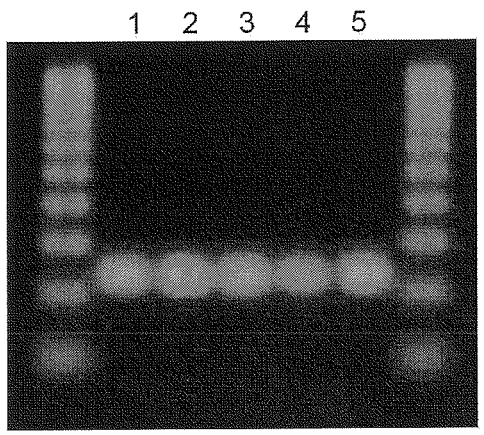
(b) Primer : Af1F/R
    (SEQ ID NO:22,23)
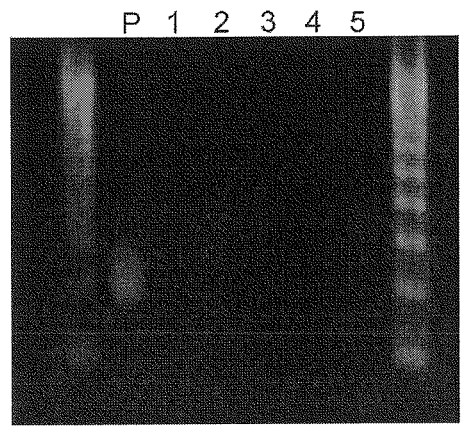
| Lane | Strain No. |
|---|---|
| 1: N. hiratsukae | IFM46953 |
| 2: N. hiratsukae | 46954 |
| 3: N. hiratsukae | 47036 |
| 4: N. hiratsukae | 49776 |
| 5: N. hiratsukae | 55915 |
| P: A.fumigatus | IFM77 (Positive Control) |

FIG. 19
(a) Primer: N2F/R
    (SEQ ID NO:14,15)
(b) Primer: Af1F/R
    (SEQ ID NO:22,23)
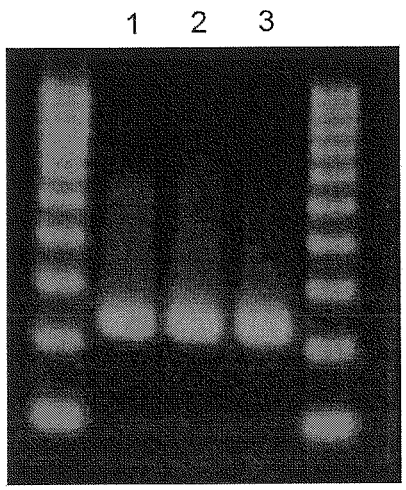
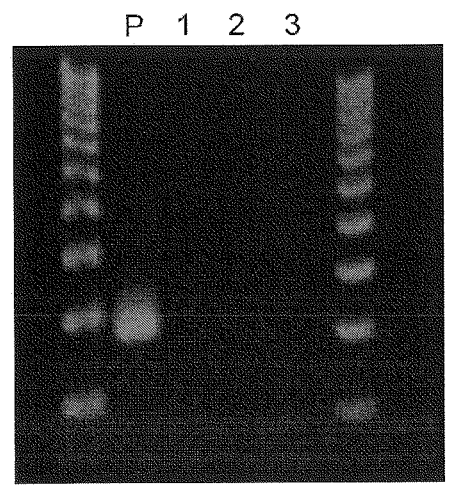
Lane                Strain No.
1: N. paulistensis  CBM-FA-191 81-GU-14-1
2: N. paulistensis  CBM-FA-608
3: N. paulistensis  CBM-FA-176
P: A. fumigatus     IFM77 (Positive Control)

FIG. 20
(a) Primer: N2F/R
    (SEQ ID NO:14,15)
(b) Primer: Af1F/R
    (SEQ ID NO:22,23)
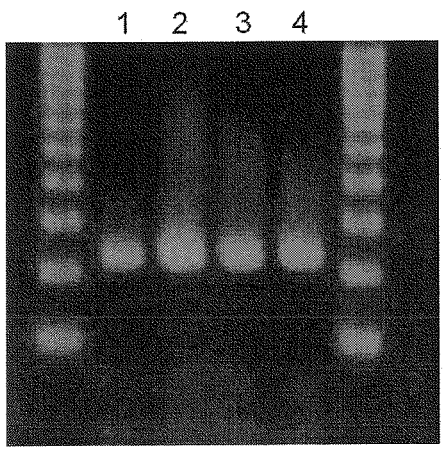
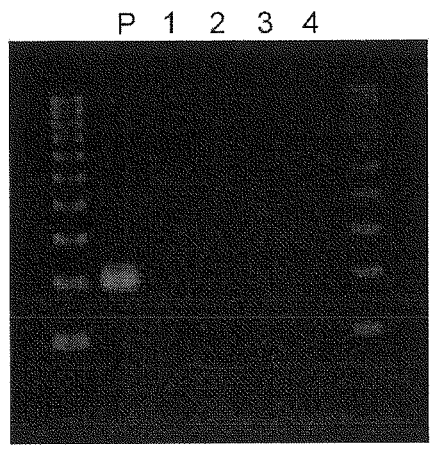
Lane            Strain No.
  1: N. spinosa    CBM-FA-892 98-TA-439-N
  2: N. spinosa    CBM-FA-678 93-BS-620-4
  3: N. spinosa    XY-9-1
  4: N. spinosa    2000-XY-325-3
  P: A. fumigatus  IFM77 (Positive Control)

Primer: H2F/H2R (SEQ ID NO: 20, 21)

| Lane | | Strain No. |
|---|---|---|
| No.9 | Hamigera striata | NBRC 6106 |
| No.10 | Hamigera striata | NBRC 9162 |
| No.11 | Hamigera striata | NBRC 9554 |
| No.12 | Hamigera striata | NBRC 31893 |

Primer: HamB7/R (SEQ ID NO: 18, 19)

| Lane | | Strain No. |
|---|---|---|
| No.13 | Hamigera striata | NBRC 6106 |
| No.14 | Hamigera striata | NBRC 9162 |
| No.15 | Hamigera striata | NBRC 9554 |
| No.16 | Hamigera striata | NBRC 31893 |

FIG. 24-2 con't
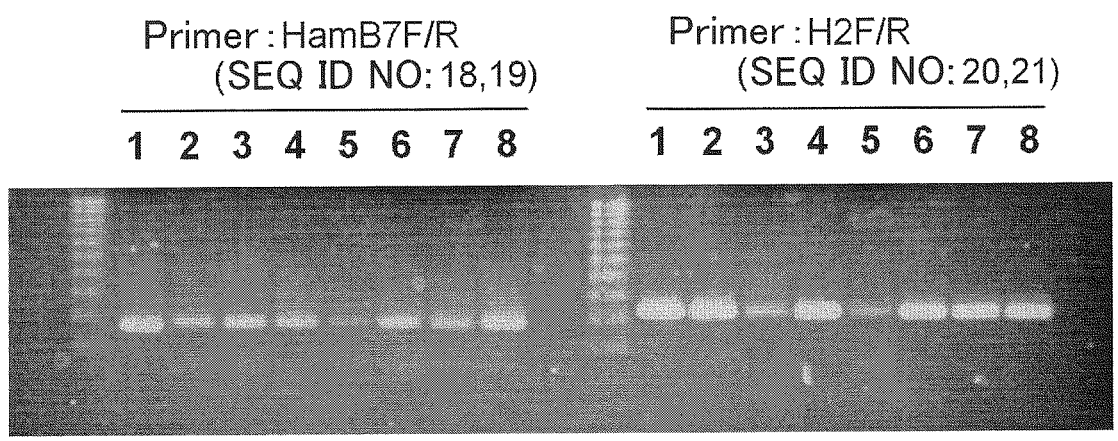
*Hamigera avellanea* Strain No.
    Lane  1. NBRC 31667
            2. NBRC 7721
            3. NBRC 8102
            4. NBRC 9853
            5. NBRC 30583
            6. NBRC 31353
            7. NBRC 31839
            8. NBRC 31892

FIG. 25-1

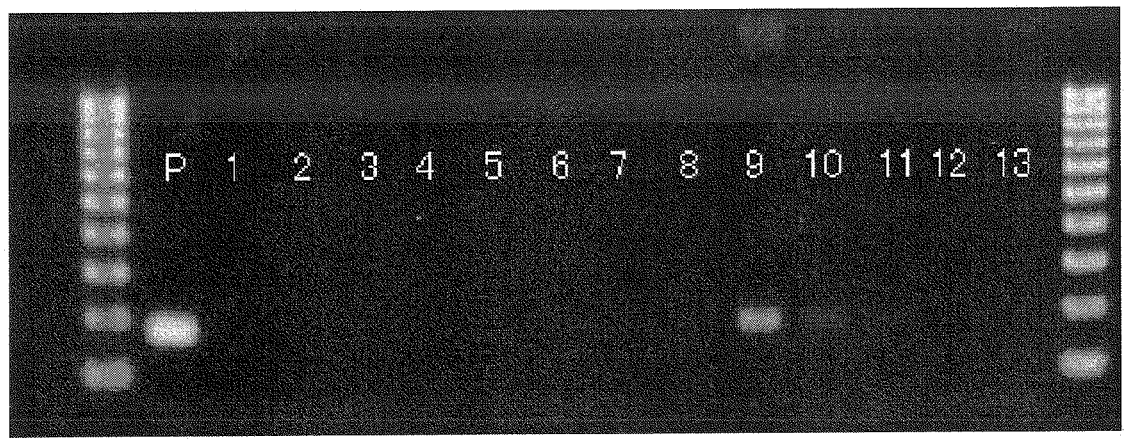

Primer: SEQ ID NO:18, 19

| Lane | Species | Strain No. |
|---|---|---|
| P | *Hamigera avellanea* | NBRC31667 |
| 1 | *Byssochlamys nivea* | NBRC8815 |
| 2 | *Byssochlamys nivea* | NBRC8972 |
| 3 | *Byssochlamys nivea* | NBRC30569 |
| 4 | *Byssochlamys nivea* | NBRC31351 |
| 5 | *Byssochlamys nivea* | NBRC31832 |
| 6 | *Byssochlamys nivea* | CBS140.65 |
| 7 | *Byssochlamys nivea* | CBS608.71 |
| 8 | *Byssochlamys fulva* | NBRC7901 |
| 9 | *Byssochlamys fulva* | NBRC31877 |
| 10 | *Byssochlamys fulva* | NBRC31878 |
| 11 | *Byssochlamys fulva* | JCM12804 |
| 12 | *Byssochlamys fulva* | JCM12805 |
| 13 | *Byssochlamys fulva* | JCM12806 |

FIG. 25-2 con't
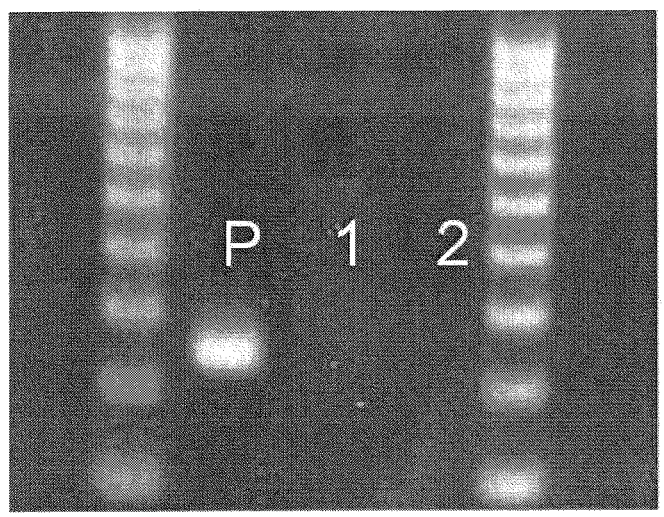
Primer: SEQ ID NO: 20, 21
| Lane | Species | Strain No. |
|---|---|---|
| P | *Hamigera avellanea* | NBRC31667 |
| 1 | *Byssochlamys fulva* | NBRC31877 |
| 2 | *Byssochlamys fulva* | NBRC31878 |

FIG. 26

Partial nucleotide sequence of the ITS region and D1/D2 region of 28S rDNA of *Byssochlamys fulva*

```
     <ITS---------------------------------------------------------------------------
   1 GTGGCCCAAC CTCCCACCCG TGTTGACCGA CACCTGTTGC TTCGGCGGGC CGCCAGGGC TCCCGCCCGG CCGCCGGGGG   80
     ********** ********** ********** ********** ********** ********** ********** **********

81 GCCCCGTCGC CCCCGGGCCC GCGCCCGCCG AAGACCCCTC GAACGCTGCC TCGAAGGTTG CCGTCTGAGT ATGAAATCAA  160
     ********** ********** ********** ********** ********** ********** ********** **********

161 TCGTTAAAAC TTTCAACAAC GGATCTCTTG GTTCCGGCAT CGATGAAGAA CGCAGCGAAA TGCGATAAGT AATGTGAATT  240
     ********** ********** ********** ********** ********** ********** ********** **********

241 GCAGAATTCC GTGAATCATC GAATCTTTGA ACGCACATTG CGCCCCCTGG CATTCCGGGG GGCATGCCTG TCCGAGCGTC  320
     ********** ********** ********** ********** ********** ********** ********** **********

321 ATTGCTAACC CTCCAGCCCG GCTGGTGTGT TGGGCCGCCG TCCCCTCCGG GGACGGGCC CGAAAGGCAG CGGCGGCGCC  400
     ********** ********** ********** ********** ********** ********** ********** **********

<==== ===F3===== ==>  <==== ===F2===== ==>
 401 GCGTCCGGTC CTCGAGCGTA TGGGGCTTTG TCACGCGCTC TGGTAGGCCC GGCCGGCTTG CTGGCCAACG ACCTCACGGT  480
     ********** ********** ********** ********** ********** ********** ********** **********
                                                                                  <== =====F1c=
     --------------------ITS>                 <= ======B1c =========>
 481 CACCTAACTT CTCTCTTAGG TTGACCTCGG ATCAGGTAGG GATACCCGCT GAACTTAAGC ATATCAATAA GCGGAGGAAA  560
     ********** ********** ********** ********** ********** ********** ********** **********
     =======>                                                                      <=======B
                        <D1/D2----------------------------------------------------

561 AGAAACCAAC AGGGATTGCC CCAGTAACGG CGAGTGAAGC GGCAAGAGCT CAAATTTGAA ATCTGGCCCC TCCGGGGTCC  640
     ********** ********** ********** ********** ********** ********** ********** **********
     2=======>    <======= B3======>

641 GAGTTGTAAT TTGCAGAGGA TGCTTCGGGT GCGGTCCCCA TCTAAGTGCC CTGGAACGGG CCGTCATAGA GGGTGAGAAT  720
     ********** ********** ********** ********** ********** ********** ********** **********

721 CCCGTCTGGG ATGGGCGGCC GTGCCCGTGT GAAGCTCCTT CGACGAGTCG AGTTGTTTGG GAATGCAGCT CTAAATGGGT  800
     ********** ********** ********** ********** ********** ********** ********** **********

801 GGTAAATTTC ATCTAAAGCT AAATATTGGC CGGAGACCGA TAGCGCACAA GTAGAGTGAT CGAAAGATGA AAAGAACTTT  880
     ********** ********** ********** ********** ********** ********** ********** **********

881 GAAAAGAGAG TTAAACAGCA CGTGAAATTG TTGAAAGGGA AGCGCTTGCG ACCAGACTCG CCCGCGGGGG TTCAGCCGGT  960
     ********** ********** ********** ********** ********** ********** ********** **********

961 ACTCGTACCG GTGTACTCCC CCGGGGGCGG GCCAGCCGTCG GTTTGGGCGG CCGGTCAAAG GCCCCCGGAA TGTGTCGCCT 1040
     ********** ********** ********** ********** ********** ********** ********** **********
                                                                                ----------D1/D
1041 CTCGGGGCGT CTTATAGCCG GGGGTGCAAT GCGGCCAGCC TGGACCGAGG AACGCGCTTC GGCACGGACG CTGGCGTAAT 1120
     ********** ********** ********** ********** ********** ********** ********** **********
     2>
1121 GG                                                                                    1122
     **
```

\* represents a nucleotide in the complementary strand.

FIG. 27

Partial nucleotide sequence of the β-tubulin genes of *Neosartorya fischeri*

```
  1 TGGTAAACCA AATCGGTGCT GCTTTCTGGT ATGTCTTGAC CTCAATTCTT GGATGACGGG AGATTGGGAC CTGTCTTAGC   80
    ********** ********** ********** ********** ********** ********** ********** **********

81 AGGCTGTCCT CCATGGGTTC AGCTTCGCTG TCATGGGTAT CAGCTAACAA ATCTACAGGC AGACCATCTC TGGTGAGCAC  160
    ********** ********** ********** ********** ********** ********** ********** **********

161 GGCCTTGACG GCTCTGGCCA GTAAGTTCGA CCTATATCCT CCCAATTGAG AAAGCGGCGG AAACACGAAA GGAAGGAAGA  240
    ********** ********** ********** ********** ********** ********** ********** **********

241 AGAGGACGCG TGTCTGATGG GGTTAATAGC TACAATGGCT CCTCCGATCT CCAGCTGGAG CGTATGAACG TCTACTTCAA  320
    ********** ********** ********** ********** ********** ********** ********** **********
                                           < ========F3 ========>    <===== ==F2======
321 CGAGGTGTGT GGATGAAACT CTCGACTCTA TACTATTTCG GCAACATCTC ACGATCTGAC TCGCTACTAG GCCAACGGTG  400
    ********** ********** ********** ********** ********** ********** ********** **********
    =>                                                                 <=== =====B1c==
401 ACAAGTATGT TCCTCGTGCC GTTCTGGTCG ATCTCGAGCC TGGTACCATG GACGCTGTCC GTGCCGGTCC CTTCGGCGAG  480
    ********** ********** ********** ********** ********** ********** ********** **********
    <----------LF--------->    <== ======F1c= ========>
    ====>    <----------LB--------- >
481 CTCTTCCGTC CCGATAACTT CGTCTTCGGC CAGTCTGGTG CTGGTAACAA CTGGGCCAAG GGTCACTACA CTGAGGGGT   559
    ********** ********** ********** ********** ********** ********** ********** *********
                                    <======== B2======== >    <== ======B3== ======>
```

\* represents a nucleotide in the complementary strand.

FIG. 28

Partial nucleotide sequence of the β-tubulin genes of
Aspergillus fumigatus

```
              <== =====F3=== =====>                                    <=== =====F2=== =====>
  1 AGGGTAACCA AATTGGTGCC GCTTTCTGGT ATGTCTTGAC CTCAAAGCTT GGATGACGGG TGATTGGGAT CTCTCATCTT   80
    ********** ********** ********** ********** ********** ********** ********** **********
                                                                          <===== ===B1c===
 81 AGCAGGCTAC CTCCATGGGT TCAGCCTCAC TGTCATGGGT ATCAGCTAAC AAATCTACAG GCAGACCATC TCTGGTGAGC  160
    ********** ********** ********** ********** ********** ********** ********** **********
                   <=== =====F1c= =======>
    ====>         <--------- -LB------- ---->
161 ATGGCCTTGA CGGCTCTGGC CAGTAAGTTC GACCTATATC CTCCCAATTG AGAAAGCGGC GGAAACACGG AAAACAAGGA  240
    ********** ********** ********** ********** ********** ********** ********** **********
                                                        <== =====B2=== ====>  <== ======B3==
241 AGAAGCGGAC GCGTGTCTGA TGGGAAATAA TAGCTACAAT GGCTCCTCCG ATCTCCAGCT GGAGCGTATG AACGTCTATT  320
    ********** ********** ********** ********** ********** ********** ********** **********
    ======>
321 TCAACGAGGT GTGTGGATGA AACTCTTGAT TTATACTATT TCGGCAACAT CTCACGATCT GACTCGCTAC TAGGCCAACG  400
    ********** ********** ********** ********** ********** ********** ********** **********

401 GTGACAAATA TGTTCCTCGT GCCGTTCTGG TCGATCTCGA GCCTGGTACC ATGGACGCTG TCCGTGCCGG TCCCTTCGGC  480
    ********** ********** ********** ********** ********** ********** ********** **********

481 GAGCTATTCC GTCCCGACAA CTTCGTCTTC GGCCAGTCCG GTGCTGGTAA CAACTGGGCC AAGGGTCACT ACACCGAGGG  560
    ********** ********** ********** ********** ********** ********** ********** **********

561 CG                                                                                        562
    **
```

\* represents a nucleotide in the complementary strand.

FIG. 29

Partial nucleotide sequence of the β-tubulin genes of *Hamigera avellanea*

```
ggtaacccaa atcggtgctg ctttctggta cgttgacaaa tccaaacgag gagacaaaat    60
******** ****** ****** ****** ****** ******** aaatcccaac ttctcgaaac accaatttga gacaaattgg gtcgaagaaa aaagatctta   120
******** ****** ****** ****** ****** ******** tactgacaat ctttataggc agaccatctc tggcgagcac ggtcttgatg gctccggtgt   180
******** ****** ****** ****** ****** ******** gtaagtgcaa cccacgcttt cggtcctgac aacaatacaa ccagatcaat tctgatgata   240
******** ****** ****** ****** ****** ******** aaaacagtta caatggcacc tccgacctcc agttggagcg tatgaacgtt tacttcaacg   300
******** ****** ****** ****** ****** ********
                                 F3
aggttcgtga attgaacatt tggatccgac tacgacgtgt caaatgctga tatatcatca   360
********** ********** ********** ********** ********** **********
      F2
ggccagcggt aacaagtatg tccccgtgc cgtccttggt cgatctcgag cctggcacca   420
********** ********** ********** ********** ********** **********
                     LF                              F1c
                     B1c                             LB
tggacgccgt ccgtgccggt ccttttggcc agctcttccg ccccgacaac ttcgttttcg   480
******** ****** ****** ****** ****** ******** gccagtctgg tgccggtaac aactgggcca agggtcacta cactg                   525
******** ****** ****** ****** ***
        B2                       B3
```

\* represents a nucleotide in the complementary strand.

FIG. 30

Partial nucleotide sequence of the β-tubulin genes of *Talaromyces flavus*

```
ggtaaccaaa tcggtgctgc tttctggtga gtttgactct cgaccgaaac tctcaattgt    60
******** ****** ****** ****** ****** ******** cgcgacaaca cgctgacttt tccaggcaaa tcatctccgc tgagcacggt ctggacggct   120
******** ****** ****** ****** ****** ******** ccggtgtgta agtattacac gattcaaatc cagattacga tccaacaata tctgataatc   180
******** ****** ****** ****** ****** ********
                                 F3                    F2
aacagctaca atggctcctc cgacctccag ttggagcgta tgaacgttta cttcaacgag   240
******** ****** ****** ****** ****** ******** gtgcgtcaaa ccactccacc taataaacgg aagacaaact catgatcgat ataggcttcc   300
******** ****** ****** ****** ****** ********
                                       B1c              F1c
ggcaacaaat atgtccctcg tgctgtcctc gtcgacttgg agcccggtac catggacgcc   360
********** ********** ********** ********** ********** **********
             LB
gtccgcgctg gtccctttgg tcagctcttc cgtcccgaca actttgtttt cggtcagtcc   420
********** ********** ********** ********** ********** **********
                                 B2
ggtgctggta acaactgggc caagggtcac tacactg                            457
********** ********** ********** *******
    B3
```

＊ represents a nucleotide in the complementary strand.

FIG. 31

Partial nucleotide sequence of the β-tubulin genes of *Talaromyces wortmannii*

```
  1 TTAATACGAC TCACTATAGG GCGAATTGGG CCCGACGTCG CATGCTCCCG GCCGCCATGG CGGCCGCGGG AATTCGATTG   80
    ********** ********** ********** ********** ********** ********** ********** **********

81 GTAACCAAAT CGGTGCTGCT TTCTGGTGAG TTGCGGATAA ACAATGGCAC AAAAAAACAT TCGTTAACGT TGTACAGGCA  160
    ********** ********** ********** ********** ********** ********** ********** **********

<== =====F3=== =====>           < ========F2 ========>
161 AACTATCTCT GGCGAGCACG GCCTCGATGG CTCCGGAATG TGAGTTATAG TGATTTTCAA AATTTCGACA TCCCACCCTG  240
    ********** ********** ********** ********** ********** ********** ********** **********
                                                                                <========
241 ATCATTTCCA GTTACAATGG CACCTCCGAC CTCCAGTTGG AGCGTATGAA CGTCTACTTC AACGAGGTGC GTGGAATCTG  320
    ********** ********** ********** ********** ********** ********** ********** **********
    <========  =LF======= ===><===== ===F1c==== ===>
    =B1c====== ==>         <---------- LB------- --->
321 CCCCGCGACA TTCGGAAATA TACTCATATC GTATAGGCTA GCGGCAACAA GTACGTCCCC CGTGCCGTCC TCGTCGATTT  400
    ********** ********** ********** ********** ********** ********** ********** **********
                                                  <===== ==B2====== => <====== =B3========
401 GGAGCCTGGC ACCATGGACG CTGTCCGCGC TGGTCCCTTC GGTCAGCTCT TCCGTCCCGA CAACTTCGTC TTCGGCCAGT  480
    ********** ********** ********** ********** ********** ********** ********** **********
    >
481 CGGGTGCTGG TAACAACTGG GCCAAGGGTC ACTACACTGA GGGTAATCAC TAGTGAATTC GCGGCCGCCT GCAGGTCGAC  560
    ********** ********** ********** ********** ********** ********** ********** **********

561 CATATGGGAG AGCTCCCAAC GCGTTGGATG CATAGCTTGA GTATTCTATA GTGTCACCTA AATAATCGAA TTCC         634
    ********** ********** ********** ********** ********** ********** ********** ****
```

\* represents a nucleotide in the complementary strand.

FIG. 32

Partial nucleotide sequence of the β-tubulin genes of *Talaromyces luteus*

```
  1 GGTAACCAAA TCGGTGCTGC GTCCTGGTAA GCTATTGATG AACCTGGGAA CGGTACAAAA TCAACATATC AGAAGAAATA   80
    ********** ********** ********** ********** ********** ********** ********** **********

81 TTTACTGACA TAGATTGTCT TCTAGGCAAA CTATCTCCGG CGAGCACGGT CTTGATGGAT CCGGCATGTG AGTGAGGTAG  160
    ********** ********** ********** ********** ********** ********** ********** **********

<======= =F3======= =>                     < ========F2 ========>
161 CTCGACACTC GACGAATCAC CACTGATGGG AAAATAGTTA CAATGGCTCT TCCGACCTCC AGTTAGACGG GATGAACGTC  240
    ********** ********** ********** ********** ********** ********** ********** **********
                                                                                <=======
                                                                    <==== =====B1c==
241 TATTTCAACG AGGTCCGTCA ATTGTGAATC ATTACCGACC GACAGCACGA ATTCTTACGG TCATATAGGC TAGCGGCAAC  320
    ********** ********** ********** ********** ********** ********** ********** **********
    ==LF======= ===>             < ========F 1c======== >
    ======>
321 AAGTACGTCC CTCGTGCCGT CCTCATCGAT CTGGAGCCCG GTACTATGGA TGCTGTCCGT GCTGGTCCTT TCGGTCAGCT  400
    ********** ********** ********** ********** ********** ********** ********** **********
                                        <== ======B2== ======>              <===== ===B3=====
401 CTTCCGTCCC GACAACTTCG TCTTCGGCCA GTCCGGTGCC GGTAACAACT GGGCCAAGGG TCACTACACT G           471
    ********** ********** ********** ********** ********** ********** ********** *
    ===>
```

\* represents a nucleotide in the complementary strand.

FIG. 33

Partial nucleotide sequence of the ITS region and D1/D2 region of 28S rDNA of *Talaromyces flavus*

```
<ITS----------------------------------------------------------------------------
  1 GCGGCCCAAC CTCCCACCCT TGTCTCTATA CACCTGTTGC TTTGGCGGGC CCACCGGGGC CACCTGGTCG CCGGGGGACG   80
    ********** ********** ********** ********** ********** ********** ********** **********

81 TCGTCTCGGG GCCCGCGCCT GCCGAAGCGC TCTGTGAACC CTGATGAAGA TGGGCTGTCT GAGTACTATG AAAATTGTCA  160
    ********** ********** ********** ********** ********** ********** ********** **********

161 AAACTTTCAA CAATGGATCT CTTGGTTCCG GCATCGATGA AGAACGCAGC GAAATGCGAT AAGTAATGTG AATTGCAGAA  240
    ********** ********** ********** ********** ********** ********** ********** **********

<  ======F3=
241 TTCCGTGAAT CATCGAATCT TTGAACGCAC ATTGCGCCCC CTGGCATTCC GGGGGGCATG CCTGTCCGAG CGTCATTTCT  320
    ********** ********** ********** ********** ********** ********** ********** **********

======>   <======F 2======>
321 GCCCTCAAGC ACGGCTTGTG TGTTGGGTGC GGTCCCCCCG GGGACCTGCC CAAAAGGCAG CGGCGACGCC CGTCTGGTCC  400
    ********** ********** ********** ********** ********** ********** ********** **********
                                                           <====== L F====== >   < ======F1c
                 <==== ====B1c=== =====>                   <= ======L B ========= ==>
401 TCGAGCGTAT GGGGCTCTGT CACTCGCTCG GGAAGGACCT GCGGGGGTTG GTCACACCAC TATATTTTAC CACGGTTGAC  480
    ********** ********** ********** ********** ********** ********** ********** **********
    ======>                                                                         <======
    ------ITS>
481 CTCGGATCAG GTAGGAGTTA CCCGCTGAAC TTAAGCATAT CAATAAGCGG AGGAAAAGAA ACCAACCGGG ATTGCCTCAG  560
    ********** ********** ********** ********** ********** ********** ********** **********
    =B2====== =><====== B3====== >
    <D1/D2------

561 TAACGGCGAG TGAAGCGGCA AGAGCTCAAA TTTGAAATCT GGCCCCTTTG GGGTCCGAGT TGTAATTTGC AGAGGATGCT  640
    ********** ********** ********** ********** ********** ********** ********** **********

641 TCGGGTGCGG TCCCCATCTA AGTGCCCTGG AACGGGCCGT CATAGAGGGT GAGAATCCCG TCTGGGATGG GCGGCCGCGC  720
    ********** ********** ********** ********** ********** ********** ********** **********

721 CCGTGTGAAG CTCCTTCGAC GAGTCGAGTT GTTTGGGAAT GCAGCTCTAA GCGGGTGGTA AATTTCATCT AAAGCTAAAT  800
    ********** ********** ********** ********** ********** ********** ********** **********

801 ACTGGCCGGA GACCGATAGC GCACAAGTAG AGTGATCGAA AGATGAAAAG AACTTTGAAA AGAGAGTTAA ACAGCACGTG  880
    ********** ********** ********** ********** ********** ********** ********** **********

881 AAATTGTTGA AAGGGAAGCG TTGTCCACCA GACTCGCCCG GGGGGGTTCA GCCGGCACTT GTGCCGGTGT ACTCCTCTCC  960
    ********** ********** ********** ********** ********** ********** ********** **********

961 GGGCGGGCCA GCATCGGTTT GGGCGGCTGG TGAAAGGCCC CGGGAATGTA ACACCCCTCG GGTGCCTTA TAGCCCGGGG 1040
    ********** ********** ********** ********** ********** ********** ********** **********
                                                            ------D1/D2>
1041 TGCCATACAG CCAGCCTGGA CCGAGGCCCG CGCTTCGGCG AGGATGCTGG CGTAATGG                        1098
     ********** ********** ********** ********** ********** ********
```

* represents a nucleotide in the complementary strand.

FIG. 34

Partial nucleotide sequences of the ITS region and D1/D2 region of 28S rDNA of *Talaromyces trachyspermus* and *Talaromyces flavus*

```
                              <ITS―――――――――――――――――――――――――――――――――――
Talaromyces trachyspermus     TGGGCCCAACCTCCCACCCGTGTCTCTTGCGTACTTTGTTGCTTTGGCGG 50
Talaromyces flavus            GCGGCCCAACCTCCCACCCTTGTCTCTATA-C-ACCTGTTGCTTTGGCGG 48
                                ****************** *******     ** *************

Talaromyces trachyspermus     GCCCACTGGGT-----CACTCCGGTCGCCGGGGAGCG--CTATGCTCCCGG 94
Talaromyces flavus            GCCCACCGGGG-----CCACCT-GGTCGCCGGGGGAC--GTC-GTCTCCGG 90
                              ****** ***     ***    *********** * *  * * ****

Talaromyces trachyspermus     GCCCGTGCCCGCCAGAGCACCCCTGTGAACCCTGA---TGAAGAGAGGCTG 142
Talaromyces flavus            GCCCGCGCCTGCCGAAG-CGCTCTGTGAACCCTGA---TGAAGATGGGCTG 137
                              ***** *** ***  **  * ************** ****** *****

Talaromyces trachyspermus     TCTGAG-----TCCCACGATAATCGTTAAAACTTTCAACAATGGATCTCTTG 189
Talaromyces flavus            TCTGAG-----TACTATGAAAATTGTCAAAACTTTCAACAATGGATCTCTTG 184
                              ******     * * ** *** ** *************************

Talaromyces trachyspermus     GTTCCGGCATCGATGAAGAACGCAGCGAAATGCGATAAGTAATGTGAATT 239
Talaromyces flavus            GTTCCGGCATCGATGAAGAACGCAGCGAAATGCGATAAGTAATGTGAATT 234
                              **************************************************

Talaromyces trachyspermus     GCAGAATTCCGTGAATCATCGAATCTTTGAACGCACATTGCGCCCCTGG 289
Talaromyces flavus            GCAGAATTCGCTGAATCATCGAATCTTTGAACGCACATTGCGCCCCTGG 284
                              **************************************************

<======F3= =======> <=
Talaromyces trachyspermus     CATTCCGGGGGGCATGCCTGTCCGAGCGTCATTTCTG-CCCTCAAGCGCG 338
Talaromyces flavus            CATTCCGGGGGGCATGCCTGTCCGAGCGTCATTTCTG-CCCTCAAGCACG 333
                              *************************************  ********* **

=====F 2======>
Talaromyces trachyspermus     GCTTGTGTGTTGG-GCGTGGTCCCCCTGGCTTTGGCGGGGACCTGCCCGA 387
Talaromyces flavus            GCTTGTGTGTTGGGT-GCGGTCCCC----CC------GGGGACCTGCCCAA 373
                              *************  * *******  *        ************ *
                                                                  <=========

<==== =
Talaromyces trachyspermus     AAGGCAGCGGCGACGTCCCGCCTAGTCCTCGAGCGTATGGGGCTCTGTCA 437
Talaromyces flavus            AAGGCAGCGGCGACGCC-CGTCTGGTCCTCGAGCGTATGGGGCTCTGTCA 422
                              *************** * ** **  **************************
                              LF=====>         <======F1c =======>

===B1c=== ===>              <== ======LB== =========
Talaromyces trachyspermus     CGCGCTCGGGAGGGACTGGTGGGC--GTTGGTCACC-----------C-CT 474
Talaromyces flavus            CTCGCTCGGGAAGGACCTGCGGGG--GTTGGTCACA-----------CCAC 460
                              * ********* ****  * ***  *********           *

――――――――――――――――――――――ITS>
                              ================>
Talaromyces trachyspermus     T--ATTCTTTCT------ACGGTTGACCTCGGATCAGGTAGGAGTTACCCG 517
Talaromyces flavus            T--ATATTTTAC------CACGGTTGACCTCGGATCAGGTAGGAGTTACCCG 504
                              * ** ***          ********************************
                                              <======B2====== ><====== B3=

Talaromyces trachyspermus     CTGAACTTAAGCATATCAATAAGCGGAGGAAAAGAAACCAACCGGGATTG 567
Talaromyces flavus            CTGAACTTAAGCATATCAATAAGCGGAGGAAAAGAAACCAACCGGGATTG 554
                              **************************************************
                              =====>
                                                    * represents the same nucleotide.
```

FIG. 34-1 con't

Partial nucleotide sequences of the ITS region and D1/D2 region of 28S rDNA of *Talaromyces trachyspermus* and *Talaromyces flavus* (continuation of FIG. 34)

```
                          <D1/D2----------------------------------------------
Talaromyces trachyspermus CCTCAGTAACGGCGAGTGAAGCGGCAAGAGCTCAAATTTGAAATCTGGCC 617
Talaromyces flavus        CCTCAGTAACGGCGAGTGAAGCGGCAAGAGCTCAAATTTGAAATCTGGCC 604
                          **************************************************

Talaromyces trachyspermus CCCCCGGGGTCCGAGTTGTAATTTGGAGACGATGCTTCGGGCGCCGTTCC 667
Talaromyces flavus        CCTTTGGGGTCCGAGTTGTAATTTGCAGACGATGCTTCGGGTGCGGTCCC 654
                          **  *********************  **************  ** ** **

Talaromyces trachyspermus CGTCTAAGTGCCCCTGGAACGGGCTGTCGCAGAGGGTGAGAACCCCGTCT 717
Talaromyces flavus        CATCTAAGTGCCC-TGGAACGGGCCGTCATAGAGGGTGAGAATCCCGTCT 703
                          * ***********  ***********  ***  ************ *******

Talaromyces trachyspermus GGGACGGG-CTACGGCGCCCGTGTGAAGCTCCTTGGACGAGTCTAGTTGT 766
Talaromyces flavus        GGGATGGG-CGGCCGCGCCCGTGTGAAGCTCCTTCGACGAGTCGAGTTGT 752
                          ****  *** *  *  ********************  ********  ******

Talaromyces trachyspermus TTGGGAATGCAGCTCTAAGCGGGTGGTAAATTTCATCTAAAGCTAAATAC 816
Talaromyces flavus        TTGGGAATGCAGCTCTAAGCGGGTGGTAAATTTCATCTAAAGCTAAATAC 802
                          **************************************************

Talaromyces trachyspermus TGGCCGGAGACCGATAGCGCACAAGTAGAGTGATCGAAAGATGAAAAGCA 866
Talaromyces flavus        TGGCCGGAGACCGATAGCGCACAAGTAGAGTGATCGAAAGATGAAAAGAA 852
                          ************************************************* *

Talaromyces trachyspermus CTTTGAAAATAGAGTCAAACAGCACGTGAAATTGTTGAAAGGGAAGCGTT 916
Talaromyces flavus        CTTTGAAAAGAGAGTTAAACAGCACGTGAAATTGTTGAAAGGGAAGCGTT 902
                          *********  *****  ********************************

Talaromyces trachyspermus GGCCGCCAGACGCGCCCGGGAGGGCTCAGCCGGCACGTGTGCCGGTGTAC 966
Talaromyces flavus        GTCCACCAGACTCGCCCGGGGGGGTTCAGCCGGCACTTGTGCCGGTGTAC 952
                          * ** ******  ********  ***  ***********  **************

Talaromyces trachyspermus TCTCTCCCGGGCGGGCCAGCATCGGTTTGGGCGGTCGCTGAAAGGCCCCG 1016
Talaromyces flavus        TCCTCTCCGGGCGGGCCAGCATCGGTTTGGGCGGCTGGTGAAAAGGCCCCG 1002
                          **   *******************************  *  ***********

Talaromyces trachyspermus GGAATGTAGCACCCTACCGGGGTGCCTTATAGCCCGGGGCGGCATGCGGC 1066
Talaromyces flavus        GGAATGTAACACCCC-TCGGGGTGCCTTATAGCCCGGGGTGCCATACAGC 1051
                          ********  *****   ********************* *  *** *  **
                                                                      ---------D1/D2>
Talaromyces trachyspermus CCGCCGGGACCGAGGCCCCGCGCTTCGGCGAGGATGCTGGCGTAATGG 1113
Talaromyces flavus        CAGCCTGGACCGAGGCCCCGCGCTTCGGCGAGGATGCTGGCGTAATGG 1098
                          * ***  ****************************************
```

* represents the same nucleotide.

FIG. 36-1 con't
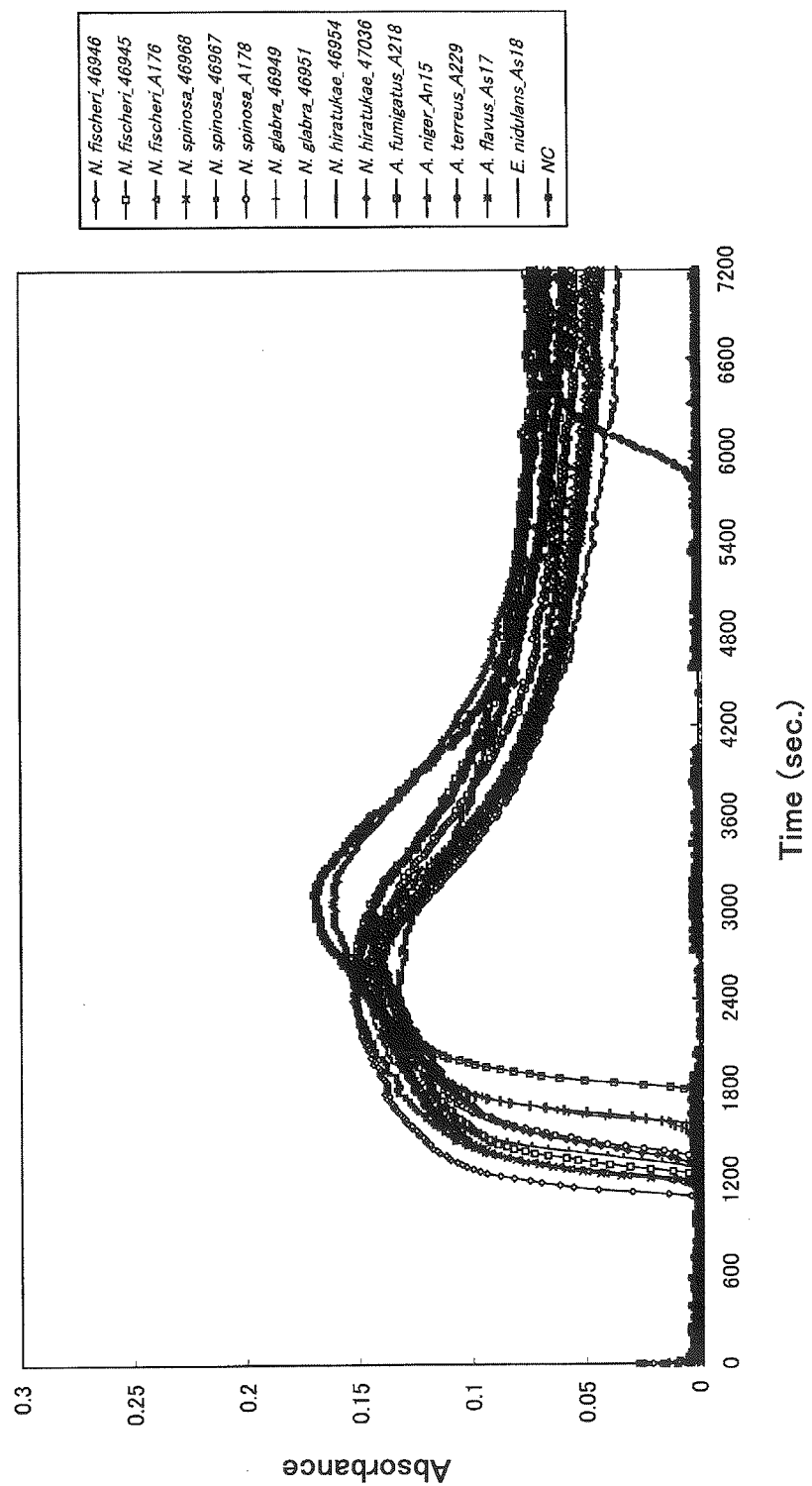

METHOD OF DETECTING HEAT-RESISTANT FUNGUS

REFERENCE TO SEQUENCE LISTING SUBMITTED ELECTRONICALLY

The content of the electronically submitted substitute sequence listing, file name: 2537_0420000_subSE-QIDListing_ascii; size: 27,956 bytes; and date of creation: Oct. 2, 2013, filed herewith, is incorporated herein by reference in its entirety.

TECHNICAL FIELD

The present invention relates to a method of detecting a heat-resistant fungus.

BACKGROUND ART

Heat-resistant fungi are widely distributed throughout nature, and the fungi grow proliferously in agricultural crops such as vegetables and fruits and contaminate foods and drinks made from the agricultural crops. Moreover, the heat-resistant fungi have high heat resistance compared with general other fungi. For example, the heat-resistant fungi may survive and grow proliferously even after a heat sterilization treatment of an acidic drink and may cause mold growth. Therefore, there are concerns about the heat-resistant fungi as important harmful fungi causing severe accidents.

As major heat-resistant fungi causing contamination accidents, which may be detected from foods and drinks after a heat sterilization treatment, heat-resistant fungi belonging to the genera *Byssochlamys, Talaromyces, Neosartorya*, and *Hamigera* are known. Compared with other heat-resistant fungi which form ascospores, the fungi belonging to the above-mentioned four genera have very high heat resistance and are likely to survive after heat sterilization. On the other hand, heat-resistant fungi other than the above-mentioned four genera can be killed under usual sterilization conditions and hence are less likely to cause contamination accidents unless sterilization fails. Therefore, to prevent the accidents by such heat-resistant fungi in foods and drinks and raw materials thereof, it is particularly important to detect and discriminate the heat-resistant fungi belonging to the four genera.

Moreover, to perform accident cause investigation and countermeasure in the case of a harmful accident, it is necessary to identify a fungus causing the accident. Therefore, if the heat-resistant fungi of the above-mentioned four genera can be discriminated, the fungus causing the accident can be detected and discriminated more rapidly.

As a conventional method of detecting and discriminating heat-resistant fungi, a method involving culturing a sample in PDA medium or the like and detecting fungi is known. However, in this method, it takes about seven days until colonies are confirmed. Moreover, identification of the species of the fungi is performed based on the morphology of the fungal organ characteristic to each fungus, and hence it is necessary to continue the culture for further seven days until morphological characters appear. Therefore, according to the method, it takes for about 14 days to detect and discriminate heat-resistant fungi. Such method which requires a long period of time to detect and discriminate heat-resistant fungi is not necessarily satisfactory in terms of sanitary management of foods and drinks, freshness keeping of raw materials, and distribution constraint. Therefore, it is required to establish a method of detecting and discriminating heat-resistant fungi more rapidly.

As a method of rapidly detecting and discriminating fungi, detection methods using a polymerase chain reaction (PCR) are known (e.g., see Patent Documents 1 to 4). However, such methods have problems in that it is difficult to detect specific heat-resistant fungi specifically and rapidly.

PRIOR ART DOCUMENT

Patent Document

[Patent Document 1] JP-T-11-505728 ("JP-T" means published Japanese translation of PCT application)
[Patent Document 2] JP-A-2006-61152 ("JP-A" means unexamined published Japanese patent application)
[Patent Document 3] JP-A-2006-304763
[Patent Document 4] JP-A-2007-174903

SUMMARY OF INVENTION

The present invention is to provide a method of specifically and rapidly detecting and discriminating a heat-resistant fungus which is a main fungus causing contamination of foods and drinks.

The difficulty in detection of a heat-resistant fungi as described above is caused by false positive and false negative results in the PCR method using known conventional primers.

In view of such problems, the inventors of the present invention have made extensive studies to search a novel DNA region capable of specifically detecting and discriminating the specific heat-resistant fungi. As a result, the inventors have found out that the β-tubulin gene or the ITS region and D1/D2 region of 28S rDNA of the heat-resistant fungi includes a region having a specific nucleotide sequence which can be clearly different from that of another fungus (hereinafter, also referred to as "variable region"). Moreover, the inventors have found out that such the heat-resistant fungi can be detected specifically and rapidly by targeting the variable region. The present invention has been completed based on the findings.

According to the present invention, there is provided the following means:

The present invention resides in a method of detecting a heat-resistant fungus selected from the group consisting of fungi belonging to the genus *Byssochlamys*, fungi belonging to the genus *Talaromyces*, fungi belonging to the genus *Neosartorya, Aspergillus fumigates*, and fungi belonging to the genus *Hamigera*, which has at least one step selected from the group consisting of the following steps 1) to 4):

1) a step of identifying a fungus belonging to the genus *Byssochlamys* using the following nucleic acid (A-I) or (A-II):

(A-I) a nucleic acid including a nucleotide sequence set forth in SEQ ID NO: 24 or 25, or a complementary sequence thereof; or (A-II) a nucleic acid including a nucleotide sequence resulting from a deletion, substitution, or addition of one to several nucleotides in the nucleotide sequence set forth in SEQ ID NO: 24 or 25 and being capable of detecting the fungus belonging to the genus *Byssochlamys*, or a complementary sequence thereof;

2) a step of identifying a fungus belonging to the genus *Talaromyces* using the following nucleic acid (B-I) or (B-II):

(B-I) a nucleic acid including a nucleotide sequence set forth in any one of SEQ ID NOS: 26 to 31, or a complementary sequence thereof; or (B-II) a nucleic acid including a nucleotide sequence resulting from a deletion, substitution, or addition of one to several nucleotides in the nucleotide sequence set forth in any one of SEQ ID NOS: 26 to 31 and being capable of detecting the fungus belonging to the genus *Talaromyces*, or a complementary sequence thereof;

3) a step of identifying a fungus belonging to the genus *Neosartorya* and/or *Aspergillus fumigatus* using the following nucleic acid (C-I) or (C-II):

(C-I) a nucleic acid including a nucleotide sequence set forth in any one of SEQ ID NOS: 32 to 34 and 83 to 86, or a complementary sequence thereof; or (C-II) a nucleic acid including a nucleotide sequence resulting from a deletion, substitution, or addition of one to several nucleotides in the nucleotide sequence set forth in any one of SEQ ID NOS: 32 to 34 and 83 to 86 and being capable of detecting the fungus belonging to the genus *Neosartorya* and/or *Aspergillus fumigatus*, or a complementary sequence thereof; and 4) a step of identifying a fungus belonging to the genus *Hamigera* using the following nucleic acid (D-I) or (D-II):

(D-I) a nucleic acid including a nucleotide sequence set forth in SEQ ID NO: 35, or a complementary sequence thereof; or (D-II) a nucleic acid including a nucleotide sequence resulting from a deletion, substitution, or addition of one to several nucleotides in the nucleotide sequence set forth in SEQ ID NO: 35 and being capable of detecting the fungus belonging to the genus *Hamigera*, or a complementary sequence thereof.

Further, the present invention resides in a nucleic acid represented by the following (I) or (II) for detecting a heat-resistant fungus:

(I) a nucleic acid including a nucleotide sequence set forth in any one of SEC) ID NOS: 24 to 35 and 83 to 86, or a complementary sequence thereof; or (II) a nucleic acid including a nucleotide sequence resulting from a deletion, substitution, or addition of one to several nucleotides in the nucleotide sequence set forth in any one of SEQ ID NOS: 24 to 35 and 83 to 86 and being capable of detecting the heat-resistant fungus, or a complementary sequence thereof.

Further, the present invention resides in an oligonucleotide for detecting a heat-resistant fungus, which is capable of hybridizing with the nucleic acid (I) or (II) described above and has a function as a nucleic acid probe or nucleic acid primer for specifically detecting the heat-resistant fungus.

Moreover, the present invention resides in a kit for detecting a heat-resistant fungus containing the above-mentioned oligonucleotides for detection as a nucleic acid probe or a nucleic acid primer.

According to the present invention, it is possible to provide a method of specifically and rapidly detecting and discriminating a heat-resistant fungus which is a main fungus causing contamination of foods and drinks.

BRIEF DESCRIPTION OF DRAWINGS

FIG. 1 is a diagram for comparing partial nucleotide sequences of the β-tubulin genes of *Aspergillus fumigatus* (SEQ ID NO:34 bases 1-99 and 200-299), *Neosartorya fischeri fischeri* bases 1-97 (SEQ ID NO: 83) and bases 198 to 295 (SEQ ID NO: 84), and *Neosartorya fischeri spinosa* bases 1-100 (SEQ ID NO: 85) and bases 201 to 299 (SEQ ID NO: 86).

FIG. 2 is a diagram illustrating nucleotide sequences of the β-tubulin genes of *Hamigera avellanea* (SEQ ID NO:35) and *Cladosporium cladosporoides* (SEQ ID NO:87).

FIG. 3(*a*) shows an electrophoretogram of samples of the fungi shown in Table 1, and FIG. 3(*b*) shows an electrophoretogram of samples of the fungi shown in Table 2. The numbers in the electrophoretograms correspond the sample numbers in the tables, and represent samples obtained by using DNAs extracted from the fungi having the corresponding sample numbers in the tables.

FIG. 7(*a*) shows an electrophoretogram of samples of the fungi shown in Table 4, and FIG. 7(*b*) shows an electrophoretogram of samples of the fungi shown in Table 5. The numbers in the electrophoretograms correspond the sample numbers in each table, and represent samples obtained by using DNAs extracted from the fungi having the corresponding sample numbers in the tables.

FIG. 9-1 is an electrophoretogram in Example 1(B-3).

FIG. 9-2 is an electrophoretogram in Example 1(B-4).

FIG. 13(*a*) shows an electrophoretogram of samples of the fungi shown in Table 8, and FIG. 13(*b*) shows an electrophoretogram of samples of the fungi shown in Table 9. The numbers in the electrophoretograms correspond the sample numbers in the tables, and represent samples obtained by using DNAs extracted from the fungi having the corresponding sample numbers in the tables.

FIG. 15 is an electrophoretogram showing discrimination results of *Aspergillus fumigatus* from fungi belonging to the genus *Neosartorya* and *Aspergillus fumigatus* in Example 1(C-3).

FIG. 16 is an electrophoretogram in the case of using strains of *Neosartorya fischeri fischeri* in Example 1(C-4). FIG. 16 (*a*) and (*b*) show electrophoretograms of samples of strains of *Neosartorya fischeri fischer*. FIG. 16(*a*): Primers N2F/R represented by the nucleotide sequences set forth in SEQ ID NOS: 14 and 15 were used. FIG. 16(*b*): Primers Af1F/R represented by the nucleotide sequences set forth in SEQ ID NOS: 22 and 23 were used. The following strains were used in each of FIG. 16(a) and (b): lane 1: *N. fisheri* CBM-FA-839 96-PE-92-1; lane 2: *N. fisheri* CBM-FA-181 90-BP-127-1; lane 3: *N. fisheri* XY-243-1; lane 4: *N. fisheri* 2000-XY-247-3; lane 5: *N. fisheri* XY-296-1; and lane 6: *N. fisheri* XY-298-1. "P" was the positive control: *A. fumigatus* strain IFM77.

FIG. 17 is an electrophoretogram in the case of using strains of *Neosartorya fischeri glabra* in Example 1(C-4). FIG. 17 (a) and (b) show electrophoretograms of samples of strains of *Neosartorya glabra*. FIG. 17(A): Primers N2F/R represented by the nucleotide sequences set forth in SEQ ID NOS: 14 and 15 were used. FIG. 17(b): Primers Af1F/R represented b the nucleotide sequences set forth in SEQ ID NOS: 22 and 23 were used. The following strains were used in each of FIG. 17(a) and (b): lane 1: *N glabra* CBM-FA-665 93-BS590-3; lane 2: *N glabra* CBM-FA-657 93-BS-1164-3; lane 3: *N glabra* CBF158; lane 4: *N glabra* CBM-FA-189; lane 5: *N glabra* IFM47148; lane 6: *N glabra* IFM53839; lane 7: *N. glabra* IFM53841 and lane 8: *N glabra* IFM55914. "P" was the positive control: *A. fumigatus* strain IFM77.

FIG. 18 is an electrophoretogram in the case of using strains of *Neosartorya hiratsukae* in Example 1(C-4). FIG. 18 (a) and (b) show electrophoretograms of samples of strains of *Neosartorya hiratsukae fischeri*. FIG. 18(a): Primers N2F/R represented by the nucleotide sequences set forth in SEQ ID NOS: 14 and 15 were used. FIG. 18(b): Primers Af1F/R represented by the nucleotide sequences set forth in SEQ ID NOS: 22 and 23 were used. The following strains were used in each of FIG. 18(a) and (b): lane 1: *N. hiratsukae* IFM46953; lane 2: *N. hiratsukae* 46954; lane 3: *N. hiratsukae* 47036; lane 4: *N. hiratsukae* 49776; and lane 5: *N. hiratsukae* 55915. "P" was the positive control: *A. fumigatus* strain IFM77.

FIG. 19 is an electrophoretogram in the case of using strains of *Neosartorya paulistensis* in Example 1(C-4). FIG. 19 (a) and (b) show electrophoretograms of samples of strains of *Neosartorya paulistensis*. FIG. 19(a): Primers N2F/R represented by the nucleotide sequences set forth in SEQ ID NOS: 14 and 15 were used. FIG. 19(b): Primers Af1F/R represented by the nucleotide sequences set forth in SEQ ID NOS: 22 and 23 were used. The following strains were used in each of FIG. 19 (a) and (b): lane 1: *N. paulistensis* CBM-FA-191 81-GU-14-1; lane 2: *N. paulistensis* CBM-FA-608; and lane 3: *N. paulistensis* CBM-FA-176. "P" was the positive control: *A. fumigatus* strain IFM77.

FIG. 20 is an electrophoretogram in the case of using strains of *Neosartorya fischeri spinosa* in Example 1(C-4). FIG. 20 (a) and (b) show electrophoretograms of samples of strains of *Neosartorya spinosa*. FIG. 20(a): Primers N2F/R represented by the nucleotide sequences set forth in SEQ ID NOS: 14 and 15 were used. FIG. 20(b): Primers Af1F/R represented by the nucleotide sequences set forth in SEQ ID NOS: 22 and 23 were used. The following strains were used in each of FIG. 20(a) and (b): lane 1: *N. spinosa* CBM-FA-892 98-TA-439-N; lane 2: *N. spinosa* CBM-FA-678 93-BS-620-4; lane 3: *N spinosa* XY-9-1; and lane 4: *N spinosa* 2000-XY-325-3. "P" was the positive control: *A. fumigatus* strain IFM77.

FIG. 24-1 is an electrophoretogram in the case of using strains of *Hamigera striata* in Example 1(D-4).

FIG. 24-2 is an electrophoretogram in the case of using strains of *Hamigera avellanea* in Example 1(D-5).

FIG. 25-1 is an electrophoretogram in the case of using fungi belonging to the genera *Hamigera* and *Byssochlamys* in Example 1(D-6).

FIG. 25-2 is an electrophoretogram in the case of using fungi belonging to the genera *Hamigera* and *Byssochlamys* in Example 1(D-6).

FIG. 26 is a diagram illustrating the position relationship of nucleotide sequences recognized by primers for detecting the genus *Byssochlamys* in the nucleotide sequences of the ITS region and D1/D2 region of 28S rDNA of fungi belonging to the genus the genus *Byssochlamys* (SEQ ID NO:25).

FIG. 27 is a diagram illustrating the position relationship of nucleotide sequences recognized by primers for detecting the genus *Neosartorya* in the nucleotide sequences of the β-tubulin genes of fungi belonging to the genus the genus *Neosartorya* (SEQ ID NO:88).

FIG. 28 is a diagram illustrating the position relationship of nucleotide sequences recognized by primers for detecting *Aspergillus fumigatus* in the nucleotide sequences of the β-tubulin genes of *Aspergillus fumigatus* (SEQ ID NO:34).

FIG. 29 is a diagram illustrating the position relationship of nucleotide sequences recognized by primers for detecting the genus *Hamigera* in the nucleotide sequences of the β-tubulin genes of fungi belonging to the genus *Hamigera* (nucleotides 1 to 525 of SEQ ID NO:35 are shown).

FIG. 30 is a diagram illustrating the position relationship of nucleotide sequences recognized by primers for detecting *Talaromyces flavus* in the nucleotide sequences of the β-tubulin genes of *Talaromyces flavus* (SEQ ID NO:26).

FIG. 31 is a diagram illustrating the position relationship of nucleotide sequences recognized by primers for detecting *Talaromyces wortmannii* in the nucleotide sequences of the β-tubulin genes of *Talaromyces wortmannii* (SEQ ID NO:29).

FIG. 32 is a diagram illustrating the position relationship of nucleotide sequences recognized by primers for detecting *Talaromyces luteus* in the nucleotide sequences of the β-tubulin genes of *Talaromyces luteus* (SEQ ID NO:27).

FIG. 33 is a diagram illustrating the position relationship of nucleotide sequences recognized by primers for detecting *Talaromyces flavus* in the nucleotide sequences of the ITS region and D1/D2 region of 28S rDNA of *Talaromyces flavus* (SEQ ID NO:30).

FIG. 34 is a diagram illustrating the position relationship of nucleotide sequences recognized by primers for detecting *Talaromyces trachyspermus* (SEQ ID NO:31) and *Talaromyces flavus* (SEQ ID NO:30) in the nucleotide sequences of the ITS region and D1/D2 region of 28S rDNA of *Talaromyces trachyspermus* and *Talaromyces flavus*. Nucleotide bases 1-567 of SEQ ID NO: 31 and nucleotide bases 1-554 of SEQ ID NO:32 are shown on FIG. 34.

FIG. 34-1 is a diagram illustrating the position relationship of nucleotide sequences recognized by primers for detecting *Talaromyces trachyspermus* (SEQ ID NO:31) and *Talaromyces flavus* (SEQ ID NO:30) in the nucleotide sequences of the ITS region and D1/D2 region of 28S rDNA of *Talaromyces trachyspermus* and *Talaromyces flavus*. (Continuation of FIG. 34). Nucleotide bases 568-1113 of SEQ ID NO: 31 and nucleotide bases 555-1098 of SEQ ID NO:32 are shown on FIG. 34-1.

FIG. 35(a) shows the results of samples Nos. 1 to 8 in Table 15, and FIG. 35(b) shows the results of samples Nos. 9 to 16 in Table 15.

FIG. 36(a) shows the results of samples Nos. 1 to 7 and FIG. 36(b) shows the results of samples Nos. 9, 11 and 14.

FIG. 36-1 is a graph illustrating the detection sensitivity of the β-tubulin genes of fungi belonging to the genus *Neosartorya* and *Aspergillus fumigatus* by real-time turbidity monitoring method in Example 3.

FIG. 39(a) shows the results of samples Nos. 1 to 8 in Table 19, and FIG. 39(b) shows the results of samples Nos. 9 to 16 in Table 19.

FIG. 41(a) shows the results of samples Nos. 1 to 8 in Table 21, and FIG. 41(b) shows the results of samples Nos. 9 to 16 in Table 21.

Figure 3:
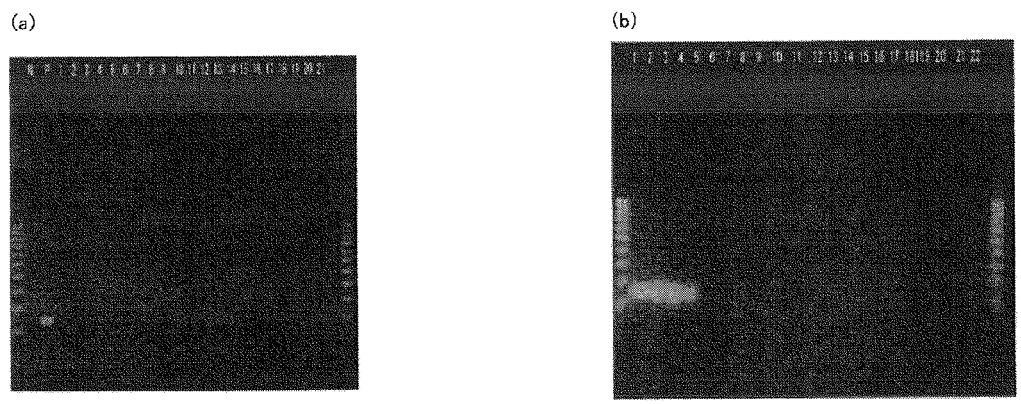
FIG. 3 is an electrophoretogram showing discrimination results of fungi belonging to the genus *Byssochlamys* in Example 1(A-1).

Other and further features and advantages of the invention will appear more fully from the following description, appropriately referring to the accompanying drawings.

MODE FOR CARRYING OUT THE INVENTION

Hereinafter, the present invention is described in detail.

The present invention relates to a method of specifically discriminating/detecting a heat-resistant fungus by identifying the heat-resistant fungus using a nucleic acid including a partial nucleotide sequence of the β-tubulin gene or nucleotide sequences of the D1/D2 region and ITS region of 28S rDNA of the heat-resistant fungus, i.e., a nucleotide sequence of a region specific to each genus of the heat-resistant fungi or a species-specific region (variable region) in the β-tubulin gene region or the D1/D2 region and ITS region of 28S rDNA of the heat-resistant fungus.

According to the present invention, it is possible to discriminate/detect a heat-resistant fungus such as a fungus belonging to the genus *Byssochlamys*, a fungus belonging to the genus *Talaromyces*, a fungus belonging to the genus *Neosartorya*, a fungus belonging to the genus *Hamigera*, or *Aspergillus fumigatus*.

More specifically, the present invention is a method of detecting a heat-resistant fungus, including at least one of the following identification/detection steps 1) to 4).

1) A step of specifically discriminating/detecting a fungus belonging to the genus *Byssochlamys* by identifying the fungus belonging to the genus *Byssochlamys* using a nucleic acid including a nucleotide sequence of a region specific to the genus *Byssochlamys* (variable region) in the β-tubulin gene region and/or the D1/D2 region and ITS region of 28S rDNA of the fungus belonging to the genus *Byssochlamys*.

2) A step of specifically discriminating/detecting a fungus belonging to the genus *Talaromyces* by identifying the fungus belonging to the genus *Talaromyces* using a nucleic acid including a nucleotide sequence of a region specific to the genus *Talaromyces* or a species-specific region (variable region) in the β-tubulin gene region and/or the D1/D2 region and ITS region of 28S rDNA of the fungus belonging to the genus *Talaromyces*.

3) A step of specifically discriminating/detecting a fungus belonging to the genus *Neosartorya* and/or *Aspergillus fumigatus* by identifying the fungus belonging to the genus *Neosartorya* and/or *Aspergillus fumigatus* using a nucleic acid including a nucleotide sequence of a region specific to the genus *Neosartorya* and/or *Aspergillus fumigatus* or a species-specific region (variable region) in the β-tubulin gene region of the fungus belonging to the genus *Neosartorya* and/or *Aspergillus fumigatus*.

4) A step of specifically discriminating/detecting a fungus belonging to the genus *Hamigera* by identifying the fungus belonging to the genus *Hamigera* using a nucleic acid including a nucleotide sequence of a region specific to the genus *Hamigera* or a species-specific region (variable region) in the β-tubulin gene region of the fungus belonging to the genus *Hamigera*.

The detection method of the present invention includes preferably at least two of the above-mentioned identification/detection steps 1) to 4), more preferably at least three of the above-mentioned identification/detection steps 1) to 4), still more preferably all the steps of the above-mentioned identification/detection steps 1) to 4). If the detection method of the present invention includes a plurality of the above-mentioned steps 1) to 4), it is possible to comprehensively detect the heat-resistant fungus which is a main fungi causing contamination of foods and drinks.

The "heat-resistant fungus" in the present invention, such as the fungus belonging to the genus *Byssochlamys*, the fungus belonging to the genus *Talaromyces*, the fungus belonging to the genus *Neosartorya*, *Aspergillus fumigatus*, and the fungus belonging to the genus *Hamigera*, is a plectomycete belonging to the family Trichocomaceae and is a heat-resistant fungus which forms ascospores which can remain viable even after a heat treatment at 75° C. for 30 minutes. Examples of the fungus belonging to the genus *Byssochlamys* include *Byssochlamys fulva* and *Byssochlamys nivea*. Examples of the fungus belonging to the genus *Talaromyces* include *Talaromyces flavus*, *Talaromyces luteus*, *Talaromyces trachyspermus*, *Talaromyces wortmannii*, *Talaromyces bacillisporus*, and *Talaromyces macrosporus*. Examples of the fungus belonging to the genus *Neosartorya* include *Neosartorya fischeri* var. *spinosa*; (hereinafter, also referred to as "*Neosartorya spinosa*"), *Neosartorya fischeri* var. *fischeri*; (hereinafter, also referred to as "*Neosartorya fischeri*"), *Neosartorya fischeri* var. *glabra*; (hereinafter, also referred to as "*Neosartorya glabra*"), *Neosartorya hiratsukae*, *Neosartorya paulistensis*, and *Neosartorya peudofischeri*. Examples of the fungus belonging to the genus *Hamigera* include *Hamigera avellanea*, and *Hamigera striata*.

The "*Aspergillus fumigatus*" in the present invention is one of deuteromycetes and is morphologically very similar to an anamorph (asexual stage) of *Neosartorya fischeri* but has no teleomorph (sexual stage).

In the present invention, the "variable region" is a region where nucleotide mutations tend to accumulate in the β-tubulin gene or in the D1/D2 region and ITS (internal transcribed spacer) region of 28S rDNA.

The "β-tubulin" is a protein which constitutes a microtubule with α-tubulin, and the "β-tubulin gene" is a gene encoding β-tubulin. The "28S rDNA" is a DNA encoding gene information of ribosome where conversion into a protein is performed. The inventors of the present invention have focused on that proteins themselves encoded by both the β-tubulin gene and 28S rDNA are universally present in fungi. Further, the inventors have discovered that nucleotide mutations tend to accumulate in the β-tubulin gene and 28S rDNA sequence and the mutations are conserved at genus- or species-level, and there is a high possibility that a specific region having a nucleotide sequence which can be used for discrimination from another genus or species is present in the β-tubulin gene or 28S rDNA sequence. Based on such findings, the inventors identified/analyzed the nucleotide sequence of the β-tubulin gene or 28S rDNA for each of fungi such as the above-mentioned heat-resistant fungi, to thereby determine the "variable regions" according to the present invention.

The nucleotide sequences of the variable regions are significantly different among the genera or species of fungi, and the variable regions in the β-tubulin genes or the D1/D2 regions and ITS regions of 28S rDNA of the fungi include nucleotide sequences specific to the fungi. Therefore, it is possible to distinguish from other genera or other species of fungi based on the nucleotide sequences of the variable regions.

The nucleotide sequence of the specific region (variable region) in the β-tubulin gene or the D1/D2 region and ITS region of 28S rDNA of a heat-resistant fungus for use in the present invention corresponds to the following nucleic acid (I) or (II).

(I) a nucleic acid including a nucleotide sequence set forth in any one of SEQ ID NOS: 24 to 35 and 83 to 86, or a complementary sequence thereof.

(II) a nucleic acid including a nucleotide sequence resulting from a deletion, substitution, or addition of one to several nucleotides in the nucleotide sequence set forth in any one of SEQ ID NOS: 24 to 35 and 83 to 86 and being capable of detecting the heat-resistant fungus; or a complementary sequence thereof.

More specifically, the following nucleic acid (A-I) or (A-II) is a nucleic acid corresponding to the nucleotide sequence of the specific region (variable region) in the β-tubulin gene and/or the D1/D2 region and ITS region of 28S rDNA of a fungus belonging to the genus *Byssochlamys*, and is used to detect the fungus belonging to the genus *Byssochlannys*.

(A-I) a nucleic acid including a nucleotide sequence set forth in SEQ ID NO: 24 or 25, or a complementary sequence thereof.

(A-II) a nucleic acid including a nucleotide sequence resulting from a deletion, substitution, or addition of one to several nucleotides in the nucleotide sequence set forth in SEQ ID NO: 24 or 25 and being capable of detecting the fungus belonging to the genus *Byssochlamys*, or a complementary sequence thereof.

The inventors of the present invention identified the nucleotide sequences of a variety of the β-tubulin genes and D1/D2 regions and ITS regions of 28S rDNA from fungi belonging to the genus *Byssochlamys* and related species of the fungi belonging to the genus *Byssochlamys*, and performed genetic distance analyses between the related genera of the genus *Byssochlamys* and the genus *Byssochlamys*, and among the fungi belonging to the genus *Byssochlamys*. Moreover, the inventors performed homology analyses of the determined β-tubulin gene sequences and the nucleotide sequences of the D1/D2 regions and ITS regions of 28S rDNA. As a result, the inventors found out variable regions specific to the fungi belonging to the genus *Byssochlamys* in the sequences. The variable region has a specific nucleotide sequence to the fungi belonging to the genus *Byssochlamys*, and hence it is possible to discriminate/identify the fungi belonging to the genus *Byssochlamys* based on the sequence of the variable region.

In the detection method of the present invention, the following nucleic acid (B-I) or (B-II) is a nucleic acid corresponding to the nucleotide sequence of the specific region (variable region) in the β-tubulin gene and/or the D1/D2 region and ITS region of 28S rDNA of a fungus belonging to the genus *Talaromyces*, and is used to detect the fungus belonging to the genus *Talaromyces*.

(B-I) a nucleic acid including a nucleotide sequence set forth in any one of SEQ ID NOS: 26 to 31, or a complementary sequence thereof.

(B-II) a nucleic acid including a nucleotide sequence resulting from a deletion, substitution, or addition of one to several nucleotides in the nucleotide sequence set forth in any one of SEQ ID NOS: 26 to 31 and being capable of detecting the fungus belonging to the genus *Talaromyces*, or a complementary sequence thereof.

The inventors of the present invention identified nucleotide sequences of a variety of the β-tubulin genes and D1/D2 regions and ITS regions of 28S rDNA from fungi belonging to the genus *Talaromyces* and related species of the fungi belonging to the genus *Talaromyces*, and performed genetic distance analyses between the related genera of the genus *Talaromyces* and the genus *Talaromyces*, and among the fungi belonging to the genus *Talaromyces*. Moreover, the inventors performed homology analyses of the determined β-tubulin gene sequences and the nucleotide sequences of the D1/D2 regions and ITS regions of 28S rDNA. As a result, the inventors found out variable regions specific to the fungi belonging to the genus *Talaromyces* in the sequences. The variable region has a specific nucleotide sequence to the fungi belonging to the genus *Talaromyces*, and hence it is possible to discriminate/identify the fungi belonging to the genus *Talaromyces* based on the sequence of the variable region.

In the detection method of the present invention, the following nucleic acid (C-I) or (C-II) is a nucleic acid corresponding to the nucleotide sequence of the specific region (variable region) in the β-tubulin gene of a fungus belonging to the genus *Neosartorya* and/or *Aspergillus fumigatus*, and is used to detect the fungus belonging to the genus *Neosartorya* and/or *Aspergillus fumigatus*.

(C-I) a nucleic acid including a nucleotide sequence set forth in any one of SEQ ID NOS: 32 to 34 and 83 to 86, or a complementary sequence thereof.

(C-II) a nucleic acid including a nucleotide sequence resulting from a deletion, substitution, or addition of one to several nucleotides in the nucleotide sequence set forth in any one of SEQ ID NOS: 32 to 34 and 83 to 86 and being capable of detecting the fungus belonging to the genus *Neosartorya* and/or *Aspergillus fumigatus*, or a complementary sequence thereof.

The inventors of the present invention identified nucleotide sequences of a variety of the β-tubulin genes from fungi belonging to the genus *Neosartorya* and/or *Aspergillus fumigatus* and related species of the fungi belonging to the genus *Neosartorya* and/or *Aspergillus fumigatus*, and performed genetic distance analyses between the related genera of the genus *Neosartorya* and the genus *Neosartorya*, among the fungi belonging to the genus *Neosartorya*, and among the related genera of the genus *Neosartorya*, the genus *Neosartorya* and *Aspergillus fumigatus*. Moreover, the inventors performed homology analyses of the determined β-tubulin gene sequences. As a result, the inventors found out variable regions specific to the fungi belonging to the genus *Neosartorya* and/or *Aspergillus fumigatus* in the sequences. The variable regions have specific nucleotide sequences to the fungi belonging to the genus *Neosartorya* and *Aspergillus fumigatus*, and hence it is possible to discriminate/identify the fungi belonging to the genus *Neosartorya* and *Aspergillus fumigatus* based on the sequence of the variable region.

In the detection method of the present invention, the following nucleic acid (D-I) or (D-II) is a nucleic acid corresponding to the nucleotide sequence of the specific region (variable region) in the β-tubulin gene of a fungus belonging to the genus *Hamigera*, and is used to detect the fungus belonging to the genus *Hamigera*.

(D-I) a nucleic acid including a nucleotide sequence set forth in SEQ ID NO: 35, or a complementary sequence thereof.

(D-II) a nucleic acid including a nucleotide sequence resulting from a deletion, substitution, or addition of one to several nucleotides in the nucleotide sequence set forth in SEQ ID NO: 35 and being capable of detecting the fungus belonging to the genus *Hamigera*, or a complementary sequence thereof.

The inventors of the present invention identified nucleotide sequences of a variety of the β-tubulin genes from fungi belonging to the genus *Hamigera* and related species of the fungi belonging to the genus *Hamigera*, and performed genetic distance analyses between the related genera of the genus *Hamigera* and the genus *Hamigera*, and among the fungi belonging to the genus *Hamigera*. Moreover, the inventors performed homology analyses of the determined β-tubulin gene sequences. As a result, the inventors found out variable regions specific to the fungi belonging to the genus *Hamigera* in the sequences. The variable region has a specific nucleotide sequence to the fungi belonging to the genus *Hamigera*, and hence it is possible to discriminate/identify the fungi belonging to the genus *Hamigera* based on the sequence of the variable region.

In the present invention, such variable regions, and nucleic acids and oligonucleotides derived from such variable regions are used as targets.

The nucleotide sequence (A-I) or (A-II) to be used in the detection method of the present invention corresponds to a partial nucleotide sequence of the β-tubulin gene or the nucleotide sequences of the variable regions of the ITS region and D1/D2 region of 28S rDNA of the fungi belonging to the genus *Byssochlamys*.

The nucleotide sequence set forth in SEQ ID NO: 24 or the complementary sequence thereof is the nucleotide sequence of the variable region in the β-tubulin gene isolated and identified from *Byssochlamys nivea*. The nucleotide sequence set forth in SEQ ID NO: 25 or the complementary sequence thereof is the nucleotide sequences of the variable regions in the ITS region and D1/D2 region of 28S rDNA isolated and identified from *Byssochlamys fulva*. The sequences are specific to the fungi belonging to the genus *Byssochlamys*, and it is possible to specifically discriminate/identify the fungi belonging to the genus *Byssochlamys* by confirming whether a sample has the nucleotide sequences or not. Moreover, it is also possible to specifically discriminate/identify the fungi belonging to the genus *Byssochlamys* by using the nucleic acid including the nucleotide sequence resulting from a deletion, substitution, or addition of one to several nucleotides in the nucleotide sequence set forth in any one of SEQ ID NOS: 24 to 25 and being capable of detecting the fungus belonging to the genus *Byssochlamys*, or the complementary sequence thereof. The nucleic acids including such nucleotide sequences are particularly preferably used for detecting *Byssochlamys nivea* and *Byssochlamys fulva*.

The nucleotide sequence (B-I) or (B-II) to be used in the detection method of the present invention corresponds to a partial nucleotide sequence of the β-tubulin gene or the nucleotide sequences of the variable regions of the ITS region and D1/D2 region of 28S rDNA of the fungi belonging to the genus *Talaromyces*.

The nucleotide sequence set forth in SEQ ID NO: 26 or the complementary sequence thereof is the nucleotide sequence of the variable region in the β-tubulin gene isolated and identified from *Talaromyces flavus*. The sequences are specific to the fungi belonging to the genus *Talaromyces*, and it is possible to specifically discriminate/identify the fungi belonging to the genus *Talaromyces* by confirming whether a sample has the nucleotide sequences or not. Moreover, it is also possible to specifically discriminate/identify the fungi belonging to the genus *Talaromyces* by using the nucleic acid including the nucleotide sequence resulting from a deletion, substitution, or addition of one to several nucleotides in the nucleotide sequence set forth in SEQ ID NO: 26 and being capable of detecting the fungi belonging to the genus *Talaromyces*, or the complementary sequence thereof. The nucleic acids including such nucleotide sequences are particularly preferably used for detecting *Talaromyces flavus* and *Talaromyces trachyspermus*.

The nucleotide sequence set forth in SEQ ID NO: 27 or the complementary sequence thereof is the nucleotide sequence of the variable region in the β-tubulin gene isolated and identified from *Talaromyces luteus*. The sequences are specific to the fungi belonging to the genus *Talaromyces*, and it is possible to specifically discriminate/identify the fungi belonging to the genus *Talaromyces* by confirming whether a sample has the nucleotide sequences or not. Moreover, it is also possible to specifically discriminate/identify the fungi belonging to the genus *Talaromyces* by using the nucleic acid including the nucleotide sequence resulting from a deletion, substitution, or addition of one to several nucleotides in the nucleotide sequence set forth in SEQ ID NO: 27 and being capable of detecting the fungi belonging to the genus *Talaromyces*, or the complementary sequence thereof. The nucleic acids including such nucleotide sequences are particularly preferably used for detecting *Talaromyces luteus*, *Talaromyces bacillisporus* and *Talaromyces wortmannii*.

The nucleotide sequence set forth in SEQ ID NO: 28 or the complementary sequence thereof is the nucleotide sequences of the variable regions in the ITS region and D1/D2 region of 28S rDNA isolated and identified from *Talaromyces wortmannii*. The sequences are specific to the fungi belonging to the genus *Talaromyces*, and it is possible to specifically discriminate/identify the fungi belonging to the genus *Talaromyces* by confirming whether a sample has the nucleotide sequences or not. Moreover, it is also possible to specifically discriminate/identify the fungi belonging to the genus *Talaromyces* by using the nucleic acid including the nucleotide sequence resulting from a deletion, substitution, or addition of one to several nucleotides in the nucleotide sequence set forth in SEQ ID NO: 28 and being capable of detecting the fungi belonging to the genus *Talaromyces*, or the complementary sequence thereof. The nucleic acids including such nucleotide sequences are particularly preferably used for detecting *Talaromyces wortmannii*, *Talaromyces flavus*, *Talaromyces trachyspermus* and *Talaromyces macrosporus*.

The nucleotide sequence set forth in SEQ ID NO: 29 or the complementary sequence thereof is the nucleotide sequence of the variable region in the β-tubulin gene isolated and identified from *Talaromyces wortmannii*. The sequences are specific to the fungi belonging to the genus *Talaromyces*, and it is possible to specifically discriminate/identify the fungi belonging to the genus *Talaromyces* by confirming whether a sample has the nucleotide sequences or not. Moreover, it is also possible to specifically discriminate/identify the fungi belonging to the genus *Talaromyces* by using the nucleic acid including the nucleotide sequence resulting from a deletion, substitution, or addition of one to several nucleotides in the nucleotide sequence set forth in SEQ ID NO: 29 and being capable of detecting the fungi belonging to the genus *Talaromyces*, or the complementary sequence thereof. The nucleic acids including such nucleotide sequences are particularly preferably used for detecting *Talaromyces wortmannii*.

The nucleotide sequence set forth in SEQ ID NO: 30 or the complementary sequence thereof is the nucleotide sequences of the variable regions in the ITS region and D1/D2 region of 28S rDNA isolated and identified from *Talaromyces flavus*. The nucleotide sequence set forth in SEQ ID NO: 31 or the complementary sequence thereof is the nucleotide sequences of the variable regions in the ITS region and D1/D2 region of 28S rDNA isolated and identified from *Talaromyces trachyspermus*. The sequences are specific to the fungi belonging to the genus *Talaromyces*, and it is possible to specifically discriminate/identify the fungi belonging to the genus *Talaromyces* by confirming whether a sample has the nucleotide sequences or not. Moreover, it is also possible to specifically discriminate/identify the fungi belonging to the genus *Talaromyces* by using the nucleic acid including the nucleotide sequence resulting from a deletion, substitution, or addition of one to several nucleotides in the nucleotide sequence set forth in SEQ ID NO: 30 or 31 and being capable of detecting the fungi belonging to the genus *Talaromyces*, or the complementary sequence thereof. The nucleic acids including such nucleotide sequences are particularly preferably used for detecting *Talaromyces flavus* and *Talaromyces trachyspermus*.

The nucleotide sequence (C-I) or (C-II) to be used in the detection method of the present invention corresponds to a partial nucleotide sequence of the β-tubulin gene of the fungi belonging to the genus *Neosartorya* or *Aspergillus fumigatus*. The nucleotide sequence set forth in SEQ ID NO: 32 or the complementary sequence thereof is the nucleotide sequence of the variable region in the β-tubulin gene isolated and identified from *Neosartorya glabra*. The nucleotide sequence set forth in SEQ ID NO: 83 or 84 or the complementary sequence thereof is the nucleotide sequence of the variable region in the β-tubulin gene isolated and identified from *Neosartorya fischeri*. The nucleotide sequence set forth in SEQ ID NO: 85 or 86 or the complementary sequence thereof is the nucleotide sequence of the variable region in the β-tubulin gene isolated and identified from *Neosartorya spinosa*. The nucleotide sequence set forth in SEQ ID NO: 33 or 34 or the complementary sequence thereof is the nucleotide sequence of the variable region in the β-tubulin gene isolated and identified from *Aspergillus fumigatus*. The sequences are specific to the fungi belonging to the genus *Neosartorya* and/or *Aspergillus fumigatus*, and it is possible to specifically discriminate/identify the fungi belonging to the genus *Neosartorya* and/or *Aspergillus fumigatus* by confirming whether a sample has the nucleotide sequences or not. Moreover, it is also possible to specifically discriminate/identify the fungi belonging to the genus *Neosartorya* and/or *Aspergillus fumigatus* by using the nucleic acid including the nucleotide sequence resulting from a deletion, substitution, or addition of one to several nucleotides in the nucleotide sequence set forth in any one of SEQ ID NOS: 32 to 34 and 83 to 86 and being capable of detecting the fungi belonging to the genus *Neosartorya* and/ or *Aspergillus fumigatus*, or the complementary sequence thereof. The nucleic acids including such nucleotide sequences are particularly preferably used for detecting *Neosartorya glabra, Neosartorya fischeri, Neosartorya spinosa, Neosartorya hiratsukae, Neosartorya paulistensis, Neosartorya pseudofischeri*, and *Aspergillus fumigatus*.

The nucleotide sequence (D-I) or (D-II) to be used in the detection method of the present invention corresponds to a partial nucleotide sequence of the β-tubulin gene of the fungi belonging to the genus *Hamigera*.

The nucleotide sequence set forth in SEQ ID NO: 35 or the complementary sequence thereof is the nucleotide sequence of the variable region in the β-tubulin gene isolated and identified from *Hamigera avellanea*. The sequences are specific to the fungi belonging to the genus *Hamigera*, and it is possible to specifically discriminate/identify the fungi belonging to the genus *Hamigera* by confirming whether a sample has the nucleotide sequences or not. Moreover, it is also possible to specifically discriminate/identify the fungi belonging to the genus *Hamigera* by using the nucleic acid including the nucleotide sequence resulting from a deletion, substitution, or addition of one to several nucleotides in the nucleotide sequence set forth in SEQ ID NO: 35 and being capable of detecting the fungi belonging to the genus *Hamigera*, or the complementary sequence thereof. The nucleic acids including such nucleotide sequences are particularly preferably used for detecting *Hamigera avellanea* and *Hamigera striata*.

Hereinafter, any one of the above nucleotide sequences (A-I) to (D-II) are also referred to as "the nucleotide sequence of the variable region according to the present invention"

In the present invention, the method of identifying the heat-resistant fungus by using the nucleic acid including the nucleotide sequence of the variable region according to the present invention is not particularly limited, and may be performed by a usual genetic engineering procedure such as a sequencing method, a hybridization method, a PCR method, or a LAMP method.

In the detection method of the present invention for identifying the heat-resistant fungus by using the nucleic acid including the nucleotide sequence of the variable region according to the present invention, a preferable embodiment includes determining a nucleotide sequence of the β-tubulin gene region or the ITS region and D1/D2 region of 28S rDNA in a sample, and then confirming whether the obtained nucleotide sequence includes any one of the nucleotide sequences (A-I) to (D-II) or not.

When identifying the fungi belonging to the genus *Byssochlamys* by using the nucleic acid including the nucleotide sequence of the variable region, it is preferable to determine a nucleotide sequence of the β-tubulin gene region or the ITS region and D1/D2 region of 28S rDNA in a sample, and then to confirm whether the obtained nucleotide sequence includes the nucleotide sequence (A-I) or (A-II) or not. In other words, the detection method of the present invention preferably includes: analyzing and determining a nucleotide sequence of the β-tubulin gene or the ITS region and D1/D2 region of 28S rDNA in a sample; comparing the determined nucleotide sequence with the nucleotide sequence (A-I) or (A-II) corresponding to the variable region in the β-tubulin gene or the ITS region and D1/D2 region of 28S rDNA; and identifying the fungi belonging to the genus *Byssochlamys* based on the matching or difference between the both nucleotide sequences.

When identifying the fungi belonging to the genus *Talaromyces* by using the nucleic acid including the nucleotide sequence of the variable region, it is preferable to determine a nucleotide sequence of the β-tubulin gene region or the ITS region and D1/D2 region of 28S rDNA in a sample, and then to confirm whether the obtained nucleotide sequence includes the nucleotide sequence (B-I) or (B-II) or not. In other words, the detection method of the present invention preferably includes: analyzing and determining a nucleotide sequence of the β-tubulin gene or the ITS region and D1/D2 region of 28S rDNA in a sample; comparing the determined nucleotide sequence with the nucleotide sequence (B-I) or (B-II) corresponding to the variable region in the β-tubulin gene or the ITS region and D1/D2 region of 28S rDNA; and identifying the fungi belonging to the genus *Talaromyces* based on the matching or difference between the both nucleotide sequences.

When identifying the fungi belonging to the genus *Neosartorya* and/or *Aspergillus fumigatus* by using the nucleic acid including the nucleotide sequence of the variable region, it is preferable to determine a nucleotide sequence of the β-tubulin gene region in a sample, and then to confirm whether the obtained nucleotide sequence includes the nucleotide sequence (C-I) or (C-II) or not. In other words, the detection method of the present invention preferably includes: analyzing and determining a nucleotide sequence of the β-tubulin gene in a sample; comparing the determined nucleotide sequence with the nucleotide sequence (C-I) or (C-II) corresponding to the variable region in the β-tubulin gene; and identifying the fungi belonging to the genus *Neosartorya* and/or *Aspergillus fumigatus* based on the matching or difference between the both nucleotide sequences.

When identifying the fungi belonging to the genus *Hamigera* by using the nucleic acid including the nucleotide sequence of the variable region, it is preferable to determine a nucleotide sequence of the β-tubulin gene region in a sample, and then to confirm whether the obtained nucleotide sequence includes the nucleotide sequence (D-I) or (D-II) or not. In other words, the detection method of the present invention preferably includes: analyzing and determining a nucleotide sequence of the β-tubulin gene in a sample; comparing the determined nucleotide sequence with the nucleotide sequence (D-I) or (D-II) corresponding to the variable region in the β-tubulin gene; and identifying the fungi belonging to the genus *Hamigera* based on the matching or difference between the both nucleotide sequences.

The method of analyzing and determining the nucleotide sequence is not particularly limited, and usual RNA or DNA sequencing means may be used.

Specific examples of the method include an electrophoresis method such as a Maxam-Gilbert method or a Sanger method, mass spectrometry, and a hybridization method. Examples of the Sanger method include a method of labeling a primer or terminator by a radiation labeling method, a fluorescent labeling method, or the like.

In the method of the present invention for detecting/identifying the heat-resistant fungus by using the nucleic acid including the nucleotide sequence of the variable region according to the present invention, an oligonucleotide for detection can be used. The oligonucleotide is capable of hybridizing with the nucleotide sequence of the variable region (i.e., any one of the nucleic acids (A-I) to (D-II)), and has a function as an oligonucleotide for specifically detecting the heat-resistant fungus.

When identifying the fungi belonging to the genus *Byssochlamys*, an oligonucleotide which is capable of hybridizing with the nucleotide sequence of the variable region (i.e., the nucleic acids (A-I) or (A-II)), and has a function as an oligonucleotide for specifically detecting the fungi belonging to the genus *Byssochlamys*, can be used.

When identifying the fungi belonging to the genus *Talaromyces*, an oligonucleotide which is capable of hybridizing with the nucleotide sequence of the variable region (i.e., the nucleic acids (B-I) or (B-II)), and has a function as an oligonucleotide for specifically detecting the fungi belonging to the genus *Talaromyces*, can be used.

When identifying the fungi belonging to the genus *Neosartorya* and/or *Aspergillus fumigatus*, an oligonucleotide which is capable of hybridizing with the nucleotide sequence of the variable region (i.e., the nucleic acids (C-I) or (C-II)), and has a function as an oligonucleotide for specifically detecting the fungi belonging to the genus *Neosartorya* and/or *Aspergillus fumigatus*, can be used.

When identifying the fungi belonging to the genus *Hamigera*, an oligonucleotide which is capable of hybridizing with the nucleotide sequence of the variable region (i.e., the nucleic acids (D-I) or (D-II)), and has a function as an oligonucleotide for specifically detecting the fungi belonging to the genus *Hamigera*, can be used.

The oligonucleotide for detection of the present invention may be one which is capable of detecting the heat-resistant fungus. That is, the oligonucleotide may be one which can be used as a nucleic acid primer or a nucleic acid probe for detection of the heat-resistant fungus, or one which is capable of hybridizing with the nucleotide sequence of the variable region in the β-tubulin gene or the ITS region and D1/D2 region of 28S rDNA of the heat-resistant fungus under stringent conditions. It should be note that, in this description, the "stringent conditions" includes, for example, the method described in Molecular Cloning—A LABORATORY MANUAL THIRD EDITION [Joseph Sambrook, David W. Russell. Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

The oligonucleotide for detection of the present invention is preferably an oligonucleotide which is capable of hybridizing with a region selected from the nucleotide sequences of the variable regions of the β-tubulin gene or the ITS region and D1/D2 region of 28S rDNA (i.e., a region in the nucleic acid (I) or (II)), and satisfies the following four conditions:

(1) the oligonucleotide includes a region containing about 10 continuous nucleotides specific to each genus of the heat-resistant fungi in the nucleic acid (I) or (II);

(2) the oligonucleotide has a GC content of about 30% to 80%;

(3) the oligonucleotide has low possibility to cause self-annealing; and (4) the oligonucleotide has a Tm value (melting temperature) of about 55° C. to 65° C.

Specifically, the oligonucleotide for detecting the fungus belonging to the genus *Byssochlamys* is preferably an oligonucleotide which is capable of hybridizing with a region in the nucleic acid (A-I) or (A-II) and satisfies the following four conditions:

(1) the oligonucleotide includes a region containing about 10 continuous nucleotides specific to a fungus belonging to the genus *Byssochlamys* in the nucleic acid (A-I) or (A-II);

(2) the oligonucleotide has a GC content of about 30% to 80%;

(3) the oligonucleotide has low possibility to cause self-annealing; and (4) the oligonucleotide has a Tm value (melting temperature) of about 55° C. to 65° C.

The oligonucleotide for detecting the fungus belonging to the genus *Talaromyces* is preferably an oligonucleotide which is capable of hybridizing with a region in the nucleic acid (B-I) or (B-II) and satisfies the following four conditions:
(1) the oligonucleotide includes a region containing about 10 continuous nucleotides specific to a fungus belonging to the genus *Talaromyces* in the nucleic acid (B-I) or (B-II);
(2) the oligonucleotide has a GC content of about 30% to 80%;
(3) the oligonucleotide has low possibility to cause self-annealing; and
(4) the oligonucleotide has a Tm value (melting temperature) of about 55° C. to 65° C.

The oligonucleotide for detecting the fungus belonging to the genus *Neosartorya* and/or *Aspergillus fumigatus* is preferably an oligonucleotide which is capable of hybridizing with a region in the nucleic acid (C-I) or (C-II) and satisfies the following four conditions:
(1) the oligonucleotide includes a region containing about 10 continuous nucleotides specific to a fungus belonging to the genus *Neosartorya* and/or *Aspergillus fumigatus* in the nucleic acid (C-I) or (C-II);
(2) the oligonucleotide has a GC content of about 30% to 80%;
(3) the oligonucleotide has low possibility to cause self-annealing; and
(4) the oligonucleotide has a Tm value (melting temperature) of about 55° C. to 65° C.

The oligonucleotide for detecting the fungus belonging to the genus *Hamigera* is preferably an oligonucleotide which is capable of hybridizing with a region in the nucleic acid (D-I) or (D-II) and satisfies the following four conditions:
(1) the oligonucleotide includes a region containing about 10 continuous nucleotides specific to a fungus belonging to the genus *Hamigera* in the nucleic acid (D-I) or (D-II);
(2) the oligonucleotide has a GC content of about 30% to 80%;
(3) the oligonucleotide has low possibility to cause self-annealing; and
(4) the oligonucleotide has a Tm value (melting temperature) of about 55° C. to 65° C.

In the (1) above, the "region containing about 10 continuous nucleotides specific to each genus of heat-resistant fungi in the nucleic acid (I) or (II)" refers to a region where the nucleotide sequences between different genera of the heat-resistant fungi are particularly poorly conserved (that is, the region has particularly high specificity to each genus of the heat-resistant fungi) in the nucleotide sequences of the variable regions of the β-tubulin gene or the ITS region and D1/D2 region of 28S rDNA, and where a nucleotide sequence including about 10 continuous nucleotides specific to each genus of the heat-resistant fungi is present.

Specifically, "the region containing about 10 continuous nucleotides specific to the fungus belonging to the genus *Byssochlamys* in the nucleic acid (A-I) or (A-II)" refers to a region where the nucleotide sequences of different fungi are particularly poorly conserved (that is, the region has particularly high specificity to the genus *Byssochlamys*) in the variable regions of the β-tubulin gene or the ITS region and D1/D2 region of 28S rDNA of the present invention and where a nucleotide sequence including about 10 continuous nucleotides specific to the genus *Byssochlamys* is present.

"The region containing about 10 continuous nucleotides specific to the fungus belonging to the genus *Talaromyces* in the nucleic acid (B-I) or (B-II)" refers to a region where the nucleotide sequences of different fungi are particularly poorly conserved (that is, the region has particularly high specificity to the genus *Talaromyces*) in the variable regions of the β-tubulin gene or the ITS region and D1/D2 region of 28S rDNA of the present invention and where a nucleotide sequence including about 10 continuous nucleotides specific to the genus *Talaromyces* is present.

"The region containing about 10 continuous nucleotides specific to the fungus belonging to the genus *Neosartorya* and/or *Aspergillus fumigatus* in the nucleic acid (C-I) or (C-II)" refers to a region where the nucleotide sequences of different fungi are particularly poorly conserved (that is, the region has particularly high specificity to the genus *Neosartorya* and/or *Aspergillus fumigatus*) in the variable regions of the β-tubulin gene of the present invention and where a nucleotide sequence including about 10 continuous nucleotides specific to the genus *Neosartorya* and/or *Aspergillus fumigatus* is present.

"The region containing about 10 continuous nucleotides specific to the fungus belonging to the genus *Hamigera* in the nucleic acid (D-I) or (D-II)" refers to a region where the nucleotide sequences of different fungi are particularly poorly conserved (that is, the region has particularly high specificity to the genus *Hamigera*) in the variable regions of the β-tubulin gene of the present invention and where a nucleotide sequence including about 10 continuous nucleotides specific to the genus *Hamigera* is present.

Moreover, in the (3) above, the "oligonucleotide has low possibility to cause self-annealing" means that the primers are expected not to bind to each other from the nucleotide sequences of the primers.

The number of nucleotides in the oligonucleotide for detection of the present invention is not particularly limited, and is preferably 13 to 30, more preferably 18 to 23. The Tm value of the oligonucleotide in hybridization is preferably in a range of 55° C. to 65° C., more preferably 59° C. to 62° C. The GC content in the oligonucleotide is preferably 30% to 80%, more preferably 45% to 65%, most preferably about 55%.

The oligonucleotide for detection of the present invention is preferably an oligonucleotide including the nucleotide sequence set forth in any one of SEQ ID NOS: 1 to 23 and 36 to 78, or the complementary sequence thereof, or an oligonucleotide including a nucleotide sequence which has 70% or more homology to the nucleotide sequence set forth in any one of SEQ ID NOS: 1 to 23 and 36 to 78, or the complementary sequence thereof, and is capable of detecting the heat-resistant fungi (an oligonucleotide which has a function as an oligonucleotide for detection). The oligonucleotide which is capable of detecting the heat-resistant fungi may be one including a nucleotide sequence which has 70% or more homology to the nucleotide sequence set forth in any one of SEQ ID NOS: 1 to 23 and 36 to 78 and has a function as a nucleic acid primer or nucleic acid probe for detecting the heat-resistant fungi, or may include a nucleotide sequence which can hybridize with the β-tubulin gene or the ITS region and D1/D2 region of 28S rDNA of each of the heat-resistant fungi under stringent conditions.

It should be note that, in this description, the "stringent conditions" includes, for example, the method described in Molecular Cloning—A LABORATORY MANUAL THIRD EDITION [Joseph Sambrook, David W. Russell. Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

In such oligonucleotide of the present invention, the homology is more preferably 75% or more, still more preferably 80% or more, even more preferably 85% or more, further more preferably 90% or more, especially preferably 95% or more as long as the oligonucleotide is capable of detecting the above-mentioned heat-resistant fungi.

The nucleotide sequence homology is calculated, for example, by Lipman-Pearson method (Science, 227, 1435, (1985)). Specifically, it can be calculated by performing analysis using a homology analysis (Search homology) program of genetic information processing software Genetyx-Win (Software Development) while the unit size to compare (ktup) parameter is set to 2.

Further, the oligonucleotide for detection of the present invention includes an oligonucleotide obtained by performing a mutation or modification such as a deletion, insertion, or substitution of nucleotide(s) for the oligonucleotide including the nucleotide sequence set forth in any one of SEQ ID NOS: 1 to 23 and 36 to 78 as long as the oligonucleotide is capable of detecting the heat-resistant fungi. The oligonucleotide of the present invention may be including a nucleotide sequence one which obtained by performing a mutation or modification such as a deletion, insertion, or substitution of nucleotide(s) for the oligonucleotide including the nucleotide sequence set forth in any one of SEQ ID NOS: 1 to 23 and 36 to 78 and has a function as a nucleic acid primer or nucleic acid probe for detecting the heat-resistant fungi, or may include a nucleotide sequence which can hybridize with the β-tubulin gene or the ITS region and D1/D2 region of 28SrDNA of each of the heat-resistant fungi under stringent conditions.

It should be note that, in this description, the "stringent conditions" includes, for example, the method described in Molecular Cloning—A LABORATORY MANUAL THIRD EDITION [Joseph Sambrook, David W. Russell. Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

The oligonucleotide obtained by performing a mutation or modification such as a deletion, insertion, or substitution of nucleotide(s) includes an oligonucleotide including a nucleotide sequence modified by a mutation or modification such as a deletion, insertion or substitution of one to several, preferably one to five, more preferably one to four, still more preferably one to three, even more preferably one to two, particularly preferably one nucleotide, to the nucleotide sequences set forth in any one of SEQ ID NOS: 1 to 23 and 36 to 78 or the complementary sequence thereof. Moreover, an appropriate nucleotide sequence may be added to the nucleotide sequence set forth in any one of SEQ ID NOS: 1 to 23 and 36 to 78 or the complementary sequence thereof.

In the present invention, among the above-mentioned oligonucleotides for detection, it is preferable to use an oligonucleotide including the nucleotide sequence set forth in any one of SEQ ID NOS: 1 to 23 and 36 to 78, or an oligonucleotide including the nucleotide sequence which has 70% or more homology to the nucleotide sequence and has a function as an oligonucleotide for detection; and more preferable to use an oligonucleotide including the nucleotide sequence set forth in any one of SEQ ID NOS: 1 to 23 and 36 to 78.

More specifically, when identifying/detecting the fungi belonging to the genus *Byssochlamys* of the heat-resistant fungi, it is preferable to use an oligonucleotide including the nucleotide sequence set forth in any one of SEQ ID NOS: 1, 2 and 36 to 39, or the complementary sequence thereof; or an oligonucleotide including the nucleotide sequence which has 70% or more homology to the nucleotide sequence set forth in any one of SEQ ID NOS: 1, 2 and 36 to 39 or the complementary sequence thereof, and which has a function as an oligonucleotide for detection; more preferably an oligonucleotide including the nucleotide sequence set forth in any one of SEQ ID NOS: 1, 2 and 36 to 39; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 1, 2 and 36 to 39.

When identifying/detecting the fungi belonging to the genus *Talaromyces*, it is preferable to use an oligonucleotide including the nucleotide sequence set forth in any one of SEQ ID NOS: 3 to 11 and 57 to 78, or the complementary sequence thereof; or an oligonucleotide including the nucleotide sequence which has 70% or more homology to the nucleotide sequence set forth in any one of SEQ ID NOS: 3 to 11 and 57 to 78 or the complementary sequence thereof, and which has a function as an oligonucleotide for detection; more preferably an oligonucleotide including the nucleotide sequence set forth in any one of SEQ ID NOS: 3 to 11 and 57 to 78; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 3 to 11 and 57 to 78.

When identifying/detecting the fungi belonging to the genus *Neosartorya* and/or *Aspergillus fumigatus*, it is preferable to use an oligonucleotide including the nucleotide sequence set forth in any one of SEQ ID NOS: 12 to 15, 22, 23 and 40 to 50, or the complementary sequence thereof; or an oligonucleotide including the nucleotide sequence which has 70% or more homology to the nucleotide sequence set forth in any one of SEQ ID NOS: 12 to 15, 22, 23 and 40 to 50 or the complementary sequence thereof, and which has a function as an oligonucleotide for detection; more preferably an oligonucleotide including the nucleotide sequence set forth in any one of SEQ ID NOS: 12 to 15, 22, 23 and 40 to 50, or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 12 to 15, 22, 23 and 40 to 50.

When identifying/detecting the fungi belonging to the genus *Hamigera*, it is preferable to use an oligonucleotide including the nucleotide sequence set forth in any one of SEQ ID NOS: 16 to 21 and 51 to 56, or the complementary sequence thereof; or an oligonucleotide including the nucleotide sequence which has 70% or more homology to the nucleotide sequence set forth in any one of SEQ ID NOS: 16 to 21 and 51 to 56 or the complementary sequence thereof, and which has a function as an oligonucleotide for detection; more preferably an oligonucleotide including the nucleotide sequence set forth in any one of SEQ ID NOS: 16 to 21 and 51 to 56; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 16 to 21 and 51 to 56.

The above oligonucleotide for detection of the present invention can be preferably used as a nucleic acid primer and a nucleic acid probe, as described later.

The bonding pattern of the oligonucleotide for detection includes not only a phosphodiester bond in a natural nucleic acid, but also a phosphoroamidate bond, a phosphorothioate bond and the like.

The oligonucleotide for use in the present invention can be synthesized by known methods. For example, the oligonucleotide may be chemically synthesized based on designed sequences, or purchased from a manufacturer of reagents. Specifically, the oligonucleotide may be synthesized using an oligonucleotide synthesizer or the like. Moreover, after synthesis, the oligonucleotides may be purified by an adsorption column, high-performance liquid chromatography, or electrophoresis. Furthermore, an oligonucleotide having a nucleotide sequence with a substitution, deletion, insertion, or addition of one to several nucleotides may be synthesized by known methods.

In the method of the present invention for identifying the heat-resistant fungus by using the nucleic acid including the nucleotide sequence of the variable region according to the present invention, a preferable embodiment includes labeling an oligonucleotide for detection which is capable of hybridizing with any one of the nucleic acids (A-I) to (D-II) under stringent conditions; hybridizing the resultant oligonucleotide for detection with nucleic acid extracted from a test object under a stringent condition; and measuring the label of the hybridized oligonucleotide for detection.

In this case, the above-mentioned oligonucleotides for detection of the present invention can be used as the oligonucleotide for detection which is capable of hybridizing with any one of the nucleic acids (A-I) to (D-II) under stringent conditions, and preferred ranges are the same as above. Among these, it is preferable to use an oligonucleotide including the nucleotide sequence set forth in any one of SEQ ID NOS: 1 to 23 and 36 to 78, or the complementary sequence thereof; or an oligonucleotide including the nucleotide sequence which has 70% or more homology to the nucleotide sequence set forth in any one of SEQ ID NOS: 1 to 23 and 36 to 78, or the complementary sequence thereof, and which has a function as an oligonucleotide for detection; more preferable to use an oligonucleotide including the nucleotide sequence set forth in any one of SEQ ID NOS: 1 to 23 and 36 to 78, or an oligonucleotide including the nucleotide sequence which has 70% or more homology to the nucleotide sequence and which has a function as an oligonucleotide for detection; and still more preferable to use an oligonucleotide including the nucleotide sequence set forth in any one of SEQ ID NOS: 1 to 23 and 36 to 78.

More specifically, when identifying/detecting the fungi belonging to the genus *Byssochlamys* of the heat-resistant fungi, it is preferable to use an oligonucleotide including the nucleotide sequence set forth in any one of SEQ ID NOS: 1, 2 and 36 to 39, or the complementary sequence thereof; or an oligonucleotide including the nucleotide sequence which has 70% or more homology to the nucleotide sequence set forth in any one of SEQ ID NOS: 1, 2 and 36 to 39 or the complementary sequence thereof, and which has a function as an oligonucleotide for detection; more preferably an oligonucleotide including the nucleotide sequence set forth in any one of SEQ ID NOS: 1, 2 and 36 to 39, or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 1, 2 and 36 to 39.

When identifying/detecting the fungi belonging to the genus *Talaromyces*, it is preferable to use an oligonucleotide including the nucleotide sequence set forth in any one of SEQ ID NOS: 3 to 11 and 57 to 78, or the complementary sequence thereof; or an oligonucleotide including the nucleotide sequence which has 70% or more homology to the nucleotide sequence set forth in any one of SEQ ID NOS: 3 to 11 and 57 to 78 or the complementary sequence thereof, and which has a function as an oligonucleotide for detection; more preferably an oligonucleotide including the nucleotide sequence set forth in any one of SEQ ID NOS: 3 to 11 and 57 to 78, or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 3 to 11 and 57 to 78.

When identifying/detecting the fungi belonging to the genus *Neosartorya* and/or *Aspergillus fumigatus*, it is preferable to use an oligonucleotide including the nucleotide sequence set forth in any one of SEQ ID NOS: 12 to 15, 22, 23 and 40 to 50, or the complementary sequence thereof; or an oligonucleotide including the nucleotide sequence which has 70% or more homology to the nucleotide sequence set forth in any one of SEQ ID NOS: 12 to 15, 22, 23 and 40 to 50 or the complementary sequence thereof, and which has a function as an oligonucleotide for detection; more preferably an oligonucleotide including the nucleotide sequence set forth in any one of SEQ ID NOS: 12 to 15, 22, 23 and 40 to 50, or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 12 to 15, 22, 23 and 40 to 50.

When identifying/detecting the fungi belonging to the genus *Hamigera*, it is preferable to use an oligonucleotide including the nucleotide sequence set forth in any one of SEQ ID NOS: 16 to 21 and 51 to 56, or the complementary sequence thereof; or an oligonucleotide including the nucleotide sequence which has 70% or more homology to the nucleotide sequence set forth in any one of SEQ ID NOS: 16 to 21 and 51 to 56 or the complementary sequence thereof, and which has a function as an oligonucleotide for detection; more preferably an oligonucleotide including the nucleotide sequence set forth in any one of SEQ ID NOS: 16 to 21 and 51 to 56; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 16 to 21 and 51 to 56.

The oligonucleotide for detection of the present invention can be used as a nucleic acid probe. The nucleic acid probe can be prepared by labeling the above-mentioned oligonucleotide with a labeling substance. The labeling substance is not particularly limited and may include a usual labeling substance such as a radioactive substance, an enzyme, a fluorescent substance, a luminescent substance, an antigen, a hapten, an enzyme substrate, or an insoluble carrier. The oligonucleotide may be labeled at its terminal or at the sequence other than the terminals, or at the sugar, phosphate group, or base moiety. Since the nucleic acid probe can be hybridized specifically with part of the variable region in the β-tubulin gene or the ITS region and D1/D2 region of 28S rDNA of the heat-resistant fungi, it is possible to rapidly and easily detect the heat-resistant fungi in a sample. Examples of means for detecting the label include: autoradiography in the case of a nucleic acid probe labeled with a radioisotope; a fluorescent microscope in the case of a nucleic acid probe labeled with a fluorescent substance; and an analysis using a sensitive film or a digital analysis using a CCD camera in the case of a nucleic acid probe labeled with a chemiluminescent substance.

The heat-resistant fungi can be detected by hybridizing the thus-labeled oligonucleotide for detection of the present invention with a nucleic acid extracted from a test object by a usual method under stringent conditions; and measuring the label of the hybridized oligonucleotide for detection. It this case, the stringent conditions may be the same conditions as described above. As a method of measuring the label of the nucleic acid probe hybridized with nucleic acid, a usual method (such as a FISH method, a dot-blot method, a Southern-blot method, or a Northern-blot method) may be used.

Further, the oligonucleotide for use in the present invention may be bound to a solid-phase carrier and used as a capture probe. In this case, the capture probe and labeled nucleic acid probe may be combined and used in a sandwich assay, or a target nucleic acid may be labeled and captured.

An example of the detection method using the oligonucleotide of the present invention as nucleic acid probe is shown below.

In the case of detection of the fungus belonging to the genus *Neosartorya* and/or *Aspergillus fumigatus*, the following oligonucleotides (l) to (w) may be labeled to prepare nucleic acid probes. As mentioned later, the nucleic acid probes consisting of the following oligonucleotides (l) to (o) hybridize specifically with parts of the variable regions of the β-tubulin genes of the fungus belonging to the genus *Neosartorya* and *Aspergillus fumigatus*, and hence can rapidly and easily detect the fungi belonging to the genus *Neosartorya* and *Aspergillus fumigatus* in samples. The nucleic acid probe consisting of the following oligonucleotides (v) and/or (w) hybridizes specifically with part of the variable region in the β-tubulin gene of *Aspergillus fumigatus* but cannot hybridize with DNA and RNA of the fungus belonging to the genus *Neosartorya*. Therefore, it is possible to rapidly and easily discriminate the fungus in the sample as one belonging to the genus *Neosartorya* or *Aspergillus fumigatus* by confirming whether the oligonucleotides hybridize with the region or not.

In the method of the present invention for identifying the heat-resistant fungus by using the nucleic acid including the nucleotide sequence of the variable region according to the present invention, a preferable embodiment includes performing gene amplification of a nucleic acid consisting of the whole or part of the region of any one of the above nucleic acids (A-I) to (D-II), and confirming whether the amplification product is present or not. In this case, the above-mentioned oligonucleotides for detection of the present invention can be used as nucleic acid primers and a pair of nucleic acid primers, and preferred ranges are the same as above. Among these oligonucleotides, as the nucleic acid primers, it is preferable to use an oligonucleotide which is capable of hybridizing with a region in the above nucleic acid (I) or (II), and satisfies the following four conditions:
(1) the oligonucleotide includes a region containing about 10 continuous nucleotides specific to each genus of the heat-resistant fungi in the nucleic acid (I) or (II);
(2) the oligonucleotide has a GC content of about 30% to 80%;
(3) the oligonucleotide has low possibility to cause self-annealing; and
(4) the oligonucleotide has a Tm value (melting temperature) of about 55° C. to 65° C.

Further, as the nucleic acid primers, it is preferable to use an oligonucleotide including the nucleotide sequence set forth in any one of SEQ ID NOS: 1 to 23 and 36 to 78, or the complementary sequence thereof; or an oligonucleotide including the nucleotide sequence which has 70% or more homology to the nucleotide sequence set forth in any one of SEQ ID NOS: 1 to 23 and 36 to 78 or the complementary sequence thereof, and which is capable of detecting the heat-resistant fungus; more preferably an oligonucleotide including the nucleotide sequence set forth in any one of SEQ ID NOS: 1 to 23 and 36 to 78; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 1 to 23 and 36 to 78.

Specifically, when identifying/detecting the fungi belonging to the genus *Byssochlamys* of the heat-resistant fungi, it is preferable to perform gene amplification of a nucleic acid consisting of the whole or part of the region of the above nucleic acid (A-I) or (A-II), and then to confirm whether the amplification product is present or not. In this case, as the nucleic acid primers, it is preferable to use an oligonucleotide which is capable of hybridizing with a region in the nucleic acid (A-I) or (A-II) and satisfies the following four conditions:
(1) the oligonucleotide includes a region containing about 10 continuous nucleotides specific to a fungus belonging to the genus *Byssochlamys* in the nucleic acid (A-I) or (A-II);
(2) the oligonucleotide has a GC content of about 30% to 80%;
(3) the oligonucleotide has low possibility to cause self-annealing; and
(4) the oligonucleotide has a Tm value of about 55° C. to 65° C.

Further, it is preferable to use an oligonucleotide including the nucleotide sequence set forth in any one of SEQ ID NOS: 1, 2 and 36 to 39, or the complementary sequence thereof; or an oligonucleotide including the nucleotide sequence which has 70% or more homology to the nucleotide sequence set forth in any one of SEQ ID NOS: 1, 2 and 36 to 39 or the complementary sequence thereof, and which has a function as an oligonucleotide for detection; more preferably an oligonucleotide including the nucleotide sequence set forth in any one of SEQ ID NOS: 1, 2 and 36 to 39; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 1, 2 and 36 to 39.

When identifying/detecting the fungi belonging to the genus *Talaromyces* of the heat-resistant fungi, it is preferable to perform gene amplification of a nucleic acid consisting of the whole or part of the region of the above nucleic acid (B-I) or (B-II), and then to confirm whether the amplification product is present or not. In this case, as the nucleic acid primers, it is preferable to use an oligonucleotide which is capable of hybridizing with a region in the nucleic acid (B-I) or (B-II) and satisfies the following four conditions:
(1) the oligonucleotide includes a region containing about 10 continuous nucleotides specific to a fungus belonging to the genus *Talaromyces* in the nucleic acid (B-I) or (B-II);
(2) the oligonucleotide has a GC content of about 30% to 80%;
(3) the oligonucleotide has low possibility to cause self-annealing; and (4) the oligonucleotide has a Tm value of about 55° C. to 65° C.

Further, it is preferable to use an oligonucleotide including the nucleotide sequence set forth in any one of SEQ ID NOS: 3 to 11 and 57 to 78, or the complementary sequence thereof; or an oligonucleotide including the nucleotide sequence which has 70% or more homology to the nucleotide sequence set forth in any one of SEQ ID NOS: 3 to 11 and 57 to 78 or the complementary sequence thereof, and which has a function as an oligonucleotide for detection; more preferably an oligonucleotide including the nucleotide sequence set forth in any one of SEQ ID NOS: 3 to 11 and 57 to 78; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 3 to 11 and 57 to 78.

When identifying/detecting the fungi belonging to the genus *Neosartorya* and/or *Aspergillus fumigatus* of the heat-resistant fungi, it is preferable to perform gene amplification of a nucleic acid consisting of the whole or part of the region of the above nucleic acid (C-I) or (C-II), and then to confirm whether the amplification product is present or not. In this case, as the nucleic acid primers, it is preferable to use an oligonucleotide which is capable of hybridizing with a region in the nucleic acid (C-I) or (C-II) and satisfies the following four conditions:
(1) the oligonucleotide includes a region containing about 10 continuous nucleotides specific to a fungus belonging to the genus *Neosartorya* and/or *Aspergillus fumigatus* in the nucleic acid (C-I) or (C-II);
(2) the oligonucleotide has a GC content of about 30% to 80%;
(3) the oligonucleotide has low possibility to cause self-annealing; and
(4) the oligonucleotide has a Tm value of about 55° C. to 65° C.

Further, it is preferable to use an oligonucleotide including the nucleotide sequence set forth in any one of SEQ ID NOS: 12 to 15, 22, 23 and 40 to 50, or the complementary sequence thereof; or an oligonucleotide including the nucleotide sequence which has 70% or more homology to the nucleotide sequence set forth in any one of SEQ ID NOS: 12 to 15, 22, 23 and 40 to 50 or the complementary sequence thereof, and which has a function as an oligonucleotide for detection; more preferably an oligonucleotide including the nucleotide sequence set forth in any one of SEQ ID NOS: 12 to 15, 22, 23 and 40 to 50, or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 12 to 15, 22, 23 and 40 to 50.

When identifying/detecting the fungi belonging to the genus *Hamigera* of the heat-resistant fungi, it is preferable to perform gene amplification of a nucleic acid consisting of the whole or part of the region of the above nucleic acid (D-I) or (D-II), and then to confirm whether the amplification product is present or not. In this case, as the nucleic acid primers, it is preferable to use an oligonucleotide which is capable of hybridizing with a region in the nucleic acid (D-I) or (D-II) and satisfies the following four conditions:
(1) the oligonucleotide includes a region containing about 10 continuous nucleotides specific to a fungus belonging to the genus *Hamigera* in the nucleic acid (D-I) or (D-II);
(2) the oligonucleotide has a GC content of about 30% to 80%;
(3) the oligonucleotide has low possibility to cause self-annealing; and
(4) the oligonucleotide has a Tm value of about 55° C. to 65° C.

Further, it is preferable to use an oligonucleotide including the nucleotide sequence set forth in any one of SEQ ID NOS: 16 to 21 and 51 to 56, or the complementary sequence thereof; or an oligonucleotide including the nucleotide sequence which has 70% or more homology to the nucleotide sequence set forth in any one of SEQ ID NOS: 16 to 21 and 51 to 56 or the complementary sequence thereof, and which has a function as an oligonucleotide for detection; more preferably an oligonucleotide including the nucleotide sequence set forth in any one of SEQ ID NOS: 16 to 21 and 51 to 56; or an oligonucleotide including the nucleotide sequence which has 70% or more homology to the nucleotide sequence and which has a function as an oligonucleotide for detection; and still more preferably an oligonucleotide including the nucleotide sequence set forth in any one of SEQ ID NOS: 16 to 21 and 51 to 56.

The method of amplifying the nucleic acid including the nucleotide sequence of the variable region is not particularly limited, and a usual method such as PCR (polymerase chain reaction) method, LCR (ligase chain reaction) method, SDA (strand displacement amplification) method, NASBA (nucleic acid sequence-based amplification) method, RCA (rolling-circle amplification) method, or LAMP (loop mediated isothermal amplification) method may be used. In the present invention, the PCR method or the LAMP method is preferably used in view of rapidness and ease as mentioned below.

As the nucleic acid primers for use in the present invention, the above-mentioned oligonucleotides for detection of the present invention may be used without further treatment, or the oligonucleotides may be labeled with a labeling substance and used as nucleic acid primers. Examples of the labeling substance and labeling method include those in the above case of the nucleic acid probes.

In the detection method of the present invention, amplification reactions of any one of the nucleic acids (A-I) to (D-II) are preferably performed by a polymerase chain reaction (PCR) method.

Hereinafter, a detection method by the PCR method according the present invention is described in detail.

In the case where the fungi belonging to the genus *Byssochlamys* are identified/detected by the PCR method, the following oligonucleotides (a) to (b) are preferably used as a nucleic acid primer, the following oligonucleotides (a1) to (b1) are more preferably used as a nucleic acid primer, and the oligonucleotides including the nucleotide sequence set forth in SEQ ID NO: 1 or 2 are still more preferably used as a nucleic acid primer.

Moreover, the following oligonucleotides (a) and (b) are preferably used as a nucleic acid primer pair, the following oligonucleotides (a1) and (b1) are more preferably used as a nucleic acid primer pair, and the oligonucleotides including the nucleotide sequences set forth in SEQ ID NOS: 1 and 2 are still more preferably used as a nucleic acid primer pair.

(a) An oligonucleotide including a nucleotide sequence set forth in SEQ ID NO: 1 or a complementary sequence thereof; or a nucleotide sequence which has 70% or more homology to the nucleotide sequence or the complementary sequence thereof, and which has a function as an oligonucleotide for detection.

(b) An oligonucleotide including a nucleotide sequence set forth in SEQ ID NO: 2 or a complementary sequence thereof; or a nucleotide sequence which has 70% or more homology to the nucleotide sequence or the complementary sequence thereof, and which has a function as an oligonucleotide for detection.

(a1) An oligonucleotide including a nucleotide sequence set forth in SEQ ID NO: 1, or a nucleotide sequence which has 70% or more homology to the nucleotide sequence and which has a function as an oligonucleotide for detection.

(b1) An oligonucleotide including a nucleotide sequence set forth in SEQ ID NO: 2, or a nucleotide sequence which has 70% or more homology to the nucleotide sequence and which has a function as an oligonucleotide for detection.

The oligonucleotides (a) and (b) can hybridize specifically with the variable region of the β-tubulin gene of the fungi belonging to the genus *Byssochlamys*. Therefore, it is possible to specifically, rapidly, and easily detect the fungi belonging to the genus *Byssochlamys* by using the oligonucleotides.

The oligonucleotide represented by the nucleotide sequence set forth in SEQ ID NO: 1 or 2 is an oligonucleotide complementary to a nucleotide sequence which is in the β-tubulin gene region and is specific to the fungi belonging to the genus *Byssochlamys* (i.e., oligonucleotides complementary to a part of the variable region). The oligonucleotides including the nucleotide sequence set forth in SEQ ID NO: 1 or 2 can hybridize specifically with a part of DNA or RNA of the fungi belonging to the genus *Byssochlamys*.

The variable region in the β-tubulin gene of the fungus belonging to the genus *Byssochlamys* is described in detail based on the variable region of *Byssochlamys nivea* as an example. As mentioned above, the partial nucleotide sequence of the β-tubulin gene of *Byssochlamys nivea* is represented by SEQ ID NO: 24. The inventors of the present invention have found out that a nucleotide sequence of the region of position 20 to 175 in the partial nucleotide sequence of the β-tubulin gene of the fungi belonging to the genus *Byssochlamys* is particularly poorly conserved among fungi genera, and each of the genera has a specific nucleotide sequence in this region.

The oligonucleotides (a) and (b) correspond to the region of position 33 to 52 and the region of position 159 to 178 in the nucleotide sequence set forth in SEQ ID NO: 24, respectively. Therefore, it is possible to specifically detect the fungi belonging to the genus *Byssochlamys* by hybridizing the oligonucleotides with the β-tubulin gene of the fungi belonging to the genus *Byssochlamys*.

In the case where the fungi belonging to the genus *Talaromyces* are identified/detected by the PCR method, the following oligonucleotides (c) to (k) are preferably used as a nucleic acid primer, the following oligonucleotides (c1) to (k1) are more preferably used as a nucleic acid primer, and the oligonucleotides including the nucleotide sequence set forth in any one of SEQ ID NOS: 3 to 11 are still more preferably used as a nucleic acid primer.

Moreover, the oligonucleotide pair (c) and (d), the oligonucleotide pair (e) and (f), the oligonucleotide pair (g) and (h), the oligonucleotide pair (i) and (h), and the oligonucleotide pair (j) and (k) are preferably used as a nucleic acid primer pair; the oligonucleotide pair (c1) and (d1), the oligonucleotide pair (e1) and (f1), the oligonucleotide pair (g1) and (h1), the oligonucleotide pair (i1) and (h1), and the oligonucleotide pair (j1) and (k1) are more preferably used as a nucleic acid primer pair; and the oligonucleotide pair including the nucleotide sequences set forth in SEQ ID NOS: 3 and 4, the oligonucleotide pair including the nucleotide sequences set forth in SEQ ID NOS: 5 and 6, the oligonucleotide pair including the nucleotide sequences set forth in SEQ ID NOS: 7 and 8, the oligonucleotide pair including the nucleotide sequences set forth in SEQ ID NOS: 9 and 8, and the oligonucleotide pair including the nucleotide sequences set forth in SEQ ID NOS: 10 and 11 are still more preferably used as a nucleic acid primer pair.

In view of detection specificity and detection sensitivity, the oligonucleotide pair (i) and (h), and the oligonucleotide pair (j) and (k) are preferably used as a nucleic acid primer pair; the oligonucleotide pair (i1) and (h1), and the oligonucleotide pair (j1) and (k1) are more preferably used as a nucleic acid primer pair; and the oligonucleotide pair including the nucleotide sequences set forth in SEQ ID NOS: 9 and 8, and the oligonucleotide pair including the nucleotide sequences set forth in SEQ ID NOS: 10 and 11 are still more preferably used as a nucleic acid primer pair.

(c) An oligonucleotide including a nucleotide sequence set forth in SEQ ID NO: 3 or a complementary sequence thereof; or a nucleotide sequence which has 70% or more homology to the nucleotide sequence or the complementary sequence thereof, and which has a function as an oligonucleotide for detection.

(d) An oligonucleotide including a nucleotide sequence set forth in SEQ ID NO: 4 or a complementary sequence thereof; or a nucleotide sequence which has 70% or more homology to the nucleotide sequence or the complementary sequence thereof, and which has a function as an oligonucleotide for detection.

(e) An oligonucleotide including a nucleotide sequence set forth in SEQ ID NO: 5 or a complementary sequence thereof; or a nucleotide sequence which has 70% or more homology to the nucleotide sequence or the complementary sequence thereof, and which has a function as an oligonucleotide for detection.

(f) An oligonucleotide including a nucleotide sequence set forth in SEQ ID NO: 6 or a complementary sequence thereof; or a nucleotide sequence which has 70% or more homology to the nucleotide sequence or the complementary sequence thereof, and which has a function as an oligonucleotide for detection.

(g) An oligonucleotide including a nucleotide sequence set forth in SEQ ID NO: 7 or a complementary sequence thereof; or a nucleotide sequence which has 70% or more homology to the nucleotide sequence or the complementary sequence thereof, and which has a function as an oligonucleotide for detection.

(h) An oligonucleotide including a nucleotide sequence set forth in SEQ ID NO: 8 or a complementary sequence thereof; or a nucleotide sequence which has 70% or more homology to the nucleotide sequence or the complementary sequence thereof, and which has a function as an oligonucleotide for detection.

(i) An oligonucleotide including a nucleotide sequence set forth in SEQ ID NO: 9 or a complementary sequence thereof; or a nucleotide sequence which has 70% or more homology to the nucleotide sequence or the complementary sequence thereof, and which has a function as an oligonucleotide for detection.

(j) An oligonucleotide including a nucleotide sequence set forth in SEQ ID NO: 10 or a complementary sequence thereof; or a nucleotide sequence which has 70% or more homology to the nucleotide sequence or the complementary sequence thereof, and which has a function as an oligonucleotide for detection.

(k) An oligonucleotide including a nucleotide sequence set forth in SEQ ID NO: 11 or a complementary sequence thereof; or a nucleotide sequence which has 70% or more homology to the nucleotide sequence or the complementary sequence thereof, and which has a function as an oligonucleotide for detection.

(c1) An oligonucleotide including a nucleotide sequence set forth in SEQ ID NO: 3, or a nucleotide sequence which has 70% or more homology to the nucleotide sequence and which has a function as an oligonucleotide for detection.

(d1) An oligonucleotide including a nucleotide sequence set forth in SEQ ID NO: 4, or a nucleotide sequence which has 70% or more homology to the nucleotide sequence and which has a function as an oligonucleotide for detection.

(e1) An oligonucleotide including a nucleotide sequence set forth in SEQ ID NO: 5, or a nucleotide sequence which has 70% or more homology to the nucleotide sequence and which has a function as an oligonucleotide for detection.

(f1) An oligonucleotide including a nucleotide sequence set forth in SEQ ID NO: 6, or a nucleotide sequence which has 70% or more homology to the nucleotide sequence and which has a function as an oligonucleotide for detection.

(g1) An oligonucleotide including a nucleotide sequence set forth in SEQ ID NO: 7, or a nucleotide sequence which has 70% or more homology to the nucleotide sequence and which has a function as an oligonucleotide for detection.

(h1) An oligonucleotide including a nucleotide sequence set forth in SEQ ID NO: 8, or a nucleotide sequence which has 70% or more homology to the nucleotide sequence and which has a function as an oligonucleotide for detection.

(i1) An oligonucleotide including a nucleotide sequence set forth in SEQ ID NO: 9, or a nucleotide sequence which has 70% or more homology to the nucleotide sequence and which has a function as an oligonucleotide for detection.

(j1) An oligonucleotide including a nucleotide sequence set forth in SEQ ID NO: 10, or a nucleotide sequence which has 70% or more homology to the nucleotide sequence and which has a function as an oligonucleotide for detection.

(k1) An oligonucleotide including a nucleotide sequence set forth in SEQ ID NO: 11, or a nucleotide sequence which has 70% or more homology to the nucleotide sequence and which has a function as an oligonucleotide for detection.

When the pair of the oligonucleotides (c) and (d) is used, *Talaromyces flavus* and *Talaromyces trachyspermus* can be specifically detected. When the pair of the oligonucleotides (e) and (f) or the pair of the oligonucleotides (j) and (k) is used, *Talaromyces luteus, Talaromyces wortmannii* and *Talaromyces bacillisporus* can be specifically detected. When the pair of the oligonucleotides (g) and (h) is used, *Talaromyces flavus, Talaromyces wortmannii, Talaromyces trachyspermus* and *Talaromyces macrosporus* can be specifically detected. When the pair of the oligonucleotides (i) and (h) is used, *Talaromyces flavus, Talaromyces trachyspermus*, and *Talaromyces macrosporus* can be specifically detected.

The oligonucleotides (c) to (k) can hybridize specifically with the variable region in the β-tubulin gene or the ITS region and D1/D2 region of 28S rDNA of the fungi belonging to the genus *Talaromyces*. Therefore, it is possible to specifically, rapidly, and easily detect the fungi belonging to the genus *Talaromyces* by using the oligonucleotides.

The oligonucleotide represented by the nucleotide sequence set forth in SEQ ID NO: 3 or 4 is an oligonucleotide complementary to a nucleotide sequence which is in the β-tubulin gene region and is specific to *Talaromyces flavus* and *Talaromyces trachyspermus* belonging to the genus *Talaromyces* (i.e., oligonucleotides complementary to a part of the variable region). The oligonucleotide represented by the nucleotide sequence set forth in any one of SEQ ID NOS: 5 to 6 and 10 to 11 is an oligonucleotide complementary to a nucleotide sequence which is in the β-tubulin gene region and is specific to *Talaromyces luteus, Talaromyces wortmannii* and *Talaromyces bacillisporus* belonging to the genus *Talaromyces* (i.e., oligonucleotides complementary to a part of the variable region). The oligonucleotide represented by the nucleotide sequence set forth in any one of SEQ ID NOS: 7 to 8 and 9 is an oligonucleotide complementary to a nucleotide sequence which is in the ITS region and D1/D2 region of 28S rDNA and is specific to *Talaromyces flavus, Talaromyces wortmannii, Talaromyces trachyspermus* and *Talaromyces macrosporus* belonging to the genus *Talaromyces* (i.e., oligonucleotides complementary to a part of the variable region). That is, the oligonucleotides including the nucleotide sequence set forth in any one of SEQ ID NOS: 3 to 11 can hybridize specifically with a part of DNA or RNA of the fungi belonging to the genus *Talaromyces*.

The variable region in the β-tubulin gene of the fungus belonging to the genus *Talaromyces* is described in detail based on the variable region of *Talaromyces flavus* and *Talaromyces luteus* as examples. As mentioned above, the partial nucleotide sequence of the β-tubulin gene of *Talaromyces flavus* is represented by SEQ ID NO: 26. The partial nucleotide sequence of the β-tubulin gene of *Talaromyces luteus* is represented by SEQ ID NO: 27. The inventors of the present invention have found out that nucleotide sequences of the region of position 10 to 40 and the region of position 70 to 100 in the partial nucleotide sequence of the β-tubulin gene (the variable region) of *Talaromyces flavus* are particularly highly conserved in *Talaromyces flavus* and *Talaromyces trachyspermus*, and are not similar to any sequences of other fungi. The inventors of the present invention also have found out that the region of position 120 to 160 and the region of position 295 to 325 in the partial nucleotide sequence of the β-tubulin gene (the variable region) of *Talaromyces luteus* are regions having sequences highly conserved in genetically related *Talaromyces luteus, Talaromyces wortmannii*, and *Talaromyces bacillisporus*, and are not similar to any sequences of other fungi.

The oligonucleotides (c) and (d) correspond to the region of position 15 to 34 and the region of position 76 to 98 in the nucleotide sequence set forth in SEQ ID NO: 26, respectively. The oligonucleotides (e) and (f), and (j) and (k) correspond to the region of position 133 to 153 and the region of position 304 to 325 in the nucleotide sequence set forth in SEQ ID NO: 27, respectively. Therefore, it is possible to specifically detect the fungi belonging to the genus *Talaromyces* by hybridizing the oligonucleotides with the β-tubulin gene of the fungi belonging to the genus *Talaromyces*.

The variable region in the ITS region and D1/D2 region of 28S rDNA of the fungus belonging to the genus *Talaromyces* is described in detail based on the variable region of *Talaromyces wortmannii* as an example. As mentioned above, the partial nucleotide sequence of the ITS region and D1/D2 region of 28S rDNA of *Talaromyces wortmannii* is represented by SEQ ID NO: 28. The inventors of the present invention have found out that nucleotide sequences of the region of position 300 to 350 and the region of position 450 to 510 in the partial nucleotide sequence of the ITS region and D1/D2 region of 28S rDNA of the fungi belonging to the genus *Talaromyces* are particularly highly conserved in *Talaromyces wortmannii, Talaromyces trachyspermus, Talaromyces flavus* and *Talaromyces macrosporus*, and are not similar to any sequences of other fungi.

The oligonucleotides (g), (h) and (i) correspond to the region of position 326 to 345 and the region of position 460 to 478 in the nucleotide sequence set forth in SEQ ID NO: 28, respectively. Therefore, it is possible to specifically detect the fungi belonging to the genus *Talaromyces* by hybridizing the oligonucleotides with the ITS region and D1/D2 region of 28S rDNA of the fungi belonging to the genus *Talaromyces*.

In the case where the fungi belonging to the genus *Neosartorya* and/or *Aspergillus fumigatus* are identified/detected by the PCR method, the following oligonucleotides (l) to (o) and (v) to (w) are preferably used as a nucleic acid primer, the following oligonucleotides (l1) to (o1) and (v1) to (w1) are more preferably used as a nucleic acid primer, and the oligonucleotides including the nucleotide sequence set forth in any one of SEQ ID NOS: 12 to 15 and 22 to 23 are still more preferably used as a nucleic acid primer.

Moreover, the oligonucleotide pair (l) and (m), the oligonucleotide pair (n) and (o), and the oligonucleotide pair (v) and (w) are preferably used as a nucleic acid primer pair; the oligonucleotide pair (l1) and (m1), the oligonucleotide pair (n1) and (o1), and the oligonucleotide pair (v1) and (w1) are more preferably used as a nucleic acid primer pair; and the oligonucleotide pair including the nucleotide sequences set forth in SEQ ID NOS: 12 and 13, the oligonucleotide pair including the nucleotide sequences set forth in SEQ ID NOS: 14 and 15, and the oligonucleotide pair including the nucleotide sequences set forth in SEQ ID NOS: 22 and 23 are still more preferably used as a nucleic acid primer pair.

For detecting the fungi belonging to the genus *Neosartorya* and *Aspergillus fumigatus*, the oligonucleotide pair (l) and (m), and the oligonucleotide pair (n) and (o) are preferably used as a nucleic acid primer pair; the oligonucleotide pair (l1) and (m1), and the oligonucleotide pair (n1) and (o1) are more preferably used as a nucleic acid primer pair; and the oligonucleotide pair including the nucleotide sequences set forth in SEQ ID NOS: 12 and 13, and the oligonucleotide pair including the nucleotide sequences set forth in SEQ ID NOS: 14 and 15 are still more preferably used as a nucleic acid primer pair. Further, in view of detection specificity and detection sensitivity, the oligonucleotide pair (n) and (o) are preferably used as a nucleic acid primer pair; the oligonucleotide pair (n1) and (o1) are more preferably used as a nucleic acid primer pair; and the oligonucleotide pair including the nucleotide sequences set forth in SEQ ID NOS: 14 and 15 are still more preferably used as a nucleic acid primer pair.

For detecting *Aspergillus fumigatus*, the oligonucleotide pair (v) and (w) are preferably used as a nucleic acid primer pair; the oligonucleotide pair (v1) and (w1) are more preferably used as a nucleic acid primer pair; and the oligonucleotide pair including the nucleotide sequences set forth in SEQ ID NOS: 22 and 23 are still more preferably used as a nucleic acid primer pair.

(l) An oligonucleotide including a nucleotide sequence set forth in SEQ ID NO: 12 or a complementary sequence thereof; or a nucleotide sequence which has 70% or more homology to the nucleotide sequence or the complementary sequence thereof, and which has a function as an oligonucleotide for detection.

(m) An oligonucleotide including a nucleotide sequence set forth in SEQ ID NO: 13 or a complementary sequence thereof; or a nucleotide sequence which has 70% or more homology to the nucleotide sequence or the complementary sequence thereof, and which has a function as an oligonucleotide for detection.

(n) An oligonucleotide including a nucleotide sequence set forth in SEQ ID NO: 14 or a complementary sequence thereof; or a nucleotide sequence which has 70% or more homology to the nucleotide sequence or the complementary sequence thereof, and which has a function as an oligonucleotide for detection.

(o) An oligonucleotide including a nucleotide sequence set forth in SEQ ID NO: 15 or a complementary sequence thereof; or a nucleotide sequence which has 70% or more homology to the nucleotide sequence or the complementary sequence thereof, and which has a function as an oligonucleotide for detection.

(v) An oligonucleotide including a nucleotide sequence set forth in SEQ ID NO: 22 or a complementary sequence thereof; or a nucleotide sequence which has 70% or more homology to the nucleotide sequence or the complementary sequence thereof, and which has a function as an oligonucleotide for detection.

(w) An oligonucleotide including a nucleotide sequence set forth in SEQ ID NO: 23 or a complementary sequence thereof; or a nucleotide sequence which has 70% or more homology to the nucleotide sequence or the complementary sequence thereof, and which has a function as an oligonucleotide for detection.

(l1) An oligonucleotide including a nucleotide sequence set forth in SEQ ID NO: 12, or a nucleotide sequence which has 70% or more homology to the nucleotide sequence and which has a function as an oligonucleotide for detection.

(m1) An oligonucleotide including a nucleotide sequence set forth in SEQ ID NO: 13, or a nucleotide sequence which has 70% or more homology to the nucleotide sequence and which has a function as an oligonucleotide for detection.

(n1) An oligonucleotide including a nucleotide sequence set forth in SEQ ID NO: 14, or a nucleotide sequence which has 70% or more homology to the nucleotide sequence and which has a function as an oligonucleotide for detection.

(o1) An oligonucleotide including a nucleotide sequence set forth in SEQ ID NO: 15, or a nucleotide sequence which has 70% or more homology to the nucleotide sequence and which has a function as an oligonucleotide for detection.

(v1) An oligonucleotide including a nucleotide sequence set forth in SEQ ID NO: 22, or a nucleotide sequence which has 70% or more homology to the nucleotide sequence and which has a function as an oligonucleotide for detection.

(w1) An oligonucleotide including a nucleotide sequence set forth in SEQ ID NO: 23, or a nucleotide sequence which has 70% or more homology to the nucleotide sequence and which has a function as an oligonucleotide for detection.

When the pair of the oligonucleotides (l) and (m) and the pair of the oligonucleotides (n) and (o) are used, the fungus belonging to the genus *Neosartorya* such as *Neosartorya fischeri, Neosartorya spinosa, Neosartorya glabra, Neosartorya hiratsukae, Neosartorya paulistensis, Neosartorya pseudofischeri*, and *Aspergillus fumigatus* can be specifically detected. When the pair of the oligonucleotides (v) and (w) is used, *Aspergillus fumigatus* can be specifically detected.

The oligonucleotides (l) to (o) can hybridize specifically with the variable region in the β-tubulin gene of the fungi belonging to the genus *Neosartorya* and *Aspergillus fumigatus*. Therefore, it is possible to specifically, rapidly, and easily detect the fungi belonging to the genus *Neosartorya* and *Aspergillus fumigatus* by using the oligonucleotides (l) to (o).

The oligonucleotide represented by the nucleotide sequence set forth in any one of SEQ ID NOS: 12 to 15 is an oligonucleotide complementary to a nucleotide sequence which is in the β-tubulin gene region and is specific to *Neosartorya fischeri, Neosartorya spinosa, Neosartorya glabra, Neosartorya hiratsukae, Neosartorya paulistensis, Neosartorya pseudofischeri* and the like which belong to the genus *Neosartorya*, and *Aspergillus fumigatus* (i.e., oligonucleotides complementary to a part of the variable region). The oligonucleotides can hybridize specifically with a part of DNA or RNA of the fungi belonging to the genus *Neosartorya* and *Aspergillus fumigatus*.

The variable region in the β-tubulin gene of the fungus belonging to the genus *Neosartorya* is described in detail based on the variable region of *Neosartorya glabra* as an example. As mentioned above, the partial nucleotide sequence of the β-tubulin gene of Neosartorya glabra is represented by SEQ ID NO: 32. The inventors of the present invention have found out that nucleotide sequences of the region of position 1 to 110, the region of position 140 to 210 and the region of position 350 to 380 in the partial nucleotide sequence of the β-tubulin gene of the fungi belonging to the genus *Neosartorya* are particularly poorly conserved among fungi, and each of fungi genera has a specific nucleotide sequence in this region. The partial nucleotide sequence of the β-tubulin gene of *Aspergillus fumigatus* is represented by SEQ ID NO: 33. The inventors of the present invention have found out that nucleotide sequences of the region of position 1 to 110, the region of position 140 to 210 and the region of position 350 to 380 in the partial nucleotide sequence of the β-tubulin gene of *Aspergillus fumigatus* are particularly poorly conserved among fungi, and each of fungi species has a specific nucleotide sequence in this region.

The oligonucleotides (l) and (m) correspond to the region of position 84 to 103 and the region of position 169 to 188 in the nucleotide sequence set forth in SEQ ID NO: 32, and the region of position 83 to 102 and the region of position 166 to 186 in the nucleotide sequence set forth in SEQ ID NO: 33, respectively. The oligonucleotides (n) and (o) correspond to the region of position 144 to 163 and the region of position 358 to 377 in the nucleotide sequence set forth in SEQ ID NO: 32, and the region of position 141 to 160 and the region of position 356 to 376 in the nucleotide sequence set forth in SEQ ID NO: 33, respectively. Therefore, it is possible to specifically detect the fungi belonging to the genus *Neosartorya* and *Aspergillus fumigatus* by hybridizing the oligonucleotides with the β-tubulin gene of the fungi belonging to the genus *Neosartorya* and/or *Aspergillus fumigatus*.

The oligonucleotides (v) and (w) can hybridize specifically with the variable region in the β-tubulin gene of *Aspergillus fumigatus*.

The oligonucleotide represented by the nucleotide sequence set forth in SEQ ID NO: 22 or 23 is an oligonucleotide complementary to a nucleotide sequence which is in the β-tubulin gene region and is specific to *Aspergillus fumigatus* (i.e., oligonucleotides complementary to a part of the variable region). Therefore, the oligonucleotides including the nucleotide sequence set forth in SEQ ID NO: 22 or 23 can hybridize specifically with a part of DNA or RNA of *Aspergillus fumigatus*, but cannot hybridize with DNA and RNA of the fungi belonging to the genus *Neosartorya*.

Other variable region in the β-tubulin gene of *Aspergillus fumigatus* is described. The partial nucleotide sequence of the β-tubulin gene of *Aspergillus fumigatus* is represented by SEQ ID NO: 33. The inventors of the present invention have found out that the region of position 20 to 50 and the region of position 200 to 230 in the partial nucleotide sequence of the β-tubulin gene of *Aspergillus fumigatus* are poorly conserved among fungi, in particular, the fungi belonging to the genus *Neosartotya*.

Figures 1, 9:
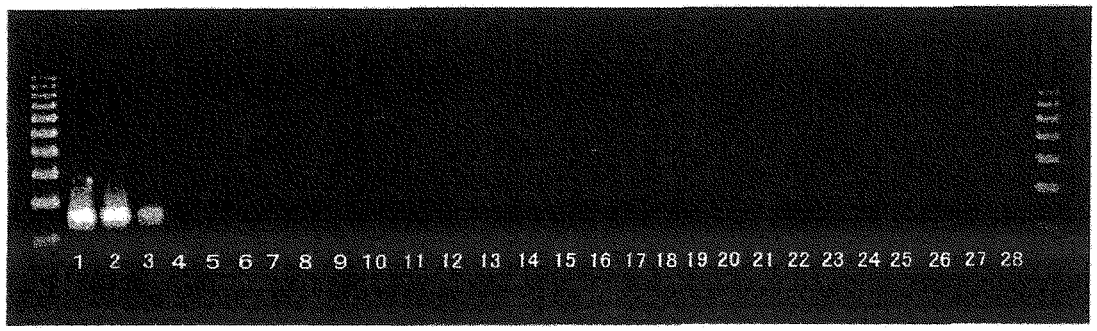

The oligonucleotides (v) and (w) correspond to the region of position 23 to 44 and the region of position 200 to 222 in the nucleotide sequence set forth in SEQ ID NO: 33, respectively. The oligonucleotides can hybridize with the β-tubulin gene of *Aspergillus fumigatus* but cannot hybridize with DNA and RNA of the fungi belonging to the genus *Neosartorya*. The fact is described in detail based on FIG. 1. FIG. 1 is a diagram for comparing partial nucleotide sequences of the β-tubulin genes of *Aspergillus fumigatus, Neosartorya fischeri*, and *Neosartorya spinosa* set forth in SEQ ID NOS: 34 and 83 to 86. As shown in FIG. 1, a comparison between the region which is in the β-tubulin gene of *Aspergillus fumigatus* and is recognized by the oligonucleotides of SEQ ID NOS: 22 and 23 and the region which corresponds to the above-mentioned region and is in the β-tubulin gene of the fungi belonging to the genus *Neosartorya* reveals that the homology of the nucleotide sequences are very low compared with other regions. Therefore, when the oligonucleotides (v) and (w) are used, it is possible to discriminate *Aspergillus fumigatus* from the fungus belonging to the genus *Neosartorya* in a sample.

An example of detecting the fungi belonging to the genus *Neosartorya* which particularly cause problems in food accidents is described below. The fungus belonging to the genus *Neosartorya* and *Aspergillus fumigatus* in samples can be detected by performing a nucleic acid amplification treatment using the pair of the oligonucleotides (l) and (m) or the pair of the oligonucleotides (n) and (o) as nucleic acid primers, and then confirming gene amplification. The samples from which the fungi belonging to the genus *Neosartorya* and *Aspergillus fumigatus* have been detected by the above process are further subjected to a nucleic acid amplification treatment using the pair of the oligonucleotides (v) and (w) as nucleic acid primers, followed by confirmation of gene amplification. As a result, it is possible to discriminate *Aspergillus fumigatus* from the fungus belonging to the genus *Neosartorya* in the sample.

Further, it is also possible to discriminate/detect the species of fungi in samples which show positive results by the above detection method using the oligonucleotides (l) to (o), based on a difference in growth temperature zones of the fungi belonging to the genus *Neosartorya* and *Aspergillus fumigatus* or by using the oligonucleotides (v) and/or (w).

The upper limit of the growth temperature of the fungi belonging to the genus *Neosartorya* is about 45° C. On the other hand, *Aspergillus fumigatus* can grow at 50° C. or higher. Based on the difference in the growth temperature zones, for example, the following procedure may be performed to discriminate between the species of fungi. However, the present invention is not limited thereto.

For samples which show positive results by the detection method using the oligonucleotides (l) to (o), hyphae from single colonies are inoculated into a PDA medium, PDB medium (potato dextrose liquid medium) or the like. Culture is performed at 48 to 52° C. for one or two days, and elongation of the hyphae is confirmed. Then, based on the difference in the growth temperature zones, the fungus can be discriminated as *Aspergillus fumigatus* in the case where proliferation is confirmed, or the fungus can be discriminated as a fungus belonging to the genus *Neosartorya* in the case where proliferation is not confirmed. It should be noted that examples of a method of confirming proliferation include, but not limited to, by confirming elongation of hyphae by a stereomicroscope, elongation of hyphae in a liquid medium, formation of fungal granules, and formation of conidia.

In the case where the fungi belonging to the genus *Hamigera* are identified/detected by the PCR method, the following oligonucleotides (p) to (u) are preferably used as a nucleic acid primer, the following oligonucleotides (p1) to (u1) are more preferably used as a nucleic acid primer, and the oligonucleotides including the nucleotide sequence set forth in any one of SEQ ID NOS: 16 to 21 are still more preferably used as a nucleic acid primer.

Moreover, the oligonucleotide pair (p) and (q), the oligonucleotide pair (r) and (s), and the oligonucleotide pair (t) and (u) are preferably used as a nucleic acid primer pair; the oligonucleotide pair (p1) and (q1), the oligonucleotide pair (r1) and (s1), and the oligonucleotide pair (t1) and (u1) are more preferably used as a nucleic acid primer pair; and the oligonucleotide pair including the nucleotide sequences set forth in SEQ ID NOS: 16 and 17, the oligonucleotide pair including the nucleotide sequences set forth in SEQ ID NOS: 18 and 19, and the oligonucleotide pair including the nucleotide sequences set forth in SEQ ID NOS: 20 and 21 are still more preferably used as a nucleic acid primer pair.

In view of detection specificity, the oligonucleotide pair (r) and (s), and the oligonucleotide pair (t) and (u) are preferably used as a nucleic acid primer pair; the oligonucleotide pair (r1) and (s1), and the oligonucleotide pair (t1) and (u1) are more preferably used as a nucleic acid primer pair; and the oligonucleotide pair including the nucleotide sequences set forth in SEQ ID NOS: 18 and 19, and the oligonucleotide pair including the nucleotide sequences set forth in SEQ ID NOS: 20 and 21 are still more preferably used as a nucleic acid primer pair. In view of detection sensitivity, the oligonucleotide pair (t) and (u) are preferably used as a nucleic acid primer pair; the oligonucleotide pair (t1) and (u1) are more preferably used as a nucleic acid primer pair; and the oligonucleotide pair including the nucleotide sequences set forth in SEQ ID NOS: 20 and 21 are still more preferably used as a nucleic acid primer pair.

(p) An oligonucleotide including a nucleotide sequence set forth in SEQ ID NO: 16 or a complementary sequence thereof; or a nucleotide sequence which has 70% or more homology to the nucleotide sequence or the complementary sequence thereof, and which has a function as an oligonucleotide for detection.

(q) An oligonucleotide including a nucleotide sequence set forth in SEQ ID NO: 17 or a complementary sequence thereof; or a nucleotide sequence which has 70% or more homology to the nucleotide sequence or the complementary sequence thereof, and which has a function as an oligonucleotide for detection.

(r) An oligonucleotide including a nucleotide sequence set forth in SEQ ID NO: 18 or a complementary sequence thereof; or a nucleotide sequence which has 70% or more homology to the nucleotide sequence or the complementary sequence thereof, and which has a function as an oligonucleotide for detection.

(s) An oligonucleotide including a nucleotide sequence set forth in SEQ ID NO: 19 or a complementary sequence thereof; or a nucleotide sequence which has 70% or more homology to the nucleotide sequence or the complementary sequence thereof, and which has a function as an oligonucleotide for detection.

(t) An oligonucleotide including a nucleotide sequence set forth in SEQ ID NO: 20 or a complementary sequence thereof; or a nucleotide sequence which has 70% or more homology to the nucleotide sequence or the complementary sequence thereof, and which has a function as an oligonucleotide for detection.

(u) An oligonucleotide including a nucleotide sequence set forth in SEQ ID NO: 21 or a complementary sequence thereof; or a nucleotide sequence which has 70% or more homology to the nucleotide sequence or the complementary sequence thereof, and which has a function as an oligonucleotide for detection.

(p1) An oligonucleotide including a nucleotide sequence set forth in SEQ ID NO: 16, or a nucleotide sequence which has 70% or more homology to the nucleotide sequence and which has a function as an oligonucleotide for detection.

(q1) An oligonucleotide including a nucleotide sequence set forth in SEQ ID NO: 17, or a nucleotide sequence which has 70% or more homology to the nucleotide sequence and which has a function as an oligonucleotide for detection.

(r1) An oligonucleotide including a nucleotide sequence set forth in SEQ ID NO: 18, or a nucleotide sequence which has 70% or more homology to the nucleotide sequence and which has a function as an oligonucleotide for detection.

(s1) An oligonucleotide including a nucleotide sequence set forth in SEQ ID NO: 19, or a nucleotide sequence which has 70% or more homology to the nucleotide sequence and which has a function as an oligonucleotide for detection.

(t1) An oligonucleotide including a nucleotide sequence set forth in SEQ ID NO: 20, or a nucleotide sequence which has 70% or more homology to the nucleotide sequence and which has a function as an oligonucleotide for detection.

(u1) An oligonucleotide including a nucleotide sequence set forth in SEQ ID NO: 21, or a nucleotide sequence which has 70% or more homology to the nucleotide sequence and which has a function as an oligonucleotide for detection.

When the pair of the oligonucleotides (p) and (q), the pair of the oligonucleotides (r) and (s), and the pair of the oligonucleotides (t) and (u) are used, *Hamigera avellanea* and *Hamigera striata* can be specifically detected.

The oligonucleotides (p) to (u) can hybridize specifically with the variable region in the β-tubulin gene of the fungi belonging to the genus *Hamigera*. Therefore, it is possible to specifically, rapidly, and easily detect the fungi belonging to the genus *Hamigera* by using the oligonucleotides.

The oligonucleotide represented by the nucleotide sequence set forth in any one of SEQ ID NOS: 16 to 21 is an oligonucleotide complementary to a nucleotide sequence which is in the β-tubulin gene region and is specific to the fungi belonging to the genus *Hamigera* (i.e., oligonucleotides complementary to a part of the variable region). The oligonucleotides including the nucleotide sequence set forth in any one of SEQ ID NOS: 16 to 21 can hybridize specifically with a part of DNA or RNA of the fungi belonging to the genus *Hamigera*.

The variable region in the β-tubulin gene of the fungus belonging to the genus *Hamigera* is described in detail based on the variable region of *Hamigera* avellanea as an example. As mentioned above, the partial nucleotide sequence of the β-tubulin gene of *Hamigera avellanea* is represented by SEQ ID NO: 35. The inventors of the present invention have found out that nucleotide sequences of the region of position 350 to 480, the region of position 1 to 25, and the region of position 180 to 2080 in the partial nucleotide sequence of the β-tubulin gene of the fungi belonging to the genus *Hamigera* are particularly poorly conserved among fungi genera, and each of the genera has a specific nucleotide sequence in this region.

The oligonucleotides (p) and (q) correspond to the region of position 358 to 377 and the region of position 440 to 459 in the nucleotide sequence set forth in SEQ ID NO: 35, respectively. The oligonucleotides (r) and (s) correspond to the region of position 2 to 22 and the region of position 181 to 200 in the nucleotide sequence set forth in SEQ ID NO: 35, respectively. The oligonucleotides (t) and (u) correspond to the region of position 172 to 191 and the region of position 397 to 416 in the nucleotide sequence set forth in SEQ ID NO: 35, respectively. Therefore, it is possible to specifically detect the fungi belonging to the genus *Hamigera* by hybridizing the oligonucleotides with the β-tubulin gene of the fungi belonging to the genus *Hamigera*.

Figures 2, 9:
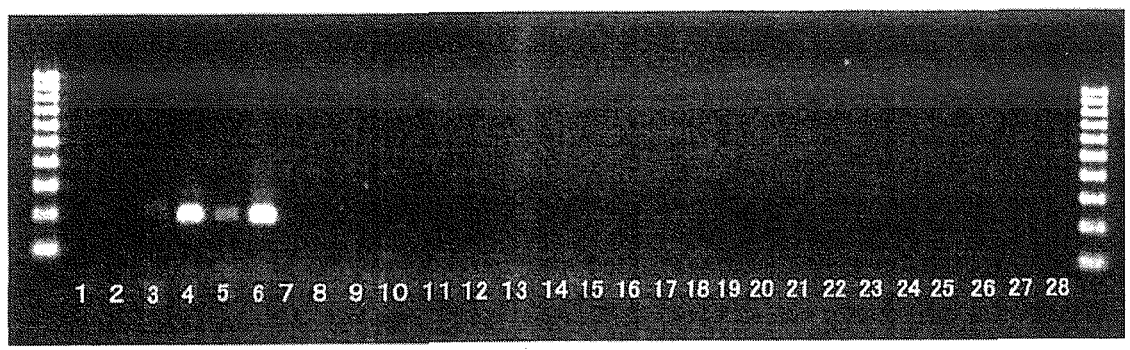

It should be noted that, as shown in FIG. 2, regions having high homology to the regions of position 358 to 377 and position 440 to 459 of the β-tubulin gene of *Hamigera avel-*

*lanea* are present in the β-tubulin gene of a fungus belonging to the genus *Cladosporium* such as *Cladosporium cladosporoides*. However, a region having high homology to the region of position 181 to 200 of the β-tubulin gene of *Hamigera avellanea* is not present in the β-tubulin gene of the fungus belonging to the genus *Cladosporium*. Therefore, when the above-mentioned oligonucleotides (p) to (u) are used in combination, it is possible to detect fungi belonging to the genus *Hamigera* and fungi belonging to the genus *Cladosporium*.

That is, the oligonucleotides (s), (t), and (u) can hybridize with the variable region in the β-tubulin gene of the fungi belonging to the genus *Hamigera* but cannot hybridize with the variable region in the β-tubulin gene of the fungi belonging to the genus *Cladosporium*. For example, for samples which show positive results by the detection method using the oligonucleotides (p) and (q), the species of the fungi in the samples can be discriminated as the genus *Hamigera* or the genus *Cladosporium* by using the oligonucleotides (r) and (s) and/or the oligonucleotides (t) and (u).

The "fungi belonging to the genus *Cladosporium*" are filamentous deuteromycetes and do not form highly heat-resistant ascospores. In addition, the fungi are widely distributed in places to live or food factories and synthesize melanin pigment, and are fungi causing black stains. Examples of the fungi belonging to the genus *Cladosporium* include *Cladosporium cladosporoides* and *Cladosporium sphaerospermum*.

Conditions of the PCR reaction are not particularly limited as long as a DNA fragment of interest can be amplified to a detectable degree. A preferred example of the conditions of PCR reaction is as follows. When detecting the fungus belonging to the genus *Byssochlamys*, a cycle including: a thermal denaturation reaction for denaturation of double-stranded DNA into single strands at 95 to 98° C. for 10 to 60 seconds; an annealing reaction for hybridization of a primer pair with the single-stranded DNA at about 59 to 61° C. for about 60 seconds; and an elongation reaction for a reaction of a DNA polymerase at about 72° C. for about 60 seconds; is repeated about 30 to 35 times. When detecting the fungus belonging to the genus *Talaromyces*, a cycle including: a thermal denaturation reaction for denaturation of double-stranded DNA into single strands at 95 to 97° C. for 10 to 60 seconds; an annealing reaction for hybridization of a primer pair with the single-stranded DNA at about 55 to 61° C. for about 60 seconds; and an elongation reaction for a reaction of a DNA polymerase at about 72° C. for about 60 seconds; is repeated about 30 to 35 times. In the case where the oligonucleotides (l) and (m), or (n) and (o) are used to detect the fungus belonging to the genus *Neosartorya* and *Aspergillus fumigatus*, a cycle including: a thermal denaturation reaction for denaturation of double-stranded DNA into single strands at 95 to 98° C. for 10 to 60 seconds; an annealing reaction for hybridization of a primer pair with the single-stranded DNA at about 59 to 61° C. for about 60 seconds; and an elongation reaction for a reaction of a DNA polymerase at about 72° C. for about 60 seconds; is repeated about 30 to 35 times. In the case where the oligonucleotides (v) and (w) are used to detect whether a fungus is the fungus belonging to the genus *Neosartorya* or *Aspergillus fumigatus*, a cycle including: a thermal denaturation reaction for denaturation of double-stranded DNA into single strands at 95 to 98° C. for 10 to 60 seconds; an annealing reaction for hybridization of a primer pair with the single-stranded DNA at about 59 to 61° C. for about 60 seconds; and an elongation reaction for a reaction of a DNA polymerase at about 72° C. for about 60 seconds; is repeated about 30 to 35 times. In the case where the oligonucleotides (p) and (q) are used to detect the fungus belonging to the genus *Hamigera*, a cycle including: a thermal denaturation reaction for denaturation of double-stranded DNA into single strands at 95 to 98° C. for 10 to 60 seconds; an annealing reaction for hybridization of a primer pair with the single-stranded DNA at about 59 to 63° C. for about 60 seconds; and an elongation reaction for a reaction of a DNA polymerase at about 72° C. for about 60 seconds; is repeated about 30 to 35 times. In the case where the oligonucleotides (r) and (s), or (t) and (u) are used to detect the fungus belonging to the genus *Hamigera*, a cycle including: a thermal denaturation reaction for denaturation of double-stranded DNA into single strands at 95 to 98° C. for 10 to 60 seconds; an annealing reaction for hybridization of a primer pair with the single-stranded DNA at about 59 to 63° C. for about 60 seconds; and an elongation reaction for a reaction of a DNA polymerase at about 72° C. for about 60 seconds; is repeated about 30 to 35 times.

In the present invention, amplification of gene fragments may be confirmed by a usual method. Examples of the method include, but not limited to, a method of integrating nucleotides labeled with a radioactive substance or the like into reaction products during an amplification reaction, a method including performing electrophoresis for PCR reaction products and confirming the existence of a band corresponding to the size of the amplified gene, a method of determining nucleotide sequences of PCR reaction products, and a method of integrating fluorescent substances into between the double strands of amplified DNA. In the present invention, the method including performing electrophoresis after a gene amplification treatment and confirming the existence of a band corresponding to the size of the amplified gene is preferred.

At position 33 to 178 in the nucleotide sequence set forth in SEQ ID NO: 24, the number of nucleotides is 146. Therefore, in the case where a sample contains the fungus belonging to the genus *Byssochlamys*, DNA fragments of about 150 bp which are specific to the fungi belonging to the genus *Byssochlamys* can be detected by performing PCR reactions using the pair of the oligonucleotides (a) and (b) as a primer set and electrophoresing the resultant PCR reaction products. By doing the above procedure, the fungi belonging to the genus *Byssochlamys* can be detected or discriminated.

At position 15 to 98 in the nucleotide sequence set forth in SEQ ID NO: 26, the number of nucleotides is 83. At position 133 to 325 in the nucleotide sequence set forth in SEQ ID NO: 27, the number of nucleotides is 192. Meanwhile, at position 326 to 478 in the nucleotide sequence set forth in SEQ ID NO: 28, the number of nucleotides is 152. Therefore, in the case where a sample contains *Talaromyces flavus* and/or *Talaromyces trachyspermus*, DNA fragments of about 80 bp which are specific to the fungi can be detected by performing PCR reactions using the pair of the oligonucleotides (c) and (d) as a primer set and electrophoresing the resultant PCR reaction products. In the case where a sample contains *Talaromyces luteus, Talaromyces wortmannii* and/or *Talaromyces bacillisporus*, DNA fragments of about 200 bp which are specific to the fungi can be detected by performing PCR reactions using the pair of the oligonucleotides (e) and (f) or the pair of the oligonucleotides (j) and (k) as a primer set and electrophoresing the resultant PCR reaction products. In the case where a sample contains *Talaromyces macrosporus, Talaromyces wortmannii, Talaromyces flavus* and/or *Talaromyces trachyspermus*, DNA fragments of about 150 bp which are specific to the fungi can be detected by performing PCR reactions using the pair of the oligonucleotides (g) and (h) as a primer set and electrophoresing the resultant PCR reaction products. In the case where a sample contains *Talaromyces macrosporus, Talaromyces flavus* and/or *Talaromyces trach*-

*yspermus*, DNA fragments of about 150 bp which are specific to the fungi can be detected by performing PCR reactions using the pair of the oligonucleotides (i) and (h) as a primer set and electrophoresing the resultant PCR reaction products. By doing the above-mentioned procedure, the fungi belonging to the genus *Talaromyces* can be detected or discriminated. It should be noted that, in the case where a sample contains *Talaromyces wortmannii*, two bands corresponding to about 200 bp and about 150 bp are confirmed by simultaneously using the pair of the oligonucleotides (e) and (f) or the oligonucleotides (j) and (k), and the pair of the oligonucleotides (g) and (h).

In the case where a sample contains the fungus belonging to the genus *Neosartorya* and/or *Aspergillus fumigatus*, DNA fragments of about 100 bp which are specific to the fungi can be detected by performing PCR reactions using the pair of the oligonucleotides (l) and (m) as a primer set and electrophoresing the resultant PCR reaction products. Also, DNA fragments of about 200 bp which are specific to the fungi can be detected by performing PCR reactions using the pair of the oligonucleotides (n) and (o) as a primer set and electrophoresing the resultant PCR reaction products. By doing the above-mentioned procedure, the fungi belonging to the genus *Neosartorya* and *Aspergillus fumigatus* can be detected or discriminated.

Further, in the case where a sample contains *Aspergillus fumigatus*, DNA fragments of about 200 bp which are specific to *Aspergillus fumigatus* can be detected by performing PCR reactions using the pair of the oligonucleotides (v) and (w) as a primer set and electrophoresing the resultant PCR reaction products. On the other hand, in the case where a sample contains the fungi belonging to the genus *Neosartorya*, even if PCR reactions are performed using the pair of the oligonucleotides (v) and (w), amplification of DNA fragments cannot be observed. Therefore, when PCR reactions are performed using the pair of the oligonucleotides (v) and (w) as a primer set, only *Aspergillus fumigatus* can be detected.

In the case where the pair of the oligonucleotides (p) and (q) are used to confirm gene amplification, the number of nucleotides at position 358 to 459 in the nucleotide sequence set forth in SEQ ID NO: 35 is about 100. Therefore, in the case where a sample contains the fungus belonging to the genus *Hamigera*, DNA fragments of about 100 bp which are specific to the fungi can be detected by performing PCR reactions using the pair of the oligonucleotides (p) and (q) as a primer set and electrophoresing the resultant PCR reaction products.

The number of nucleotides at position 2 to 200 in the nucleotide sequence set forth in SEQ ID NO: 35 is about 200. In the case where the pair of the oligonucleotides (t) and (u) are used, the number of nucleotides at position 172 to 416 in the nucleotide sequence set forth in SEQ ID NO: 35 is about 245. Therefore, in the case where a sample contains the fungus belonging to the genus *Hamigera*, DNA fragments of about 200 bp or about 240 bp which are specific to the fungi can be detected by performing PCR reactions using the pair of the oligonucleotides (r) and (s) or the pair of the oligonucleotides (t) and (u) as a primer set and electrophoresing the resultant PCR reaction products. By doing the above-mentioned procedure, the fungi belonging to the genus *Hamigera* can be detected or discriminated.

In the detection method of the present invention it is preferable to simultaneously use a detection method using the pair of the oligonucleotides (c) and (d), the pair of the oligonucleotides (g) and (h), or the pair of the oligonucleotides and (i) and (h) and a detection method using the pair of the oligonucleotides (e) and (f) or the pair of the oligonucleotides (j) and (k), for detecting the fungi belonging to the genus *Talaromyces*. When a plurality of pairs of the oligonucleotides is used in combination, the fungi belonging to the genus *Talaromyces* can be exhaustively detected. In particular, it is more preferable to use a detection method using the pair of the oligonucleotides (c1) and (d1), the pair of the oligonucleotides (g1) and (h1), or the pair of the oligonucleotides (i1) and (h1) and a detection method using the pair of the oligonucleotides (e1) and (f1) or the pair of the oligonucleotides (j1) and (k1) in combination, and it is still more preferable to use a detection method using the pair of the oligonucleotides represented by the nucleotide sequences set forth in SEQ ID NOS: 3 and 4, the pair of the oligonucleotides represented by the nucleotide sequences set forth in SEQ ID NOS: 7 and 8, or the pair of the oligonucleotides represented by the nucleotide sequences set forth in SEQ ID NOS: 9 and 8 and a detection method using the pair of the oligonucleotides represented by the nucleotide sequences set forth in SEQ ID NOS: 5 and 6 or the pair of the oligonucleotides represented by the nucleotide sequences set forth in SEQ ID NOS: 10 and 11 in combination.

When the pair of the oligonucleotides (c) and (d) is used, *Talaromyces flavus* and *Talaromyces trachyspermus* can be specifically detected. When the pair of the oligonucleotides (e) and (f) or the pair of the oligonucleotides (j) and (k) is used, *Talaromyces luteus*, *Talaromyces wortmannii* and *Talaromyces bacillisporus* can be specifically detected. When the pair of the oligonucleotides (g) and (h) is used, *Talaromyces flavus*, *Talaromyces wortmannii*, *Talaromyces trachyspermus* and *Talaromyces macrosporus* can be specifically detected. When the pair of the oligonucleotides (i) and (h) is used, *Talaromyces flavus*, *Talaromyces trachyspermus*, and *Talaromyces macrosporus* can be specifically detected. Therefore, when the pair of the oligonucleotides (c) and (d), the pair of the oligonucleotides (g) and (h), or the pair of the oligonucleotides (i) and (h) is used in combination with the pair of the oligonucleotides (e) and (f) or the pair of the oligonucleotides (j) and (k), the fungi belonging to the genus *Talaromyces* which particularly cause problems in food accidents can be exhaustively detected.

In particular, in view of detection sensitivity, it is preferred to use a detection method using the pair of oligonucleotides (i) and (h) and a detection method using the pair of oligonucleotides (j) and (k) in combination, it is more preferred to use a detection method using the pair of oligonucleotides (i1) and (h1) and a detection method using the pair of oligonucleotides (j1) and (k1) in combination, and it is still more preferred to use a detection method using the pair of the oligonucleotides represented by the nucleotide sequences set forth in SEQ ID NOS: 9 and 8 and a detection method using the pair of the oligonucleotides represented by the nucleotide sequences set forth in SEQ ID NOS: 10 and 11 in combination.

In the present invention, it should be note that the phrase "performing a gene amplification treatment by simultaneously using oligonucleotides" means that, for example, a gene amplification treatment step as mentioned above is performed by mixing two or more pairs of oligonucleotides and adding the obtained mixture to one reaction system as primers. When two pairs of oligonucleotides are simultaneously used, the fungi belonging to the genus *Talaromyces* can be rapidly and exhaustively detected. The mixing ratio of the two pairs of oligonucleotides is not particularly limited but is preferably 1:1 to 1:2.

In the detection method of the present invention, it is preferred to simultaneously use a detection method using the pair of the oligonucleotides (l) and (m) and/or the pair of the oligonucleotides and (n) and (o) and a detection method using the pair of the oligonucleotides (v) and (w). As mentioned above, the detection method using the pair of the oligonucleotides (l) and (m) or the pair of the oligonucleotides (n) and (o) can detect the fungi belonging to the genus *Neosartorya* and *Aspergillus fumigatus*, and the detection method using the pair of the oligonucleotides (v) and (w) can detect *Aspergillus fumigatus*. Therefore, when the methods are used in combination, the fungus detected from a sample can be discriminated as a fungus belonging to the genus *Neosartorya* or *Aspergillus fumigatus*. In particular, it is more preferred to use a detection method using the pair of the oligonucleotides (l1) and (m1) and/or the pair of the oligonucleotides (n1) and (o1) and a detection method using the pair of the oligonucleotides (v1) and (w1) in combination, and it is still more preferred to use a detection method using the pair of the oligonucleotides represented by the nucleotide sequences set forth in SEQ ID NOS: 12 and 13 and/or the pair of the oligonucleotides represented by the nucleotide sequences set forth in SEQ ID NOS: 14 and 15 and a detection method using the pair of the oligonucleotides represented by the nucleotide sequences set forth in SEQ ID NOS: 22 and 23 in combination.

In view of detection sensitivity, it is preferred to use a detection method using the pair of oligonucleotides (n) and (o) and a detection method using the pair of oligonucleotides (v) and (w) in combination, it is more preferred to use a detection method using the pair of oligonucleotides (n1) and (o1) and a detection method using the pair of oligonucleotides (v1) and (w1) in combination, and it is still more preferred to use a detection method using the pair of the oligonucleotides represented by the nucleotide sequences set forth in SEQ ID NOS: 14 and 15 and a detection method using the pair of the oligonucleotides represented by the nucleotide sequences set forth in SEQ ID NOS: 22 and 23 in combination.

In the detection method of the present invention, it is preferred to simultaneously use a detection method using the pair of the oligonucleotides (p) and (q) and a detection method using the pair of the oligonucleotides (r) and (s) or the pair of the oligonucleotides (t) and (u). By using the methods in combination, it is possible to specifically detect only a fungus belonging to the genus *Hamigera* from a sample. In other words, by using the methods in combination, it is possible to discriminate the fungus belonging to the genus *Hamigera* from the fungus belonging to the genus *Cladosporium* in a sample. Discrimination between the both genera enables to predict the risk of mycotoxin, because the fungi belonging to the genus *Hamigera* produce no mycotoxin. In addition, it is also possible to predict whether fungal contamination has been caused before heating or not by discriminating between the both genera, because the both genera have different heat resistances. Therefore, the above detection method can be used for finding a cause, such as revising a sterilization step or confirming airtightness of a container.

In particular, it is more preferred to use a detection method using the pair of the oligonucleotides (p1) and (q1) and a detection method using the pair of the oligonucleotides (r1) and (s1) or the pair of the oligonucleotides (t1) and (u1) in combination, and it is still more preferred to use a detection method using the pair of the oligonucleotides represented by the nucleotide sequences set forth in SEQ ID NOS: 16 and 17 and a detection method using the pair of the oligonucleotides represented by the nucleotide sequences set forth in SEQ ID NOS: 18 and 19 or the pair of the oligonucleotides represented by the nucleotide sequences set forth in SEQ ID NOS: 20 and 21 in combination.

In view of detection sensitivity, it is preferred to use a detection method using the pair of oligonucleotides (p) and (q) and a detection method using the pair of oligonucleotides (t) and (u) in combination, it is more preferred to use a detection method using the pair of oligonucleotides (p1) and (q1) and a detection method using the pair of oligonucleotides (t1) and (u1) in combination, and it is still more preferred to use a detection method using the pair of the oligonucleotides represented by the nucleotide sequences set forth in SEQ ID NOS: 16 and 17 and a detection method using the pair of the oligonucleotides represented by the nucleotide sequences set forth in SEQ ID NOS: 20 and 21 in combination.

In the detection method of the present invention, a preferred embodiment includes amplifying the whole or part of any one of the nucleic acids (A-I) to (D-II) by a loop mediated isothermal amplification method (LAMP method).

In the LAMP method, synthesis of a complementary strand can be performed under isothermal condition because periodic temperature control is not required. Therefore, a specific fungus in a sample can be detected easily and rapidly by the LAMP method.

Hereinafter, the detection method of the present invention by the LAMP method is described in detail.

The LAMP method is a loop-mediated isothermal amplification method which does not require the periodic temperature control method (WO 00/28082 A1), which allows isothermal complementary strand synthesis by annealing the 3'-end side of a primer to a nucleotide serving as a template to prepare a starting point of complementary strand synthesis, and combining a primer that anneals to a loop formed from the above annealing step. In the LAMP method, at least four primers which recognize six nucleotide sequence regions in the nucleic acid as a template are required, and these primers are designed so that the 3'-end side thereof is certainly annealed to the nucleotide as a template. By using the primers, it is possible to act a checking mechanism based on complementary binding of the nucleotide sequences, repeatedly, and then to perform a sensitive and specific nucleic acid amplification reaction.

The six nucleotide sequence regions recognized by the primers are referred to as F3, F2 and F1 in this order from the 5'-end side of the nucleotide as a template, and B3c, B2c and B1c in this order from the 3'-end side thereof. Complementary sequences of F1, F2 and F3 are called F1c, F2c and F3c, respectively. Complementary sequences of B1c, B2c and B3c are called B1, B2 and B3, respectively.

The six nucleotide sequence regions may be selected by the following procedure, but the present invention is not limited thereto.

First, alignment of a nucleotide sequence of a fungus of interest is performed. The alignment may be performed by using software such as Clustal X. Subsequently, based on the resultant alignment information, the above-mentioned six nucleotide sequence regions are selected using software such as Primer Explorer V4 (HP of Eiken Chemical Co., Ltd.) to design primers for the LAMP method.

Primers to be used in the LAMP method are designed by determining the above-mentioned six nucleotide sequence regions from a nucleotide sequence of a region for amplification (a target region), and then designing inner primers F and B and outer primers F and B as described below.

The inner primer used in the LAMP method is an oligonucleotide having, at the 3' end, a nucleotide sequence that recognizes a certain nucleotide sequence region in a target nucleotide sequence and provides a synthesis origin; and having, at the 5' end, a nucleotide sequence complementary to an arbitrary region of a nucleic acid synthesis reaction product obtained with this primer at the origin. In the inner primers, a primer having a "nucleotide sequence selected from F2"

at the 3' end and a "nucleotide sequence selected from F1c" at the 5' end is called an inner primer F (hereinafter, abbreviated to FIP), and a primer having a "nucleotide sequence selected from B2" at the 3' end and a "nucleotide sequence selected from B1c" at the 5' end is called an inner primer B (hereinafter, abbreviated to BIP). The inner primers may have arbitrary nucleotide sequences including 0 to 50 nucleotides at a position between the F2 region and the F1c region or between the B2 region and the B1c region.

The outer primer used in the LAMP method is an oligonucleotide having a nucleotide sequence that recognizes "a certain nucleotide sequence region which presents on the 5'-end side of a certain nucleotide sequence region such as the above-mentioned F2 region or B2 region" in the target nucleotide sequence and provides a synthesis origin. Examples thereof include a primer including a nucleotide sequence selected from the F3 region and a primer including a nucleotide sequence selected from the B3 region. In the outer primers, a primer containing a "nucleotide sequence selected from F3" is called an outer primer F (hereinafter, abbreviated to F3), and a primer containing a "nucleotide sequence selected from B3" is called an outer primer B (hereinafter, abbreviated to B3).

"F" in each primer means that a primer complementarily binds to the anti-sense strand of the target nucleotide sequence and provides a synthesis origin. "B" in each primer i means that a primer complementarily binds to the sense strand of the target nucleotide sequence and provides a synthesis origin.

In the amplification of the nucleic acid by the LAMP method, a loop primer(s) (hereinafter, abbreviated to LF and LB) can be preferably used in addition to the inner and outer primers. The loop primers refer to 2 primers (one for each of strands composing a double-strand) containing, at the 3' end, a nucleotide sequence complementary to a sequence in a loop formed by the annealing of complementary sequences present at the same strand of an amplification product obtained by the LAMP method. That is, the loop primer is a primer having a nucleotide sequence complementary to a nucleotide sequence of a single strand moiety of the loop structure on the 5'-end side in the dumbbell-like structure. The use of the loop primers increases nucleic acid synthesis origins in number and achieves reduction in reaction time and enhancement in detection sensitivity (WO 02/24902 Pamphlet).

The nucleotide sequence of the loop primer may be selected from nucleotide sequences in the target region or complementary strands thereof or may be another nucleotide sequence, as long as the sequence is complementary to the nucleotide sequence of the single strand moiety of the loop structure on the 5'-end side in the dumbbell-like structure. Further, one type or two types of loop primers may be used.

When a DNA fragment of the target region is amplified using at least four or more types of the above-mentioned primers, the DNA fragment can be amplified to an amount sufficient for specific and efficient detection of the DNA fragment. Therefore, a specific fungus can be detected by confirming whether the amplified product is present or not.

In the method of the present invention, when detecting the heat-resistant fungi by the RAMP method, the oligonucleotide for detecting is preferably an oligonucleotide consisting of a nucleotide sequence corresponding to any one of the following (i) to (vi). In the following (i) to (vi), nucleotide sequence regions F3. F2 and F1 are selected from the 5'-end side in a target region selected from the nucleotide sequence of the variable region in the β-tubulin gene or the D1/D2 region and ITS region of 28S rDNA of the heat-resistant fungus, nucleotide sequence regions B3c, B2c and B1c are selected from the 3'-end side in the target region, complementary nucleotide sequences of the B3c, B2c and B1c are called B3, B2 and B1, respectively, and complementary nucleotide sequences of the F3, F2 and F1 are called F3c, F2c and F1c, respectively.

(i) A nucleotide sequence having the sequence identical to that of the B2 region at the 3' terminal side and the sequence identical to that of the B1c region at the 5' terminal side
(ii) A nucleotide sequence having the sequence identical to that of the B3 region
(iii) A nucleotide sequence having the sequence identical to that of the F2 region at the 3' terminal side and the sequence identical to that of the F1c region at the 5' terminal side
(iv) A nucleotide sequence having the sequence identical to that of the F3 region
(v) A nucleotide sequence having a sequence complementary to a part between the B1 region and the B2 region
(vi) A nucleotide sequence having a sequence complementary to a part between the F1 region and the F2 region The oligonucleotide may be used not only as a primer for the LAMP method but also as, for example, a primer for the PCR method or a probe for detecting a nucleic acid.

The primer that can be used in the present invention preferably includes 15 or more nucleotides, and more preferably 20 or more nucleotides. Further, each primer may be an oligonucleotide of single nucleotide sequence or a mixture of oligonucleotides of a plurality of nucleotide sequences.

In the present invention, in the case where the heat-resistant fungus is detected by the LAMP method, the variable region in the β-tubulin gene or the D1/D2 region and ITS region of 28S rDNA of the heat-resistant fungus (i.e., the whole or part of any one of the nucleic acids (A-I) to (D-II)) is determined as a target region, and a DNA fragment including the region is amplified to confirm whether an amplification product is present or not.

A region to be amplified by the LAMP method preferably includes; a nucleotide sequence which is part of the nucleotide sequence set forth in SEQ ID NO: 25 and includes the whole or part of the nucleotide sequence of position 400 to 600 in the nucleotide sequence set forth in SEQ ID NO: 25; a nucleotide sequence which is part of the nucleotide sequence set forth in SEQ ID NO: 32 and includes the whole or part of the nucleotide sequence of position 10 to 250 and/or position 350 to 559 in the nucleotide sequence set forth in SEQ ID NO: 32; a nucleotide sequence which is part of the nucleotide sequence set forth in SEQ ID NO: 34 and includes the whole or part of the nucleotide sequence of position 10 to 250 and/or position 350 to 559 in the nucleotide sequence set forth in SEQ ID NO: 34; a nucleotide sequence which is part of the nucleotide sequence set forth in SEQ ID NO: 35 and includes the whole or part of the nucleotide sequence of position 300 to 550 in the nucleotide sequence set forth in SEQ ID NO: 35; a nucleotide sequence which is part of the nucleotide sequence set forth in SEQ ID NO: 26 and includes the whole or part of the nucleotide sequence of position 200 to 450 in the nucleotide sequence set forth in SEQ ID NO: 26; a nucleotide sequence which is part of the nucleotide sequence set forth in SEQ ID NO: 29 and includes the whole or part of the nucleotide sequence of position 150 to 420 in the nucleotide sequence set forth in SEQ ID NO: 29; a nucleotide sequence which is part of the nucleotide sequence set forth in SEQ ID NO: 27 and includes the whole or part of the nucleotide sequence of position 150 to 450 in the nucleotide sequence set forth in SEQ ID NO: 27; a nucleotide sequence which is part of the nucleotide sequence set forth in SEQ ID NO: 30 and includes the whole or part of the nucleotide sequence of position 250 to 550 in the nucleotide sequence set forth in SEQ ID NO: 30; a nucleotide sequence which is part of the nucleotide sequence set forth in SEQ ID NO: 31 and includes the whole or part of the nucleotide sequence of position 250 to 550 in the nucleotide sequence set forth in SEQ ID NO: 31; or a nucleotide sequence resulting from a deletion, substitution, or addition of one to several nucleotides in any one of the above-mentioned nucleotide sequences.

Hereinafter, primers and primer sets which are preferably used in detection of the heat-resistant fungi by the LAMP method are described.

In order to design primers for specifically detecting the fungi belonging to the genus *Byssochlamys*, the above-mentioned six nucleotide sequence regions are preferably determined from the range in the nucleotide numbers 400 to 600 of the nucleotide sequence set forth in SEQ ID NO: 25. Specifically, it is preferred to use a primer consisting of a oligonucleotide having the nucleotide sequence set forth in SEQ ID NO: 36, a primer consisting of a oligonucleotide having the nucleotide sequence set forth in SEQ ID NO: 37, a primer consisting of a oligonucleotide having the nucleotide sequence set forth in SEQ ID NO: 38, a primer consisting of a oligonucleotide having the nucleotide sequence set forth in SEQ ID NO: 39, and a primer set including the primers, and it is more preferred to use the following primer set.

Primer set for detecting the fungi belonging to the genus *Byssochlamys* (LB1 primer set)

```
LB1F3 primer:
                                    (SEQ ID NO: 36)
CGGTCCTCGAGCGTATGG LB1B3 primer:
                                    (SEQ ID NO: 37)
CCGTTACTGGGGCAATCC LB1FIP primer:
                                    (SEQ ID NO: 38)
AGTTAGGTGACCGTGAGGTCGTCTTTGTCACGCGCTCTGG LB1BIP primer:
                                    (SEQ ID NO: 39)
GGATCAGGTAGGGATACCCGCTGTTGGTTTCTTTTCCTCCGC
```

FIG. 26 illustrates positions of nucleotide sequences recognized by the above-mentioned primers in the nucleotide sequence of the ITS region and D1/D2 region of 28S rDNA of the fungi belonging to the genus *Byssochlamys*.

When the primers and primer set are used, the variable region in the ITS region and D1/D2 region of 28S rDNA of the fungi belonging to the genus *Byssochlamys* can be amplified specifically, rapidly, and sensitively by the LAMP method. Therefore, the fungi belonging to the genus *Byssochlamys* in a sample can be detected by confirming amplification of the DNA fragments.

In order to design primers for specifically detecting the fungi belonging to the genus *Neosartorya* and *Aspergillus fumigatus*, the above-mentioned six nucleotide sequence regions are preferably determined from the range in the nucleotide numbers 350 to 559 and the range in the nucleotide numbers 10 to 250 of the nucleotide sequence set forth in SEQ ID NO: 32 or 34. Specifically, it is preferred to use a primer consisting of a oligonucleotide having the nucleotide sequence set forth in SEQ ID NO: 40, a primer consisting of a oligonucleotide having the nucleotide sequence set forth in SEQ ID NO: 41, a primer consisting of a oligonucleotide having the nucleotide sequence set forth in SEQ ID NO: 42, a primer consisting of a oligonucleotide having the nucleotide sequence set forth in SEQ ID NO: 43, and a primer set including the primers, and it is more preferred to use the following primer set.

Primer set for detecting the fungi belonging to the genus *Neosartorya* and *Aspergillus fumigatus* (LN1 primer set)

```
LN1F3 primer:
                                    (SEQ D NO: 40)
GGCAACATCTCACGATCTGA LN1B3 primer:
                                    (SEQ ID NO: 41)
CCCTCAGTGTAGTGACCCTT LN1FIP primer:
                                    (SEQ ID NO: 42)
ATGGTACCAGGCTCGAGATCGATACTAGGCCAACGGTGACA LN1BIP primer:
                                    (SEQ ID NO: 43)
GTCCCTTCGGCGAGCTCTTCGTTGTTACCAGCACCAGACT
```

To detect the fungi belonging to the genus *Neosartorya* and *Aspergillus fumigatus*, loop primers are preferably used in addition to the above-mentioned primers. The following primers are preferably used as the loop primers. Moreover, the primer set preferably further includes primers consisting of oligonucleotides having the nucleotide sequences set forth in SEQ ID NOS: 44 and 45.

Loop primer for detecting the fungi belonging to the genus *Neosartorya* and *Aspergillus fumigatus* (LN1 loop primer)

```
                                    (SEQ ID NO: 44)
LN1LF loop primer:    ACGGCACGAGGAACATACT (SEQ ID NO: 45)
LN1LB loop primer:    CGATAACTTCGTCTTCGGCC
```

FIG. 27 illustrates positions of nucleotide sequences recognized by the above-mentioned primers in the nucleotide sequence of the β-tubulin gene of *Neosartorya fischeri* which belongs to the genus *Neosartorya* including *Neosartorya glabra*.

When the primers and primer set are used, the variable region in the β-tubulin gene of the fungi belonging to the genus *Neosartorya* and *Aspergillus fumigatus* can be amplified specifically, rapidly, and sensitively by the LAMP method. Therefore, the fungi belonging to the genus *Neosartorya* and/or *Aspergillus fumigatus* in a sample can be detected by confirming amplification of the DNA fragments.

In order to design primers for specifically detecting *Aspergillus fumigatus*, other than the above-mentioned primer set, it is preferred to use a primer consisting of a oligonucleotide having the nucleotide sequence set forth in SEQ ID NO: 46, a primer consisting of a oligonucleotide having the nucleotide sequence set forth in SEQ ID NO: 47, a primer consisting of a oligonucleotide having the nucleotide sequence set forth in SEQ ID NO: 48, a primer consisting of a oligonucleotide having the nucleotide sequence set forth in SEQ ID NO: 49, and a primer set including the primers, and it is more preferred to use the following primer set.

Primer set for detecting *Aspergillus fumigatus* (LAf2 primer set)

```
LAf2F3 primer:
                                    (SEQ ID NO: 46)
GCCGCTTTCTGGTATGTCT
```

```
LAf2B3 primer:
                            (SEQ ID NO: 47)
CGCTTCTTCCTTGTTTTCCG LAf2FIP primer:
                            (SEQ ID NO: 48)
CCATGACAGTGAGGCTGAACCCCGGGTGATTGGGATCTCTCA LAf2BIP primer:
                            (SEQ ID NO: 49)
ACCATCTCTGGTGAGCATGGCTTTCCGCCGCTTTCTCAA
```

To detect the fungi belonging to *Aspergillus fumigatus*, loop primers are preferably used in addition to the above-mentioned primers. The following primer is preferably used as the loop primer. Moreover, the primer set preferably further includes a primer consisting of a oligonucleotide having the nucleotide sequence set forth in SEQ ID NO: 50.

Loop primer for detecting *Aspergillus fumigatus* (LAf2 loop primer)

```
                            (SEQ ID NO: 50)
LAf2LB loop primer:   AGTAAGTTCGACCTATATCCTCCC
```

FIG. 28 illustrates positions of nucleotide sequences recognized by the above-mentioned primers in the nucleotide sequence of the β-tubulin gene of *Aspergillus fumigatus*. When the primers and primer set are used, the variable region in the β-tubulin gene of *Aspergillus fumigatus* can be amplified specifically, rapidly, and sensitively by the LAMP method. Therefore. *Aspergillus fumigatus* in a sample can be detected by confirming amplification of the DNA fragments.

It should be noted that, when the primer set is used, it is possible to specifically detect *Aspergillus fumigatus* but is impossible to detect the fungi belonging to the genus *Neosartorya*. Therefore, the fungi belonging to the genus *Neosartorya* can be discriminated from *Aspergillus fumigatus* by using the primer set for detecting the fungi belonging to the genus *Neosartorya* and *Aspergillus fumigatus* (LN1 primer set) and the primer set for detecting *Aspergillus fumigatus* (LAf2 primer set) in combination.

In order to design primers for specifically detecting the fungi belonging to the genus *Hamigera*, the above-mentioned six nucleotide sequence regions are preferably determined from the range in the nucleotide numbers 300 to 550 of the nucleotide sequence set forth in SEQ ID NO: 35. Specifically, it is preferred to use a primer consisting of a oligonucleotide having the nucleotide sequence set forth in SEQ ID NO: 51, a primer consisting of a oligonucleotide having the nucleotide sequence set forth in SEQ ID NO: 52, a primer consisting of a oligonucleotide having the nucleotide sequence set forth in SEQ ID NO: 53, a primer consisting of a oligonucleotide having the nucleotide sequence set forth in SEQ ID NO: 54, and a primer set including the primers, and it is more preferred to use the following primer set.

Primer set for detecting the fungi belonging to the genus *Hamigera* (LH2 primer set)

```
LH2F3 primer:
                            (SEQ ID NO: 51)
GGATCCGAATACGACGTGTC LH2B3 primer:
                            (SEQ ID NO: 52)
CCCTCAGTGTAGTGACCCTT LH2FIP primer:
                            (SEQ ID NO: 53)
CATGGTGCCAGGCTCGAGATCCAGGCCAGCGGTAACAAG LH2BIP primer:
                            (SEQ ID NO: 54)
CCGGTCCTTTTGGCCAGCTCTGTTACCGGCACCAGACT
```

To detect the fungi belonging to the genus *Hamigera*, loop primers are preferably used in addition to the above-mentioned primers. The following primers are preferably used as the loop primers. Moreover, the primer set preferably further includes primers consisting of oligonucleotides having the nucleotide sequences set forth in SEQ ID NOS: 55 and 56.

Loop primer for detecting the fungi belonging to the genus *Hamigera* (LH2 loop primer)

```
                            (SEQ ID NO: 55)
LH2LF loop primer:   ACGGCACGGGGGACATA (SEQ ID NO: 56)
LH2LB loop primer:   TTCCGCCCAGACAACTTCG
```

FIG. 29 illustrates positions of nucleotide sequences recognized by the above-mentioned primers in the nucleotide sequence of the β-tubulin gene of the fungi belonging to the genus *Hamigera*.

When the primers and primer set are used, the variable region in the β-tubulin gene of the fungi belonging to the genus *Hamigera* can be amplified specifically, rapidly, and sensitively by the LAMP method. Therefore, the fungi belonging to the genus *Hamigera* in a sample can be detected by confirming amplification of the DNA fragments.

In order to design primers for specifically detecting *Talaromyces flavus*, the above-mentioned six nucleotide sequence regions are preferably determined from the range in the nucleotide numbers 200 to 450 of the nucleotide sequence set forth in SEQ ID NO: 26. Specifically, it is preferred to use a primer consisting of a oligonucleotide having the nucleotide sequence set forth in SEQ ID NO: 57, a primer consisting of a oligonucleotide having the nucleotide sequence set forth in SEQ ID NO: 58, a primer consisting of a oligonucleotide having the nucleotide sequence set forth in SEQ ID NO: 59, a primer consisting of a oligonucleotide having the nucleotide sequence set forth in SEQ ID NO: 60, and a primer set including the primers, and it is more preferred to use the following primer set.

Primer set for detecting *Talaromyces flavus* (LTf2 primer set)

```
LTf2F3 primer:
                            (SEQ ID NO: 57)
CCAGTTGGAGCGTATGAACG LTf2B3 primer:
                            (SEQ ID NO: 58)
CCCAGTTGTTACCAGCACCG LTf2FIP primer:
                            (SEQ ID NO: 59)
TTGTTGCCGGAGGCCTACACTTTACTTCAACGAGGTGCGT LTf2BIP primer:
                            (SEQ ID NO: 60)
CGACTTGGAGCCCGGTACCAAAAGTTGTCGGGACGGAAGA
```

To detect *Talaromyces flavus*, loop primers are preferably used in addition to the above-mentioned primers. The following primer is preferably used as the loop primer. Moreover, the primer set preferably further includes a primer consisting of a oligonucleotide having the nucleotide sequence set forth in SEQ ID NO: 61.

Loop primer for detecting *Talaromyces flavus* (LTf2 loop primer)

```
                                          (SEQ ID NO: 61)
LTf2LB loop primer:    GCTGGTCCCTTTGGTCAGC
```

FIG. 30 illustrates positions of nucleotide sequences recognized by the above-mentioned primers in the nucleotide sequence of the β-tubulin gene of *Talaromyces flavus*. When the primers and primer set are used, the variable region in the β-tubulin gene of *Talaromyces flavus* can be amplified specifically, rapidly, and sensitively by the LAMP method. Therefore, *Talaromyces flavus* in a sample can be detected by confirming amplification of the DNA fragments.

In order to design primers for specifically detecting *Talaromyces wortmannii*, the above-mentioned six nucleotide sequence regions are preferably determined from the range in the nucleotide numbers 150 to 420 of the nucleotide sequence set forth in SEQ ID NO: 29. Specifically, it is preferred to use a primer consisting of a oligonucleotide having the nucleotide sequence set forth in SEQ ID NO: 62, a primer consisting of a oligonucleotide having the nucleotide sequence set forth in SEQ ID NO: 63, a primer consisting of a oligonucleotide having the nucleotide sequence set forth in SEQ ID NO: 64, a primer consisting of a oligonucleotide having the nucleotide sequence set forth in SEQ ID NO: 65, and a primer set including the primers, and it is more preferred to use the following primer set.

Primer set for detecting *Talaromyces wortmannii* (LTw4-3 primer set)

```
LTw4F3 primer:
                                          (SEQ ID NO: 62)
TGGCTCCGGAATGTGAGTT LTw3B3 primer:
                                          (SEQ ID NO: 63)
CAAATCGACGAGGACGGC LTw4FIP primer:
                                          (SEQ ID NO: 64)
CGCTCCAACTGGAGGTCGGAAAATTTCGACATCCCACCCT LTw3BIP primer:
                                          (SEQ ID NO: 65)
GGAATCTGCCCCGCGACATTCCGGGGGACGTACTTGTTG
```

To detect *Talaromyces wortmannii*, loop primers are preferably used in addition to the above-mentioned primers. The following primers are preferably used as the loop primers. Moreover, the primer set preferably further includes primers consisting of oligonucleotides having the nucleotide sequences set forth in SEQ ID NOS: 66 and 67.

Loop primer for detecting *Talaromyces wortmannii* (LTw4-3 loop primer)

```
                                          (SEQ ID NO: 66)
LTw4LF loop primer:    GGTGCCATTGTAACTGGAAATGA (SEQ ID NO: 67)
LTw3LB loop primer:    ACTCATATCGTATAGGCTAGCGG
```

FIG. 31 illustrates positions of nucleotide sequences recognized by the above-mentioned primers in the nucleotide sequence of the β-tubulin gene of *Talaromyces wortmannii*. When the primers and primer set are used, the variable region in the β-tubulin gene of *Talaromyces wortmannii* can be amplified specifically, rapidly, and sensitively by the LAMP method. Therefore, *Talaromyces wortmannii* in a sample can be detected by confirming amplification of the DNA fragments.

In order to design primers for specifically detecting *Talaromyces luteus*, the above-mentioned six nucleotide sequence regions are preferably determined from the range in the nucleotide numbers 150 to 450 of the nucleotide sequence set forth in SEQ ID NO: 27. Specifically, it is preferred to use a primer consisting of a oligonucleotide having the nucleotide sequence set forth in SEQ ID NO: 68, a primer consisting of a oligonucleotide having the nucleotide sequence set forth in SEQ ID NO: 69, a primer consisting of a oligonucleotide having the nucleotide sequence set forth in SEQ ID NO: 70, a primer consisting of a oligonucleotide having the nucleotide sequence set forth in SEQ ID NO: 71, and a primer set including the primers, and it is more preferred to use the following primer set.

Primer set for detecting *Talaromyces luteus* (LTI1primer set)

```
LTI1F3 primer:
                                          (SEQ ID NO: 68)
CGAATCACCACTGATGGGAA LTI1B3 primer:
                                          (SEQ ID NO: 69)
GAAGAGCTGACCGAAAGGAC LTI1FIP primer:
                                          (SEQ ID NO: 70)
TTCGTGCTGTCGGTCGGTAATGTTCCGACCTCCAGTTAGAGC LTI1BIP primer:
                                          (SEQ ID NO: 71)
TAGGCTAGCGGCAACAAGTACGATAGTACCGGGCTCCAGATC
```

To detect *Talaromyces luteus*, loop primers are preferably used in addition to the above-mentioned primers. The following primer is preferably used as the loop primer. Moreover, the primer set preferably further includes a primer consisting of a oligonucleotide having the nucleotide sequence set forth in SEQ ID NO: 72.

Loop primer for detecting *Talaromyces luteus* (LTI1 loop primer)

```
                                          (SEQ ID NO: 72)
LTI1LF loop primer:    ACCTCGTTGAAATAGACGTTCA
```

FIG. 32 illustrates positions of nucleotide sequences recognized by the above-mentioned primers in the nucleotide sequence of the β-tubulin gene of *Talaromyces luteus*. When the primers and primer set are used, the variable region in the β-tubulin gene of *Talaromyces luteus* can be amplified specifically, rapidly, and sensitively by the LAMP method. Therefore, *Talaromyces luteus* in a sample can be detected by confirming amplification of the DNA fragments.

In order to design primers for specifically detecting *Talaromyces flavus* and *Talaromyces trachyspermus*, the above-mentioned six nucleotide sequence regions are preferably determined from the range in the nucleotide numbers 250 to 550 of each nucleotide sequence set forth in SEQ ID NO: 30 or 31. Specifically, it is preferred to use a primer consisting of a oligonucleotide having the nucleotide sequence set forth in SEQ ID NO: 73, a primer consisting of a oligonucleotide having the nucleotide sequence set forth in SEQ ID NO: 74, a primer consisting of a oligonucleotide having the nucleotide sequence set forth in SEQ ID NO: 75, a primer consisting of a oligonucleotide having the nucleotide sequence set forth in SEQ ID NO: 76, and a primer set including the primers, and it is more preferred to use the following primer set.

Primer set for detecting *Talaromyces flavus* and *Talaromyces trachyspermus* (LT1primer set)

```
LT1F3 primer:
                                        (SEQ ID NO: 73)
GCGTCATTTCTGCCCTCAA LT1B3 primer:
                                        (SEQ ID NO: 74)
AGTTCAGCGGGTAACTCCT LT1FIP primer:
                                        (SEQ ID NO: 75)
TACGCTCGAGGACCAGACGGCGGCTTGTGTGTTGGGTG LT1BIP primer:
                                        (SEQ ID NO: 76)
TCTGTCACTCGCTCGGGAAGGACCTGATCCGAGGTCAACC
```

To detect *Talaromyces flavus* and *Talaromyces trachyspermus*, loop primers are preferably used in addition to the above-mentioned primers. The following primers are preferably used as the loop primers. Moreover, the primer set preferably further includes primers consisting of the oligonucleotides having the nucleotide sequences set forth in SEQ ID NOS: 77 and 78.

Loop primer for detecting *Talaromyces flavus* and *Talaromyces trachyspermus* (LT1 loop primer)

```
                                        (SEQ ID NO: 77)
LT1LF loop primer:      GCTGCCTTTTGGGCAGGTC (SEQ ID NO: 78)
LT1LB loop primer:      TGGTCACACCACTATATTTTACCAC
```

FIG. 33, FIG. 34 and FIG. 34-1 illustrate positions of nucleotide sequences recognized by the above-mentioned primers in the nucleotide sequence of the ITS region and D1/D2 region of 28S rDNA of *Talaromyces flavus* and *Talaromyces trachyspermus*.

When the primers and primer set are used, the variable region in the ITS region and D1/D2 region of 28S rDNA of *Talaromyces flavus* and *Talaromyces trachyspermus* can be amplified specifically, rapidly, and sensitively by the LAMP method. Therefore, *Talaromyces flavus* and *Talaromyces trachyspermus* in a sample can be detected by confirming amplification of the DNA fragments.

The outer primers in the above-mentioned primer sets may be used not only in the LAMP method but also in the PCR method. In the PCR method, a DNA fragment of interest can be amplified by PCR using the above-mentioned primers, the β-tubulin gene or the ITS region and D1/D2 region of 28S rDNA in a sample as a template, and a heat-stable DNA polymerase.

An enzyme used in amplification of the DNA fragment is not particularly limited as long as it is generally used, and it is preferably a template-dependent nucleic acid synthetase having strand displacement activities. Such an enzyme includes Bst DNA polymerase (large fragment), Bca (exo-) DNA polymerase, and the Klenow fragment of *E. coli* DNA polymerase I; and preferably includes Bst DNA polymerase (large fragment). The enzyme that can be used in the present invention may be purified from viruses, bacteria, or the like or may be prepared by a gene recombination technique. These enzymes may be modified by fragmentation, amino acid substitution, or the like.

The temperature for amplification by the LAMP method is not particularly limited but is preferably 60 to 65° C.

The amplification of the DNA fragment by the LAMP method can be confirmed by general method. The nucleic acid amplification products can be detected, for example, by hybridization using a labeled oligonucleotide as a probe which specifically recognizes amplified nucleotide sequences; by a fluorescent intercalator method (JP-A-2001-242169); by directly applying the reaction solution after the completion of reaction to agarose gel electrophoresis. In case of the agarose gel electrophoresis, the LAMP amplification products are detected in the form of a ladder of many bands differing in base length.

Moreover, in the LAMP method, substrates are consumed in large amounts by nucleic acid synthesis, and pyrophosphoric acid ions as by-products are converted into magnesium pyrophosphate through its reaction with coexisting magnesium ions and makes the reaction solution cloudy to the extent that can be observed visually. Thus, the nucleic acid amplification reaction may be detected by confirming this cloudiness by use of a measurement apparatus that can optically observe time-dependent rises in turbidity after the completion of reaction or during reaction, for example, by confirming changes in absorbance at 400 nm by use of a spectrophotometer (WO 01/83817 Pamphlet).

According to the detection method by the LAMP method, a procedure from a sample preparation step to a fungus detection step can be performed within a time as short as about 60 to 120 minutes.

Hereinafter, an embodiment of the method of detecting the heat-resistant fungus of the present invention will be described specifically, but the present invention is not limited thereto.

1) Analysis of Fungus Causing Accident

Foods and drinks which contain sugars and proteins and cannot be sterilized under strong conditions may cause contamination accidents by heat-resistant fungi. Examples of the foods and drinks include foods and drinks made from agricultural products such as fruits and fruit juices and animal products such as milk.

In the detection method, DNA is collected from hyphae detected from a drink or the like which has caused the accident. Thereafter, a gene amplification treatment such as PCR reactions or the LAMP method is performed using the above-mentioned oligonucleotides of the present invention as nucleic acid primers.

In the case where the gene amplification is performed by the PCR method, the pair of the oligonucleotides (a) and (b) is used as a primer pair for detecting the genus *Byssochlamys*; one or more pairs of the oligonucleotides (c) and (d), the pair of the oligonucleotides (e) and (f), the pair of the oligonucleotides (g) and (h), the pair of the oligonucleotides (i) and (h), and the pair of the oligonucleotides (j) and (k) are used as primers for detecting the genus *Talaromyces*; one or more pairs of the oligonucleotides (l) and (m) and the pair of the oligonucleotides (n) and (o) are used as primers for detecting the genus *Neosartorya* and *Aspergillus fumigatus*; and one or more pairs of the oligonucleotides (p) and (q), the pair of the oligonucleotides (r) and (s), and the pair of the oligonucleotides (t) and (u) are used as primers for detecting the genus *Hamigera*.

In the case where the gene amplification is performed by the LAMP method, the set of the oligonucleotide represented by the nucleotide sequences set forth in SEQ ID NOS: 36 to 39 is used as primers for detecting the genus *Byssochlamys*; one or more sets of the set of the oligonucleotides represented by the nucleotide sequences set forth in SEQ ID NOS: 57 to 61, the set of the oligonucleotides represented by the nucleotide sequences set forth in SEQ ID NOS: 62 to 67, the set of the oligonucleotides represented by the nucleotide sequences set forth in SEQ ID NOS: 68 to 72, and the set of the oligonucleotides represented by the nucleotide sequences set forth in SEQ ID NOS: 73 to 78 are used as primers for detecting the genus *Talaromyces*; the set of the oligonucleotides represented by the nucleotide sequences set forth in SEQ ID NOS: 40 to 45 is used as primers for detecting fungi belonging to the genus *Neosartotya* and *Aspergillus fumigatus*; and the set of the oligonucleotides represented by the nucleotide sequences set forth in SEQ ID NOS: 51 to 56 is used as primers for detecting fungi belonging to the genus *Hamigera*.

When the primer pairs and primer sets are used, the above-mentioned four genera of heat-resistant fungi can be independently detected. Moreover, when the primers for detecting the respective genera are used in appropriate combination, a plurality of genera and species in the four genera can be exhaustively detected. The primers of the present invention are specific to each genus, and hence it is possible to exhaustively detect the four genera of heat-resistant fungi and to identify fungi based on the type of primers used at genus level (detection of heat-resistant fungi in the four genera).

After the gene amplification treatment using the primers, in the case of the PCR method, electrophoresis is performed to confirm whether the amplification product is present or not, while in the case of the LAMP method, the turbidity of the reaction solution is measured to confirm whether the amplification reaction is caused or not. At the same time, part of the fungal cells collected is inoculated into chloramphenicol-supplemented PDA and cultured at 50° C.

In the case where a PCR gene amplification product is confirmed by using primers other than the primers for detecting fungi belonging to the genus *Neosartorya*, and/or in the case where a gene amplification product is confirmed by using the primers for detecting fungi belonging to the genus *Neosartorya* and hyphae do not elongate at 50° C., or no reaction product is detected after PCR reactions or LAMP reactions using the primers for discriminating *Aspergillus fumigatus* from *Neosartorya*, the sample is evaluated to be "positive for heat-resistant fungi (including fungi belonging to the genus *Neosartorya*)".

As an example, a case where a gene amplification treatment is performed by the PCR method using the pair of the oligonucleotides (a) and (b), the pair of the oligonucleotides (t) and (u), the pair of the oligonucleotides (n) and (o), the pair of the oligonucleotides (i) and (h), and the pair of the oligonucleotides (j) and (k) in combination is described in detail. In the case where a reaction product is confirmed in a system using the primers for detecting fungi belonging to the genus *Neosartorya* (the pair of the oligonucleotides (n) and (o)), elongation of hyphae cultured at 50° C. is confirmed to discriminate that the fungus is *Neosartorya* or *Aspergillus fumigatus*. Alternatively, detection is performed using the oligonucleotides for *Neosartorya* and *Aspergillus fumigatus* as nucleic acid primers. For example, PCR reactions are performed using the oligonucleotides (v) and (w) as primers, in the case where a reaction product of about 200 bp is detected, the sample is evaluated to be positive for *Aspergillus fumigatus*, while in the case where no reaction product is detected, the sample is evaluated to be positive for fungi belonging to the genus Neosartorya.

In the case where a reaction product is confirmed in a system using the primers for detecting fungi belonging to the genus *Byssochlamys* (the pair of the oligonucleotides (a) and (b)), the sample is evaluated to be positive for fungi belonging to the genus *Byssochlamys*.

In the case where a reaction product is confirmed in a system using the primers for detecting fungi belonging to the genus *Hamigera* (the pair of the oligonucleotides (t) and (u)), the sample is evaluated to be positive for fungi belonging to the genus *Hamigera*.

In the case where a reaction product is confirmed in a system using the primers for detecting fungi belonging to the genus *Talaromyces* (the pair of the oligonucleotides (j) and (k) and/or the pair of the oligonucleotides (i) and (h)), the sample is evaluated to be positive for fungi belonging to the genus *Talaromyces*.

The heat-resistant fungi survive under heat sterilization conditions, and hence it is highly likely that the heat-resistant fungi were mixed in the sample from raw materials and steps. Therefore, in the case where the sample is positive for the heat-resistant fungi, it is necessary to further test the cleanliness level of the raw materials and production environment. On the other hand, in the case where the sample is negative for the heat-resistant fungi, it is necessary to revise the sterilization step or to confirm airtightness of a container because the contamination was caused by a fault in sterilization or mixing of the fungi in the sample after sterilization (investigation into the cause).

2) Microorganism Inspection of Raw Material

A usual fungus inspection of raw materials requires two tests for general fungi (a sample is not subjected to a heat shock treatment) and for heat-resistant fungi (a sample is subjected to a heat shock treatment). In contrast, it is not necessary to perform the heat shock treatment for the sample according to the present invention. That is, the test for general fungi is only performed, and then, in the case where hyphae are confirmed, the hyphae may be used to evaluate whether the fungi are heat-resistant fungi or not by the method of 1) above. In a conventional method, it takes about seven days to detect heat-resistant fungi. In contrast, according to the present invention, it is possible to reduce the time for detection by two days because it takes about three days to confirm the hyphae and at most two days to detect the fungi. Moreover, in the conventional method, it further takes about seven days to identify the species of the fungi after detection of the heat-resistant fungi, while in the method of the present invention, it is possible to simultaneously perform detection and identification at genus level.

The sample to be used for the detection method of the present invention is not particularly limited, and may be a food or drink itself, a raw material of the food or drink, an isolated fungus, a cultured fungus, or the like.

A method of preparing DNA from a sample is not particularly limited as long as DNA can be obtained at a sufficient purification degree and in a sufficient amount for detecting the heat-resistant fungi. DNA obtained by reverse transcriptase from RNA contained in a sample may be used. While the sample may be used without purification, the sample may be subjected to a pre-treatment such as separation, extraction, concentration, or purification before use. For example, the sample may be purified by phenol and chloroform extraction or using a commercially available extraction kit to increase the purity of the nucleic acid before use.

According to the method of the present invention, a procedure from a sample preparation step to a fungus detection step can be performed within a time as short as about 5 to 12 hours.

The kit for detecting a heat-resistant fungus of the present invention includes the above-mentioned oligonucleotides for detection as a nucleic acid probe or a nucleic acid primer. Specifically, the kit for detecting a heat-resistant fungus of the present invention includes, as a nucleic acid probe or a nucleic acid primer, at least one oligonucleotide selected from the group consisting of oligonucleotides which can hybridize with the nucleic acid (I) or (II) and can act as oligonucleotides for specifically detecting the heat-resistant fungus. The kit particularly preferably includes, as a nucleic acid probe or a nucleic acid primer, at least one oligonucleotide selected from the group consisting of an oligonucleotide including the nucleotide sequence set forth in any one of SEQ ID NOS: 1 to 23 or 36 to 78 or a complementary sequence thereof and an oligonucleotide including a nucleotide sequence which has 70% or more homology to the nucleotide sequence or the complementary sequence thereof and can act as an oligonucleotide for detection. The kit can be used for detection of the heat-resistant fungi. The kit of the present invention may include not only the above-mentioned nucleic acid probes or nucleic acid primers but also, depending on purpose, substances which are usually used for detecting a fungus, such as a label-detecting substance, a buffer, a nucleic acid synthetase (such as a DNA polymerase, an RNA polymerase, or a reverse transcriptase), and an enzyme substrate (such as dNTP or rNTP).

For example, the kit for detecting the heat-resistant fungus by LAMP method preferably includes theabove-mentioned primer set, a variety of oligonucleotide(s) necessary as a loop primer, four types of dNTPs serving as substrates of nucleic acid synthesis (dATP, dCTP, dGTP, and dTTP), a DNA polymerase such as a template-dependent nucleic acid synthetase having strand displacement activity, a buffer which provides preferred conditions for enzymatic reactions, a salt serving as a cofactor (such as a magnesium salt or a manganese salt), and a protecting agent for stabilizing an enzyme or a template, and if necessary, reagents necessary for detection of reaction products. The kit of the present invention may include a positive control for confirming whether gene amplification proceeds normally by the oligonucleotides for detection of the present invention. The positive control is, for example, DNA including a region which is amplified by the oligonucleotides for detection of the present invention.

EXAMPLES

Hereinafter, the present invention will be described more in detail with reference to Examples, but it should be understood that the technological scope of the present invention is not particularly limited by the following Examples.

Example 1

(A-1) Detection and Discrimination of Fungi Belonging to the Genus Byssochlamys 1. Determination of Partial Nucleotide Sequence of β-Tubulin Gene Nucleotide sequences of the β-tubulin gene of each variety of fungi belonging to the genus Byssochlamys were determined by the following method.

A test fungus was cultured in the dark on a potato dextrose agar slant at 30° C. for 7 days. DNA was extracted from the fungus using GenTorukun™ (manufactured by TAKARA BIO INC.). PCR amplification of a target site was performed using PuRe Taq™ Ready-To-Go PCR Beads (manufactured by GE Health Care UK LTD); and primers Bt2a (5'-GG-TAACCAAATCGGTGCTGCTTTC-3', SEQ ID NO: 79) and Bt2b (5'-ACCCTCAGTGTAGTGACCCTTGGC-3', SEQ ID NO: 80) (Glass and Donaldson, Appl Environ Microbiol 61: 1323-1330, 1995). Amplification of β-tubulin partial length was performed under conditions including a denaturation temperature of 95° C., an annealing temperature of 59° C., an elongation temperature of 72° C., and 35 cycles. PCR products were purified using Auto Seg™ G-50 (manufactured by Amersham Pharmacia Biotech). The PCR products were labeled with BigDye (registered trademark) terminator Ver. 1.1 (manufactured by Applied Biosystems), and electrophoresis was performed using ABI PRISM 3130 Genetic Analyzer (manufactured by Applied Biosystems). Nucleotide sequences from fluorescence signals in electrophoresis were determined using the software "ATGC Ver. 4" (manufactured by Genetyx).

Based on the nucleotide sequence information of the β-tubulin gene of Byssochlamys nivea and known nucleotide sequence information of the β-tubulin gene of a variety of fungi, alignment analyses were performed using DNA analysis software (product name: DNAsis pro, manufactured by Hitachi Software Engineering Co., Ltd.), to thereby determine a specific region in the β-tubulin gene including nucleotide sequences specific to the fungi belonging to the genus Byssochlamys (SEQ ID NO: 24).

2. Detection of Fungi Belonging to the Genus Byssochlamys and Identification of the Fungi at Genus Level (1) Design of Primers From regions having particularly high specificity to the fungi belonging to the genus Byssochlamys on the 3'-end side in the determined nucleotide sequence region specific to the fungi belonging to the genus Byssochlamys, partial regions which satisfy the following four conditions were searched:
1) including several nucleotides which is specific to the genus;
2) having a GC content of about 30% to 80%;
3) having low possibility to cause self-annealing; and
4) having a Tm value of about 55 to 65° C.

Based on the nucleotide sequences of the above regions, one primer pair was designed to search the effectiveness of detection of the genus Byssochlamys and identification of the genus by PCR reactions using DNAs extracted from the fungi as templates. Specifically, it was examined that a DNA amplification reaction is observed at a position corresponding to the size of about 150 bp in the case of a reaction using DNA of the fungi of the genus Byssochlamys as a template, while no amplification product is observed in the cases of reactions using genomic DNAs of other fungi as templates. As a result, DNA amplification was observed at a position corresponding to the size of about 150 bp specifically to Byssochlamys nivea and Byssochlamys fulva, while no amplification product was observed in the cases of reactions using genomic DNAs of other fungi as templates. The results reveal that it is possible to exhaustively detect the fungi of the genus Byssochlamys, and to identify the genus Byssochlamys at genus level. The primer pair confirmed to have the effectiveness is one which consists of the oligonucleotides represented by the nucleotide sequences set forth in SEQ ID NOS: 1 and 2. The primers used were synthesized by Sigma-Aldrich Japan (desalted products, 0.02 μmol scale) and purchased.

(2) Preparation of Samples

The fungi belonging to the genus Byssochlamys, other heat-resistant fungi, and general fungi shown in Table 1 and Table 2 were used as fungi to be used for evaluation of the effectiveness of the designed primers. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. (for general fungi) or 30° C. (for heat-resistant fungi and *Aspergillus fumigatus*) for 7 days.

TABLE 1

| Sample No. | Species | Strain No. (IFM) |
|---|---|---|
| N | (Negative Control) | — |
| P | *Byssochlamys nivea* | 48421 |
| 1 | *Aureobasidium pullulans* | 41408 |
| 2 | *Aureobasidium pullulans* | 41409 |
| 3 | *Aureobasidium pullulans* | 41410 |
| 4 | *Alternaria alternata* | 41348 |
| 5 | *Alternaria alternata* | 52225 |
| 6 | *Chaetomium globosum* | 40868 |
| 7 | *Chaetomium globosum* | 40869 |
| 8 | *Chaetomium globosum* | 40873 |
| 9 | *Paecilomyces variotii* | 40913 |
| 10 | *Paecilomyces variotii* | 50292 |
| 11 | *Paecilomyces variotii* | 40915 |
| 12 | *Trichoderma viride* | 40938 |
| 13 | *Trichoderma viride* | 51045 |
| 14 | *Cladosporium cladosporioides* | 41450 |
| 15 | *Fusarium oxysporium* | 41530 |
| 16 | *Fusarium oxysporium* | 50002 |
| 17 | *Aspergillus fumigatus* | 07-77 |
| 18 | *Aspergillus fumigatus* | 07-81 |
| 19 | *Aspergillus fumigatus* | 07-87 |
| 20 | *Aspergillus fumigatus* | 07-91 |
| 21 | *Aspergillus fumigatus* | 07-93 |

TABLE 2

| Sample No. | Species | Strain No. (IFM) |
|---|---|---|
| 1 | *Byssochlamys fulva* | 48421 |
| 2 | *Byssochlamys fulva* | 51213 |
| 3 | *Byssochlamys nivea* | 51244 |
| 4 | *Byssochlamys nivea* | 51245 |
| 5 | *Talaromyces flavus* | 42243 |
| 6 | *Talaromyces flavus* | 52233 |
| 7 | *Talaromyces luteus* | 53241 |
| 8 | *Talaromyces luteus* | 53242 |
| 9 | *Talaromyces trachyspermus* | 42247 |
| 10 | *Talaromyces trachyspermus* | 52252 |
| 11 | *Talaromyces wortmannii* | 52255 |
| 12 | *Talaromyces wortmannii* | 52262 |
| 13 | *Neosartorya fischeri* | 46945 |
| 14 | *Neosartorya fischeri* | 46946 |
| 15 | *Neosartorya glabra* | 46949 |
| 16 | *Neosartorya glabra* | 46951 |
| 17 | *Neosartorya spinosa* | 46967 |
| 18 | *Neosartorya spinosa* | 46968 |
| 19 | *Neosartorya hiratsukae* | 46954 |
| 20 | *Neosartorya hiratsukae* | 47036 |
| 21 | *Hamigera avellanea* | 42323 |
| 22 | *Hamigera avellanea* | 52241 |

(3) Preparation of Genomic DNA

The respective fungi were collected from the agar media using platinum loops.

Genomic DNA solutions were prepared from the collected fungi using a genomic DNA preparation kit (trade name: PrepMan ultra, manufactured by Applied Biosystems). The concentration of each DNA solution was adjusted to 50 ng/μL.

(4) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEC) ID NO: 1 (0.02 pmol/μL) and 0.5 μL of the primer represented by the nucleotide sequence set forth in SEQ ID NO: 2 (0.02 pmol/μL) were added thereto, to thereby prepare 25 μL of a PCR reaction solution.

The PCR reaction solution was subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(5) Confirmation of Amplified Gene Fragment

After the PCR reaction, 2 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 3(*a*) and FIG. 3(*b*). Note that, FIG. 3(*a*) shows an electrophoretogram of samples of the fungi shown in Table 1, and FIG. 3(*b*) shows an electrophoretogram of samples of the fungi shown in Table 2. The numbers in the electrophoretograms correspond the sample numbers in the tables, and represent samples obtained by using DNAs extracted from the fungi having the corresponding sample numbers in the tables.

As a result, in the case of the samples containing the genomic DNA of the fungi belonging to the genus *Byssochlamys*, amplification of gene fragments of about 150 bp was confirmed (lanes 1 to 4 in FIG. 3(*b*)). On the other hand, in the case of the samples containing no genomic DNA of the fungi belonging to the genus *Byssochlamys*, amplification of gene fragments was not confirmed. From the above-described results, it is understood that the fungi belonging to the genus *Byssochlamys* can be specifically detected by using the oligonucleotides (a) and (b) of the present invention.

(A-2) Detection and Discrimination of Fungi Belonging to the Genus *Byssochlamys*

(1) Preparation of Primers

The primers consisting of the oligonucleotides represented by the nucleotide sequences set forth in SEQ ID NOS: 1 and 2, designed in Example 1(A-1), were used.

(2) Preparation of Samples

Figure 4:
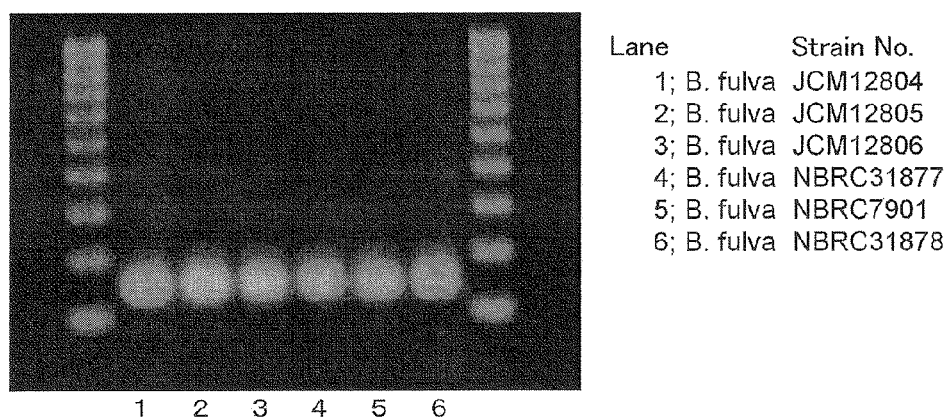
FIG. 4 is an electrophoretogram in the case of using strains of *Byssochlamys fulva* in Example 1(A-2).
Figure 5:
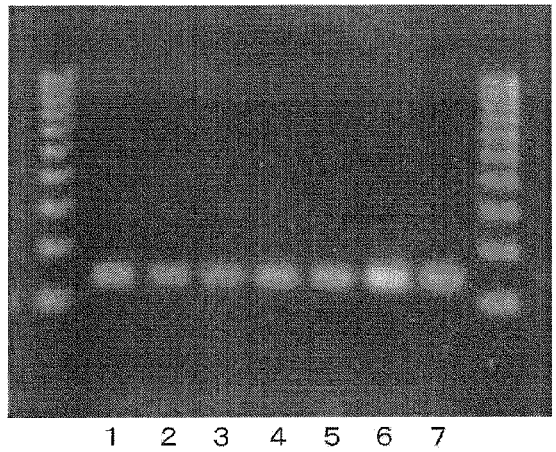
FIG. 5 is an electrophoretogram in the case of using strains of *Byssochlamys nivea* in Example 1(A-2).

To confirm detection specificity of the oligonucleotides (a) and (b) to the fungi belonging to the genus *Byssochlamys*, the respective strains of *Byssochlamys fulva* shown in FIG. 4 and the respective strains of *Byssochlamys nivea* shown in FIG. 5 were used. As the fungi, fungi available from fungus deposition institutes, such as fungi stored in National Institute of Technology and Evaluation based on NBRC numbers and fungi stored in The Centraalbureau voor Schimmelcultures based on CBS numbers were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. for 7 days.

(3) Preparation of Genomic DNA

The respective fungi were collected from the agar media using platinum loops.

Genomic DNA solutions were prepared from the collected fungi using a genomic DNA preparation kit (trade name: PrepMan ultra, manufactured by Applied Biosystems). The concentration of each DNA solution was adjusted to 50 ng/μL.

(4) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 1 (0.02 pmol/μL) and 0.5 μL of the primer represented by the nucleotide sequence set forth in SEQ ID NO: 2 (0.02 pmol/μL) were added thereto, to thereby prepare 25 μL of a PCR reaction solution.

The PCR reaction solution was subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(5) Confirmation of Amplified Gene Fragment

After the PCR reaction, 4 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 4 and FIG. 5. Note that, FIG. 4 shows an electrophoretogram of samples of strains of *Byssochlamys fulva*, and FIG. 5 shows an electrophoretogram of samples o of strains of *Byssochlamys nivea*.

As a result, in all of the strains of *Byssochlamys fulva* and *Byssochlamys nivea* used, specific amplified DNA fragments were confirmed. Therefore, it is understood that the fungi belonging to the genus *Byssochlamys* can be specifically detected with high accuracy regardless of the strains by using the oligonucleotides of the present invention.

(B-1) Detection and Discrimination of Fungi Belonging to the Genus *Talaromyces*

1. Analysis of Nucleotide Sequence Specific to Fungi Belonging to the Genus *Talaromyces*

Nucleotide sequences of the β-tubulin gene and the ITS region and D1/D2 region of 28S rDNA of each variety of fungi belonging to the genus *Talaromyces* were determined by the following method.

A test fungus was cultured in the dark on a potato dextrose agar slant at 25° C. for 7 days. DNA was extracted from the fungus using GenTorukun™ (manufactured by TAKARA BIO INC.). PCR amplification of a target site was performed using PuRe Taq™ Ready-To-Go PCR Beads (manufactured by GE Health Care UK LTD); and primers Bt2a (5'-GGTAACCAAATCGGTGCTGCTTTC-3', SEQ ID NO: 79) and Bt2b (5'-ACCCTCAGTGTAGTGACCCTTGGC-3', SEQ ID NO: 80) (Glass and Donaldson, Appl Environ Microbiol 61: 1323-1330, 1995) as primers for the β-tubulin gene; or primers NL1 (5'-GCATATCAATAAGCGGAGGAAAAG-3', SEQ ID NO: 81) and NL4 (5'-GGTCCGTGTTTCAAGACGG-3', SEQ ID NO: 82) (The fungal homorph:Mitotic and plemorphic speciation in fungal systematics, Wallingford: CAB international.) as primers for the D1/D2 region of 28S rDNA. Amplification of β-tubulin partial length was performed under conditions including a denaturation temperature of 95° C., an annealing temperature of 59° C., an elongation temperature of 72° C., and 35 cycles. Amplification of ITS region and D1/D2 region of 28S rDNA was performed under conditions including a denaturation temperature of 95° C., an annealing temperature of 55° C., an elongation temperature of 72° C., and 35 cycles. PCR products were purified using Auto Seg™ G-50 (manufactured by Amersham Pharmacia Biotech). The PCR products were labeled with BigDye (registered trademark) terminator Ver. 1.1 (manufactured by Applied Biosystems), and electrophoresis was performed using ABI PRISM 3130 Genetic Analyzer (manufactured by Applied Biosystems). Nucleotide sequences from fluorescence signals in electrophoresis were determined using the software "ATGC Ver. 4" (manufactured by Genetyx).

Based on nucleotide sequence information of the β-tubulin gene and ITS region and D1/D2 region of 28S rDNA of a variety of fungi (*Talaromyces flavus*, *Talaromyces luteus*, and *Talaromyces wortmannii*) and known nucleotide sequence information of the β-tubulin gene and ITS region and D1/D2 region of 28S rDNA of a variety of fungi, alignment analyses were performed using DNA analysis software (product name: DNAsis pro, manufactured by Hitachi Software Engineering Co., Ltd.), to thereby determine specific regions in the β-tubulin gene and ITS region and D1/D2 region of 28S rDNA including nucleotide sequences specific to the fungi belonging to the genus *Talaromyces* (SEQ ID NOS: 26 to 28).

2. Detection of Fungi Belonging to the Genus *Talaromyces* and Identification of the Fungi at Genus Level (1) Design of Primers From regions having particularly high specificity to the fungi belonging to the genus *Talaromyces* on the 3'-end side in the determined nucleotide sequence regions specific to the fungi belonging to the genus *Talaromyces* (SEQ ID NOS: 26 to 28), partial regions which satisfy the following four conditions were searched:

1) including several nucleotides which is specific to the genus;
2) having a GC content of about 30% to 80%;
3) having low possibility to cause self-annealing; and
4) having a Tm value of about 55 to 65° C.

Based on the nucleotide sequences of the above regions, five primer pairs were designed for the β-tubulin gene, and five primer pairs were designed for the ITS region and D1/D2 region of 28S rDNA to search the effectiveness of detection of the fungi of the genus *Talaromyces* and identification of the genus by PCR reactions using DNAs extracted from the fungi as templates. As a result, in the case of using one of the five pairs for the β-tubulin gene primers, amplification of DNA was observed specifically to *Talaromyces flavus* and *Talaromyces trachyspermus* at a position corresponding to the size expected from the designed primer pairs. The primer pair confirmed to have the effectiveness is the pair of SEQ ID NOS: 3 and 4.

Subsequently, it was examined that the fungi of the genus *Talaromyces* can be exhaustively detected by using a plurality of primer pairs in combination. Specifically, a DNA amplification reaction is observed at a position corresponding to the size expected from the designed primer pairs in the case of a reaction using DNA of the fungi of the genus *Talaromyces* as a template, while no amplification product is observed in the cases of reactions using genomic DNAs of other fungi as templates. As a result, it was confirmed that the fungi of the genus *Talaromyces* can be exhaustively detected and the genus *Talaromyces* can be identified at genus level by using a mixture of two of the five pairs of the primers for the β-tubulin gene and two of the five pairs of the primers for the ITS region and D1/D2 region of 28S rDNA. The primer pairs confirmed to have the effectiveness are ones each of which consists of any two oligonucleotides represented by the nucleotide sequences set forth in SEQ ID NOS: 5 to 11. The primers used were synthesized by Sigma-Aldrich Japan (desalted products, 0.02 μmol scale) and purchased.

(2) Preparation of Samples

The fungi belonging to the genus *Talaromyces*, other heat-resistant fungi, and general fungi shown in Table 3 were used as fungi to be used for evaluation of the effectiveness of the designed primers. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. (for general fungi) or 30° C. (for heat-resistant fungi) for 7 days.

TABLE 3

| Sample No. | Species | Strain No. |
| --- | --- | --- |
| N | (Negative Control) | — |
| 1 | Talaromyces flavus | T38 |
| 2 | Talaromyces trachyspermus | T24 |
| 3 | Neosartorya ficheri | A183 |
| 4 | Byssochlamys fulva | IFM48421 |
| 5 | Byssochlamys nivea | IFM51244 |
| 6 | Penicillium griseofulvum | P14 |
| 7 | Penicillium citirinum | P15 |
| 8 | Penicillium paneum | P16 |
| 9 | Penicillium oxalicum | P17 |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(4) PCR Reaction

1 μL of the genormic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 3 (20 pmol/μL) and 0.5 μL of the primer represented by the nucleotide sequence set forth in SEQ ID NO: 4 (20 pmol/μL) were added thereto, to thereby prepare 25 μL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 95° C. for 10 seconds, (ii) an annealing reaction at 59° C. for 1 minute, and (iii) an elongation reaction at 72° C. for 1 minute.

(5) Confirmation of Amplified Gene Fragment

After the PCR reaction, 10 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 6.

Figure 6:
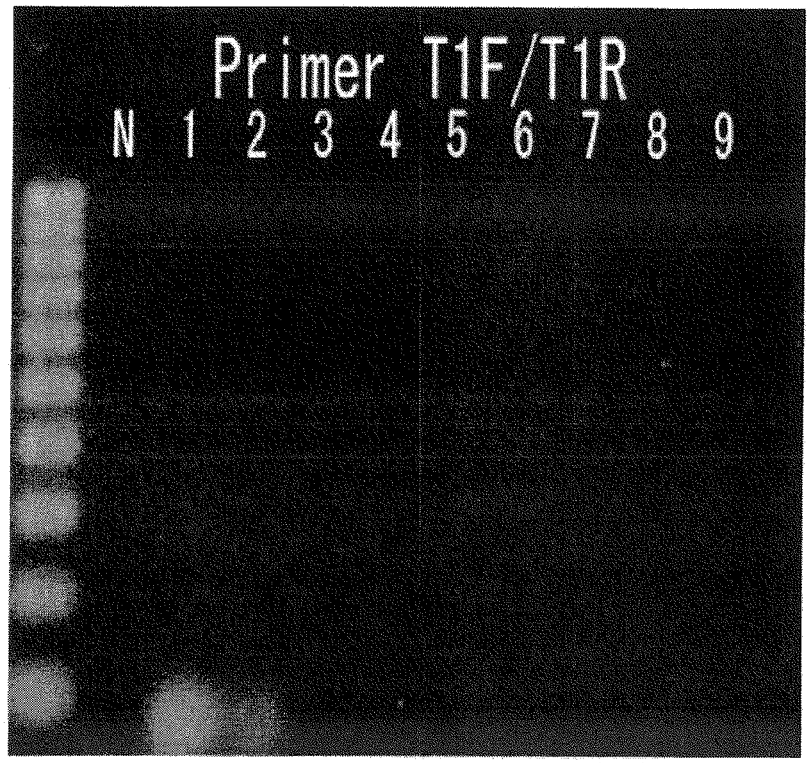
FIG. 6 is an electrophoretogram showing discrimination results of fungi belonging to the genus *Talaromyces* in Example 1(B-1).

As a result, in the case of the samples containing the genomic DNA of Talaromyces flavus and Talaromyces trachyspermus, amplification of gene fragments of about 80 bp was confirmed (lanes 1 and 2 in FIG. 6). On the other hand, in the case of the samples containing no genomic DNA of the fungi belonging to the genus Talaromyces, amplification of gene fragments was not confirmed. From the above-described results, it is understood that the fungi belonging to the genus Talaromyces can be specifically detected by using the above-described oligonucleotides (c) and (d).

(B-2) Detection and Discrimination of Fungi Belonging to the Genus Talaromyces (1) Preparation of Primers The primers consisting of the oligonucleotides represented by the nucleotide sequences set forth in SEQ ID NOS: 5 to 8, designed in Example 1(B-1), were used.

(2) Preparation of Samples

As the fungi belonging to the genus Talaromyces, Talaromyces flavus, Talaromyces trachyspermus, Talaromyces wortmannii, and Talaromyces luteus were used. To confirm specificity of the oligonucleotides (e) to (h) to the β-tubulin genes of the fungi belonging to the genus Talaromyces, the fungi shown in Tables 4 and 5 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. for 7 days.

TABLE 4

| Sample No. | Species | Strain No. |
| --- | --- | --- |
| 1 | Talaromyces flavus | 42243 |
| 2 | Talaromyces flavus | 52233 |
| 3 | Talaromyces luteus | 53242 |
| 4 | Talaromyces luteus | 53241 |
| 5 | Talaromyces trachyspermus | 42247 |
| 6 | Talaromyces trachyspermus | 52252 |
| 7 | Talaromyces wortmannii | 52255 |
| 8 | Talaromyces wortmannii | 52262 |
| 9 | Byssochlamys fluva | 51213 |
| 10 | Byssochlamys nivea | 51245 |
| 11 | Hamigera avellanea | 42323 |
| 12 | Hamigera avellanea | 52241 |

TABLE 5

| Sample No. | Species | Strain No. |
| --- | --- | --- |
| 1 | Talaromyces flavus | 42243 |
| 2 | Talaromyces flavus | 52233 |
| 3 | Talaromyces luteus | 53242 |
| 4 | Talaromyces luteus | 53241 |
| 5 | Talaromyces trachyspermus | 42247 |
| 6 | Talaromyces trachyspermus | 52252 |
| 7 | Talaromyces wortmannii | 52255 |
| 8 | Talaromyces wortmannii | 52262 |
| 9 | Alternaria alternata | 52225 |
| 10 | Aureobasidium pullulans | 41409 |
| 11 | Chaetomium globosum | 40869 |
| 12 | Hamigera avellanea | 42323 |
| 13 | Paecilomyces variotii | 40913 |
| 14 | (Negative Control) | — |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(4) PCR Reaction

1 μL of the genomic DNA solution prepared above as a DNA template, 25 μL of Pre Mix Taq (trade name, manufactured by TAKARA BIO INC.) and 20 μL of sterile distilled water were mixed, and 1.0 µL of the primer represented by the nucleotide sequence set forth in SEQ ID NO: 5 (20 pmol/µL), 1.0 µL of the primer represented by the nucleotide sequence set forth in SEQ ID NO: 6 (20 pmol/µL), 1.0 µL of the primer represented by the nucleotide sequence set forth in SEQ ID NO: 7 (20 pmol/µL), and 1.0 µL of the primer represented by the nucleotide sequence set forth in SEQ ID NO: 8 (20 pmol/µL) were added thereto, to thereby prepare 50 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 97° C. for 10 seconds, (ii) an annealing reaction at 59° C. for 1 minute, and (iii) an elongation reaction at 72° C. for 1 minute.

(5) Confirmation of Amplified Gene Fragment

Figure 7:
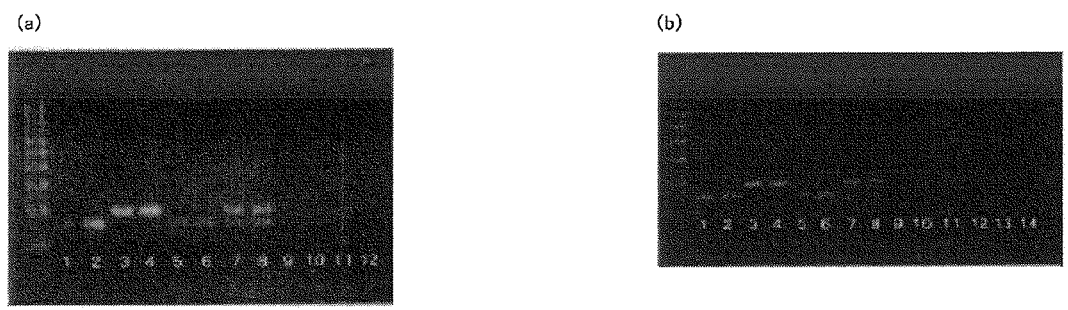
FIG. 7 is an electrophoretogram showing discrimination results of fungi belonging to the genus *Talaromyces* in Example 1(B-2).
Figure 8:
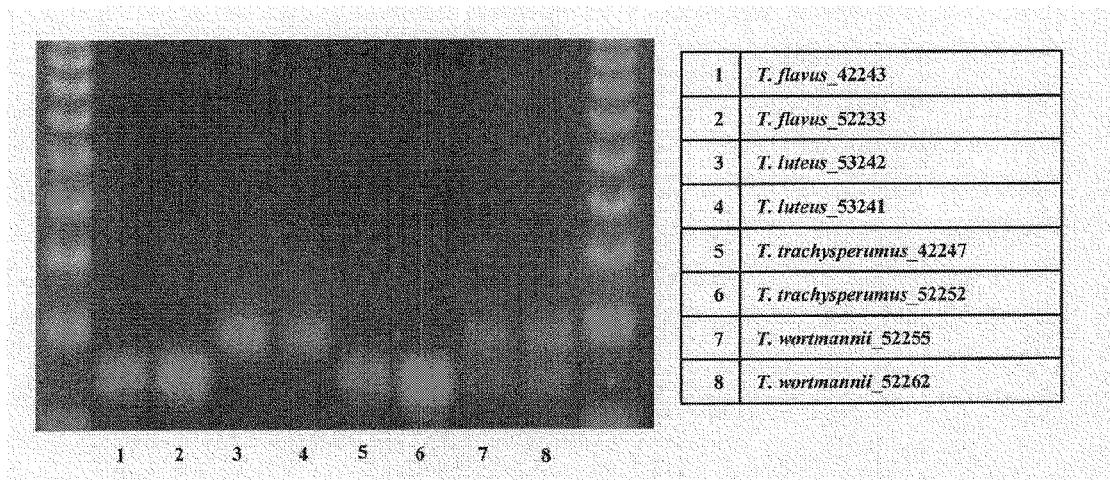
FIG. 8 is an electrophoretogram showing discrimination results of fungi belonging to the genus *Talaromyces* in Example 1(B-2).

After the PCR reaction, 2 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 7(*a*), FIG. 7(*b*) and FIG. 8. Note that, FIG. 7(*a*) shows an electrophoretogram of samples of the fungi shown in Table 4, and FIG. 7(*b*) shows an electrophoretogram of samples of the fungi shown in Table 5. The numbers in the electrophoretograms correspond the sample numbers in each table, and represent samples obtained by using DNAs extracted from the fungi having the corresponding sample numbers in the tables. FIG. 8 shows an electrophoretogram of samples only of the fungi belonging to the genus *Talaromyces*.

As a result, in the samples containing genomic DNA of *Talaromyces flavus*, *Talaromyces trachyspermus*, or *Talaromyces wortmannii* of the fungi belonging to the genus *Talaromyces* (the lanes 1 to 2 and 5 to 8 in FIG. 7(*a*) and the lanes 1 to 2 and 5 to 8 in FIG. 7(*b*)), amplification of gene fragments of about 150 bp was confirmed. The gene fragments were obtained by amplification using the primers represented by the nucleotide sequences of SEQ ID NOS: 7 and 8. Meanwhile, in the samples containing genomic DNA of *Talaromyces wortmannii* or *Talaromyces luteus* (the lanes 3 to 4 and 7 to 8 in FIG. 7(*a*) and the lanes 3 to 4 and 7 to 8 in FIG. 7(*b*)), amplification of gene fragments of about 200 bp was confirmed. The gene fragments were obtained by amplification using the primers represented by the nucleotide sequences of SEQ ID NOS: 5 and 6. On the other hand, in the sample containing no genomic DNA of the fungi belonging to the genus *Talaromyces*, amplification of gene fragments were not confirmed. From the above-described results, it is understood that the fungi belonging to the genus *Talaromyces* can be specifically and exhaustively detected by simultaneously using the oligonucleotides (e) and (f) and the oligonucleotides (g) and (h).

(B-3) Detection and Discrimination of Fungi Belonging to the Genus *Talaromyces*

(1) Preparation of Primers

The primers consisting of the oligonucleotides represented by the nucleotide sequences set forth in SEQ ID NOS: 8 and 9, designed in Example 1(B-1), were used.

(2) Preparation of Samples

To confirm detection specificity of the oligonucleotides (h) and (i) to the fungi belonging to the genus *Talaromyces* and other fungus shown in FIG. 6 were used. As the fungi, fungi available from fungus deposition institutes, such as fungi stored in National Institute of Technology and Evaluation based on NBRC numbers and fungi stored in The Centraalbureau voor Schimmelcultures based on CBS numbers were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. (for heat-resistant fungi contains the genus *Talaromyces* and *Aspergillus fumigatus*) or 25° C. (for general fungi) for 7 days.

TABLE 6

| | Species | Strain |
|---|---|---|
| No. 1 | *Talaromyces flavus* | CBS 310.38 ex type |
| No. 2 | *Talaromyces macrosporus* | NBRC7132 |
| No. 3 | *Talaromyces trachysperumus* | CBS373.48 ex type |
| No. 4 | *Talaromyces bacillisporus* | CBS294.48 ex type |
| No. 5 | *Talaromyces wortmannii* | CBS391.48 ex type |
| No. 6 | *Talaromyces luteus* | CBS348.51 ex neotype |
| No. 7 | *Geosmithia argillacea* | CBM-FA0940 ex type |
| No. 8 | *Geosmithia emersonii* | CBS393.64 ex type |
| No. 9 | *Byssochlamys fluva* | CBS132.33 ex type |
| No. 10 | *Byssochlamys nivea* | CBS100.11 ex type |
| No. 11 | *Byssochlamys spectabilis* | CBS101.075 ex type |
| No. 12 | *Hamigera avellanea* | CBS295.48 ex type |
| No. 13 | *Hamigera striata* | CBS377.48 ex type |
| No. 14 | *Thermoascus aurantiacus* | NBRC6766 |
| No. 15 | *Thermoascus crustaceus* | NBRC9129 |
| No. 16 | *Neosartorya fischeri* | NRRL181 ex type |
| No. 17 | *Neosartorya spinosa* | IFO8782 ex type |
| No. 18 | *Aspergillus fumigatus* | IAM13869 ex type |
| No. 19 | *Aspergillus niger* | CBS554.65 ex type |
| No. 20 | *Aspergillus flavus* | IFO30107 ex neotype |
| No. 21 | *Eupenicillium brefeldianum* | IFO31730 ex type |
| No. 22 | *Penicillium griseofulvum* | CBS185.27 ex neotype |
| No. 23 | *Alternaria alternata* | CBS103.33 |
| No. 24 | *Aurerobasidium pullulans* | CBS105.22 |
| No. 25 | *Chaetomium globosum* | CBS148.51 |
| No. 26 | *Fusarium oxysporum* | IFM50002 |
| No. 27 | *Tricoderma viride* | CBS433.34 |
| No. 28 | *Cladosporium cladosporioides* | CBS170.54 ex neotype |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(4) PCR Reaction

1 µL of the genomic DNA solution prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 8 (20 pmol/µL) and 0.5 µL of the primer represented by the nucleotide sequence set forth in SEQ ID NO: 9 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 95° C. for 1 minute, (ii) an annealing reaction at 59° C. for 1 minute, and (iii) an elongation reaction at 72° C. for 1 minute.

(5) Confirmation of Amplified Gene Fragment

After the PCR reaction, 10 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 9-1. The numbers in the electrophoretogram correspond the sample numbers in Table 6, and represent samples obtained by using DNAs extracted from the fungi having the corresponding sample numbers in Table 6.

As a result, only in the samples containing genomic DNAs of *Talaromyces flavus*, *Talaromyces macrospores*, and *Talaromyces trachyspermus* of the fungi belonging to the genus *Talaromyces* (lanes 1 to 3), amplification of gene fragments of about 150 bp was confirmed. On the other hand, in the sample containing no genomic DNA of the fungi belonging to the genus *Talaromyces*, amplification of gene fragments was not confirmed. From the above-described results, it is understood that only a specific species of fungus of the fungi belonging to the genus *Talaromyces* can be specifically detected by using the oligonucleotides of the present invention.

(B-4) Detection and Discrimination of Fungi Belonging to the Genus *Talaromyces*

(1) Primers

The primers consisting of the oligonucleotides represented by the nucleotide sequences set forth in SEQ ID NOS: 10 and 11, designed in Example 1(B-1), were used.

(2) Preparation of Samples

To confirm detection specificity of the oligonucleotides (j) and (k) to the same fungi belonging to the genus *Talaromyces* and other fungus shown in Table 6 of Example 1(B-3) were used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. (for heat-resistant fungi contains the genus *Talaromyces* and *Aspergillus fumigatus*) or 25° C. (for general fungi) for 7 days.

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(4) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 10 (20 pmol/μL) and 0.5 μL of the primer represented by the nucleotide sequence set forth in SEQ ID NO: 11 (20 pmol/μL) were added thereto, to thereby prepare 25 μL of a PCR reaction solution.

The PCR reaction solution was subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 55° C. for 1 minute, and (iii) an elongation reaction at 72° C. for 1 minute.

(5) Confirmation of Amplified Gene Fragment

After the PCR reaction, 10 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 9-2. The numbers in the electrophoretogram correspond the sample numbers in Table 6, and represent samples obtained by using DNAs extracted from the fungi having the corresponding sample numbers in Table 6.

As a result, only in the samples containing genomic DNAs of *Talaromyces bacillisporus*, *Talaromyces wortmannii*, and *Talaromyces luteus* of the fungi belonging to the genus *Talaromyces* (lanes 4 to 6), amplification of gene fragments of about 200 bp was confirmed. On the other hand, in the sample containing no genomic DNA of the fungi belonging to the genus *Talaromyces*, amplification of gene fragments was not confirmed. From the above-described results, it is understood that only a specific species of fungus of the fungi belonging to the genus *Talaromyces* can be specifically detected by using the oligonucleotides of the present invention.

(B-5) Detection and Discrimination of Fungi Belonging to the Genus *Talaromyces*

(1) Preparation of Primers

The primers consisting of the oligonucleotides represented by the nucleotide sequences set forth in SEQ ID NOS: 7 and 8, designed in Example 1(B-1), were used.

(2) Preparation of Samples

Figure 10:
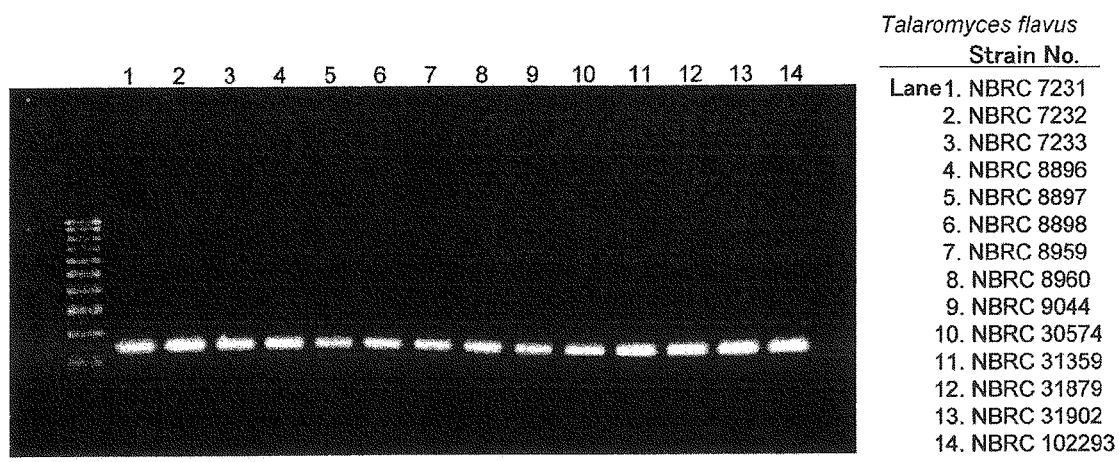
FIG. 10 is an electrophoretogram in the case of using strains of *Talaromyces flavus* in Example 1(B-5).
Figure 11:
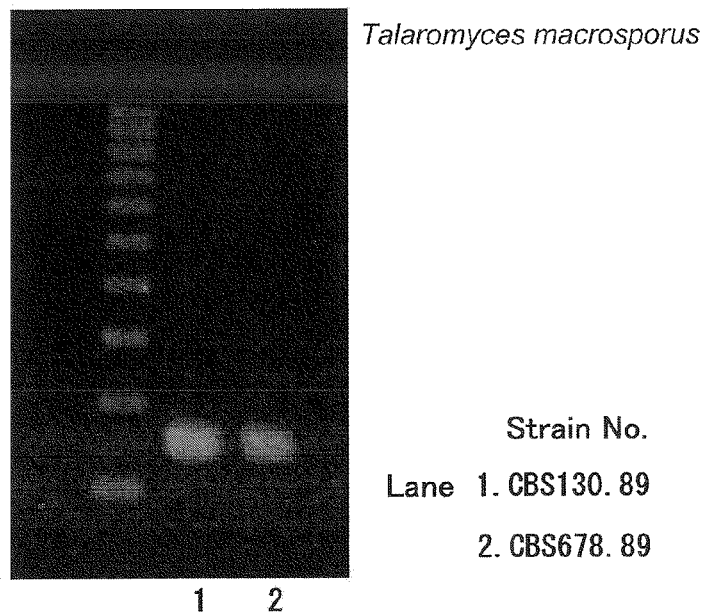
FIG. 11 is an electrophoretogram in the case of using strains of *Talaromyces macrosporus* in Example 1(B-5).

To confirm detection specificity to the oligonucleotides (g) and (h) against the fungi belonging to the genus *Talaromyces*, the strains of *Talaromyces flavus* shown in FIG. 10 and strains of *Talaromyces macrosporus* shown in FIG. 11 were used. As the fungi, fungi available from fungus deposition institutes, such as fungi stored in National Institute of Technology and Evaluation based on NBRC numbers and fungi stored in The Centraalbureau voor Schimmelcultures based on CBS numbers were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/μL.

(4) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 7 (20 pmol/μL) and 0.5 μL of the primer represented by the nucleotide sequence set forth in SEQ ID NO: 8 (20 pmol/μL) were added thereto, to thereby prepare 25 μL of a PCR reaction solution.

The PCR reaction solution was subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 61° C. for 1 minute, and (iii) an elongation reaction at 72° C. for 1 minute.

(5) Confirmation of Amplified Gene Fragment

After the PCR reaction, 4 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 10 and FIG. 11.

As a result, in the cases of all of the strains of *Talaromyces flavus* and *Talaromyces macrospores* used, specific amplified DNA fragments were confirmed. Therefore, it is understood that the fungi belonging to the genus *Talaromyces* can be specifically detected with high accuracy regardless of the strains by using the oligonucleotides of the present invention.

(C-1) Detection and Discrimination of Fungi Belonging to the Genus *Neosartorya* and *Aspergillus fumigatus*

1. Determination of Partial Nucleotide Sequence of β-Tubulin Gene

Nucleotide sequences of the β-tubulin gene of *Neosartorya glabra, Neosartotya fischeri, Neosartorya spinosa* and *Aspergillus fumigatus* were determined by the following method.

A test fungus was cultured in the dark on a potato dextrose agar slant at 30° C. for 7 days. DNA was extracted from the fungus using GenTorukun™ (manufactured by TAKARA BIO INC.). PCR amplification of a target site was performed using PuRe Taq™ Ready-To-Go PCR Beads (manufactured by GE Health Care UK LTD); and primers Bt2a (5'-GG-TAACCAAATCGGTGCTGCTTTC-3', SEQ ID NO: 79) and Bt2b (5'-ACCCTCAGTGTAGTGACCCTTGGC-3', SEQ ID NO: 80) (Glass and Donaldson, Appl Environ Microbiol 61: 1323-1330, 1995). Amplification of β-tubulin partial length was performed under conditions including a denaturation temperature of 95° C., an annealing temperature of 59° C., an elongation temperature of 72° C., and 35 cycles. PCR products were purified using Auto Seg™ G-50 (manufactured by Amersham Pharmacia Biotech). The PCR products were labeled with BigDye (registered trademark) terminator Ver. 1.1 (manufactured by Applied Biosystems), and electrophoresis was performed using ABI PRISM 3130 Genetic Analyzer (manufactured by Applied Biosystems). Nucleotide sequences from fluorescence signals in electrophoresis were determined using the software "ATGC Ver. 4" (manufactured by Genetyx).

Based on the nucleotide sequences of the β-tubulin gene of *Neosartorya glabra, Neosartorya fischeri, Neosartorya spinosa* and *Aspergillus fumigatus*, and known nucleotide sequence information of the β-tubulin gene of a variety of fungi, alignment analyses were performed using DNA analysis software (product name: DNAsis pro, manufactured by Hitachi Software Engineering Co., Ltd.), to thereby determine specific regions in the β-tubulin gene including nucleotide sequences specific to the fungi belonging to the genus *Neosartorya* and *Aspergillus fumigatus* (SEQ ID NOS: 32 to 34 and 83 to 86).

2. Detection of Fungi Belonging to the Genus *Neosartorya* and *Aspergillus fumigatus*

(1) Design of Primers

From regions having particularly high specificity to the fungi belonging to the genus *Neosartorya* and *Aspergillus fumigatus* on the 3'-end side in the determined nucleotide sequence regions specific to the preserving property for the both fungi, partial regions which satisfy the following four conditions were searched:

1) including several nucleotides which is specific to the genus;
2) having a GC content of about 30% to 80%;
3) having low possibility to cause self-annealing; and
4) having a Tm value of about 55 to 65° C.

Based on the nucleotide sequences of the above regions, four pairs of primers were designed to examine effectiveness of simultaneous detection of the genus *Neosartorya* and *Aspergillus fumigatus* by PCR reactions using DNAs extracted from a variety of fungi as templates. Specifically, it was examined that DNA amplification reactions are observed at positions corresponding to the sizes expected from the designed primer pairs in reactions using DNAs of the genus *Neosartorya* and *Aspergillus fumigatus* as templates, while no amplification product is observed in reactions using genomic DNAs of other fungi. As a result, in the cases of two pairs of primers, DNA amplification was observed specifically to the genus *Neosartorya* and *Aspergillus fumigatus*, while, in the cases of the reactions using the genomic DNAs of other fungi, no amplification product was observed. That is, the two pairs of primers can simultaneously detect the genus *Neosartorya* and *Aspergillus fumigatus*. The primer pairs confirmed to have the effectiveness are ones each of which consists of any two oligonucleotides represented by the nucleotide sequences set forth in SEQ ID NOS: 12 and 13, and the nucleotide sequences set forth in SEQ ID NOS: 14 and 15. The primers used were synthesized by Sigma-Aldrich Japan (desalted products, 0.02 μmol scale) and purchased.

(2) Preparation of Samples

The fungi belonging to the genus *Neosartorya* and *Aspergillus fumigatus* in Table 7 were used. To confirm specificity of the oligonucleotides (l) and (m) to the β-tubulin genes of these fungi, other fungi shown in Tables 7 were used. It should be noted that the strains were obtained from strains stored in RIKEN based on JCM numbers, strains stored in Institute of Molecular and Cellular Biosciences, The University of Tokyo based on IAM numbers and strains stored in Institute for Fermentation. Osaka based on IFO numbers and used for evaluation.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. (for heat-resistant fungi and *Aspergillus fumigatus*) or 25° C. (for general fungi) for 7 days.

TABLE 7

| Sample No. | Species | Strain No. |
|---|---|---|
| 1 | *Neosartorya ficheri* | A183 |
| 2 | *Neosartorya spinosa* | N121 |
| 3 | *Byssochlamys fulva* | JCM12805 |
| 4 | *Byssochlamys nivea* | IAM51244 |
| 5 | *Talaromyces macrosporus* | IFO30070 |
| 6 | *Talaromyces flavus* | IAM42243 |
| 7 | *Aspergillus fumigatus* | 07-77 |
| 8 | *Aspergillus niger* | IFO6662 |
| 9 | *Aspergillus flavus* | IFO7600 |
| 10 | *Aspergillus terreus* | IFO8835 |
| 11 | *Emericella nidulans* | IFO6083 |
| 12 | *Candida albicans* | IFO1385 |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(4) PCR Reaction

1 µL of the genomic DNA solution prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 12 (20 pmol/µL) and 0.5 µL of the primer represented by the nucleotide sequence set forth in SEQ ID NO: 13 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 98° C. for 10 seconds, (ii) an annealing reaction at 59° C. for 1 minute, and (iii) an elongation reaction at 72° C. for 1 minute.

(5) Confirmation of Amplified Gene Fragment

Figure 12:
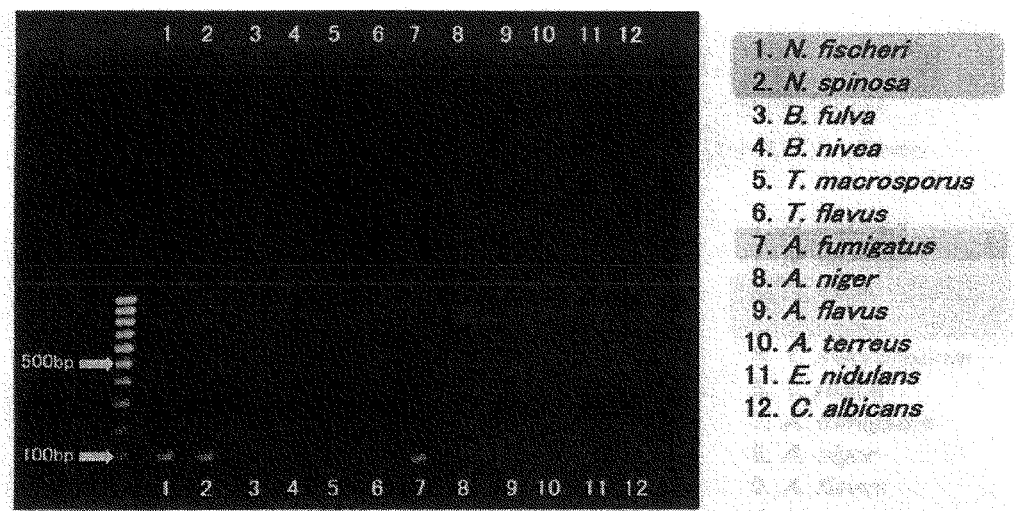
FIG. 12 is an electrophoretogram showing discrimination results of fungi belonging to the genus *Neosartorya* and *Aspergillus fumigatus* in Example 1(C-1).

After the PCR reaction, 10 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 12.

As a result, in the case of the samples containing the genomic DNA of the fungi belonging to the genus *Neosartorya* or *Aspergillus fumigatus*, amplification of gene fragments of about 100 bp was confirmed (lanes 1, 2 and 7). On the other hand, in the case of the samples containing no genomic DNA of the fungi belonging to the genus *Neosartorya* or *Aspergillus fumigatus*, amplification of gene fragments was not confirmed. From the above-described results, it is understood that the fungi belonging to the genus *Neosartarya* and *Aspergillus fumigatus* can be specifically detected by using the above-described oligonucleotides (l) and (m).

(6) Discrimination Based on Difference in Growth Temperatures Between Fungi Belonging to the Genus *Neosartorya* and *Aspergillus fumigatus*

For samples where amplification of gene fragments was confirmed by the above-mentioned method, hyphae from single colonies were inoculated into a PDA medium (product name: Potato dextrose medium, manufactured by Eiken Chemical Co., Ltd.), and the fungi were cultured at 50° C. for one day and then observed by a method of confirming hyphae using a stereomicroscope. As a result, in samples where *Aspergillus fumigatus* was inoculated, active growth of the hyphae was observed, while in samples where the fungi belonging to the genus *Neosartorya* were inoculated, growth of the hyphae was not observed. The results reveal that it is possible to discriminate only *Aspergillus fumigatus* from the fungi belonging to the genus *Neosartotya* and *Aspergillus fumigatus* based on a difference in growth temperature zones.

(C-2) Detection and Discrimination of the Fungi Belonging to the Genus *Neosartorya* and *Aspergillus fumigatus*

(1) Preparation of Primers

The primers consisting of the oligonucleotides represented by the nucleotide sequences set forth in SEQ ID NOS: 14 and 15, designed in Example 1(C-1), were used.

(2) Preparation of Samples

The fungi belonging to the genus *Neosartorya* and *Aspergillus fumigatus* shown in Table 8 and Table 9 were used. To confirm specificity of the oligonucleotides (n) and (o) to the β-tubulin genes of the fungi belonging to the genus *Neosartorya* and *Aspergillus fumigatus*, other fungi shown in Table 8 and Table 9 were used. These fungi were stored in Medical Mycology Research Center (MMRC), Chiba University, and the fungi deposited based on numbers were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. (for heat-resistant fungi and *Aspergillus fumigatus*) or 25° C. (for general fungi) for 7 days.

TABLE 8

| Sample No. | Species | Strain No. |
|---|---|---|
| 1 | Neosartorya ficheri | A176 |
| 2 | Neosartorya spinosa | A176 |
| 3 | Aspergillus fumigatus | A218 |
| 4 | Neosartorya glabra | N153 |
| 5 | Neosartorya glabra | N129 |
| 6 | Neosartorya hiratsukae | N14 |
| 7 | Aspergillus niger | An15 |
| 8 | Aspergillus terreus | A229 |
| 9 | Aspergillus flavus | As17 |
| 10 | Emericella nidulans | As18 |
| 11 | N.C. (negative control) | |

TABLE 9

| Sample No. | Species | Strain No. |
|---|---|---|
| 1 | Neosartorya ficheri | A176 |
| 2 | Neosartorya hiratsukae | N14 |
| 3 | Talaromyces luteus | T58 |
| 4 | Talaromyces flavus | T38 |
| 5 | Talaromyces trachyspermus | T24 |
| 6 | Talaromyces wortmannii | T77 |
| 7 | Byssochlamys fluva | B3 |
| 8 | Byssochlamys nivea | B7 |
| 9 | Paecilomyces lilacinus | 54312 |
| 10 | Penicillium griseofulvum | 54313 |
| 11 | Penicillium citirinum | 54314 |
| 12 | Penicillium paneum | 55885 |
| 13 | Penicillium oxalicum | 55886 |
| 14 | N.C. (negative control) | |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(4) PCR Reaction

1 µL of the genomic DNA solution prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 14 (20 pmol/µL) and 0.5 µL of the primer represented by the nucleotide sequence set forth in SEQ ID NO: 15 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 97° C. for 10 seconds, (ii) an annealing reaction at 59° C. for 1 minute, and (iii) an elongation reaction at 72° C. for 1 minute.

(5) Confirmation of Amplified Gene Fragment

Figure 13:
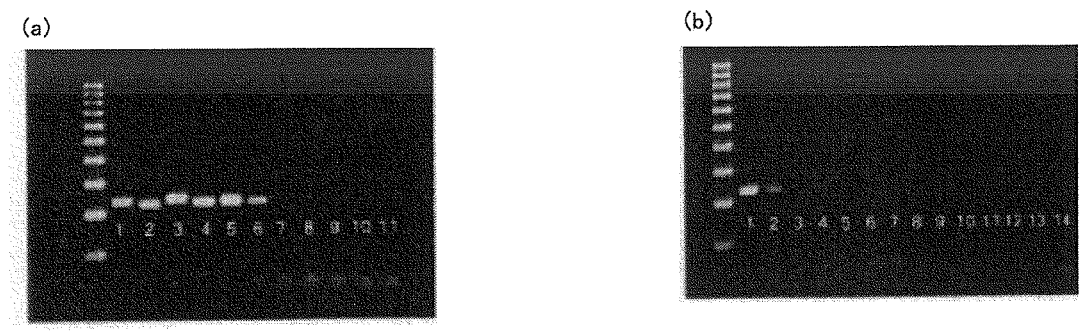
FIG. 13 is an electrophoretogram showing discrimination results of fungi belonging to the genus *Neosartorya* and *Aspergillus fumigatus* in Example 1(C-2).

After the PCR reaction, 2μL of a sample was collected from the PCR reaction solution and electrophoresed using a 2% agarose gel, and DNA was stained with SYBR Safe DNA gel stain in 1 33 TAE (Invitrogen), to thereby confirm whether the amplified DNA fragment was present or not. The electrophoretograms in the agarose gel are shown in FIG. 13(a) and FIG. 13(b). Note that, FIG. 13(a) shows an electrophoretogram of samples of the fungi shown in Table 8, and FIG. 13(b) shows an electrophoretogram of samples of the fungi shown in Table 9. The numbers in the electrophoretograms correspond the sample numbers in the tables, and represent samples obtained by using DNAs extracted from the fungi having the corresponding sample numbers in the tables.

As a result, in the case of the samples containing the genomic DNA of the fungi belonging to the genus *Neosartorya* and *Aspergillus fumigatus*, amplification of gene fragments of about 200 bp was confirmed. On the other hand, in the case of the samples containing no genomic DNA of the fungi belonging to the genus *Neosartorya* or *Aspergillus fumigatus*, amplification of gene fragments was not confirmed. From the above-described results, it is understood that the fungi belonging to the genus *Neosartorya* and *Aspergillus fumigatus* can be specifically detected by using the above-described oligonucleotides (n) and (o).

(6) Discrimination Based on Difference in Growth Temperatures Between Fungi Belonging to the Genus Neosartotya and *Aspergillus fumigatus*

For samples where amplification of gene fragments was confirmed by the above-mentioned method, hyphae from single colonies were inoculated into a PDA medium (product name: Potato dextrose medium, manufactured by Eiken Chemical Co., Ltd.), and the fungi were cultured at 50° C. for one day and observed by a method of confirming hyphae using a stereomicroscope. As a result, in samples where *Aspergillus fumigatus* was inoculated, active growth of the hyphae was observed, while in samples where the fungi belonging to the genus *Neosattorya* were inoculated, growth of the hyphae was not observed. The results reveal that it is possible to discriminate only *Aspergillus fumigatus* from the fungi belonging to the genus *Neosartorya* and *Aspergillus fumigatus* based on a difference in growth temperature zones.

(C-3) Discrimination of *Aspergillus fumigatus* from Fungi Belonging to the Genus *Neosartorya* Using Oligonucleotides (v) and (w)

(1) Design of Primers for Detection of *Aspergillus fumigatus*

Alignment analyses (DNAsis Pro) of the nucleotide sequences of the β-tubulin genes of *Neosartorya glabra*, *Aspergillus fumigatus*, *Neosartorya fischeri*, and *Neosartorya spinosa* represented by SEQ ID NOS: 32 to 34 and 83 to 86 were performed to determine regions where differences in nucleotide sequences of both the fungi belonging to the genus *Neosartorya* and *Aspergillus fumigatus* were present. From regions having particularly high specificity to *Aspergillus fumigatus* on the 3'-end side in the determined nucleotide sequence regions, partial regions which satisfy the following four conditions were searched:

1) including several nucleotides which is specific to *Aspergillus fumigatus*;
2) having a GC content of about 30% to 80%;
3) having low possibility to cause self-annealing; and
4) having a Tm value of about 55 to 65° C.

Based on the nucleotide sequences of the above regions, two pairs of primers were designed to examine effectiveness of discrimination of *Aspergillus fumigatus* from the genus *Neosartorya* and *Aspergillus fumigatus* by PCR reactions using DNAs extracted from a variety of fungi as templates. Specifically, it was examined that, in reactions using DNAs of *Aspergillus fumigatus* as templates, DNA amplification reactions are observed at positions corresponding to the sizes expected from the designed primer pairs, while in reactions using genomic DNAs of the fungi belonging to the genus *Neosartorya*, no amplification product is observed. As a result, in the cases of one pair of primers, DNA amplification was observed specifically to *Aspergillus fumigatus*, while, in the cases of the reactions using the genomic DNAs of other fungi, no amplification product was observed. The primer pair confirmed to have the effectiveness is one each of which consists of any two oligonucleotides represented by the nucleotide sequences set forth in SEQ ID NOS: 22 and 23. The primers used were synthesized by Sigma-Aldrich Japan (desalted products, 0.02 μmol scale) and purchased.

(2) Preparation of Samples

The fungi belonging to the genus *Neosartorya* and *Aspergillus fumigatus* shown in Table 10 and Table 11 were used. Fungi other than the fungi belonging to the genus *Neosartorya* and *Aspergillus fumigatus*, shown in Tables 10 and 11, were used as references. These strains of fungi were stored in Medical Mycology Research Center (MMRC), Chiba University, and the fungi deposited based on numbers were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. (for heat-resistant fungi and *Aspergillus fumigatus*) or 25° C. (for general fungi) for 7 days.

TABLE 10

| No. 1 | A125 | A. fumigatus |
| No. 2 | A211 | A. fumigatus |
| No. 3 | A212 | A. fumigatus |
| No. 4 | A108 | A. fumigatus var. ellipticus |
| No. 5 | IFM46945 | N. fischeri |
| No. 6 | IFM46946 | N. fischeri |
| No. 7 | IFM46967 | N. spinosa |
| No. 8 | IFM46968 | N. spinosa |
| No. 9 | IFM46949 | N. glabra |
| No. 10 | IFM46951 | N. glabra |
| No. 11 | IFM46954 | N. hiratukae |
| No. 12 | IFM47037 | N. hiratukae |

TABLE 11

| No. 1 | A209 | A. fumigatus |
| No. 2 | A213 | A. fumigatus |
| No. 3 | A215 | A. fumigatus |
| No. 4 | A176 | N. fischeri |
| No. 5 | A239 | N. fischeri |
| No. 6 | A270 | N. fischeri |
| No. 7 | A178 | N. spinosa |
| No. 8 | A129 | A. brevipes |
| No. 9 | A133 | A. duricaulis |
| No. 10 | A252 | A. fumigatiaffinis |
| No. 11 | A234 | A. fumisynnematus |

TABLE 11-continued

| No. 12 | A170 | *A. lentulus* |
| No. 13 | A223 | *A. novofumigatus* |
| No. 14 | A221 | *A. udagawae* |
| No. 15 | A131 | *A. unilateralis* |
| No. 16 | A132 | *A. viridinutaus* |
| No. 17 | An15 | *A. niger* |
| No. 18 | A229 | *A. terreus* |
| No. 19 | As17 | *A. flavus* |
| No. 20 | As18 | *E. nidulans* |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(4) PCR Reaction

1 µL of the genomic DNA solution prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 22 (20 pmol/µL) and 0.5 µL of the primer represented by the nucleotide sequence set forth in SEQ ID NO: 23 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(5) Confirmation of Amplified Gene Fragment

Figure 14:
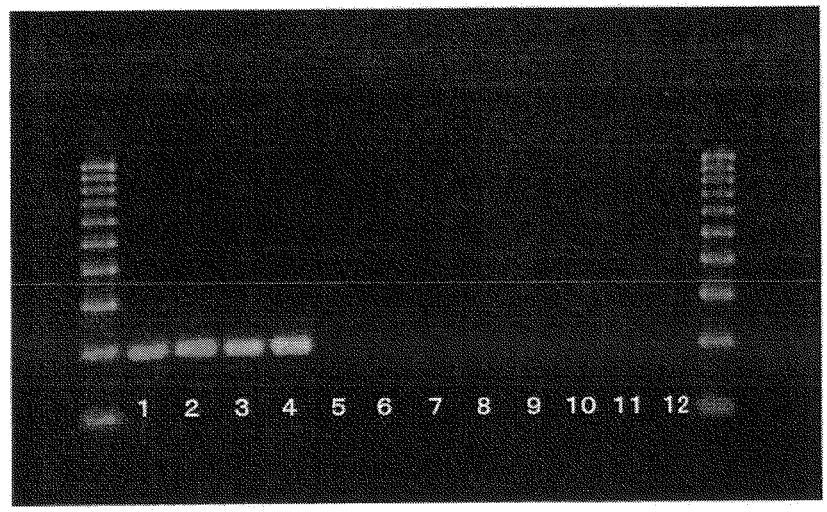
FIG. 14 is an electrophoretogram showing discrimination results of *Aspergillus fumigatus* from fungi belonging to the genus *Neosartorya* and *Aspergillus fumigatus* in Example 1(C-3).

After the PCR reaction, 2.5 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 14 and FIG. 15. Note that, FIG. 14 shows an electrophoretogram of samples of the fungi shown in Table 10, and FIG. 15 shows an electrophoretogram of samples of the fungi shown in Table 11. The numbers in the electrophoretograms correspond the sample numbers in the tables, and represent samples obtained by using DNAs extracted from the fungi having the corresponding sample numbers in the tables.

As shown in FIGS. 14 and 15, only in the samples containing genomic DNA of *Aspergillus fumigatus*, amplified fragments of about 200 bp were clearly confirmed. On the other hand, in the samples containing genomic DNAs of other fungi including the fungi of the genus *Neosartorya*, the amplified fragments of about 200 bp were not confirmed.

From the above-described results, it is understood that *Aspergillus fumigatus* can be specifically detected by performing gene amplification treatment using the above-described oligonucleotides (v) and (w) and then confirming the amplified fragments.

(C-4) Detection and Discrimination of the Fungi Belonging to the Genus *Neosartotya* and *Aspergillus fumigatus*

(1) Preparation of Primers

The primers consisting of the oligonucleotides represented by the nucleotide sequences set forth in SEQ ID NOS: 14 to 15 and the primers consisting of the oligonucleotides represented by the nucleotide sequences set forth in SEQ ID NOS: 22 to 23, designed in Example (C-1) and Example (C-3), were used.

(2) Preparation of Samples

To confirm detection specificity of the oligonucleotides (n) and (o) to the fungi belonging to the genus *Neosartorya* and detection specificity of the oligonucleotides (v) and (w) to *Aspergillus fumigatus*, the strains of *Neosartorya fischeri* shown in FIG. 16, strains of *Neosartorya glabra* shown in FIG. 17, strains of *Neosartotya hiratsukae* shown in FIG. 18, strains of *Neosartorya paulistensis* shown in FIG. 19, and strains of *Neosartorya spinosa* shown in FIG. 20 were used. In addition, *Aspergillus fumigatus* was used as a positive control for a reaction system including the oligonucleotides (v) and (w). It should be noted that, fungi available from fungus deposition institutes, such as fungi stored in National Institute of Technology and Evaluation based on NBRC numbers and fungi stored in The Centraalbureau voor Schimmelcultures based on CBS numbers, and fungi stored in Medical Mycology Research Center, Chiba University based on IFM numbers were obtained and used as test fungi.

The respective fungi were cultured under optimum conditions. The culture was performed using a potato dextrose medium (trade name: Pearlcore potato dextrose agar medium, manufactured by Eiken Chemical Co., Ltd.) under culture conditions of 30° C. (for heat-resistant fungi and *Aspergillus fumigatus*) or 25° C. (for general fungi) for 14 days.

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(4) PCR Reaction

1 µL of the genomic DNA solution prepared above as a DNA template, 13 µL of Pre Mix Tact (trade name, manufactured by TAKARA BIO INC.) and 10 µL of sterile distilled water were mixed, and 0.5 µL of the primer represented by the nucleotide sequence set forth in SEQ ID NO: 14 (0.02 pmol/µL) and 0.5 µL of the primer represented by the nucleotide sequence set forth in SEQ ID NO: 15 (0.02 pmol/µL) were added thereto, to thereby prepare 25 µL of a PCR reaction solution. Further, a PCR reaction solution was prepared in the same way as above except that 0.5 µl of the primer represented by the nucleotide sequence set forth in SEQ ID NO: 22 (20 pmol/µl) and 0.5 µl of the primer represented by the nucleotide sequence set forth in SEQ ID NO: 23 (20 pmol/µl) were used instead of the above-mentioned primers.

The PCR reaction solutions were subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(5) Confirmation of Amplified Gene Fragment

After the PCR reaction, 4 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIG. 16 to FIG. 20. Note that, FIG. 16 shows an electrophoretogram of samples of strains of *Neosartorya fischeri fischeri*, FIG. 17 shows an electrophoretogram of samples of strains of *Neosartorya glabra*, FIG. 18 shows an electrophoretogram of samples of strains of *Neosartorya hiratsukae fischeri*, FIG. 19 shows an electrophoretogram of samples of strains of *Neosatiorya paulistensis*, and FIG. 20 shows an electrophoretogram of samples of strains of *Neosartorya spinosa*.

As a result, in the reaction systems including the primers represented by the nucleotide sequences set forth in SEQ ID NOS: 14 and 15, specific amplified DNA fragments were confirmed in all of the strains used, *Neosartorya fischeri, Neosartorya glabra, Neosartorya hiratsukae, Neosartorya paulistensis*, and *Neosartorya spinosa* (FIG. 16(*a*), FIG. 17(*a*), FIG. 18(*a*), FIG. 19(*a*), and FIG. 20(*a*)). Therefore, it is understood that the fungi belonging to the genus *Neosartorya* can be specifically detected with high accuracy regardless of the strains by using the oligonucleotides of the present invention.

In the reaction systems including the primers represented by the nucleotide sequences set forth in SEQ ID NOS: 22 and 23, specific amplified DNA fragments were confirmed only in the samples containing genomic DNA of *Aspergillus fumigatus* as a template. On the other hand, in all of the samples containing the respective strains of the genus *Neosartorya*, amplification of DNA fragments was not confirmed (FIG. 16(*b*), FIG. 17(*b*), FIG. 18(*b*), FIG. 19(*b*), and FIG. 20(*b*)). From the above-described results, it is understood that *Aspergillus fumigatus* can be specifically detected by performing gene amplification treatment using the above-described oligonucleotides (v) and (w) and then confirming the amplified fragments.

(D-1) Detection and Discrimination of Fungi Belonging to the Genus *Hamigera*

1. Determination of Partial Nucleotide Sequence of β-Tubulin Gene

Nucleotide sequences of the β-tubulin gene of *Hamigera avellanea* and *Cladosporium cladosporioides* were determined by the following method.

A test fungus was cultured in the dark on a potato dextrose agar slant at 30° C. for *Hamigera avellanea* and 25° C. for *Cladosporium cladosporioides* for 7 days. DNA was extracted from the fungus using GenTorukun™ (manufactured by TAKARA BIO INC.). PCR amplification of a target site was performed using PuRe Taq™ Ready-To-Go PCR Beads (manufactured by GE Health Care UK LTD); and primers Bt2a (5'-GGTAACCAAATCGGTGCTGCTTTC-3', SEQ ID NO: 79) and Bt2b (5'-ACCCTCAGTGTAGTGAC-CCTTGGC-3', SEQ ID NO: 80) (Glass and Donaldson, Appl Environ Microbiol 61: 1323-1330, 1995). Amplification of β-tubulin partial length was performed under conditions including a denaturation temperature of 95° C., an annealing temperature of 59° C., an elongation temperature of 72° C., and 35 cycles. PCR products were purified using Auto Seg™ G-50 (manufactured by Amersham Pharmacia Biotech). The PCR products were labeled with BigDye (registered trademark) terminator Ver. 1.1 (manufactured by Applied Biosystems), and electrophoresis was performed using ABI PRISM 3130 Genetic Analyzer (manufactured by Applied Biosystems). Nucleotide sequences from fluorescence signals in electrophoresis were determined using the software "ATGC Ver. 4" (manufactured by Genetyx).

Based on the nucleotide sequences information of the β-tubulin gene of *Hamigera avellanea* and *Cladosporium cladosporioides* and known nucleotide sequence information of the β-tubulin gene of a variety of fungi, alignment analyses were performed using DNA analysis software (product name: DNAsis pro, manufactured by Hitachi Software Engineering Co., Ltd.), to thereby determine specific regions in the β-tubulin gene including nucleotide sequences specific to *Hamigera avellanea* which belongs to the genus *Hamigera* (SEQ ID NOS: 35).

2. Detection of Fungi Belonging to the Genus *Hamigera*

(1) Design of Primers

From regions having particularly high specificity to *Hamigera avellanea* on the 3'-end side in the determined nucleotide sequence regions, partial regions which satisfy the following four conditions were searched:

1) including several nucleotides which is specific to the genus;
2) having a GC content of about 30% to 80%;
3) having low possibility to cause self-annealing; and
4) having a Tm value of about 55 to 65° C.

Based on the nucleotide sequences of the above regions, five primer pairs were designed to search the effectiveness of detection of the fungi belonging to genus *Hamigera* by PCR reactions using DNAs extracted from the fungi as templates. As a result, in the case of using one of the five primer pairs, amplification of DNA was observed specifically to *Hamigera avellanea* and *Cladosporium cladosporioides*, and no amplification of DNA was observed to genomic DNAs extracted from other fungi as templates. That is, it was confirmed that the fungi belonging to the genus *Hamigera* can be detected. The primer pair confirmed to have the effectiveness is one which consists of the oligonucleotides represented by the nucleotide sequences set forth in SEQ ID NOS: 16 and 17. The primers used were synthesized by Sigma-Aldrich Japan (desalted products, 0.02 µmol scale) and purchased.

(2) Preparation of Samples

The fungi belonging to the genus *Hamigera*, other heat-resistant fungi, and general fungi shown in Table 12 were used as fungi to be used for evaluation of the effectiveness of the designed primers. These fungi were stored in Medical Mycology Research Center (MMRC), Chiba University, and the fungi deposited based on IFM numbers and T numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. (for general fungi) or 30° C. (for heat-resistant fungi) for 7 days.

TABLE 12

| Sample No. | Species | Strain No. |
| --- | --- | --- |
| N | (Negative Control) | — |
| 1 | *Hamigera avellanea* | T34 |
| 2 | *Byssochlamys fulva* | IAM12805 |
| 3 | *Byssochlamys nivea* | IAM12806 |
| 4 | *Talaromyces flavus* | T38 |
| 5 | *Talaromyces trachyspermus* | T24 |
| 6 | *Penicillium griseofulvum* | P14 |
| 7 | *Penicillium citirinum* | P15 |

TABLE 12-continued

| Sample No. | Species | Strain No. |
|---|---|---|
| 8 | Penicillium paneum | P16 |
| 9 | Penicillium oxalicum | P17 |

(3) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(4) PCR Reaction

1 µL of the genomic DNA solution prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 16 (20 pmol/µL) and 0.5 µL of the primer represented by the nucleotide sequence set forth in SEQ ID NO: 17 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 98° C. for 10 seconds, (ii) an annealing reaction at 63° C. for 1 minute, and (iii) an elongation reaction at 72° C. for 1 minute.

(5) Confirmation of Amplified Gene Fragment

Figure 21:
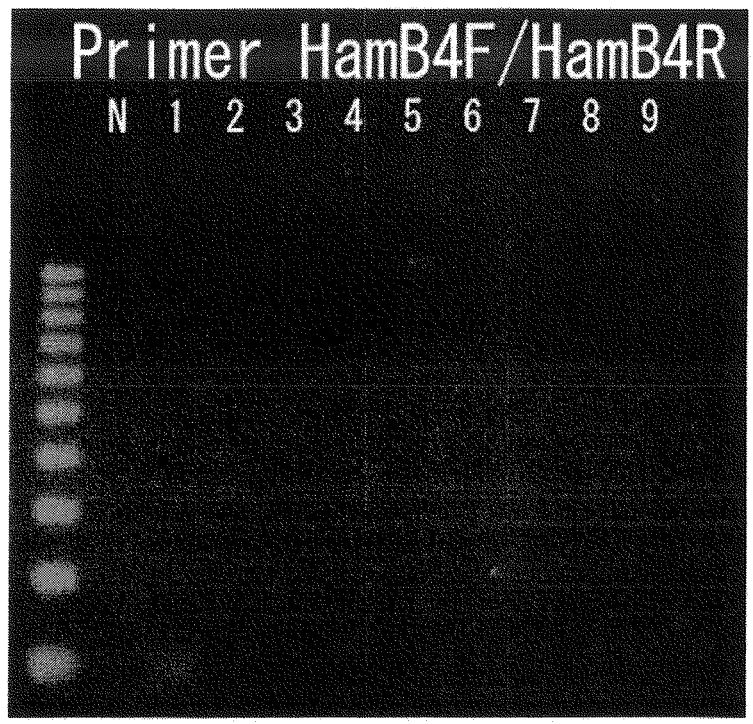
FIG. 21 is an electrophoretogram showing discrimination results of fungi belonging to the genus *Hamigera* in Example 1(D-1).

After the PCR reaction, 10 µL of a sample was collected from the PCR reaction solution and electrophoresed using a 2% agarose gel, and DNA was stained with S^/BR Safe DNA gel stain in 1×TAE (Invitrogen), to thereby confirm whether the amplified DNA fragment was present or not. The electrophoretogram in the agarose gel is shown in FIG. 21. The numbers in the electrophoretogram correspond the sample numbers in Table 12, and represent samples obtained by using DNAs extracted from the fungi having the corresponding sample numbers in Table 12.

As a result, in the case of the samples containing the genomic DNA of fungi belonging to the genus *Hamigera*, amplification of gene fragments of about 100 bp was confirmed (lane 1). On the other hand, in the case of the samples containing no genomic DNA of fungi belonging to the genus *Hamigera*, amplification of gene fragments was not confirmed. From the above-described results, it is understood that fungi belonging to the genus *Hamigera* can be specifically detected by using the above-described oligonucleotides (p) and (q).

(D-2) Detection and Discrimination of Fungi Belonging to the Genus *Hamigera*

(a) Preparation of Primers

The primers consisting of the oligonucleotides represented by the nucleotide sequences set forth in SEQ ID NOS: 16 and 17, designed in Example 1(D-1), were used.

(b) Preparation of Samples

As the fungi belonging to the genus *Hamigera* and the fungi belonging to the genus *Cladosporium*, *Hamigera avellanea* and *Cladosporium cladosporioides* shown in Table 13 were used. To confirm specificity of the oligonucleotides (p) to (q) to the β-tubulin genes of the fungi belonging to the genus *Hamigera* and the fungi belonging to the genus *Cladosporium*, other fungi shown in Tables 13 were used. These fungi were stored in Medical Mycology Research Center (MMRC), Chiba University, and the fungi deposited based on IFM numbers and T numbers or the like were obtained and used. As a positive control, *Hamigera avellanea* (the name of strains: T34) was used as a template of DNA.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. (for general fungi) or 30° C. (for heat-resistant fungi and *Aspergillus fumigatus*) for 7 days.

TABLE 13

| Sample No. | Species | Strain No. |
|---|---|---|
| P | Hamigera avellanea (Positive Control) | T34 |
| 1 | Hamigera avellanea | IAM42323 |
| 2 | Hamigera avellanea | IAM52241 |
| 3 | Aureobasidium pullulans | IAM41408 |
| 4 | Aureobasidium pullulans | IAM41409 |
| 5 | Aureobasidium pullulans | IAM41410 |
| 6 | Alternaria alternate | IAM41348 |
| 7 | Alternaria alternate | IAM52225 |
| 8 | Chaetomium globosum | IAM40868 |
| 9 | Chaetomium globosum | IAM4040873 |
| 10 | Paecilomyces variotii | IAM40913 |
| 11 | Paecilomyces variotii | IAM40915 |
| 12 | Paecilomyces variotii | IAM50292 |
| 13 | Trichoderma viride | IAM40938 |
| 14 | Trichoderma viride | IAM51045 |
| 15 | Cladosporium cladosporioides | IAM41450 |
| 16 | Fusarium oxysporium | IAM41530 |
| 17 | Fusarium oxysporium | IAM50002 |
| 18 | Aspergillus fumigatus | 07-77 |
| 19 | Aspergillus fumigatus | 07-81 |
| 20 | Aspergillus fumigatus | 07-87 |
| 21 | Aspergillus fumigatus | 07-91 |
| 22 | Aspergillus fumigatus | 07-93 |

(c) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(d) PCR Reaction

1 µL of the genomic DNA solution prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 16 (20 pmol/µL) and 0.5 µL of the primer represented by the nucleotide sequence set forth in SEQ ID NO: 17 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 97° C. for 10 seconds, (ii) an annealing reaction at 63° C. for 1 minute, and (iii) an elongation reaction at 72° C. for 1 minute.

(e) Confirmation of Amplified Gene Fragment

Figure 22:
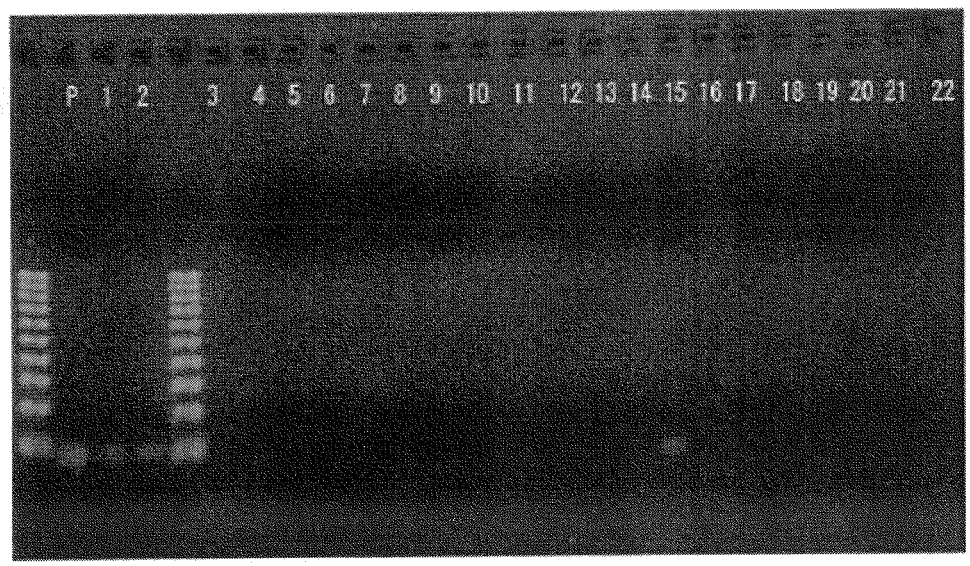
FIG. 22 is an electrophoretogram showing discrimination results of fungi belonging to the genus *Hamigera* in Example 1(D-2).

After the PCR reaction, 2 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 22. The numbers in the electrophoretogram correspond the sample numbers in Table 13, and represent samples obtained by using DNAs extracted from the fungi having the corresponding sample numbers in Table 13.

As a result, in the case of the samples containing the genomic DNA of fungi belonging to the genus *Hamigera* and the fungi belonging to the genus *Cladosporium*, amplification of gene fragments of about 100 bp was confirmed. On the other hand, in the case of the samples containing no genomic DNA of the fungi belonging to the genus *Hamigera* or the fungi belonging to the genus *Cladosporium*, amplification of gene fragments was not confirmed. From the above-described results, it is understood that the fungi belonging to the genus *Hamigera* and the fungi belonging to the genus *Cladosporium* can be specifically detected by using the above-described oligonucleotides (p) and (q).

(D-3) Detection and Discrimination of Fungi Belonging to the Genus *Hamigera*

(a) Design of Primers

Alignment analyses (DNAsis Pro) of nucleotide sequences of the β-tubulin genes of fungi including *Cladosporium* cladosporioides and *Hamigera avellanea* represented by SEQ ID NOS: 35 were performed to determine regions where significant differences in the nucleotide sequences were present. From regions having particularly high specificity to *Hamigera avellanea* on the 3'-end side in the determined nucleotide sequence regions, partial regions which satisfy the following four conditions were searched:
1) including several nucleotides which is specific to the genus;
2) having a GC content of about 30% to 80%;
3) having low possibility to cause self-annealing; and
4) having a Tm value of about 55 to 65° C.

Based on the nucleotide sequences of the above regions, seven pairs of primers were designed to examine effectiveness of discrimination of the genus *Hamigera* and *Cladosporium cladosporioides* by PCR reactions using DNAs extracted from a variety of fungi as templates. Specifically, it was examined that, in reactions using DNAs of the genus *Hamigera* as templates, DNA amplification products are observed at positions corresponding to the sizes expected from the designed primer pairs, while in reactions using genomic DNAs of the other fungi, no amplification product is observed. As a result, it was confirmed that the fungi belonging to the genus *Hamigera* and *Cladosporium cladosporioides* can be detected. The primer pairs confirmed to have the effectiveness are ones each of which consists of any two oligonucleotides represented by the nucleotide sequences set forth in SEQ ID NOS: 18 and 19, and the nucleotide sequences set forth in SEQ ID NOS: 20 and 21. The primers used were synthesized by Sigma-Aldrich Japan (desalted products, 0.02 µmol scale) and purchased.

(b) Preparation of Samples

The fungi belonging to the genus *Hamigera*, other heat-resistant fungi, and general fungi shown in Table 14 were used as fungi to be used for evaluation of the effectiveness of the designed primers. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: PearIcore potato dextrose agar medium, manufactured by Eiken Chemical Co., Ltd.) under culture conditions of 25° C. (for general fungi) or 30° C. (for heat-resistant fungi) for 7 days.

TABLE 14

| Sample No. | Species | Strain No. |
|---|---|---|
| N | (Negative Control) | — |
| 1 | Hamigera avellanea | T34 |
| 2 | Hamigera avellanea | IAM42323 |
| 3 | Hamigera avellanea | IAM52241 |
| 4 | Aureobasidium pullulans | IAM41408 |
| 5 | Aureobasidium pullulans | IAM41409 |
| 6 | Aureobasidium pullulans | IAM41410 |
| 7 | Alternaria alternate | IAM41348 |
| 8 | Alternaria alternate | IAM52220 |
| 9 | Chaetomium globosum | IAM40868 |
| 10 | Chaetomium globosum | IAM40869 |
| 11 | Chaetomium globosum | IAM40873 |
| 12 | Paecilomyces variotii | IAM40913 |
| 13 | Paecilomyces variotii | IAM40915 |
| 14 | Paecilomyces variotii | IAM50292 |
| 15 | Trichoderma viride | IAM40938 |
| 16 | Trichoderma viride | IAM51045 |
| 17 | Cladosporium cladosporioides | IAM41450 |
| 18 | Fusarium oxysporium | IAM41530 |
| 19 | Fusarium oxysporium | IAM50002 |

(c) Preparation of Genomic DNA

The respective fungi were collected from the agar media using platinum loops.

Genomic DNA solutions were prepared from the collected fungi using a genomic DNA preparation kit (PrepMan ultra (trade name) manufactured by Applied Biosystems). The concentration of each DNA solution was adjusted to 50 ng/µL.

(d) PCR Reaction

1 µL of the genomic DNA solution of *Hamigera avellanea* or *Cladosporium cladosporioides* prepared above as a DNA template, 13 µL of Pre Mix Taq (trade name, manufactured by TAKARA BIO INC.) and 10 µL of sterile distilled water were mixed, and 0.5 µL of the primer represented by the nucleotide sequence set forth in SEQ ID NO: 18 (20 pmol/µL) and 0.5 µL of the primer represented by the nucleotide sequence set forth in SEQ ID NO: 19 (20 pmol/µL) were added thereto, to thereby prepare 25 µL of a PCR reaction solution.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 97° C. for 10 seconds, (ii) an annealing reaction at 60° C. for 1 minute, and (iii) an elongation reaction at 72° C. for 1 minute.

(e) Confirmation of Amplified Gene Fragment

Figure 23:
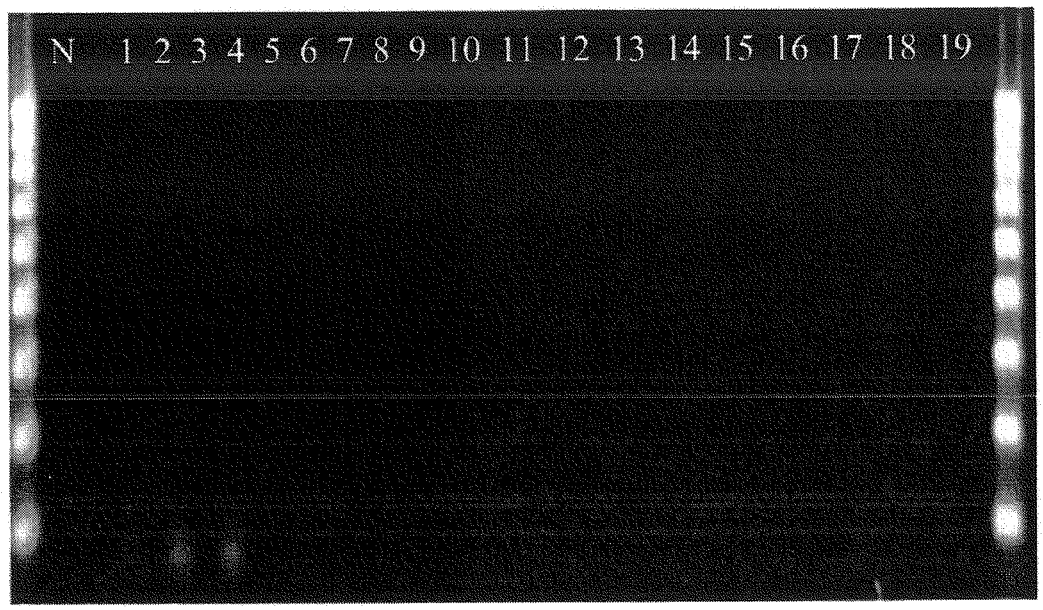
FIG. 23 is an electrophoretogram showing discrimination results of fungi belonging to the genus *Hamigera* in Example 1(D-3).

After the PCR reaction, 2 µL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 23. The numbers in the electrophoretogram correspond the sample numbers in Table 14, and represent samples obtained by using DNAs extracted from the fungi having the corresponding sample numbers in Table 14.

As a result, in the case of the samples containing the genomic DNA of the fungus belonging to the genus *Hamigera*, amplification of gene fragments of about 200 bp was confirmed (Sample Nos. 1 to 3). On the other hand, in the case of the sample containing the genomic DNA of the fungus belonging to the genus *Cladosporium* (Sample No. 17) and the samples containing no genomic DNA of the fungus belonging to the genus *Hamigera*, amplification of gene fragments was not confirmed. As is clear from the results, it is understood that the fungi in samples can be discriminated as the fungi belonging to the genus *Hamigera* or as the fungi belonging to the genus *Cladosporium* by using the oligonucleotides (r) and (s).

(D-4) Detection and Discrimination of Fungi Belonging to the Genus *Hamigera*

(a) Preparation of Primers

The primers consisting of the oligonucleotides represented by the nucleotide sequences set forth in SEQ ID NOS: 18 to 21, designed in Example 1(D-3), were used.

(b) Preparation of Samples

Figures 1, 24:
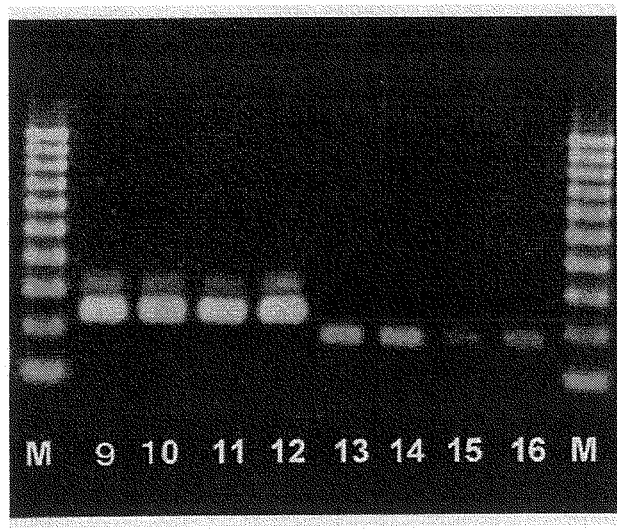

To confirm specificity of the oligonucleotides (r) to (u) to the β-tubulin genes of the fungi belonging to the genus *Hamigera*, each strains of *Hamigera striata* shown in FIG. 24-1 were used as the fungi belonging to the genus *Hamigera*.

The respective fungi were cultured in the same way as in (D-1) above.

(c) Preparation of Genomic DNA

Genomic DNA solutions were prepared in the same way as in (D-1) above. The concentration of each of the DNA solutions was adjusted to 50 ng/μl.

(d) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 18 (20 pmol/μL) and 0.5 μL of the primer represented by the nucleotide sequence set forth in SEQ ID NO: 19 (20 pmol/μL) were added thereto, to thereby prepare 25 μL of a PCR reaction solution. Further, a PCR reaction solution was prepared in the same way as above except that 0.5 μl of the primer represented by the nucleotide sequence set forth in SEQ ID NO: 20 (20 pmol/μl) and 0.5 μl of the primer represented by the nucleotide sequence set forth in SEQ ID NO: 21 (20 pmol/μl) were used instead of the above-mentioned primers.

The PCR reaction solutions were subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 61° C. to 59° C. for 1 minute, and (iii) an elongation reaction at 72° C. for 1 minute.

(e) Confirmation of Amplified Gene Fragment

After the PCR reaction, 4 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 24-1.

As a result, in either case of the reaction systems including the primers represented by the nucleotide sequences set forth in SEQ ID NOS: 18 and 19 and the primers represented by the nucleotide sequences set forth in SEQ ID NOS: 20 and 21, specific amplified DNA fragments were confirmed in all of the used strains of *Hamigera striata* (lanes 9 to 16). The bands were detected more clearly (lanes 9 to 12) in the cases of the reaction system including the primers represented by the nucleotide sequences set forth in SEQ ID NOS: 20 and 21. From the above-described results, it is understood that the fungi belonging to the genus *Hamigera* can be specifically detected with high accuracy regardless of the strains by using the oligonucleotides of the present invention.

(D-5) Detection and Discrimination of Fungi Belonging to the Genus *Hamigera*

(a) Preparation of Primers

The primers consisting of the oligonucleotides represented by the nucleotide sequences set forth in SEQ ID NOS: 18 to 21, designed in Example 1(D-3), were used.

(b) Preparation of Samples

To confirm specificity of the oligonucleotides (r) to (u) to the β-tubulin genes of the fungi belonging to the genus *Hamigera*, each strains of *Hamigera avellanea* shown in FIG. 24-2 were used as the fungi belonging to the genus *Hamigera*.

The respective fungi were cultured in the same way as in (D-1) above.

(c) Preparation of Genomic DNA

Genomic DNA solutions were prepared in the same way as in (D-1) above. The concentration of each of the DNA solutions was adjusted to 50 ng/μl.

(d) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 18 (20 pmol/μL) and 0.5 μL of the primer represented by the nucleotide sequence set forth in SEQ ID NO: 19 (20 pmol/μL) were added thereto, to thereby prepare 25 μL of a PCR reaction solution. Further, a PCR reaction solution was prepared in the same way as above except that 0.5 μl of the primer represented by the nucleotide sequence set forth in SEQ ID NO: 20 (20 pmol/μl) and 0.5 μl of the primer represented by the nucleotide sequence set forth in SEQ ID NO: 21 (20 pmol/μl) were used instead of the above-mentioned primers.

The PCR reaction solutions were subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(e) Confirmation of Amplified Gene Fragment

After the PCR reaction, 2 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretogram in the agarose gel is shown in FIG. 24-2.

As a result, in either case of the reaction systems including the primers represented by the nucleotide sequences set forth in SEQ ID NOS: 18 and 19 and the primers represented by the nucleotide sequences set forth in SEQ ID NOS: 20 and 21, specific amplified DNA fragments were confirmed in all of the used strains of *Hamigera avellanea* (lanes 1 to 8). From the above-described results, it is understood that the fungi belonging to the genus *Hamigera* can be specifically detected with high accuracy regardless of the strains by using the oligonucleotides of the present invention.

(D-6) Detection and Discrimination of Fungi Belonging to the Genus *Hamigera*

(a) Primers

The primers consisting of the oligonucleotides represented by the nucleotide sequences set forth in SEQ ID NOS: 18 to 21, designed in Example 1(D-3), were used.

(b) Preparation of Samples

To confirm specificity of the oligonucleotides (r) to (u) to the fungi belonging to the genus *Hamigera*, each strains of *Byssochlamys nivea* and *Byssochlamys fulva* shown in FIGS. 25-1 and 25-2 were used as the fungi of the genus *Byssochlamys* closely related to the genus *Hamigera*. As the fungi, fungi available from fungus deposition institutes, such as fungi stored in National Institute of Technology and Evaluation based on NBRC numbers and fungi stored in The Centraalbureau voor Schimmelcultures based on CBS numbers were obtained and used.

The respective fungi were cultured in the same way as in Example 1(D-1) above.

(c) Preparation of Genomic DNA

Genomic DNA solutions were prepared in the same way as in Example 1(D-1) above. The concentration of each of the DNA solutions was adjusted to 50 ng/μL.

(d) PCR Reaction

1 μL of the genomic DNA solution prepared above as a DNA template, 13 μL of Pre Mix Taq (trade name, manufactured by TAKARA BIO INC.) and 10 μL of sterile distilled water were mixed, and 0.5 μL of the primer represented by the nucleotide sequence set forth in SEQ ID NO: 18 (20 pmol/μL) and 0.5 μL of the primer represented by the nucleotide sequence set forth in SEQ ID NO: 19 (20 pmol/μL) were added thereto, to thereby prepare 25 μL of a PCR reaction solution. Further, a PCR reaction solution was prepared in the same way as above except that 0.5 μl of the primer represented by the nucleotide sequence set forth in SEQ ID NO: 20 (20 pmol/μl) and 0.5 μl of the primer represented by the nucleotide sequence set forth in SEQ ID NO: 21 (20 pmol/μl) were used instead of the above-mentioned primers.

The PCR reaction solutions were subjected to a gene amplification treatment using an automatic gene amplification device thermal cycler DICE (TAKARA BIO INC.). PCR reaction conditions were 35 cycles of (i) a thermal denaturation reaction at 95° C. for 1 minute, (ii) an annealing reaction at 59° C. for 1 minute, and (iii) an elongation reaction at 72° C. for 1 minute.

(e) Confirmation of Amplified Gene Fragment

After the PCR reaction, 2 μL of a sample was collected from the PCR reaction solution and electrophoresed using a 2% agarose gel, and DNA was stained with SYBR Safe DNA gel stain in 1×TAE (Invitrogen), to thereby confirm whether the amplified DNA fragment was present or not. The electrophoretograms in the agarose gel are shown in FIGS. 25-1 and 25-2.

As shown in FIG. 25-1, in the reaction system including the primers represented by the nucleotide sequences set forth in SEQ ID NOS: 18 and 19, gene amplification was observed at a position corresponding to the size of 200 bp not only in the case of *Hamigera avellanea* used as a positive control but also in the cases of part of the strains of *Byssochlamys fulva* (NBRC31877 and NBRC31878; lanes 9 and 10), while gene amplification was not observed in the cases of the other fungi belonging to the genus *Byssochlamys*. It is presumed that gene amplification of NBRC31877 and 31878 was observed because the strains are genetically related to the genus *Hamigera* compared with the other strains.

On the other hand, as shown in FIG. 25-2, in the reaction system including the primers represented by the nucleotide sequences set forth in SEQ ID NOS: 20 and 21, gene amplification was not observed in *Byssochlamys fulva* NBRC31877 and NBRC31878. From the above-described results, it is understood that only the fungi belonging to the genus *Hamigera* can be specifically detected with high accuracy without detecting the fungi belonging to the genus *Byssochlamys* by using the oligonucleotides set forth in SEQ ID NOS: 20 and 21.

As the above, it is understood that the heat-resistant fungi can be detected by using the oligonucleotides of the present invention. Specifically, the fungi belonging to the genus *Byssochlamys* can be discriminated by using the oligonucleotides of SEQ ID NOS: 1 and 2. The fungi belonging to the genus *Talaromyces* can be discriminated by using the oligonucleotides SEQ ID NOS: 3 to 11. The fungi belonging to the genus *Neosartorya* and *Aspergillus fumigatus* can be discriminated by using the oligonucleotides SEQ ID NOS: 12 to 15. Further, the fungi belonging to the genus *Neosartorya* can be discriminated from *Aspergillus fumigatus*. The fungi belonging to the genus *Hamigera* can be discriminated by using the oligonucleotides SEQ ID NOS: 16 to 21. Therefore, it is possible to discriminate the heat-resistant fungi by performing at least two, preferably all of the steps of detecting the heat-resistant fungi using the above oligonucleotides of the present invention.

Example 2

Detection of Fungi Belonging to the Genus *Byssochlamys*

(1) Design and Synthesis of Primers

Nucleotide sequence information of the ITS region and D1/D2 region of 28S rDNA of a variety of fungi (*Paecilomyces variotii*, *Hamigera avellanea*, *Talaromyces flavus*, *Talaromyces luteus*, *Talaromyces trachyspermus*, *Byssochlamys nivea*, *Byssochlamys fulva*, and *Neosartorya fischeri*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to the fungi belonging to the genus *Byssochlamys*. Based on the specified nucleotide sequence, primers consisting of oligonucleotides represented by the nucleotide sequences set forth in SEQ ID NOS: 36 to 39 were designed, and the primers were synthesized by E Genome order (FUJITSU SYSTEM SOLUTIONS LIMITED) (SEQ ID NOS: 36 and 37; 5 pmol scale, SEQ ID NOS: 38 and 39; 40 pmol scale; all of the primers are column-purified products) and purchased.

(2) Preparation of Samples

As the fungi belonging to the genus *Byssochlamys*. *Byssochlamys fulva* and *Byssochlamys* nivea were used. To confirm the specificity of the primers consisting of oligonucleotides represented by the nucleotide sequences of SEQ ID NOS: 36 to 39 to the ITS region and D1/D2 region of 28S rDNA of the fungi belonging to the genus *Byssochlamys*, the fungi shown in Table 15 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 15

| Sample No. | Species | Strain No. (IFM) |
|---|---|---|
| 1 | Byssochlamys fulva | 48421 |
| 2 | Byssochlamys nivea | 51244 |
| 3 | Talaromyces flavus | 42243 |
| 4 | Talaromyces luteus | 53241 |
| 5 | Talaromyces trachyspermus | 42247 |
| 6 | Talaromyces wortmannii | 52262 |
| 7 | Neosartorya ficheri | 46945 |
| 8 | Neosartorya spinosa | 46967 |
| 9 | Neosartorya glabra | 46949 |
| 10 | Neosartorya hiratsukae | 47036 |
| 11 | Alternaria alternata | 41348 |
| 12 | Aureobasidium pullulans | 41409 |
| 13 | Chaetomium globosum | 40869 |
| 14 | Fusarium oxysporium | 50002 |
| 15 | Trichoderma viride | 40938 |
| 16 | Cladosporium cladosporioides | 41450 |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 µL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/µL. The genomic DNA solution was used as a template DNA in the following LAMP reaction.

(4) Preparation of Reaction Solution for LAMP Reaction 12.5 µL of 2× Reaction Mix (Tris-HCl (pH 8.8) 40 mM, KCl 20 mM, $MgSO_4$ 16 mM, $(NH_4)_2SO_4$ 20 mM, 0.2% Tween20, Betaine 1.6 M, dNTPs 2.8 mM: Eiken Chemical Co., Ltd.; Loopamp DNA amplification reagent kit), 1 µL of the primer consisting of the oligonucleotide represented by the nucleotide sequence set forth in SEQ ID NO: 36 (LB1F3 primer: 5 pmol/µL), 1 µL of the primer consisting of the oligonucleotide represented by the nucleotide sequence set forth in SEQ ID NO: 37 (LB1B3 primer: 5 pmol/µL), 1 µL of the primer consisting of the oligonucleotide represented by the nucleotide sequence set forth in SEQ ID NO: 38 (LB1FIP primer: 40 pmol/µL), 1 µL of the primer consisting of the oligonucleotide represented by the nucleotide sequence set forth in SEQ ID NO: 39 (LB1BIP primer: 40 pmol/µL), 1 µL of Bst DNA Polymerase (8 U/25 µL, manufactured by Eiken Chemical Co., Ltd.) and 1 µL of the template DNA prepared above were mixed, and distilled water was added thereto, to thereby prepare a total of 25 µL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 35:
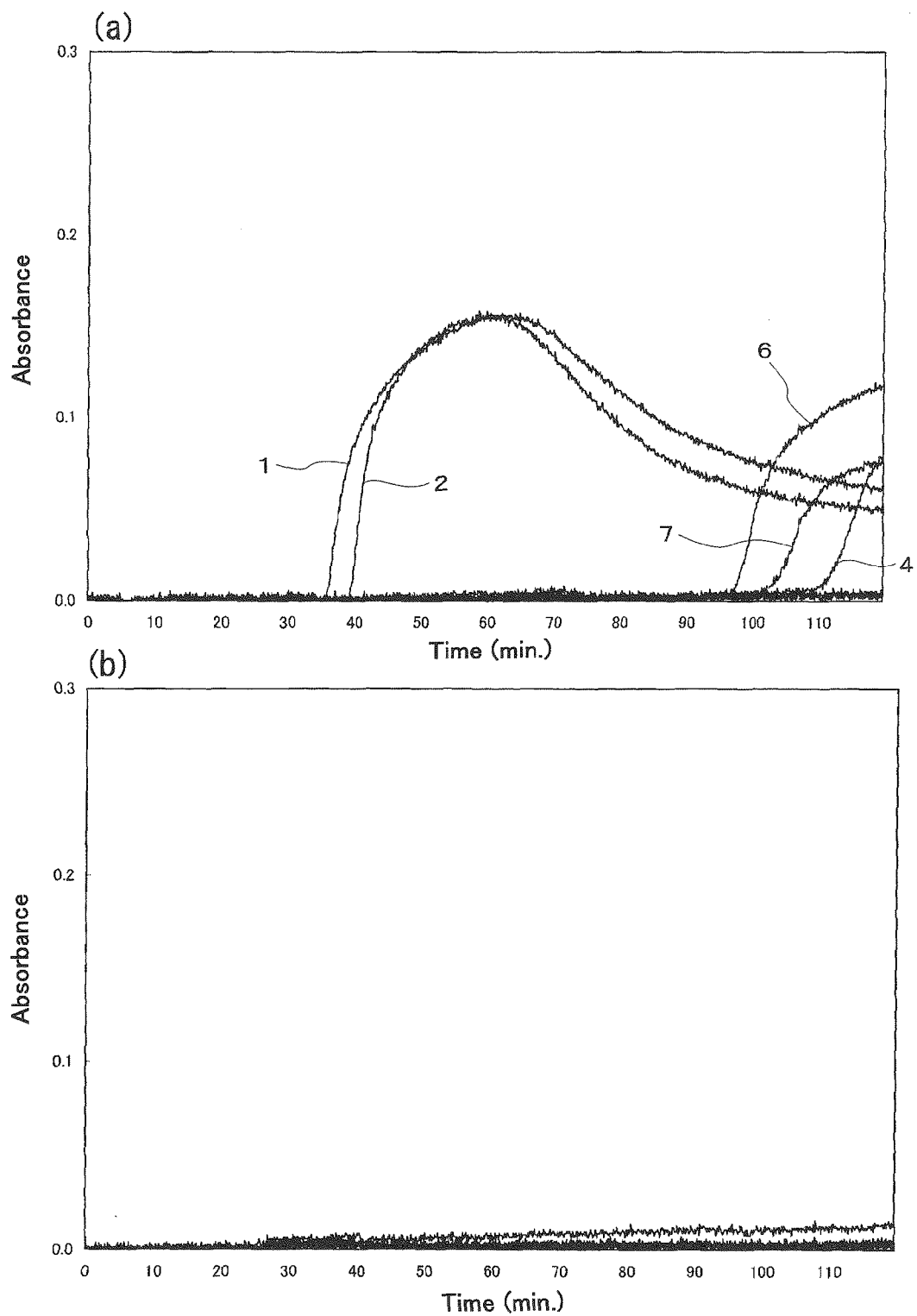
FIG. 35 is a graph illustrating the detection sensitivity of the ITS region and D1/D2 region of 28S rDNA of fungi belonging to the genus *Byssochlamys* by real-time turbidity monitoring method in Example 2. The numeral 1 denotes the detection sensitivity of a sample including genomic DNA derived from *Byssochlamys fulva* IFM48421 strain; the numeral 2 denotes the detection sensitivity of a sample including genomic DNA derived from *Byssochlamys nivea* IFM51244 strain, the numeral 4 denotes the detection sensitivity of a sample including genomic DNA derived from *Talaromyces luteus* IFM53241 strain, the numeral 6 denotes the detection sensitivity of a sample including genomic DNA derived from *Talaromyces wortmannii* IFM52262 strain, and the numeral 7 denotes the detection sensitivity of a sample including genomic DNA derived from *Neosartorya fischeri* IFM46945 strain.

Amplification of DNA was confirmed by an increase in turbidity of the reaction solution. The measurement results of the turbidity of the reaction solutions are shown in FIG. 35(a) and FIG. 35(b). Note that, FIG. 35(a) shows the results of samples Nos. 1 to 8 in Table 15, and FIG. 35(b) shows the results of samples Nos. 9 to 16 in Table 15.

As a result, the turbidity increases (i.e. the DNA synthesis and amplification reactions) were observed from about 30 minutes after the initiation of the reaction only in the systems where the genomic DNAs of the fungi belonging to the genus Byssochlamys were used as templates. The increase in the turbidity reached a peak 60 to 70 minutes after the start of the reaction, and then the turbidity was in a gradual decline.

On the other hand, in the systems where the genomic DNAs of the fungi other than the genus Byssochlamys were used, the turbidity increases in the reaction solutions were not observed for 90 minutes after the initiation of the reaction. It should be noted that, in the systems including genomic DNAs of fungi other than the genus Byssochlamys, the turbidity increases in the reaction solutions were observed from about 100 minutes after the start of the reaction. This is caused by amplification by reactions of the primers or annealing of a small amount of primers to sequences other than the target sequences due to a longer reaction time.

As is apparent from the above results, according to the present invention, it is possible to detect the genus Byssochlamys easily, rapidly, and specifically.

Example 3

Detection of Fungi Belonging to the Genus Neosartorya and Aspergillus fumigatus (1) Design and Synthesis of Primers Nucleotide sequence information of the β-tubulin genes of a variety of fungi (Neosartorya fischeri, Neosartorya glabra, Paecilomyces variotii, Hamigera avellanea, Talaromyces flavus, Talaromyces luteus, Talaromyces trachyspermus, Byssochlamys nivea, and Byssochlamys fulva) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to the fungi belonging to the genus Neosartorya and Aspergillus fumigatus. Based on the nucleotide sequences, primers consisting of oligonucleotides represented by the nucleotide sequences set forth in SEQ ID NOS: 40 to 45 were designed, and the primers were synthesized by E Genome order (FUJITSU SYSTEM SOLUTIONS LIMITED) (SEQ ID NOS: 40 and 41; 5 pmol scale, SEQ ID NOS: 42 and 43; 40 pmol scale, SEQ ID NOS: 44 and 45: 20 pmol scale; all of the primers are column-purified products) and purchased.

(2) Preparation of Samples

The fungi belonging to the genus Neosartorya and Aspergillus fumigatus shown in Tables 16 and 16-1 were used. To confirm the specificity of the primers consisting of oligonucleotides represented by the nucleotide sequences of SEQ ID NOS: 40 to 45 to the β-tubulin genes of the fungi, the fungi shown in Tables 16 and 16-1 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 16

| Sample No. | Species | Strain No. (IFM) |
|---|---|---|
| 1 | *Neosartorya ficheri* | 46945 |
| 2 | *Neosartorya spinosa* | 46967 |
| 3 | *Neosartorya glabra* | 46949 |
| 4 | *Neosartorya hiratsukae* | 47036 |
| 5 | *Talaromyces flavus* | 42243 |
| 6 | *Talaromyces luteus* | 53242 |
| 7 | *Talaromyces trachyspermus* | 42247 |
| 8 | *Talaromyces wortmannii* | 52262 |
| 9 | *Byssochlamys fulva* | 48421 |
| 10 | *Hamigera avellanea* | 42323 |
| 11 | *Alternaria alternata* | 41348 |
| 12 | *Aureobasidium pullulans* | 41409 |
| 13 | *Chaetomium globosum* | 40869 |
| 14 | *Fusarium oxysporium* | 50002 |
| 15 | *Trichoderma viride* | 40938 |
| 16 | *Cladosporium cladosporioides* | 41450 |

TABLE 16-1

| Sample No. | Species | Strain No. |
|---|---|---|
| 1 | *Neosartorya ficheri* | IFM46946 |
| 2 | *Neosartorya ficheri* | IFM46945 |
| 3 | *Neosartorya ficheri* | A176 |
| 4 | *Neosartorya spinosa* | IFM46968 |
| 5 | *Neosartorya spinosa* | IFM46967 |
| 6 | *Neosartorya spinosa* | A178 |
| 7 | *Neosartorya glabra* | IFM46949 |
| 8 | *Neosartorya glabra* | IFM46951 |
| 9 | *Neosartorya hiratsukae* | IFM46954 |
| 10 | *Neosartorya hiratsukae* | IFM47036 |
| 11 | *Aspergillus fumigatus* | A218 |
| 12 | *Aspergillus niger* | An15 |
| 13 | *Aspergillus terreus* | A229 |
| 14 | *Aspergillus flavus* | As17 |
| 15 | *Emericella nidulans* | As18 |
| 16 | NC (Negative Control) | DW |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 µL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/µL. The genomic DNA solution was used as a template DNA in the following LAMP reaction.

(4) Preparation of Reaction Solution for LAMP Reaction 12.5 µL of 2× Reaction Mix (Tris-HCl (pH 8.8) 40 mM, KCl 20 mM, MgSO$_4$ 16 mM, (NH$_4$)$_2$SO$_4$ 20 mM, 0.2% Tween20, Betaine 1.6 M, dNTPs 2.8 mM: Eiken Chemical Co., Ltd.; Loopamp DNA amplification reagent kit), 1 µL of the primer consisting of the oligonucleotide represented by the nucleotide sequence set forth in SEQ ID NO: 40 (LN1F3 primer: 5 pmol/µL), 1 µL of the primer consisting of the oligonucleotide represented by the nucleotide sequence set forth in SEQ ID NO: 41 (LN1B3 primer: 5 pmol/µL), 1 µL of the primer consisting of the oligonucleotide represented by the nucleotide sequence set forth in SEQ ID NO: 42 (LN1FIP primer: 40 pmol/µL), 1 µL of the primer consisting of the oligonucleotide represented by the nucleotide sequence set forth in SEQ ID NO: 43 (LN1BIP primer: 40 pmol/µL), 1 µL of the primer consisting of the oligonucleotide represented by the nucleotide sequence set forth in SEQ ID NO: 44 (LN1LF loop primer: 20 pmol/µL), 1 µL of the primer consisting of the oligonucleotide represented by the nucleotide sequence set forth in SEQ ID NO: 45 (LN1LB loop primer: 20 pmol/µL), 1 µL of Bst DNA Polymerase (8 U/25 µL, manufactured by Eiken Chemical Co., Ltd.) and 1 µL of the template DNA prepared above were mixed, and distilled water was added thereto, to thereby prepare a total of 25 µL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 36:
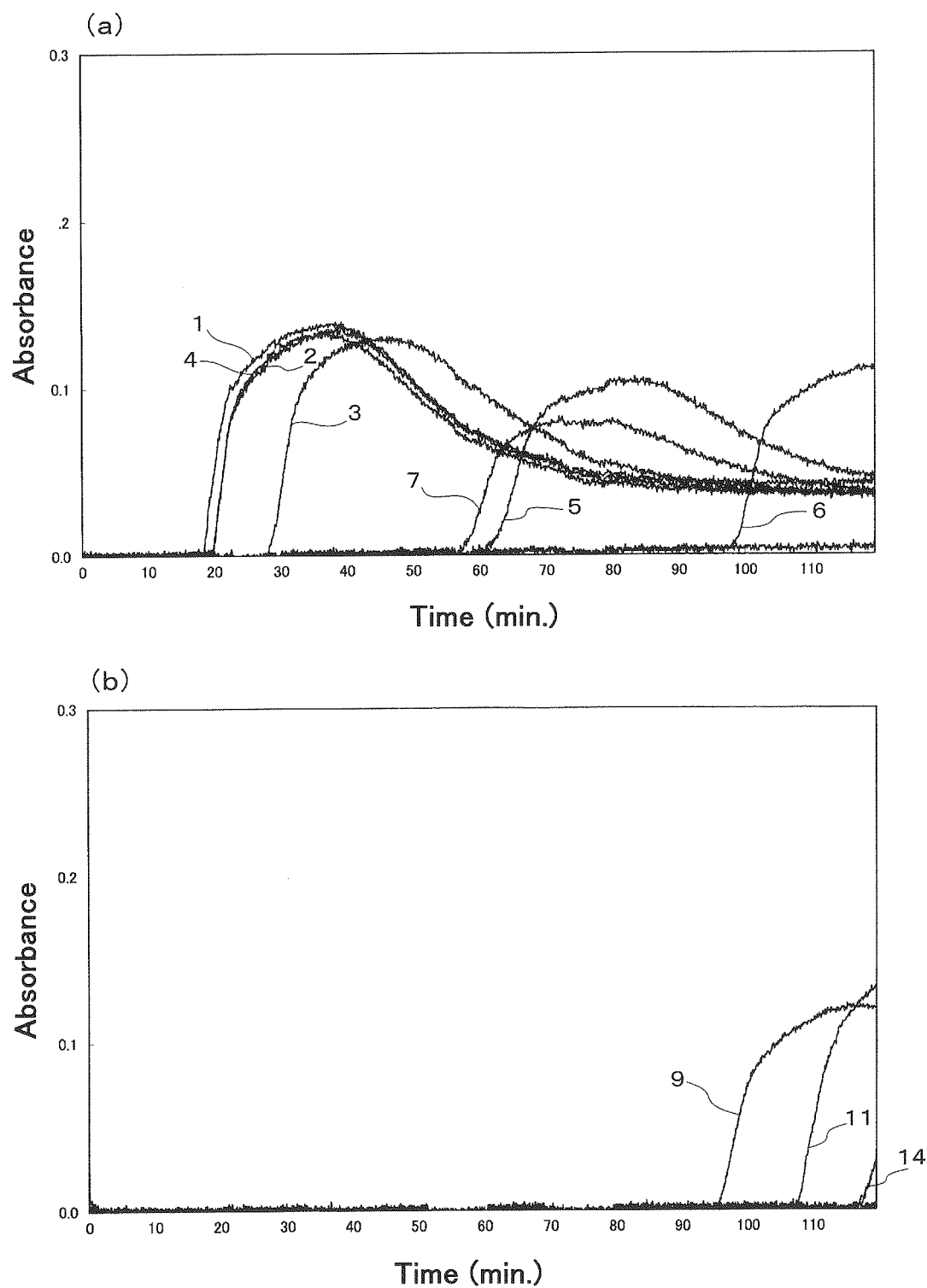
FIG. 36 is a graph illustrating the detection sensitivity of the β-tubulin genes of fungi belonging to the genus *Neosartorya* by real-time turbidity monitoring method in Example 3. The numeral 1 denotes the detection sensitivity of a sample including genomic DNA derived from *Neosartorya fischeri* IFM46945 strain; the numeral 2 denotes the detection sensitivity of a sample including genomic DNA derived from *Neosartorya spinosa* IFM46967 strain; the numeral 3 denotes the detection sensitivity of a sample including genomic DNA derived from *Neosartorya glabra* IFM46949 strain; the numeral 4 denotes the detection sensitivity of a sample including genomic DNA derived from *Neosartorya hiratsukae* IFM47036 strain; the numeral 5 denotes the detection sensitivity of a sample including genomic DNA derived from *Talaromyces flavus* IFM42243 strain; the numeral 6 denotes the detection sensitivity of a sample including genomic DNA derived from *Talaromyces luteus* IFM53242 strain; the numeral 7 denotes the detection sensitivity of a sample including genomic DNA derived from *Talaromyces trachyspermus* IFM42247 strain; the numeral 9 denotes the detection sensitivity of a sample including genomic DNA derived from *Byssochlamys fulva* IFM48421 strain; the numeral 11 denotes the detection sensitivity of a sample including genomic DNA derived from *Alternaria alternate* IFM41348 strain; the numeral 14 denotes the detection sensitivity of a sample including genomic DNA derived from *Fusarium oxysporium* IFM50002 strain.

Amplification of DNA was confirmed by an increase in turbidity of the reaction solution. The measurement results of the turbidity of the reaction solutions are shown in FIG. 36 and FIG. 36-1.

As a result, the turbidity increases (i.e. the DNA synthesis and amplification reactions) were observed from about 20 minutes after the initiation of the reaction only in the systems where the genomic DNAs of the fungi belonging to the genus *Neosartorya* (*Neosartorya spinosa*, *Neosartorya hiratsukae*, *Neosartorya ficheri*, and *Neosartorya glabra*) and *Aspergillus fumigatus* were used as templates.

On the other hand, in the systems where the genomic DNAs of the fungi other than the genus *Neosartorya* and *Aspergillus fumigatus* were used, the turbidity increases in the reaction solutions were not observed for 50 minutes after the initiation of the reaction. It should be noted that, in the systems including genomic DNAs of the fungi other than the genus *Neosartorya* and *Aspergillus fumigatus*, the turbidity increases in the reaction solutions were observed from about 60 minutes after the start of the reaction. This is caused by amplification by reactions of the primers or annealing of a small amount of primers to sequences other than the target sequences due to a longer reaction time.

As is apparent from the above results, according to the present invention, it is possible to detect the fungi belonging to the genus *Neosartorya* and *Aspergillus fumigatus* easily, rapidly, and specifically.

Example 4

Detection of Fungi Belonging to the Genus *Hamigera*

(1) Design and Synthesis of Primers

Nucleotide sequence information of the β-tubulin genes of a variety of fungi (*Paecilomyces variotii*, *Hamigera avellanea*, *Talaromyces flavus*, *Talaromyces luteus*, *Talaromyces trachyspermus*, *Byssochlamys nivea*, *Byssochlamys fulva*, and *Neosartorya fischeri*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to the fungi belonging to the genus *Hamigera*. Based on the specific nucleotide sequence, primers consisting of oligonucleotides represented by the nucleotide sequences set forth in SEQ ID NOS: 51 to 56 were designed, and the primers were synthesized by E Genome order (FUJITSU SYSTEM SOLUTIONS LIMITED) (SEQ ID NOS: 51 and 52; 5 pmol scale, SEQ ID NOS: 53 and 54; 40 pmol scale, SEQ ID NOS: 55 and 56: 20 pmol scale; all of the primers are column-purified products) and purchased.

(2) Preparation of Samples

As the fungi belonging to the genus *Hamigera*, *Hamigera avellanea* shown in Table 17 were used. To confirm the specificity of the primers consisting of oligonucleotides represented by the nucleotide sequences of SEQ ID NOS: 51 to 56 to the β-tubulin genes of the fungi belonging to the genus *Hamigera*, the other fungi shown in Table 17 were also used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 17

| Sample No. | Species | Strain No. (IFM) |
|---|---|---|
| 1 | Hamigera avellanea | 42323 |
| 2 | Hamigera avellanea | 52241 |
| 3 | Hamigera avellanea | 52957 |
| 4 | Byssochlamys fulva | 51213 |
| 5 | Byssochlamys nivea | 51245 |
| 6 | Paecilomyces variotii | 40913 |
| 7 | Paecilomyces variotii | 40915 |
| 8 | DW (Negative Control) | — |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 μL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/μL. The genomic DNA solution was used as a template DNA in the following LAMP reaction.

(4) Preparation of Reaction Solution for LAMP Reaction 12.5 μL of 2× Reaction Mix (Tris-HCl (pH 8.8) 40 mM, KCl 20 mM, $MgSO_4$ 16 mM, $(NH_4)_2SO_4$ 20 mM, 0.2% Tween20, Betaine 1.6 M, dNTPs 2.8 mM: Eiken Chemical Co., Ltd.; Loopamp DNA amplification reagent kit), 1 μL of the primer consisting of the oligonucleotide represented by the nucleotide sequence set forth in SEQ ID NO: 51 (LH2F3 primer: 5 pmol/μL), 1 μL of the primer consisting of the oligonucleotide represented by the nucleotide sequence set forth in SEQ ID NO: 52 (LH2B3 primer: 5 pmol/μL), 1 μL of the primer consisting of the oligonucleotide represented by the nucleotide sequence set forth in SEQ ID NO: 53 (LH2FIP primer: 40 pmol/μL), 1 μL of the primer consisting of the oligonucleotide represented by the nucleotide sequence set forth in SEQ ID NO: 54 (LH2BIP primer: 40 pmol/μL), 1 μL of the primer consisting of the oligonucleotide represented by the nucleotide sequence set forth in SEQ ID NO: 55 (LH2LF loop primer: 20 pmol/μL), 1 μL of the primer consisting of the oligonucleotide represented by the nucleotide sequence set forth in SEQ ID NO: 56 (LH2LB loop primer: 20 pmol/μL), 1 μL of Bst DNA Polymerase (8 U/25 μL, manufactured by Liken Chemical Co., Ltd.) and 1 μL of the template DNA prepared above were mixed, and distilled water was added thereto, to thereby prepare a total of 25 μL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simu)taneously, the turbidity of the reaction solution was measured (wavelength: 400 nm).

(6) Confirmation of DNA Amplification

Figure 37:
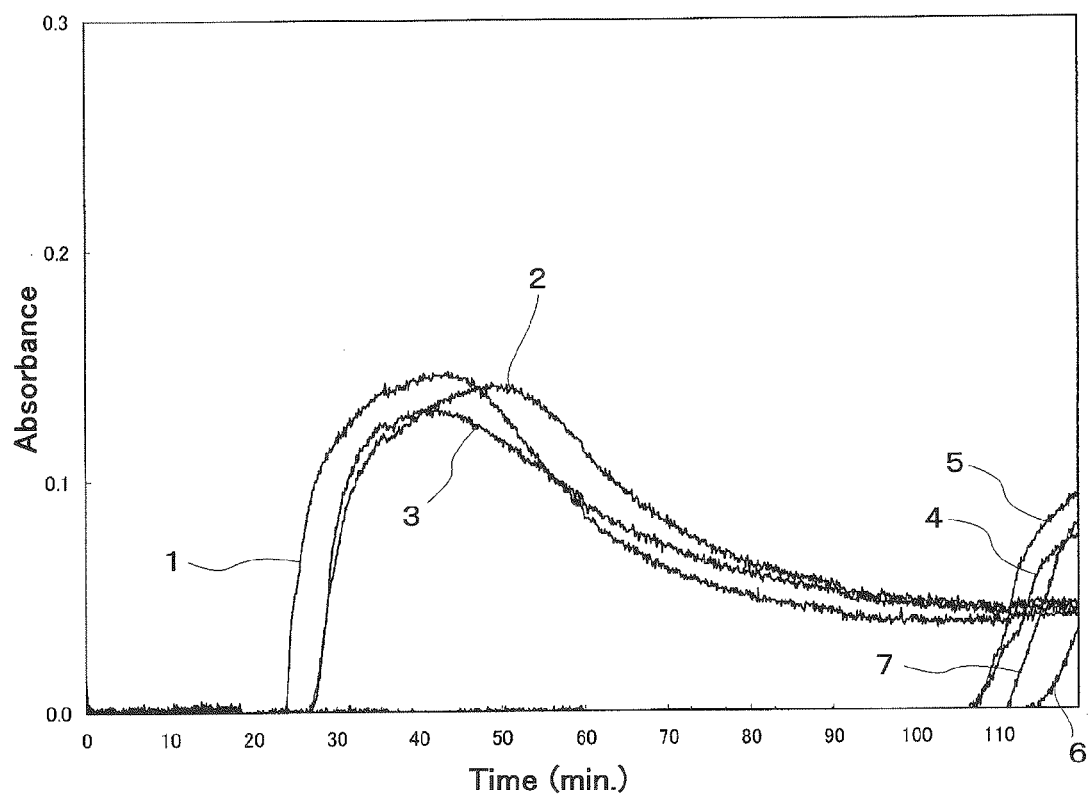
FIG. 37 is a graph illustrating the detection sensitivity of the β-tubulin genes of fungi belonging to the genus *Hamigera* by real-time turbidity monitoring method in Example 4. The numeral 1 denotes the detection sensitivity of a sample including genomic DNA derived from *Hamigera avellanea* IFM42323 strain; the numeral 2 denotes the detection sensitivity of a sample including genomic DNA derived from *Hamigera avellanea* IFM52241 strain; the numeral 3 denotes the detection sensitivity of a sample including genomic DNA derived from *Hamigera avellanea* IFM52957 strain; the numeral 4 denotes the detection sensitivity of a sample including genomic DNA derived from *Byssochlamys fulva* IFM51213 strain; the numeral 5 denotes the detection sensitivity of a sample including genomic DNA derived from *Byssochlamys nivea* IFM51245 strain; the numeral 6 denotes the detection sensitivity of a sample including genomic DNA derived from *Paecilomyces variotii* IFM40913 strain; the numeral 7 denotes the detection sensitivity of a sample including genomic DNA derived from *Paecilomyces variotii* IFM40915 strain.

Amplification of DNA was confirmed by an increase in turbidity of the reaction solution. The measurement results of the turbidity of the reaction solutions are shown in FIG. 37.

As a result, the turbidity increases (i.e. the DNA synthesis and amplification reactions) were observed from about 25 minutes after the initiation of the reaction only in the systems where the genomic DNAs of the fungi belonging to the genus *Hamigera* (*Hamigera avellanea*) were used as templates.

On the other hand, in the systems where the genomic DNAs of the fungi other than the fungi belonging to the genus *Hamigera* were used, the turbidity increases in the reaction solutions were not observed for 100 minutes after the initiation of the reaction. It should be noted that, in the systems including genomic DNAs of the fungi other than the genus *Hamigera*, the turbidity increases in the reaction solutions were observed from about 110 minutes after the start of the reaction. This is caused by amplification by reactions of the primers or annealing of a small amount of primers to sequences other than the target sequences due to a longer reaction time.

As is apparent from the above results, according to the present invention, it is possible to detect the fungi belonging to the genus *Hamigera* easily, rapidly, and specifically.

Example 5

Detection *Aspergillus fumigatus* (Discrimination *Aspergillus fumigatus* from the Fungi Belonging to the Genus *Neosartorya*)

(1) Design and Synthesis of Primers

Nucleotide sequence information of the β-tubulin genes of a variety of fungi (*Aspergillus fumigatus*, *Neosartorya fischeri*, and *Neosartorya spinosa*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to *Aspergillus fumigatus*. Based on the specified nucleotide sequence, primers consisting of oligonucleotides represented by the nucleotide sequences set forth in SEQ ID NOS: 46 to 50 were designed, and the primers were synthesized by E Genome order (FUJITSU SYSTEM SOLUTIONS LIMITED) (SEQ ID NOS: 46 and 47; 5 pmol scale, SEQ ID NOS: 48 and 49; 40 pmol scale, SEQ ID NO: 50: 20 pmol scale; all of the primers are column-purified products) and purchased.

(2) Preparation of Samples

The fungi belonging to the genus *Neosartorya* and *Aspergillus fumigatus* shown in Table 18 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 18

| Sample No. | Species | Strain No. |
| --- | --- | --- |
| 1 | Aspergillus fumigatus | A209 |
| 2 | Aspergillus fumigatus | A213 |
| 3 | Aspergillus fumigatus | A215 |
| 4 | Neosartorya ficheri | IFM46945 |
| 5 | Neosartorya ficheri | IFM46946 |
| 6 | Neosartorya spinosa | IFM46967 |
| 7 | Neosartorya spinosa | IFM46968 |
| 8 | DW (Negative Control) | — |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 µL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/µL. The genomic DNA solution was used as a template DNA in the following LAMP reaction.

(4) Preparation of Reaction Solution for LAMP Reaction 12.5 µL of 2× Reaction Mix (Tris-HCl (pH 8.8) 40 mM, KCl 20 mM, MgSO$_4$ 16 mM, (NH$_4$)$_2$SO$_4$ 20 mM, 0.2% Tween20, Betaine 1.6 M, dNTPs 2.8 mM: Eiken Chemical Co., Ltd.; Loopamp DNA amplification reagent kit), 1 µL of the primer consisting of the oligonucleotide represented by the nucleotide sequence set forth in SEQ ID NO: 46 (LAf2F3 primer: 5 pmol/µL), 1 µL of the primer consisting of the oligonucleotide represented by the nucleotide sequence set forth in SEQ ID NO: 47 (LAf2B3 primer: 5 pmol/µL), 1 µL of the primer consisting of the oligonucleotide represented by the nucleotide sequence set forth in SEQ ID NO: 48 (LAf2FIP primer: 40 pmol/µL), 1 µL of the primer consisting of the oligonucleotide represented by the nucleotide sequence set forth in SEQ ID NO: 49 (LAf2BIP primer: 40 pmol/µL), 1 µL of the primer consisting of the oligonucleotide represented by the nucleotide sequence set forth in SEQ ID NO: 50 (LAf2LB loop primer: 20 pmol/µL), 1 µL of Bst DNA Polymerase (8 U/25 µL, manufactured by Eiken Chemical Co., Ltd.) and 1 µL of the template DNA prepared above were mixed, and distilled water was added thereto, to thereby prepare a total of 25 µL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 38:
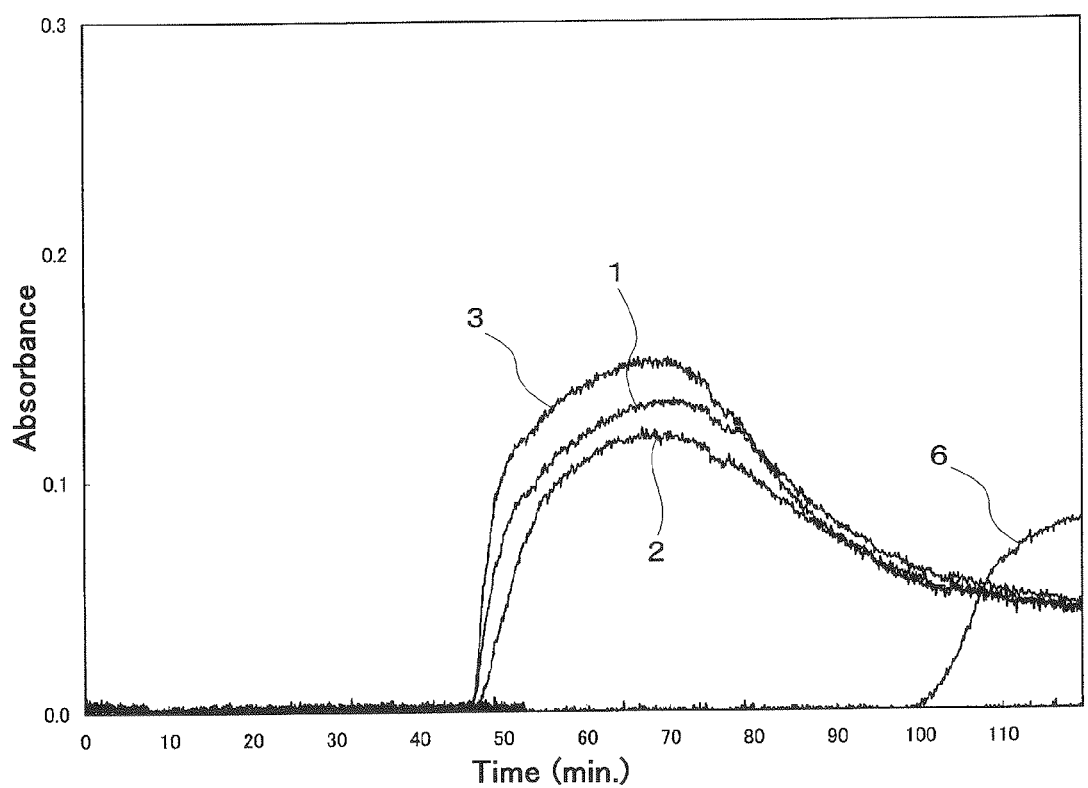
FIG. 38 is a graph illustrating the detection sensitivity of the β-tubulin genes of *Aspergillus fumigatus* by real-time turbidity monitoring method in Example 5. The numeral 1 denotes the detection sensitivity of a sample including genomic DNA derived from *Aspergillus fumigatus* A209 strain; the numeral 2 denotes the detection sensitivity of a sample including genomic DNA derived from *Aspergillus fumigatus* A213 strain; the numeral 3 denotes the detection sensitivity of a sample including genomic DNA derived from *Aspergillus fumigatus* A215 strain; the numeral 6 denotes the detection sensitivity of a sample including genomic DNA derived from *Neosartorya spinosa* IFM46967 strain.

Amplification of DNA was confirmed by an increase in turbidity of the reaction solution. The measurement results of the turbidity of the reaction solutions are shown in FIG. 38.

As a result, the turbidity increases (i.e. the DNA synthesis and amplification reactions) were observed from about 45 minutes after the initiation of the reaction only in the systems where the genomic DNAs of Aspergillus fumigatus were used as templates.

On the other hand, in the systems where the genomic DNAs of the fungi belonging to the genus Neosartorya were used, the turbidity increases in the reaction solutions were not observed for 90 minutes after the initiation of the reaction. It should be noted that, in the systems including genomic DNAs of the fungi belonging to the genus Neosartorya, the turbidity increases in the reaction solutions were observed from about 100 minutes after the start of the reaction. This is caused by amplification by reactions of the primers or annealing of a small amount of primers to sequences other than the target sequences due to a longer reaction time.

As is apparent from the above results, according to the present invention, it is possible to detect Aspergillus fumigatus easily, rapidly, and specifically.

In addition, it is possible to discrimination the fungi belonging to the genus Neosartorya from Aspergillus fumigatus by utilizing the method of detecting Aspergillus fumigatus shown in the present Example and the method of using primers consisting of oligonucleotides represented by the nucleotide sequences set forth in SEQ ID NOS: 40 to 45 shown in Example 3.

Example 6

Detection of *Talaromyces flavus*

(1) Design and Synthesis of Primers

Nucleotide sequence information of the β-tubulin genes of a variety of fungi (*Paecilomyces variotii, Hamigera avellanea, Talaromyces flavus, Talaromyces luteus, Talaromyces trachyspermus, Byssochlamys nivea, Byssochlamys fulva*, and *Neosartorya fischeri*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to *Talaromyces flavus*. Based on the specified nucleotide sequence, primers consisting of oligonucleotides represented by the nucleotide sequences set forth in SEQ ID NOS: 57 to 61 were designed, and the primers were synthesized by E Genome order (FUJITSU SYSTEM SOLUTIONS LIMITED) (SEQ ID NOS: 57 and 58; 5 pmol scale, SEQ ID NOS: 59 and 60; 40 pmol scale, SEQ ID NO: 61: 20 pmol scale; all of the primers are column-purified products) and purchased.

(2) Preparation of Samples

*Talaromyces flavus* shown in Table 19 were used. To confirm the specificity of the primers consisting of oligonucleotides represented by the nucleotide sequences of SEQ ID NOS: 57 to 61 to the β-tubulin genes of *Talaromyces flavus*, the other fungi shown in Table 19 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 19

| Sample No. | Species | Strain No. (IFM) |
| --- | --- | --- |
| 1 | Talaromyces flavus | 42243 |
| 2 | Talaromyces flavus | 52233 |
| 3 | Talaromyces luteus | 53242 |
| 4 | Talaromyces luteus | 53241 |
| 5 | Talaromyces trachyspermus | 42247 |
| 6 | Talaromyces trachyspermus | 52252 |
| 7 | Talaromyces wortmannii | 52255 |
| 8 | Talaromyces wortmannii | 52262 |
| 9 | Byssochlamys fulva | 48421 |

TABLE 19-continued

| Sample No. | Species | Strain No. (IFM) |
|---|---|---|
| 10 | Byssochlamys fluva | 51213 |
| 11 | Byssochlamys nivea | 51244 |
| 12 | Byssochlamys nivea | 51245 |
| 13 | Hamigera avellanea | 42323 |
| 14 | Hamigera avellanea | 52241 |
| 15 | Paecilomyces variotii | 40913 |
| 16 | Paecilomyces variotii | 40915 |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 μL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/μL. The genomic DNA solution was used as a template DNA in the following LAMP reaction.

(4) Preparation of Reaction Solution for LAMP Reaction 12.5 μL of 2× Reaction Mix (Tris-HCl (pH 8.8) 40 mM, KCl 20 mM, $MgSO_4$ 16 mM, $(NH_4)_2SO_4$ 20 mM, 0.2% Tween20, Betaine 1.6 M, dNTPs 2.8 mM: Eiken Chemical Co., Ltd.; Loopamp DNA amplification reagent kit), 1 μL of the primer consisting of the oligonucleotide represented by the nucleotide sequence set forth in SEQ ID NO: 57 (LTf2F3 primer: 5 pmol/μL), 1 μL of the primer consisting of the oligonucleotide represented by the nucleotide sequence set forth in SEQ ID NO: 58 (LTf2B3 primer: 5 pmol/μL), 1 μL of the primer consisting of the oligonucleotide represented by the nucleotide sequence set forth in SEQ ID NO: 59 (LTf2FIP primer: 40 pmol/μL), 1 μL of the primer consisting of the oligonucleotide represented by the nucleotide sequence set forth in SEQ ID NO: 60 (LTf2BIP primer: 40 pmol/μL), 1 μL of the primer consisting of the oligonucleotide represented by the nucleotide sequence set forth in SEQ ID NO: 61 (LTf2LB loop primer: 20 pmol/μL), 1 μL of Bst DNA Polymerase (8 U/25 μL, manufactured by Eiken Chemical Co., Ltd.) and 1 μL of the template DNA prepared above were mixed, and distilled water was added thereto, to thereby prepare a total of 25 μL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 39:
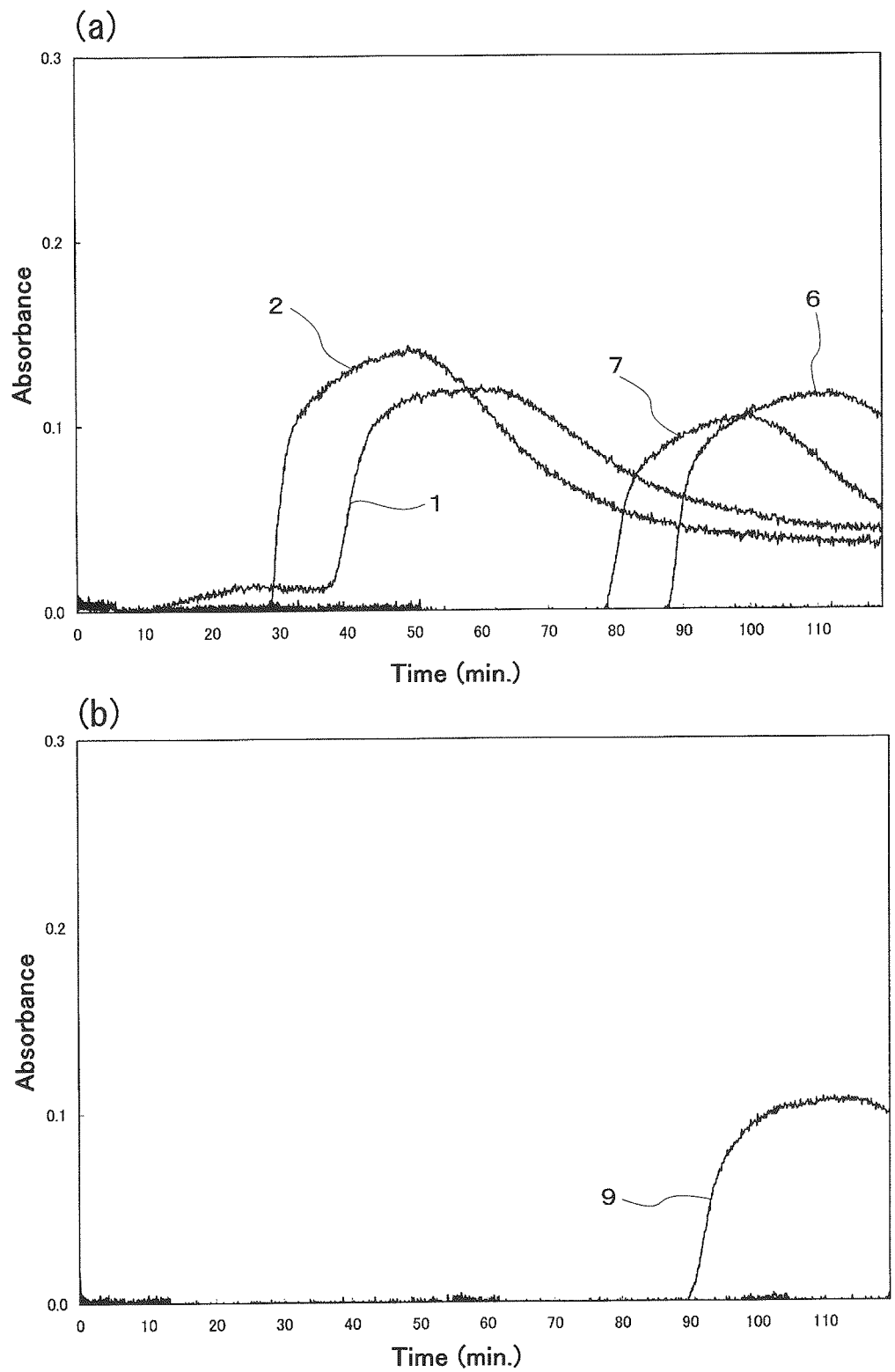
FIG. 39 is a graph illustrating the detection sensitivity of the β-tubulin genes of *Talaromyces flavus* by real-time turbidity monitoring method in Example 6. The numeral 1 denotes the detection sensitivity of a sample including genomic DNA derived from *Talaromyces flavus* IFM42243 strain; the numeral 2 denotes the detection sensitivity of a sample including genomic DNA derived from *Talaromyces flavus* IFM52233 strain; the numeral 6 denotes the detection sensitivity of a sample including genomic DNA derived from *Talaromyces trachyspermus* IFM52252 strain; the numeral 7 denotes the detection sensitivity of a sample including genomic DNA derived from *Talaromyces wortmannii* IFM52255 strain; the numeral 9 denotes the detection sensitivity of a sample including genomic DNA derived from *Byssochlarnys fulva* IFM48421 strain.

Amplification of DNA was confirmed by an increase in turbidity of the reaction solution. The measurement results of the turbidity of the reaction solutions are shown in FIG. 39(*a*) and FIG. 39(*b*). Note that, FIG. 39(*a*) shows the results of samples Nos. 1 to 8 in Table 19, and FIG. 39(*b*) shows the results of samples Nos. 9 to 16 in Table 19.

As a result, the turbidity increases (i.e. the DNA synthesis and amplification reactions) were observed from about 30 minutes after the initiation of the reaction only in the systems where the genomic DNAs of *Talaromyces flavus* were used as templates.

On the other hand, in the systems where the genomic DNAs of the fungi other than *Talaromyces flavus* were used, the turbidity increases in the reaction solutions were not observed for 70 minutes after the initiation of the reaction. It should be noted that, in the systems including genomic DNAs of the fungi other than *Talaromyces flavus*, increases in the turbidity of the reaction solutions were observed from about 80 minutes after the start of the reaction. This is caused by amplification by reactions of the primers or annealing of a small amount of primers to sequences other than the target sequences due to a longer reaction time.

As is apparent from the above results, according to the method of the present invention, it is possible to easily and rapidly detect *Talaromyces flavus* by measuring the turbidity in a reaction solution for a period from the start of the reaction to the time point of about 60 minutes, at which the turbidity significantly increases by DNA amplification of only *Talaromyces flavus*.

Example 7

Detection of *Talaromyces wortmannii*

(1) Design and Synthesis of Primers

Nucleotide sequence information of the β-tubulin genes of a variety of fungi (*Talaromyces wortmannii, Paecilomyces variotii, Hamigera avellanea, Talaromyces flavus, Talaromyces luteus, Talaromyces trachyspermus, Byssochlamys nivea, Byssochlamys fulva*, and *Neosartorya fischeri*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to *Talaromyces wortmannii*. Based on the specified nucleotide sequence regions, primers consisting of oligonucleotides represented by the nucleotide sequences set forth in SEQ ID NOS: 62 to 67 were designed, and the primers were synthesized by E Genome order (FUJITSU SYSTEM SOLUTIONS LIMITED) (SEQ ID NOS: 62 and 63; 5 pmol scale, SEQ ID NOS: 64 and 65; 40 pmol scale, SEQ ID NOS: 66 and 67: 20 pmol scale; all of the primers are column-purified products) and purchased.

(2) Preparation of Samples

*Talaromyces wortmannii* shown in Table 20 were used. To confirm the specificity of the primers consisting of oligonucleotides represented by the nucleotide sequences of SEQ ID NOS: 62 to 67 to the β-tubulin genes of *Talaromyces wortmannii*, the other fungi shown in Table 20 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 20

| Sample No. | Species | Strain No. (IFM) |
|---|---|---|
| 1 | Talaromyces wortmannii | 52255 |
| 2 | Talaromyces wortmannii | 52262 |
| 3 | Talaromyces flavus | 42243 |
| 4 | Talaromyces luteus | 53241 |
| 5 | Talaromyces trachyspermus | 42247 |
| 6 | Byssochlamys fulva | 48421 |
| 7 | Byssochlamys nivea | 51244 |
| 8 | Hamigera avellanea | 42323 |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 µL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/µL. The genomic DNA solution was used as a template DNA in the following LAMP reaction.

(4) Preparation of Reaction Solution for LAMP Reaction 12.5 µL of 2× Reaction Mix (Tris-HCl (pH 8.8) 40 mM, KCl 20 mM, MgSO$_4$ 16 mM, (NH$_4$)$_2$SO$_4$ 20 mM, 0.2% Tween20, Betaine 1.6 M, dNTPs 2.8 mM: Eiken Chemical Co., Ltd.; Loopamp DNA amplification reagent kit), 1 µL of the primer consisting of the oligonucleotide represented by the nucleotide sequence set forth in SEQ ID NO: 62 (LTw4F3 primer: 5 pmol/µL), 1 µL of the primer consisting of the oligonucleotide represented by the nucleotide sequence set forth in SEQ ID NO: 63 (LTw3B3 primer: 5 pmol/µL), 1 µL of the primer consisting of the oligonucleotide represented by the nucleotide sequence set forth in SEQ ID NO: 64 (LTw4FIP primer: 40 pmol/µL), 1 µL of the primer consisting of the oligonucleotide represented by the nucleotide sequence set forth in SEQ ID NO: 65 (LTw3BIP primer: 40 pmol/µL), 1 µL of the primer consisting of the oligonucleotide represented by the nucleotide sequence set forth in SEQ ID NO: 66 (LTw4LF loop primer: 20 pmol/µL), 1 µL of the primer consisting of the oligonucleotide represented by the nucleotide sequence set forth in SEQ ID NO: 67 (LTw3LB loop primer: 20 pmol/µL), 1 µL of Bst DNA Polymerase (8 U/25 µL, manufactured by Eiken Chemical Co., Ltd.) and 1 µL of the template DNA prepared above were mixed, and distilled water was added thereto, to thereby prepare a total of 25 µL of a reaction solution.

(5) LAMP Reaction

The reaction solution prepared above was subjected to a DNA amplification reaction at 63±2° C. for 60 minutes using a rea)-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 40:
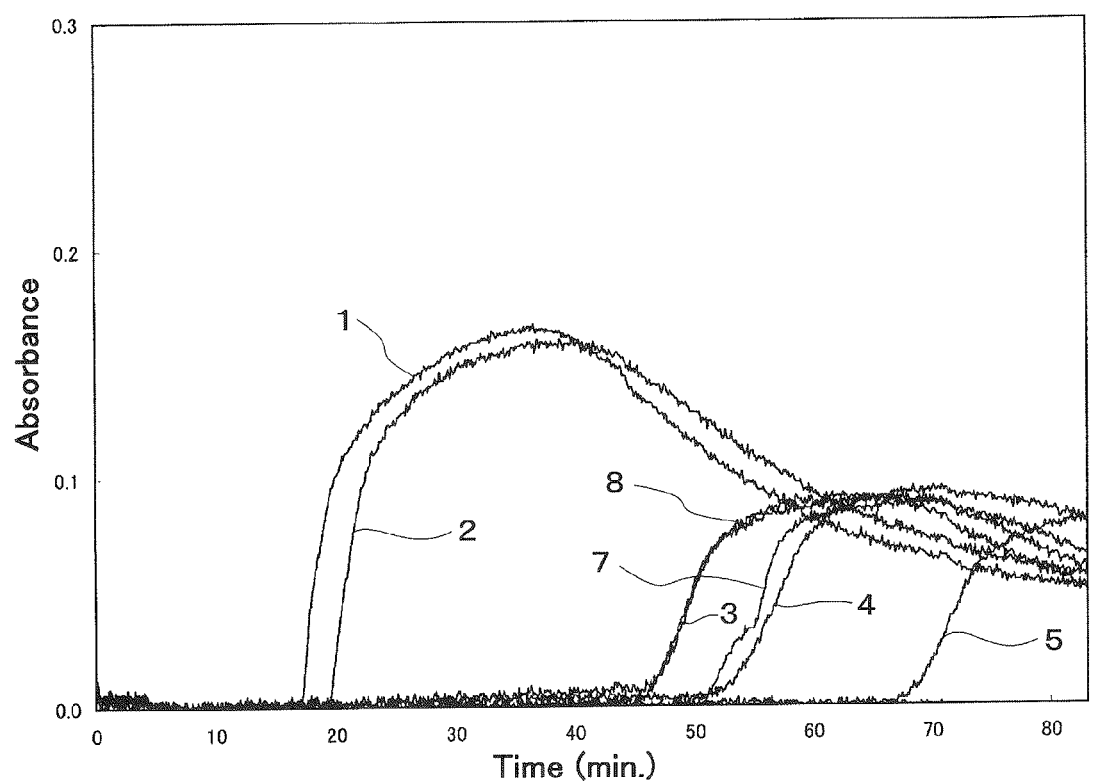
FIG. 40 is a graph illustrating the detection sensitivity of the β-tubulin genes of *Talaromyces wortmannii* by real-time turbidity monitoring method in Example 7. The numeral 1 denotes the detection sensitivity of a sample including genomic DNA derived from *Talaromyces wortmannii* IFM52255 strain; the numeral 2 denotes the detection sensitivity of a sample including genomic DNA derived from *Talaromyces wortmannii* IFM52262 strain; the numeral 3 denotes the detection sensitivity of a sample including genomic DNA derived from *Talaromyces flavus* IFM42243 strain; the numeral 4 denotes the detection sensitivity of a sample including genomic DNA derived from *Talaromyces luteus* IFM53241 strain; the numeral 5 denotes the detection sensitivity of a sample including genomic DNA derived from *Talaromyces trachyspermus* IFM42247 strain; the numeral 7 denotes the detection sensitivity of a sample including genomic DNA derived from *Byssochlamys nivea* IFM51244 strain; the numeral 8 denotes the detection sensitivity of a sample including genomic DNA derived from *Hamigera avellanea* IFM42323 strain.

Amplification of DNA was confirmed by an increase in turbidity of the reaction solution. The measurement results of the turbidity of the reaction solutions are shown in FIG. 40.

As a result, the turbidity increases (i.e. the DNA synthesis and amplification reactions) were observed from about 20 minutes after the initiation of the reaction only in the systems where the genomic DNAs of *Talaromyces wortmannii* were used as templates.

On the other hand, in the systems where the genomic DNAs of the fungi other than *Talaromyces wortmannii* were used, the turbidity increases in the reaction solutions were not observed for 40 minutes after the initiation of the reaction. It should be noted that, in the systems including genomic DNAs of the fungi other than *Talaromyces wortmannii*, increases in the turbidity of the reaction solutions were observed from about 50 minutes after the start of the reaction. This is caused by amplification by reactions of the primers or annealing of a small amount of primers to sequences other than the target sequences due to a longer reaction time.

As is apparent from the above results, according to the present invention, it is possible to detect *Talaromyces wortmannii* easily, rapidly, and specifically.

Example 8

Detection of *Talaromyces luteus*

(1) Design and Synthesis of Primers

Nucleotide sequence information of the β-tubulin genes of a variety of fungi (*Talaromyces luteus, Paecilomyces variotii, Hamigera avellanea, Talaromyces flavus, Talaromyces wortmannii, Talaromyces trachyspermus, Byssochlamys nivea, Byssochlamys fulva*, and *Neosartorya fischeri*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to *Talaromyces luteus*. Based on the specified nucleotide sequence, primers consisting of oligonucleotides represented by the nucleotide sequences set forth in SEQ ID NOS: 68 to 72 were designed, and the primers were synthesized by E Genome order (FUJITSU SYSTEM SOLUTIONS LIMITED) (SEQ ID NOS: 68 and 69; 5 pmol scale, SEQ ID NOS: 70 and 71; 40 pmol scale, SEQ ID NO: 72: 20 pmol scale; all of the primers are column-purified products) and purchased.

(2) Preparation of Samples

*Talaromyces luteus* shown in Table 21 were used. To confirm the specificity of the primers consisting of oligonucleotides represented by the nucleotide sequences of SEQ ID NOS: 68 to 72 to the β-tubulin genes of *Talaromyces luteus*, the other fungi shown in Table 21 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 21

| Sample No. | Species | Strain No. (IFM) |
|---|---|---|
| 1 | *Talaromyces luteus* | 53242 |
| 2 | *Talaromyces luteus* | 53241 |
| 3 | *Talaromyces flavus* | 42243 |
| 4 | *Talaromyces trachyspermus* | 42247 |
| 5 | *Talaromyces wortmannii* | 52262 |
| 6 | *Byssochlamys fulva* | 48421 |
| 7 | *Neosartorya ficheri* | 46945 |
| 8 | *Neosartorya spinosa* | 46967 |
| 9 | *Neosartorya glabra* | 46949 |
| 10 | *Neosartorya hiratsukae* | 47036 |
| 11 | *Alternaria alternata* | 41348 |
| 12 | *Aureobasidium pullulans* | 41409 |
| 13 | *Chaetomium globosum* | 40869 |
| 14 | *Fusarium oxysporium* | 50002 |
| 15 | *Trichoderma viride* | 40938 |
| 16 | *Cladosporium cladosporioides* | 41450 |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 µL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/μL. The genomic DNA solution was used as a template DNA in the following LAMP reaction.

(4) Preparation of Reaction Solution for LAMP Reaction 12.5 μL of 2× Reaction Mix (Tris-HCl (pH 8.8) 40 mM, KCl 20 mM, $MgSO_4$ 16 mM, $(NH_4)_2SO_4$ 20 mM, 0.2% Tween20, Betaine 1.6 M, dNTPs 2.8 mM: Eiken Chemical Co., Ltd.; Loopamp DNA amplification reagent kit), 1 μL of the primer consisting of the oligonucleotide represented by the nucleotide sequence set forth in SEQ ID NO: 68 (LTl1F3 primer: 5 pmol/μL), 1 μL of the primer consisting of the oligonucleotide represented by the nucleotide sequence set forth in SEQ ID NO: 69 (LTl1B3 primer: 5 pmol/μL), 1 μL of the primer consisting of the oligonucleotide represented by the nucleotide sequence set forth in SEQ ID NO: 70 (LTl1FIP primer: 40 pmol/μL), 1 μL of the primer consisting of the oligonucleotide represented by the nucleotide sequence set forth in SEQ ID NO: 71 (LTl1BIP primer: 40 pmol/μL), 1 μL of the primer consisting of the oligonucleotide represented by the nucleotide sequence set forth in SEQ ID NO: 72 (LTl1LF loop primer: 20 pmol/μL), 1 μL of Bst DNA Polymerase (8 U/25 μL, manufactured by Eiken Chemical Co., Ltd.) and 1 μL of the template DNA prepared above were mixed, and distilled water was added thereto, to thereby prepare a total of 25 μL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 41:
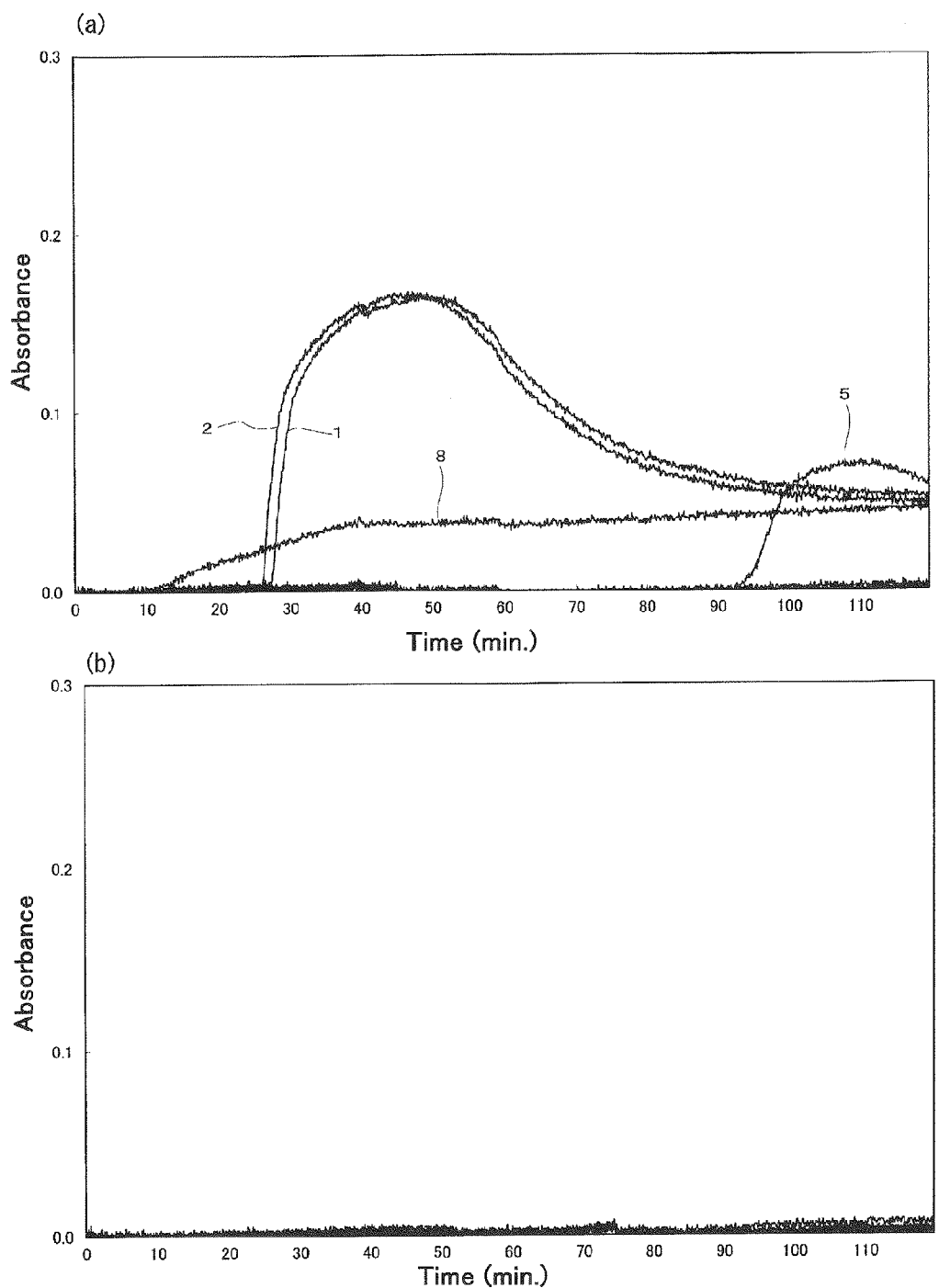
FIG. 41 is a graph illustrating the detection sensitivity of the β-tubulin genes of *Talaromyces luteus* by real-time turbidity monitoring method in Example 8. The numeral 1 denotes the detection sensitivity of a sample including genomic DNA derived from *Talaromyces luteus* IFM53242 strain; the numeral 2 denotes the detection sensitivity of a sample including genomic DNA derived from *Talaromyces luteus* IFM53241 strain; the numeral 5 denotes the detection sensitivity of a sample including genomic DNA derived from *Talaromyces wortmannii* IFM52262 strain; the numeral 8 denotes the detection sensitivity of a sample including genomic DNA derived from *Neosartorya spinosa* IFM46967 strain.

Amplification of DNA was confirmed by an increase in turbidity of the reaction solution. The measurement results of the turbidity of the reaction solutions are shown in FIG. 41(*a*) and FIG. 41(*b*). Note that, FIG. 41(*a*) shows the results of samples Nos. 1 to 8 in Table 21, and FIG. 41(*b*) shows the results of samples Nos. 9 to 16 in Table 21.

As a result, the sudden turbidity increases (i.e. the DNA synthesis and amplification reactions) were observed from about 25 minutes after the initiation of the reaction only in the systems where the genomic DNAs of *Talaromyces luteus* were used as templates.

On the other hand, in the systems where the genomic DNAs of the fungi other than *Talaromyces luteus* were used, the turbidity increases in the reaction solutions were not observed for 80 minutes after the initiation of the reaction. It should be noted that, in the systems including genomic DNAs of the fungi other than *Talaromyces luteus*, increases in the turbidity of the reaction solutions were observed from about 90 minutes after the start of the reaction. This is caused by amplification by reactions of the primers or annealing of a small amount of primers to sequences other than the target sequences due to a longer reaction time. Although a gradual increase in the turbidity was observed from 10 minutes after the start of the reaction in the sample number 8, the increase is considered to be caused not by amplification of the gene corresponding to the nucleotide sequence specific to the genomic DNA but by gradual gene amplification by a reaction of the primers. The gradual gene amplification reaction can be clearly differentiated from the conventional LAMP reaction, because the measurement results between the both reactions are clearly different. That is, the LAMP reaction shows the results obtained by amplification caused by annealing of primers, while the gradual gene amplification shows the results having no peak of the turbidity increase.

As is apparent from the above results, according to the present invention, it is possible to identify *Talaromyces luteus* easily, rapidly, and specifically.

Example 9

Detection of *Talaromyces flavus* and *Talaromyces trachyspermus*

(1) Design and Synthesis of Primers

Nucleotide sequence information of the ITS region and D1/D2 region of 28S rDNA of a variety of fungi (*Talaromyces flavus, Talaromyces trachyspermus, Paecilomyces variotii, Hamigera avellanea, Talaromyces wortmannii, Byssochlamys nivea, Byssochlamys fulva,* and *Neosartorya fischeri*) was determined by a sequencing method. Based on the sequence information, alignment analyses were performed using DNA analysis software (product name: DNAsis pro, manufactured by Hitachi Software Engineering Co., Ltd.), to thereby determine nucleotide sequences specific to *Talaromyces flavus* and *Talaromyces trachyspermus*. Based on the specified nucleotide sequence, primers consisting of oligonucleotides represented by the nucleotide sequences set forth in SEQ ID NOS: 73 to 78 were designed, and the primers were synthesized by E Genome order (FUJITSU SYSTEM SOLUTIONS LIMITED) (SEQ ID NOS: 73 and 74; 5 pmol scale, SEQ ID NOS: 75 and 76; 40 pmol scale, SEQ ID NOS: 77 and 78; 20 pmol scale; all of the primers are column-purified products) and purchased.

(2) Preparation of Samples

*Talaromyces flavus* and *Talaromyces trachyspermus* shown in Table 22 were used. To confirm the specificity of the primers consisting of oligonucleotides represented by the nucleotide sequences of SEQ ID NOS: 73 to 78 to the ITS region and D1/D2 region of 28S rDNA of the fungi, the other fungi shown in Table 22 were used. These fungi were stored in Medical Mycology Research Center (MMRC), Chiba University, and the fungi deposited based on IFM numbers or the like were obtained and used.

The respective fungi were cultured under optimum conditions. The culture was performed using a potato dextrose medium (trade name: Pearlcore potato dextrose agar medium, manufactured by Eiken Chemical Co., Ltd.) under culture conditions of 25° C. for 7 days.

TABLE 22

| Sample No. | Species | Strain No. |
|---|---|---|
| 1 | *Talaromyces flavus* | IFM42243 |
| 2 | *Talaromyces flavus* | IFM52233 |
| 3 | *Talaromyces flavus* | T38 |
| 4 | *Talaromyces luteus* | IFM53242 |
| 5 | *Talaromyces luteus* | IFM53241 |
| 6 | *Talaromyces trachyspermus* | IFM42247 |
| 7 | *Talaromyces trachyspermus* | IFM52252 |
| 8 | *Talaromyces wortmannii* | IFM52262 |
| 9 | *Talaromyces wortmannii* | IFM52255 |
| 10 | *Byssochlamys fulva* | IFM48421 |
| 11 | *Byssochlamys nivea* | IFM51245 |
| 12 | *Penicillium griseofulvum* | IFM54313 |
| 13 | *Penicillium citirinum* | IFM54314 |
| 14 | *Hamigera avellanea* | IFM42323 |
| 15 | *Neosartorya ficheri* | IFM46945 |
| 16 | NC (Negative Control) | DW |

(3) Preparation of Genomic DNA

Genomic DNA solutions were prepared from the collected fungi using a genomic DNA preparation kit (PrepMan ultra (trade name) manufactured by Applied Biosystems). Specifically, several colonies were collected from each medium, and the fungus was suspended in 200 μL of a reagent supplied with the kit and dissolved by a heat treatment at 100° C. for 10 minutes. Centrifugation was performed at 14,800 rpm for 5 minutes, and the supernatant was collected. The concentration of the resultant genomic DNA solution was adjusted to 50 ng/μL. The genomic DNA solution was used as a template DNA in the following LAMP reaction.

(4) Preparation of Reaction Solution for LAMP Reaction 12.5 μL of 2× Reaction Mix (Tris-HCl (pH 8.8) 40 mM, KCl 20 mM, MgSO$_4$ 16 mM, (NH$_4$)$_2$SO$_4$ 20 mM, 0.2% Tween20, Betaine 1.6 M, dNTPs 2.8 mM: Eiken Chemical Co., Ltd.; Loopamp DNA amplification reagent kit), 1 μL of the primer consisting of the oligonucleotide represented by the nucleotide sequence set forth in SEQ ID NO: 73 (LT1F3 primer: 5 pmol/μL), 1 μL of the primer consisting of the oligonucleotide represented by the nucleotide sequence set forth in SEQ ID NO: 74 (LT1B3 primer: 5 pmol/μL), 1 μL of the primer consisting of the oligonucleotide represented by the nucleotide sequence set forth in SEQ ID NO: 75 (LT1HP primer: 40 pmol/μL), 1 μL of the primer consisting of the oligonucleotide represented by the nucleotide sequence set forth in SEQ ID NO: 76 (LT1BIP primer: 40 pmol/μL), 1 μL of the primer consisting of the oligonucleotide represented by the nucleotide sequence set forth in SEQ ID NO: 77 (LT1LF primer: 20 pmol/μL), 1 μL of the primer consisting of the oligonucleotide represented by the nucleotide sequence set forth in SEQ ID NO: 78 (LT1LB loop primer: 20 pmol/μL), 1 μL of Bst DNA Polymerase (8 U/25 μL, manufactured by Eiken Chemical Co., Ltd.) and 1 μL of the template DNA prepared above were mixed, and distilled water was added thereto, to thereby prepare a total of 25 μL of a reaction solution.

(5) LAMP Reaction

The reaction solution prepared above was subjected to a DNA amplification reaction at 63±2° C. for 60 minutes using a real-time turbidity measuring apparatus Loopamp RT-160C (manufactured by Eiken Chemical Co., Ltd.). Simultaneously, the turbidity of the reaction solution was measured (wavelength: 400 nm).

(6) Confirmation of DNA Amplification

Figure 42:
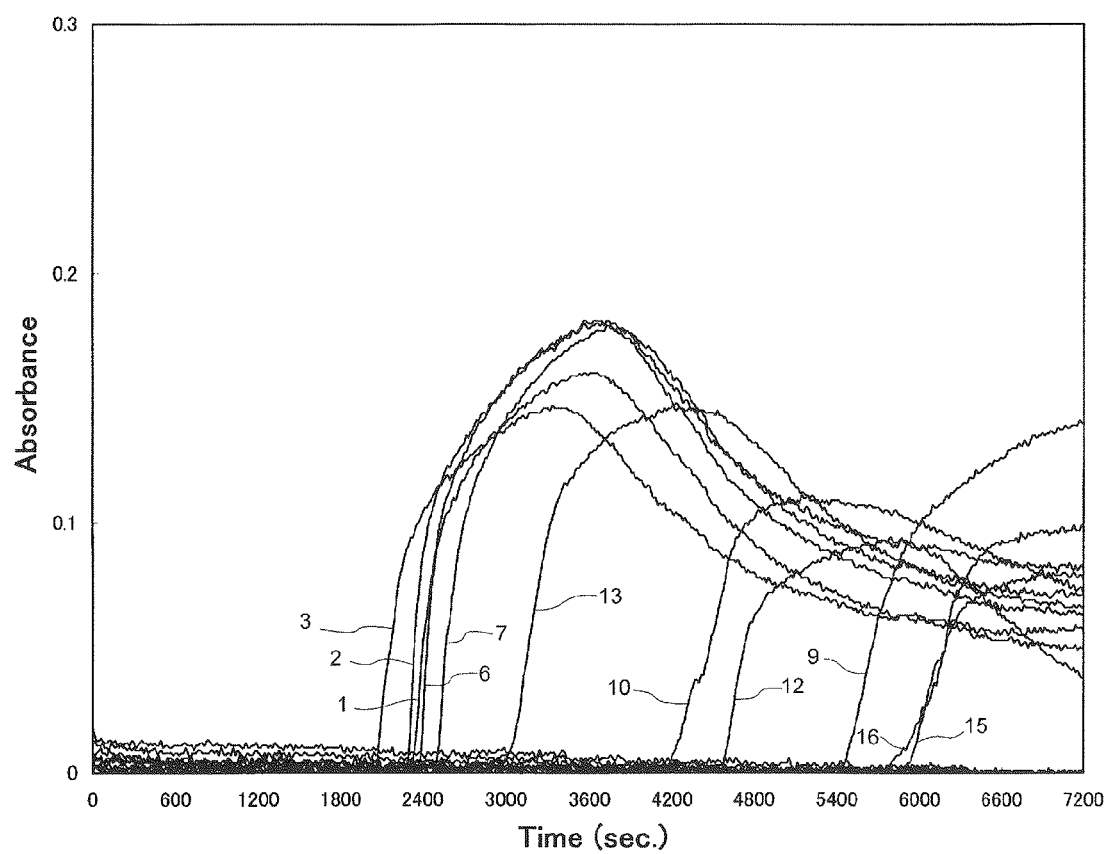
FIG. 42 is a graph illustrating the detection sensitivity of the ITS region and D1/D2 region of 28S rDNA of *Talaromyces flavus* and *Talaromyces trachyspermus* by real-time turbidity monitoring method in Example 9. The numeral 1 denotes the detection sensitivity of a sample including genomic DNA derived from *Talaromyces flavus* IFM42243 strain; the numeral 2 denotes the detection sensitivity of a sample including genomic DNA derived from *Talaromyces flavus* IFM52233 strain; the numeral 3 denotes the detection sensitivity of a sample including genomic DNA derived from *Talaromyces flavus* T38 strain; the numeral 6 denotes the detection sensitivity of a sample including genomic DNA derived from *Talaromyces trachyspermus* IFM42247 strain; the numeral 7 denotes the detection sensitivity of a sample including genomic DNA derived from *Talaromyces trachyspermus* IFM52252 strain; the numeral 9 denotes the detection sensitivity of a sample including genomic DNA derived from *Talaromyces wortmannii* IFM52255 strain; the numeral 10 denotes the detection sensitivity of a sample including genomic DNA derived from *Byssochlamys fulva* IFM48421 strain; the numeral 12 denotes the detection sensitivity of a sample including genomic DNA derived from *Penicillium griseofulvum* IFM54313 strain; the numeral 13 denotes the detection sensitivity of a sample including genomic DNA derived from *Penicillium citirinum* IFM54314 strain; the numeral 15 denotes the detection sensitivity of a sample including genomic DNA derived from *Neosartorya ficheri* IFM46945 strain; the numeral 16 denotes the detection sensitivity of a sample utilizing DW as a negative control.

Amplification of DNA was confirmed by an increase in turbidity of the reaction solution. The measurement results of the turbidity of the reaction solutions are shown in FIG. 42.

As a result, the turbidity increases (i.e. the DNA synthesis and amplification reactions) were observed from about 40 minutes after the initiation of the reaction only in the systems where the genomic DNAs of *Talaromyces flavus* and *Talaromyces trachyspermus* were used as templates.

On the other hand, in the systems where the genomic DNAs of the fungi other than *Talaromyces flavus* and *Talaromyces trachyspermus* were used, the turbidity increases in the reaction solutions were not observed for 45 minutes after the initiation of the reaction. It should be noted that, in the systems including genomic DNAs of the fungi other than *Talaromyces flavus* and *Talaromyces trachyspermus*, increases in the turbidity of the reaction solutions were observed from about 50 minutes after the start of the reaction. This is caused by amplification by reactions of the primers or annealing of a small amount of primers to sequences other than the target sequences due to a longer reaction time.

As is apparent from the above results, according to the present invention, it is possible to detect *Talaromyces flavus* and *Talaromyces trachyspermus* easily, rapidly, and specifically.

As shown in Examples 6 to 9, it is possible to detect the fungi of the genus *Talaromyces* at species level according to the method of the present invention.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2008-139995 filed in Japan on May 28, 2008, Patent Application No. 2008-139996 filed in Japan on May 28, 2008, Patent Application No. 2008-139997 filed in Japan on May 28, 2008, Patent Application No. 2008-139998 filed in Japan on May 28, 2008, Patent Application No. 2008-139999 filed in Japan on May 28, 2008, and Patent Application No. 2008-141499 filed in Japan on May 29, 2008, each of which is entirely herein incorporated by reference.

[Sequence Listing]
P2008-1007WO00.ST25.txt

---

What is claimed is:

1. A method of detecting whether a heat-resistant fungus belonging to the genus *Byssochlamys* is present in a sample, which comprises steps of:
   (i) adding, to the sample, or adding to nucleic acid obtained from the sample, both oligonucleotide (a) and oligonucleotide (b), wherein
   oligonucleotide (a) consists of a labeled or unlabeled nucleotide sequence that has 95% or more homology to SEQ ID NO: 1 and
   oligonucleotide (b) consists of a labeled or unlabeled nucleotide sequence that has 95% or more homology to SEQ ID NO: 2;
   (ii) hybridizing oligonucleotide (a) and oligonucleotide (b) to nucleic acid in the sample or to nucleic acid obtained from the sample, under conditions in which both oligonucleotide (a) and oligonucleotide (b) hybridize specifically to *Byssochlamys* nucleic acid that is in the sample or was obtained from the sample, or,
   hybridizing oligonucleotide (a) and oligonucleotide (b) to nucleic acid in the sample or to nucleic acid obtained from the sample, under conditions in which both oligonucleotide (a) and oligonucleotide (b) hybridize specifically to *Byssochlamys* nucleic acid that is in the sample or was obtained from the sample and performing amplification of nucleic acid using oligonucleotide (a) and oligonucleotide (b) as a primer pair for the amplification, and
   (iii) determining whether oligonucleotide (a) and oligonucleotide (b) hybridized to nucleic acid in step (ii), or, determining whether an amplification product was produced in step (ii),
   wherein determining that oligonucleotide (a) and oligonucleotide (b) hybridized to the nucleic acid, or, when gene amplification was performed, determining that an amplification product was produced by the amplification, detects the presence, in the sample, of a fungus belonging to the genus *Byssochlamys*.

2. The method of detecting a heat-resistant fungus according to claim 1, wherein at least one of oligonucleotide (a) and oligonucleotide (b) is labeled.

3. The method according to claim 1, wherein step (ii) is said hybridizing oligonucleotide (a) and oligonucleotide (b) to nucleic acid in the sample or to nucleic acid obtained from the sample, and step (iii) is said determining whether oligonucleotide (a) and oligonucleotide (b) hybridized to nucleic acid in step (ii).

4. The method of claim 1, wherein the nucleotide sequence of oligonucleotide (a) is that of SEQ ID NO: 1 and the nucleotide sequence of oligonucleotide (b) is that of SEQ ID NO: 2.

5. The method of claim 1, wherein the fungus is *Byssochlamys nivea*.

6. The method of claim 1, wherein step (ii) is said hybridizing oligonucleotide (a) and oligonucleotide (b) to nucleic acid in the sample or to nucleic acid obtained from the sample and performing amplification of the nucleic acid using oligonucleotide (a) and oligonucleotide (b) as a primer pair for the amplification and step (iii) is said determining whether an amplification product was produced in step (ii).

* * * * *

SEQUENCE LISTING

```
<160> NUMBER OF SEQ ID NOS: 88

<210> SEQ ID NO 1
<211> LENGTH: 20
<212> TYPE: DNA
<213> ORGANISM: Artificial sequence
<220> FEATURE:
<223> OTHER INFORMATION: Synthesized

<400> SEQUENCE: 1
ttgggaccaa acaagagaca                                               20

<210> SEQ ID NO 2
<211> LENGTH: 20
<212> TYPE: DNA
<213> ORGANISM: Artificial sequence
<220> FEATURE:
<223> OTHER INFORMATION: Synthesized

<400> SEQUENCE: 2
tgtgcactta cacaccagca                                               20
```

<210> SEQ ID NO 3
<211> LENGTH: 20
<212> TYPE: DNA
<213> ORGANISM: Artificial sequence
<220> FEATURE:
<223> OTHER INFORMATION: Synthesized

<400> SEQUENCE: 3
tgctgctttc tggtgagttt                                          20

<210> SEQ ID NO 4
<211> LENGTH: 20
<212> TYPE: DNA
<213> ORGANISM: Artificial sequence
<220> FEATURE:
<223> OTHER INFORMATION: Synthesized

<400> SEQUENCE: 4
ggagatgatt tgcctggaaa                                          20

<210> SEQ ID NO 5
<211> LENGTH: 21
<212> TYPE: DNA
<213> ORGANISM: Artificial sequence
<220> FEATURE:
<223> OTHER INFORMATION: Synthesized

<400> SEQUENCE: 5
tgatggatcc ggcatgtgag t                                        21

<210> SEQ ID NO 6
<211> LENGTH: 22
<212> TYPE: DNA
<213> ORGANISM: Artificial sequence
<220> FEATURE:
<223> OTHER INFORMATION: Synthesized

<400> SEQUENCE: 6
tacttgttgc cgctagccta ta                                       22

<210> SEQ ID NO 7
<211> LENGTH: 20
<212> TYPE: DNA
<213> ORGANISM: Artificial sequence
<220> FEATURE:
<223> OTHER INFORMATION: Synthesized

<400> SEQUENCE: 7
ttgaaaggga agcgttggcc                                          20

<210> SEQ ID NO 8
<211> LENGTH: 19
<212> TYPE: DNA
<213> ORGANISM: Artificial sequence
<220> FEATURE:
<223> OTHER INFORMATION: Synthesized

<400> SEQUENCE: 8
ccccgggcta taaggcacc                                           19

<210> SEQ ID NO 9
<211> LENGTH: 21
<212> TYPE: DNA
<213> ORGANISM: Artificial sequence
<220> FEATURE:

```
<223> OTHER INFORMATION: Synthesized

<400> SEQUENCE: 9
gttgaaaggg aagcgttgtc c                                              21

<210> SEQ ID NO 10
<211> LENGTH: 21
<212> TYPE: DNA
<213> ORGANISM: Artificial sequence
<220> FEATURE:
<223> OTHER INFORMATION: Synthesized

<400> SEQUENCE: 10
tgatggatcc ggartstgag t                                              21

<210> SEQ ID NO 11
<211> LENGTH: 21
<212> TYPE: DNA
<213> ORGANISM: Artificial sequence
<220> FEATURE:
<223> OTHER INFORMATION: Synthesized

<400> SEQUENCE: 11
cttgttgccg ctagcctata t                                              21

<210> SEQ ID NO 12
<211> LENGTH: 20
<212> TYPE: DNA
<213> ORGANISM: Artificial sequence
<220> FEATURE:
<223> OTHER INFORMATION: Synthesized

<400> SEQUENCE: 12
gtcatgggta tcagctaaca                                                20

<210> SEQ ID NO 13
<211> LENGTH: 20
<212> TYPE: DNA
<213> ORGANISM: Artificial sequence
<220> FEATURE:
<223> OTHER INFORMATION: Synthesized

<400> SEQUENCE: 13
ctttctcaat tgggaggata                                                20

<210> SEQ ID NO 14
<211> LENGTH: 20
<212> TYPE: DNA
<213> ORGANISM: Artificial sequence
<220> FEATURE:
<223> OTHER INFORMATION: Synthesized

<400> SEQUENCE: 14
ggctctggcc agtaagttcg                                                20

<210> SEQ ID NO 15
<211> LENGTH: 20
<212> TYPE: DNA
<213> ORGANISM: Artificial sequence
<220> FEATURE:
<223> OTHER INFORMATION: Synthesized

<400> SEQUENCE: 15
ttgtcaccgt tggcctagta                                                20
```

```
<210> SEQ ID NO 16
<211> LENGTH: 20
<212> TYPE: DNA
<213> ORGANISM: Artificial sequence
<220> FEATURE:
<223> OTHER INFORMATION: Synthesized

<400> SEQUENCE: 16
tcaggccagc ggtaacaagt                                               20

<210> SEQ ID NO 17
<211> LENGTH: 20
<212> TYPE: DNA
<213> ORGANISM: Artificial sequence
<220> FEATURE:
<223> OTHER INFORMATION: Synthesized

<400> SEQUENCE: 17
ggaagagctg gccaaaagga                                               20

<210> SEQ ID NO 18
<211> LENGTH: 20
<212> TYPE: DNA
<213> ORGANISM: Artificial sequence
<220> FEATURE:
<223> OTHER INFORMATION: Synthesized

<400> SEQUENCE: 18
gtaaccaaat cggtgctgct                                               20

<210> SEQ ID NO 19
<211> LENGTH: 20
<212> TYPE: DNA
<213> ORGANISM: Artificial sequence
<220> FEATURE:
<223> OTHER INFORMATION: Synthesized

<400> SEQUENCE: 19
aaagcgtggg ttgcacttac                                               20

<210> SEQ ID NO 20
<211> LENGTH: 20
<212> TYPE: DNA
<213> ORGANISM: Artificial sequence
<220> FEATURE:
<223> OTHER INFORMATION: Synthesized

<400> SEQUENCE: 20
ctccggtgtg taagtgcaac                                               20

<210> SEQ ID NO 21
<211> LENGTH: 20
<212> TYPE: DNA
<213> ORGANISM: Artificial sequence
<220> FEATURE:
<223> OTHER INFORMATION: Synthesized

<400> SEQUENCE: 21
gccaggctcg agatcgacca                                               20

<210> SEQ ID NO 22
<211> LENGTH: 22
<212> TYPE: DNA
<213> ORGANISM: Artificial sequence
<220> FEATURE:
<223> OTHER INFORMATION: Synthesized
```

<400> SEQUENCE: 22
gatgacgggt gattgggatc tc                                          22

<210> SEQ ID NO 23
<211> LENGTH: 23
<212> TYPE: DNA
<213> ORGANISM: Artificial sequence
<220> FEATURE:
<223> OTHER INFORMATION: Synthesized

<400> SEQUENCE: 23
gcgtccgctt cttccttgtt ttc                                         23

<210> SEQ ID NO 24
<211> LENGTH: 511
<212> TYPE: DNA
<213> ORGANISM: Byssochlamys nivea

<400> SEQUENCE: 24
ggtaacccaa atcggtgctg ctttctggta tgttgggacc aaacaagaga caggaagagc    60
ctggatgtct atttggagtg tggaaggctc gaggtgtgag attgaggatg ctaacaattc   120
tacaggcaga ccatctccgg tgagcacggt ctcgacggtg ctggtgtgta agtgcacacg   180
atgttttggc gtctatgaga tgaggaatcg agagtgactg acgctaattt agctacaatg   240
gctcctccga cctccagctg gagcgcatga acgtctactt caacgaggtt gttgttgact   300
tccctgatga tcgcgataag acgctccata tgctgaccct cctcctaggc tgccggcaag   360
aagtatgttc cccgtgccgt cctcgtcgac cttgagcctg gtaccatgga cgctgtccgt   420
gccggtcctt tcggccagca cttccgccat gacaacttcg tcttcggtca gtccggtgct   480
ggtaacaact gggccaaggg tcactacact g                                 511

<210> SEQ ID NO 25
<211> LENGTH: 1122
<212> TYPE: DNA
<213> ORGANISM: Byssochlamys fulva

<400> SEQUENCE: 25
gtggcccaac ctcccacccg tgttgaccga cacctgttgc ttcggcgggc ccgccagggc    60
tcccgcccgg ccgccggggg gccccgtcgc ccccgggccc gcgcccgccg aagacccctc   120
gaacgctgcc tcgaaggttg ccgtctgagt atgaaatcaa tcgttaaaac tttcaacaac   180
ggatctcttg gttccggcat cgatgaagaa cgcagcgaaa tgcgataagt aatgtgaatt   240
gcagaattcc gtgaatcatc gaatctttga acgcacattg cgccccctgg cattccgggg   300
ggcatgcctg tccgagcgtc attgctaacc ctccagcccg gctggtgtgt gggccgccg   360
tccccctccgg gggacgggcc cgaaaggcag cggcggcgcc gcgtccggtc ctcgagcgta   420
tggggctttg tcacgcgctc tggtaggccc ggcggcttg ctggccaacg acctcacggt   480
cacctaactt ctctcttagg ttgacctcgg atcaggtagg ataccccgct gaacttaagc   540
atatcaataa gcggaggaaa agaaaccaac agggattgcc ccagtaacgg cgagtgaagc   600
ggcaagagct caaatttgaa atctggcccc tccggggtcc gagttgtaat ttgcagagga   660
tgcttcgggt gcggtcccca tctaagtgcc ctggaacggg ccgtcataga gggtgagaat   720
cccgtctggg atgggcggcc gtgccgtgt gaagctcctt cgacgagtcg agttgtttgg   780
gaatgcagct ctaaatgggt ggtaaatttc atctaaagct aaatattggc cggagaccga   840
tagcgcacaa gtagagtgat cgaaagatga aaagaacttt gaaaagagag ttaaacagca   900

```
cgtgaaattg ttgaaaggga agcgcttgcg accagactcg cccgcggggg ttcagccggt    960
actcgtaccg gtgtactccc ccgggggcgg gccagcgtcg gtttgggcgg ccggtcaaag   1020
gcccccggaa tgtgtcgcct ctcggggcgt cttatagccg ggggtgcaat gcggccagcc   1080
tggaccgagg aacgcgcttc ggcacggacg ctggcgtaat gg                      1122

<210> SEQ ID NO 26
<211> LENGTH: 457
<212> TYPE: DNA
<213> ORGANISM: Talaromyces flavus

<400> SEQUENCE: 26
ggtaaccaaa tcggtgctgc tttctggtga gtttgactct cgaccgaaac tctcaattgt     60
cgcgacaaca cgctgacttt tccaggcaaa tcatctccgc tgagcacggt ctggacggct    120
ccggtgtgta agtattacac gattcaaatc cagattacga tccaacaata tctgataatc    180
aacagctaca atggctcctc cgacctccag ttggagcgta tgaacgttta cttcaacgag    240
gtgcgtcaaa ccactccacc taataaacgg aagacaaact catgatcgat ataggcttcc    300
ggcaacaaat atgtccctcg tgctgtcctc gtcgacttgg agcccggtac catgacgcc     360 gtccgcgctg gtccctttgg tcagctcttc cgtcccgaca actttgtttt cggtcagtcc    420
ggtgctggta acaactgggc caagggtcac tacactg                            457

<210> SEQ ID NO 27
<211> LENGTH: 471
<212> TYPE: DNA
<213> ORGANISM: Talaromyces luteus

<400> SEQUENCE: 27
ggtaaccaaa tcggtgctgc gtcctggtaa gctattgatg aacctgggaa cggtacaaaa     60
tcaacatatc agaagaaata tttactgaca tagattgtct tctaggcaaa ctatctccgg    120
cgagcacggt cttgatggat ccggcatgtg agtgaggtag ctcgacactc gacgaatcac    180
cactgatggg aaaatagtta caatggctct tccgacctcc agttagagcg gatgaacgtc    240
tatttcaacg aggtccgtca attgtgaatc attaccgacc gacagcacga attcttacgg    300
tcatataggc tagcggcaac aagtacgtcc ctcgtgccgt cctcatcgat ctggagcccg    360
gtactatgga tgctgtccgt gctggtcctt tcggtcagct cttccgtccc gacaacttcg    420
tcttcggcca gtccggtgcc ggtaacaact gggccaaggg tcactacact g             471

<210> SEQ ID NO 28
<211> LENGTH: 549
<212> TYPE: DNA
<213> ORGANISM: Talaromyces wortmannii

<400> SEQUENCE: 28
aacggcgagt gaagcggcaa gagctcaaat ttgaaatctg gctccttcgg ggcccgagtt     60
gtaatttgga gaggatgctt cgggcgtggc ccctatctaa gtgccctgga acgggccgtc    120
atagagggtg agaatcccgt ctgggatagg tggtcccgcc cgtgtgaagc tccttcgaag    180
agtcgagttg tttgggaatg cagctctaag agggtggtaa atttcatcta aagctaaata    240
ttggccggag accgatagcg cacaagtaga gtgatcgaaa gatgaaaagc actttgaaaa    300
gagagttaaa cagcacgtga aattgttgaa agggaagcat tggcaaccag acttgcttgg    360
ggaggctcag ccggcacgtg tgccggtgca ctcctcccg gcaggccagc gtcggtttgg    420
```

| | |
|---|---|
| gcggtcggtc aaaggccctg ggaatgtagc actcttcggg gtgccttata gcccggggtg | 480 |
| ccatgcgacc tgcccggacc gaggaacgcg cttcggctcg gacgctggcg taatggttgt | 540 |
| caatggccc | 549 |

```
<210> SEQ ID NO 29
<211> LENGTH: 634
<212> TYPE: DNA
<213> ORGANISM: Talaromyces wortmannii

<400> SEQUENCE: 29
```

| | |
|---|---|
| ttaatacgac tcactatagg gcgaattggg cccgacgtcg catgctcccg gccgccatgg | 60 |
| cggccgcggg aattcgattg gtaaccaaat cggtgctgct ttctggtgag ttgcggataa | 120 |
| acaatggcac aaaaaaacat tcgttaacgt tgtacaggca aactatctct ggcgagcacg | 180 |
| gcctcgatgg ctccggaatg tgagttatag tgattttcaa aatttcgaca tcccaccctg | 240 |
| atcatttcca gttacaatgg cacctccgac ctccagttgg agcgtatgaa cgtctacttc | 300 |
| aacgaggtgc gtggaatctg ccccgcgaca ttcggaaata tactcatatc gtataggcta | 360 |
| gcggcaacaa gtacgtcccc cgtgccgtcc tcgtcgattt ggagcctggc accatggacg | 420 |
| ctgtccgcgc tggtcccttc ggtcagctct tccgtcccga caacttcgtc ttcggccagt | 480 |
| cgggtgctgg taacaactgg gccaagggtc actacactga gggtaatcac tagtgaattc | 540 |
| gcggccgcct gcaggtcgac catatgggag agctcccaac gcgttggatg catagcttga | 600 |
| gtattctata gtgtcaccta ataatcgaa ttcc | 634 |

```
<210> SEQ ID NO 30
<211> LENGTH: 1098
<212> TYPE: DNA
<213> ORGANISM: Talaromyces flavus

<400> SEQUENCE: 30
```

| | |
|---|---|
| gcggcccaac ctcccaccct tgtctctata cacctgttgc tttggcgggc ccaccggggc | 60 |
| cacctggtcg ccgggggacg tcgtctccgg gcccgcgcct gccgaagcgc tctgtgaacc | 120 |
| ctgatgaaga tgggctgtct gagtactatg aaaattgtca aaactttcaa caatggatct | 180 |
| cttggttccg gcatcgatga agaacgcagc gaaatgcgat aagtaatgtg aattgcagaa | 240 |
| ttccgtgaat catcgaatct ttgaacgcac attgcgcccc ctggcattcc ggggggcatg | 300 |
| cctgtccgag cgtcatttct gccctcaagc acggcttgtg tgttgggtgc ggtcccccg | 360 |
| gggacctgcc caaaaggcag cggcgacgcc cgtctggtcc tcgagcgtat ggggctctgt | 420 |
| cactcgctcg ggaaggacct gcggggggttg gtcacaccac tatatttac cacggttgac | 480 |
| ctcggatcag gtaggagtta cccgctgaac ttaagcatat caataagcgg aggaaaagaa | 540 |
| accaaccggg attgcctcag taacggcgag tgaagcggca agagctcaaa tttgaaatct | 600 |
| ggccccttg gggtccgagt tgtaatttgc agaggatgct tcgggtgcgg tccccatcta | 660 |
| agtgccctgg aacgggccgt catagagggt gagaatcccg tctgggatgg gcggccgcgc | 720 |
| ccgtgtgaag ctccttcgac gagtcgagtt gtttgggaat gcagctctaa gcgggtggta | 780 |
| aatttcatct aaagctaaat actggccgga gaccgatagc gcacaagtag agtgatcgaa | 840 |
| agatgaaaag aactttgaaa agagagttaa acagcacgtg aaattgttga agggaagcg | 900 |
| ttgtccacca gactcgcccg gggggttca gccggcactt gtgccggtgt actcctctcc | 960 |
| gggcgggcca gcatcggttt gggcggctgg tgaaggcccc gggaatgta acacccctcg | 1020 |
| gggtgcctta tagcccgggg tgccatacag ccagcctgga ccgaggcccg cgcttcggcg | 1080 | aggatgctgg cgtaatgg                                                    1098

<210> SEQ ID NO 31
<211> LENGTH: 1113
<212> TYPE: DNA
<213> ORGANISM: Talaromyces trachyspermus

<400> SEQUENCE: 31
tgggcccaac ctcccacccg tgtctcttgc gtactttgtt gctttggcgg gcccactggg      60
tcactccggt cgccggggag cgctatgctc ccgggcccgt gcccgccaga gcacccctgt     120
gaaccctgat gaagagaggc tgtctgagtc ccacgataat cgttaaaact ttcaacaatg     180
gatctcttgg ttccggcatc gatgaagaac gcagcgaaat gcgataagta atgtgaattg     240
cagaattccg tgaatcatcg aatctttgaa cgcacattgc gccccctggc attccggggg     300
gcatgcctgt ccgagcgtca tttctgccct caagcgcggc ttgtgtgttg ggcgtggtcc     360
ccctggcttt ggcggggacc tgcccgaaag gcagcggcga cgtcccgcct agtcctcgag     420 cgtatgggc tctgtcacgc gctcgggagg gactggtggg cgttggtcac cccttattct      480
ttctacggtt gacctcggat caggtaggag ttacccgctg aacttaagca tatcaataag     540
cggaggaaaa gaaaccaacc gggattgcct cagtaacggc gagtgaagcg gcaagagctc     600
aaatttgaaa tctggcccc ccggggtccg agttgtaatt tggagaggat gcttcgggcg      660
ccgttcccgt ctaagtgccc ctggaacggg ctgtcgcaga gggtgagaac ccgtctggg      720 acgggctacg gcgcccgtgt gaagctcctt ggacgagtct agttgtttgg gaatgcagct     780
ctaagcgggt ggtaaatttc atctaaagct aaatactggc cggagaccga tagcgcacaa     840
gtagagtgat cgaaagatga aaagcacttt gaaaatagag tcaaacagca cgtgaaattg     900
ttgaaaggga agcgttggcc gccagacgcg cccggggaggg ctcagccggc acgtgtgccg    960
gtgtactctc tcccggggcgg gccagcatcg gtttgggcgg tcgctgaaag gccccgggaa   1020
tgtagcaccc taccggggtg ccttatagcc cggggcggca tgcggcccgc cgggaccgag   1080
gcccgcgctt cggcgaggat gctggcgtaa tgg                                 1113

<210> SEQ ID NO 32
<211> LENGTH: 454
<212> TYPE: DNA
<213> ORGANISM: Neosartorya glabra

<400> SEQUENCE: 32
tatgtcttga cctcaaagct tggatgacgg gtgattggga tctctcatct tagcaggcta     60
cctccatggg ttcagcctca ctgtcatggg tatcagctaa caaatctaca ggcagaccat    120
ctctggtgag catggccttg acggctctgg ccagtaagtt cgacctatat cctcccaatt    180
gagaaagcgg cagaaacacg gaaaacaagg aagaagcgga cgcgtgtctg atgggaaata    240
atagctacaa tggctcctcc gatctccagc tggagcgtat gaacgtctat ttcaacgagg    300
tgtgtggatg aaactcttga tttatactat ttcggcaaca tctcacgatc tgactcgcta    360
ctaggccaac ggtgacaaat atgttcctcg tgccgttctg gtcgatctcg agcctggtac    420
catggacgct gtccgtgccg gtcccttcgg cgag                                454

<210> SEQ ID NO 33
<211> LENGTH: 451
<212> TYPE: DNA
<213> ORGANISM: Aspergillus fumigatus

<400> SEQUENCE: 33

```
tatgtcttga cctcaaagct tggatgacgg gtgattggga tctctcatct tagcaggcta    60
cctccatggg ttcagcctca ctgtcatggg tatcagctaa caaatctaca ggcagaccat   120
ctctggtgag catggcctta cggctctggc cagtaagttc gacctatatc ctcccaattg   180
agaaagcggc agaaacacgg aaaacaagga agaagcggac gcgtgtctga tgggaaataa   240
tagctacaat ggctcctccg atctccagct ggagcgtatg aacgtctatt caacgaggtg   300
tgtggatgaa actcttgatt tatactattt cggcaacatc tcacgatctg actcgctact   360
aggccaacgg tgacaaatat gttcctcgtg ccgttctggt cgatctcgag cctggtacca   420
tggacgctgt ccgtgccggt cccttcgcga g                                  451
```

<210> SEQ ID NO 34
<211> LENGTH: 562
<212> TYPE: DNA
<213> ORGANISM: Aspergillus fumigatus

<400> SEQUENCE: 34

```
agggtaaccaa aattggtgcc gctttctggt atgtcttgac ctcaaagctt ggatgacggg    60
tgattgggat ctctcatctt agcaggctac ctccatgggt tcagcctcac tgtcatgggt   120
atcagctaac aaatctacag gcagaccatc tctggtgagc atggccttga cggctctggc   180
cagtaagttc gacctatatc ctcccaattg agaaagcggc ggaaacacgg aaaacaagga   240
agaagcggac gcgtgtctga tgggaaataa tagctacaat ggctcctccg atctccagct   300
ggagcgtatg aacgtctatt caacgaggtg tgtggatgaa actcttgatt ttatactatt   360
tcggcaacat ctcacgatct gactcgctac taggccaacg tgacaaata tgttcctcgt   420
gccgttctgg tcgatctcga gcctggtacc atggacgctg tccgtgccgg tcccttcggc   480
gagctattcc gtcccgacaa cttcgtcttc ggccagtccg tgctggtaa caactgggcc   540
aagggtcact acaccgaggg cg                                             562
```

<210> SEQ ID NO 35
<211> LENGTH: 530
<212> TYPE: DNA
<213> ORGANISM: Hamigera avellanea

<400> SEQUENCE: 35

```
ggtaacccaa atcggtgctg ctttctggta cgttgacaaa tccaaacgag gagacaaaat    60
aaatcccaac ttctcgaaac accaatttga gacaaattgg gtcgaagaaa aagatctta   120
tactgacaat ctttataggc agaccatctc tggcgagcac ggtcttgatg ctccggtgt   180
gtaagtgcaa cccacgcttt cggtcctgac aacaatacaa ccagatcaat tctgatgata   240
aaaacagtta caatggcacc tccgacctcc agttggagcg tatgaacgtt tacttcaacg   300
aggttcgtga attgaacatt tggatccgac tacgacgtgt caaatgctga tatatcatca   360
ggccagcggt aacaagtatg tccccgtgc cgtccttggt cgatctcgag cctggcacca   420
tggacgccgt ccgtgccggt cctttggcc agctcttccg ccccgacaac ttcgtttcg   480
gccagtctgg tgccggtaac aactgggcca agggtcacta cactgagggt             530
```

<210> SEQ ID NO 36
<211> LENGTH: 18
<212> TYPE: DNA
<213> ORGANISM: Artificial sequence
<220> FEATURE:
<223> OTHER INFORMATION: Synthesized

<400> SEQUENCE: 36
cggtcctcga gcgtatgg                                                        18

<210> SEQ ID NO 37
<211> LENGTH: 18
<212> TYPE: DNA
<213> ORGANISM: Artificial sequence
<220> FEATURE:
<223> OTHER INFORMATION: Synthesized

<400> SEQUENCE: 37
ccgttactgg ggcaatcc                                                        18

<210> SEQ ID NO 38
<211> LENGTH: 40
<212> TYPE: DNA
<213> ORGANISM: Artificial sequence
<220> FEATURE:
<223> OTHER INFORMATION: Synthesized

<400> SEQUENCE: 38
agttaggtga ccgtgaggtc gtctttgtca cgcgctctgg                                40

<210> SEQ ID NO 39
<211> LENGTH: 42
<212> TYPE: DNA
<213> ORGANISM: Artificial sequence
<220> FEATURE:
<223> OTHER INFORMATION: Synthesized

<400> SEQUENCE: 39
ggatcaggta gggatacccg ctgttggttt cttttcctcc gc                             42

<210> SEQ ID NO 40
<211> LENGTH: 20
<212> TYPE: DNA
<213> ORGANISM: Artificial sequence
<220> FEATURE:
<223> OTHER INFORMATION: Synthesized

<400> SEQUENCE: 40
ggcaacatct cacgatctga                                                      20

<210> SEQ ID NO 41
<211> LENGTH: 20
<212> TYPE: DNA
<213> ORGANISM: Artificial sequence
<220> FEATURE:
<223> OTHER INFORMATION: Synthesized

<400> SEQUENCE: 41
ccctcagtgt agtgaccctt                                                      20

<210> SEQ ID NO 42
<211> LENGTH: 41
<212> TYPE: DNA
<213> ORGANISM: Artificial sequence
<220> FEATURE:
<223> OTHER INFORMATION: Synthesized

<400> SEQUENCE: 42
atggtaccag gctcgagatc gatactaggc caacggtgac a                              41

<210> SEQ ID NO 43

```
<211> LENGTH: 40
<212> TYPE: DNA
<213> ORGANISM: Artificial sequence
<220> FEATURE:
<223> OTHER INFORMATION: Synthesized

<400> SEQUENCE: 43
gtcccttcgg cgagctcttc gttgttacca gcaccagact                              40

<210> SEQ ID NO 44
<211> LENGTH: 19
<212> TYPE: DNA
<213> ORGANISM: Artificial sequence
<220> FEATURE:
<223> OTHER INFORMATION: Synthesized

<400> SEQUENCE: 44
acggcacgag gaacatact                                                    19

<210> SEQ ID NO 45
<211> LENGTH: 20
<212> TYPE: DNA
<213> ORGANISM: Artificial sequence
<220> FEATURE:
<223> OTHER INFORMATION: Synthesized

<400> SEQUENCE: 45
cgataacttc gtcttcggcc                                                   20

<210> SEQ ID NO 46
<211> LENGTH: 19
<212> TYPE: DNA
<213> ORGANISM: Artificial sequence
<220> FEATURE:
<223> OTHER INFORMATION: Synthesized

<400> SEQUENCE: 46
gccgctttct ggtatgtct                                                    19

<210> SEQ ID NO 47
<211> LENGTH: 20
<212> TYPE: DNA
<213> ORGANISM: Artificial sequence
<220> FEATURE:
<223> OTHER INFORMATION: Synthesized

<400> SEQUENCE: 47
cgcttcttcc ttgttttccg                                                   20

<210> SEQ ID NO 48
<211> LENGTH: 42
<212> TYPE: DNA
<213> ORGANISM: Artificial sequence
<220> FEATURE:
<223> OTHER INFORMATION: Synthesized

<400> SEQUENCE: 48
ccatgacagt gaggctgaac cccgggtgat tgggatctct ca                          42

<210> SEQ ID NO 49
<211> LENGTH: 39
<212> TYPE: DNA
<213> ORGANISM: Artificial sequence
<220> FEATURE:
<223> OTHER INFORMATION: Synthesized

<400> SEQUENCE: 49
```

```
accatctctg gtgagcatgg ctttccgccg ctttctcaa                              39

<210> SEQ ID NO 50
<211> LENGTH: 24
<212> TYPE: DNA
<213> ORGANISM: Artificial sequence
<220> FEATURE:
<223> OTHER INFORMATION: Synthesized

<400> SEQUENCE: 50
agtaagttcg acctatatcc tccc                                             24

<210> SEQ ID NO 51
<211> LENGTH: 20
<212> TYPE: DNA
<213> ORGANISM: Artificial sequence
<220> FEATURE:
<223> OTHER INFORMATION: Synthesized

<400> SEQUENCE: 51
ggatccgaat acgacgtgtc                                                  20

<210> SEQ ID NO 52
<211> LENGTH: 20
<212> TYPE: DNA
<213> ORGANISM: Artificial sequence
<220> FEATURE:
<223> OTHER INFORMATION: Synthesized

<400> SEQUENCE: 52
ccctcagtgt agtgaccctt                                                  20

<210> SEQ ID NO 53
<211> LENGTH: 39
<212> TYPE: DNA
<213> ORGANISM: Artificial sequence
<220> FEATURE:
<223> OTHER INFORMATION: Synthesized

<400> SEQUENCE: 53
catggtgcca ggctcgagat ccaggccagc ggtaacaag                             39

<210> SEQ ID NO 54
<211> LENGTH: 38
<212> TYPE: DNA
<213> ORGANISM: Artificial sequence
<220> FEATURE:
<223> OTHER INFORMATION: Synthesized

<400> SEQUENCE: 54
ccggtccttt tggccagctc tgttaccggc accagact                              38

<210> SEQ ID NO 55
<211> LENGTH: 17
<212> TYPE: DNA
<213> ORGANISM: Artificial sequence
<220> FEATURE:
<223> OTHER INFORMATION: Synthesized

<400> SEQUENCE: 55
acggcacggg ggacata                                                     17

<210> SEQ ID NO 56
<211> LENGTH: 19
<212> TYPE: DNA
```

<213> ORGANISM: Artificial sequence
<220> FEATURE:
<223> OTHER INFORMATION: Synthesized

<400> SEQUENCE: 56
ttccgcccag acaacttcg                                                    19

<210> SEQ ID NO 57
<211> LENGTH: 20
<212> TYPE: DNA
<213> ORGANISM: Artificial sequence
<220> FEATURE:
<223> OTHER INFORMATION: Synthesized

<400> SEQUENCE: 57
ccagttggag cgtatgaacg                                                   20

<210> SEQ ID NO 58
<211> LENGTH: 20
<212> TYPE: DNA
<213> ORGANISM: Artificial sequence
<220> FEATURE:
<223> OTHER INFORMATION: Synthesized

<400> SEQUENCE: 58
cccagttgtt accagcaccg                                                   20

<210> SEQ ID NO 59
<211> LENGTH: 40
<212> TYPE: DNA
<213> ORGANISM: Artificial sequence
<220> FEATURE:
<223> OTHER INFORMATION: Synthesized

<400> SEQUENCE: 59
ttgttgccgg aggcctacac tttacttcaa cgaggtgcgt                              40

<210> SEQ ID NO 60
<211> LENGTH: 40
<212> TYPE: DNA
<213> ORGANISM: Artificial sequence
<220> FEATURE:
<223> OTHER INFORMATION: Synthesized

<400> SEQUENCE: 60
cgacttggag cccggtacca aaagttgtcg ggacggaaga                              40

<210> SEQ ID NO 61
<211> LENGTH: 19
<212> TYPE: DNA
<213> ORGANISM: Artificial sequence
<220> FEATURE:
<223> OTHER INFORMATION: Synthesized

<400> SEQUENCE: 61
gctggtccct ttggtcagc                                                    19

<210> SEQ ID NO 62
<211> LENGTH: 19
<212> TYPE: DNA
<213> ORGANISM: Artificial sequence
<220> FEATURE:
<223> OTHER INFORMATION: Synthesized

<400> SEQUENCE: 62
tggctccgga atgtgagtt                                                    19

<210> SEQ ID NO 63
<211> LENGTH: 18
<212> TYPE: DNA
<213> ORGANISM: Artificial sequence
<220> FEATURE:
<223> OTHER INFORMATION: Synthesized

<400> SEQUENCE: 63
caaatcgacg aggacggc                                                  18

<210> SEQ ID NO 64
<211> LENGTH: 40
<212> TYPE: DNA
<213> ORGANISM: Artificial sequence
<220> FEATURE:
<223> OTHER INFORMATION: Synthesized

<400> SEQUENCE: 64
cgctccaact ggaggtcgga aaatttcgac atcccaccct                          40

<210> SEQ ID NO 65
<211> LENGTH: 39
<212> TYPE: DNA
<213> ORGANISM: Artificial sequence
<220> FEATURE:
<223> OTHER INFORMATION: Synthesized

<400> SEQUENCE: 65
ggaatctgcc ccgcgacatt ccgggggacg tacttgttg                           39

<210> SEQ ID NO 66
<211> LENGTH: 23
<212> TYPE: DNA
<213> ORGANISM: Artificial sequence
<220> FEATURE:
<223> OTHER INFORMATION: Synthesized

<400> SEQUENCE: 66
ggtgccattg taactggaaa tga                                            23

<210> SEQ ID NO 67
<211> LENGTH: 23
<212> TYPE: DNA
<213> ORGANISM: Artificial sequence
<220> FEATURE:
<223> OTHER INFORMATION: Synthesized

<400> SEQUENCE: 67
actcatatcg tataggctag cgg                                            23

<210> SEQ ID NO 68
<211> LENGTH: 20
<212> TYPE: DNA
<213> ORGANISM: Artificial sequence
<220> FEATURE:
<223> OTHER INFORMATION: Synthesized

<400> SEQUENCE: 68
cgaatcacca ctgatgggaa                                                20

<210> SEQ ID NO 69
<211> LENGTH: 20
<212> TYPE: DNA
<213> ORGANISM: Artificial sequence
<220> FEATURE:

<223> OTHER INFORMATION: Synthesized

<400> SEQUENCE: 69
gaagagctga ccgaaaggac                                          20

<210> SEQ ID NO 70
<211> LENGTH: 42
<212> TYPE: DNA
<213> ORGANISM: Artificial sequence
<220> FEATURE:
<223> OTHER INFORMATION: Synthesized

<400> SEQUENCE: 70
ttcgtgctgt cggtcggtaa tgttccgacc tccagttaga gc                 42

<210> SEQ ID NO 71
<211> LENGTH: 42
<212> TYPE: DNA
<213> ORGANISM: Artificial sequence
<220> FEATURE:
<223> OTHER INFORMATION: Synthesized

<400> SEQUENCE: 71
taggctagcg gcaacaagta cgatagtacc gggctccaga tc                 42

<210> SEQ ID NO 72
<211> LENGTH: 22
<212> TYPE: DNA
<213> ORGANISM: Artificial sequence
<220> FEATURE:
<223> OTHER INFORMATION: Synthesized

<400> SEQUENCE: 72
acctcgttga aatagacgtt ca                                       22

<210> SEQ ID NO 73
<211> LENGTH: 19
<212> TYPE: DNA
<213> ORGANISM: Artificial sequence
<220> FEATURE:
<223> OTHER INFORMATION: Synthesized

<400> SEQUENCE: 73
gcgtcatttc tgccctcaa                                           19

<210> SEQ ID NO 74
<211> LENGTH: 19
<212> TYPE: DNA
<213> ORGANISM: Artificial sequence
<220> FEATURE:
<223> OTHER INFORMATION: Synthesized

<400> SEQUENCE: 74
agttcagcgg gtaactcct                                           19

<210> SEQ ID NO 75
<211> LENGTH: 38
<212> TYPE: DNA
<213> ORGANISM: Artificial sequence
<220> FEATURE:
<223> OTHER INFORMATION: Synthesized

<400> SEQUENCE: 75
tacgctcgag gaccagacgg cggcttgtgt gttgggtg                      38

<210> SEQ ID NO 76
<211> LENGTH: 40
<212> TYPE: DNA
<213> ORGANISM: Artificial sequence
<220> FEATURE:
<223> OTHER INFORMATION: Synthesized

<400> SEQUENCE: 76
tctgtcactc gctcgggaag gacctgatcc gaggtcaacc                              40

<210> SEQ ID NO 77
<211> LENGTH: 19
<212> TYPE: DNA
<213> ORGANISM: Artificial sequence
<220> FEATURE:
<223> OTHER INFORMATION: Synthesized

<400> SEQUENCE: 77
gctgcctttt gggcaggtc                                                     19

<210> SEQ ID NO 78
<211> LENGTH: 25
<212> TYPE: DNA
<213> ORGANISM: Artificial sequence
<220> FEATURE:
<223> OTHER INFORMATION: Synthesized

<400> SEQUENCE: 78
tggtcacacc actatatttt accac                                              25

<210> SEQ ID NO 79
<211> LENGTH: 24
<212> TYPE: DNA
<213> ORGANISM: Artificial sequence
<220> FEATURE:
<223> OTHER INFORMATION: Synthesized

<400> SEQUENCE: 79
ggtaaccaaa tcggtgctgc tttc                                               24

<210> SEQ ID NO 80
<211> LENGTH: 24
<212> TYPE: DNA
<213> ORGANISM: Artificial sequence
<220> FEATURE:
<223> OTHER INFORMATION: Synthesized

<400> SEQUENCE: 80
accctcagtg tagtgaccct tggc                                               24

<210> SEQ ID NO 81
<211> LENGTH: 24
<212> TYPE: DNA
<213> ORGANISM: Artificial sequence
<220> FEATURE:
<223> OTHER INFORMATION: Synthesized

<400> SEQUENCE: 81
gcatatcaat aagcggagga aaag                                               24

<210> SEQ ID NO 82
<211> LENGTH: 19
<212> TYPE: DNA
<213> ORGANISM: Artificial sequence
<220> FEATURE:
<223> OTHER INFORMATION: Synthesized

<400> SEQUENCE: 82

```
ggtccgtgtt tcaagacgg                                                 19
```

<210> SEQ ID NO 83
<211> LENGTH: 97
<212> TYPE: DNA
<213> ORGANISM: Neosartorya fischeri

<400> SEQUENCE: 83

```
tggtaaacca atcggtgct gctttctggt atgtcttgac ctcaattctt ggatgacggg    60
agattgggac ctgtcttagc aggctgtcct ccatggg                            97
```

<210> SEQ ID NO 84
<211> LENGTH: 98
<212> TYPE: DNA
<213> ORGANISM: Neosartorya fischeri

<400> SEQUENCE: 84

```
cctcccaatt gagaaagcgg cggaaacacg aaaggaagga agaagaggac gcgtgtctga    60
tggggttaat agctacaatg gctcctccga tctccagc                           98
```

<210> SEQ ID NO 85
<211> LENGTH: 100
<212> TYPE: DNA
<213> ORGANISM: Neosartorya spinosa

<400> SEQUENCE: 85

```
tggtaaacca atcggtgct gctttctggt atgtctcaac ctcaatgctt ggatgatggg    60
agattaggac ctgtcatctc agcaggctgt cctccatggg                         100
```

<210> SEQ ID NO 86
<211> LENGTH: 99
<212> TYPE: DNA
<213> ORGANISM: Neosartorya spinosa

<400> SEQUENCE: 86

```
cctcccaatt gagaaagccg ggggaaacac gaaaggcaag caggaagagg acgcgtgcct    60
gacgggataa tagctacaat ggcacctccg acctccagc                          99
```

<210> SEQ ID NO 87
<211> LENGTH: 619
<212> TYPE: DNA
<213> ORGANISM: Cladosporium cladosporoides

<400> SEQUENCE: 87

```
aggttcacct tcagaccggc cagtgtgtac gttgagcgcc tcgatcccga tggcagtgaa    60
gagctggtga ttaacatgtg caaagggcaa ccaaattggt gctgctttct ggcagaccat   120
ctccggcgag catggcctcg acggctccgg cgtgtatgtt tacatcgcca gaaagaatac   180
attgggcttc atctgacacc tgctaggtac aatggcacgt ctgacctcca gctggagcgc   240
atgaacgtct acttcaatga ggtacaaatg ccaaggcaa tcgcatactc cgatagcacg    300
cactgacctt ctgcgatttc aggcttccgg caacaagtac gtcccgcgtg ccgtcctcgt   360
cgacttggag cccggtacca tggacgctgt ccgtgccggt cccttcggcc agctcttccg   420
tcccgacaac ttcgtcttcg gccagtccgg cgccggcaac aactgggcca agggtcacta   480
cactgagggt gccgagctcg tcgaccaagt ccttgatgtc gtccgtcgcg aggcagaggg   540
ctgcgactgc ctccagggtt tccagatcac ccactctctc ggtggtggta ccggtgccgg   600
```

```
                                                  -continued tatgggtact cttctcatc                                                  619

<210> SEQ ID NO 88
<211> LENGTH: 559
<212> TYPE: DNA
<213> ORGANISM: Neosartorya fischeri

<400> SEQUENCE: 88
tggtaaacca aatcggtgct gctttctggt atgtcttgac ctcaattctt ggatgacggg      60
agattgggac ctgtcttagc aggctgtcct ccatgggttc agcttcgctg tcatgggtat     120
cagctaacaa atctacaggc agaccatctc tggtgagcac ggccttgacg gctctggcca    180
gtaagttcga cctatatcct cccaattgag aaagcggcgg aaacacgaaa ggaaggaaga    240
agaggacgcg tgtctgatgg ggttaatagc tacaatggct cctccgatct ccagctggag    300
cgtatgaacg tctacttcaa cgaggtgtgt ggatgaaact ctcgactcta tactatttcg    360
gcaacatctc acgatctgac tcgctactag gccaacggtg acaagtatgt tcctcgtgcc    420
gttctggtcg atctcgagcc tggtaccatg gacgctgtcc gtgccggtcc cttcggcgag    480
ctcttccgtc ccgataactt cgtcttcggc cagtctggtg ctggtaacaa ctgggccaag    540
ggtcactaca ctgaggggt                                                559
```